(12) United States Patent
Narayan et al.

(10) Patent No.: US 11,230,593 B2
(45) Date of Patent: Jan. 25, 2022

(54) COMPOSITIONS AND METHODS FOR TREATING AND PREVENTING INFLUENZA

(71) Applicant: VISTERRA, INC., Waltham, MA (US)

(72) Inventors: Kristin Narayan, Lexington, MA (US); Susan Sloan, Newton, MA (US); Jill Yarbrough, Pittsboro, NC (US); David William Oldach, Jamaica Plain, MA (US); Zachary Shriver, Winchester, MA (US)

(73) Assignee: VISTERRA, INC., Waltham, MA (US)

( * ) Notice: Subject to any disclaimer, the term of this patent is extended or adjusted under 35 U.S.C. 154(b) by 0 days.

(21) Appl. No.: 16/829,519

(22) Filed: Mar. 25, 2020

(65) Prior Publication Data

US 2020/0308257 A1    Oct. 1, 2020

Related U.S. Application Data

(60) Provisional application No. 62/890,938, filed on Aug. 23, 2019, provisional application No. 62/873,401, filed on Jul. 12, 2019, provisional application No. 62/823,426, filed on Mar. 25, 2019.

(51) Int. Cl.

| | |
|---|---|
| *A61K 39/00* | (2006.01) |
| *A61K 39/145* | (2006.01) |
| *C12N 7/00* | (2006.01) |
| *A61K 39/12* | (2006.01) |
| *C07K 14/005* | (2006.01) |
| *C07K 16/10* | (2006.01) |
| *A61P 31/16* | (2006.01) |
| *A61K 31/53* | (2006.01) |
| *A61K 45/06* | (2006.01) |

(52) U.S. Cl.
CPC .......... *C07K 16/1018* (2013.01); *A61K 31/53* (2013.01); *A61P 31/16* (2018.01); *A61K 45/06* (2013.01); *A61K 2039/505* (2013.01); *A61K 2039/54* (2013.01); *A61K 2039/545* (2013.01)

(58) Field of Classification Search
CPC .......... C12N 7/00; C12N 2760/16134; A61P 31/16; A61P 31/12; A61K 39/12
See application file for complete search history.

(56) References Cited

U.S. PATENT DOCUMENTS

| | | | |
|---|---|---|---|
| 4,474,757 A | 10/1984 | Amon et al. | |
| 4,625,015 A | 11/1986 | Green et al. | |
| 5,589,174 A | 12/1996 | Okuno et al. | |
| 5,631,350 A | 5/1997 | Okuno et al. | |
| 5,684,146 A | 11/1997 | Okuno et al. | |
| 6,337,070 B1 | 1/2002 | Okuno et al. | |
| 6,720,409 B2 | 4/2004 | Okuno et al. | |
| 7,255,859 B1 | 8/2007 | Emrich et al. | |
| 7,527,800 B2 | 5/2009 | Yang et al. | |
| 7,537,768 B2 | 5/2009 | Luke et al. | |
| 7,566,454 B2 | 7/2009 | Lu et al. | |
| 7,566,458 B2 | 7/2009 | Yang et al. | |
| 7,572,620 B2 | 8/2009 | Olsen et al. | |
| 7,879,326 B2 | 2/2011 | Foung et al. | |
| 8,124,092 B2 | 2/2012 | Lanzavecchia | |
| 8,192,927 B2 | 6/2012 | Van Den Brink et al. | |
| 8,383,121 B2 | 2/2013 | Qian et al. | |
| 8,444,986 B2 | 5/2013 | Qian et al. | |
| 8,470,327 B2 | 6/2013 | Throsby et al. | |
| 8,486,406 B2 | 7/2013 | Burioni et al. | |
| 8,540,994 B2 | 9/2013 | Ho et al. | |
| 8,540,995 B2 | 9/2013 | Mookkan et al. | |
| 8,540,996 B2 | 9/2013 | Qian et al. | |
| 8,574,581 B2 | 11/2013 | Qian et al. | |
| 8,574,830 B2 | 11/2013 | Mookkan et al. | |
| 8,603,467 B2 | 12/2013 | Chen et al. | |
| 8,637,456 B2 | 1/2014 | Sasisekharan et al. | |
| 8,637,644 B2 | 1/2014 | Ho et al. | |
| 8,637,645 B2 | 1/2014 | Ho et al. | |
| 8,802,110 B2 | 8/2014 | Raman et al. | |
| 8,871,207 B2 | 10/2014 | Lanzavecchia | |
| 8,877,200 B2 | 11/2014 | Shriver et al. | |
| 9,096,657 B2 | 8/2015 | Shriver et al. | |
| 9,278,998 B2 | 3/2016 | Jayaraman et al. | |
| 9,334,309 B2 | 5/2016 | Sasisekharan et al. | |
| 9,572,861 B2 | 2/2017 | Sasisekharan et al. | |
| 9,587,010 B2 | 3/2017 | Lanzavecchia | |
| 9,683,030 B2 | 6/2017 | Raguram et al. | |
| 9,709,567 B2 | 7/2017 | Jayaraman et al. | |
| 9,745,352 B2 | 8/2017 | Raman et al. | |
| 9,969,794 B2 | 5/2018 | Shriver et al. | |
| 9,982,037 B2 | 5/2018 | Raguram et al. | |
| 10,226,527 B2 | 3/2019 | Tharakaraman et al. | |

(Continued)

FOREIGN PATENT DOCUMENTS

| | | |
|---|---|---|
| CA | 2872308 A1 | 11/2013 |
| CN | 104602709 A | 5/2015 |

(Continued)

OTHER PUBLICATIONS

Pierce et al., "M-ZDOCK: a grid-based approach for Cn symmetric multimer docking," Bioinformatics (2005) vol. 21, No. 8, pp. 1472-1478.

Plans-Rubio, "The vaccination coverage required to establish herd immunity against influenza viruses," Preventive Medicine (2012) vol. 55, pp. 72-77.

Powers et al., "Expression of single-chain Fv-Fc fusions in Pichia pastoris", J. Immunol. Methods, 2001, vol. 251, pp. 123-135.

Rogers and Paulson "Receptor determinants of human and animal influenza virus isolates: differences in receptor specificity of the H3 hemagglutinin based on species of origin" Virology. 127(2)361-373 (1983).

(Continued)

*Primary Examiner* — Barry A Chestnut
(74) *Attorney, Agent, or Firm* — Lando & Anastasi, LLP

(57) ABSTRACT

This disclosure relates to binding agents, e.g., antibodies and antigen-binding fragments thereof, that bind hemagglutinin protein of influenza viruses, and methods of their use.

20 Claims, 34 Drawing Sheets

Specification includes a Sequence Listing.

(56) References Cited

U.S. PATENT DOCUMENTS

| | | |
|---|---|---|
| 10,513,553 B2 | 12/2019 | Wollacott et al. |
| 10,538,578 B2 | 1/2020 | Raguram et al. |
| 10,800,835 B2 | 10/2020 | Shriver et al. |
| 2002/0054882 A1 | 5/2002 | Okuno et al. |
| 2005/0042229 A1 | 2/2005 | Yang et al. |
| 2005/0287172 A1 | 12/2005 | Yang et al. |
| 2006/0153871 A1 | 7/2006 | Olsen et al. |
| 2006/0217338 A1 | 9/2006 | Lu et al. |
| 2007/0286869 A1 | 12/2007 | Luke et al. |
| 2008/0014205 A1 | 1/2008 | Horowitz et al. |
| 2008/0241918 A1 | 10/2008 | Sasisekharan et al. |
| 2009/0060949 A1 | 3/2009 | Ho et al. |
| 2009/0081193 A1 | 3/2009 | Sasisekharan et al. |
| 2009/0092620 A1 | 4/2009 | Moste et al. |
| 2009/0106864 A1 | 4/2009 | Henry et al. |
| 2009/0136530 A1 | 5/2009 | Yang et al. |
| 2009/0234096 A1 | 9/2009 | Garry et al. |
| 2009/0264362 A1 | 10/2009 | Garry et al. |
| 2009/0269342 A1 | 10/2009 | Sasisekharan et al. |
| 2009/0291472 A1 | 11/2009 | Lu et al. |
| 2009/0311265 A1 | 12/2009 | Van Den Brink et al. |
| 2010/0021489 A1 | 1/2010 | Amon et al. |
| 2010/0036096 A1 | 2/2010 | Roosild et al. |
| 2010/0040635 A1 | 2/2010 | Horowitz et al. |
| 2010/0041740 A1 | 2/2010 | Wong et al. |
| 2010/0061990 A1 | 3/2010 | Sasisekharan et al. |
| 2010/0061995 A1 | 3/2010 | Carragher et al. |
| 2010/0080813 A1 | 4/2010 | Lanzavecchia |
| 2010/0086555 A1 | 4/2010 | Lanzavecchia |
| 2010/0145031 A1 | 6/2010 | Lanzavecchia et al. |
| 2010/0278834 A1 | 11/2010 | Lanzavecchia |
| 2010/0316654 A1 | 12/2010 | Horowitz et al. |
| 2011/0014187 A1 | 1/2011 | Burioni et al. |
| 2011/0033490 A1 | 2/2011 | Jayaraman et al. |
| 2011/0038935 A1 | 2/2011 | Marasco et al. |
| 2011/0065095 A1 | 3/2011 | Kida et al. |
| 2011/0201547 A1 | 8/2011 | Sasisekharan et al. |
| 2011/0274702 A1 | 11/2011 | Lanzavecchia |
| 2011/0319600 A1 | 12/2011 | Ikuta et al. |
| 2012/0020971 A1 | 1/2012 | Kauvar et al. |
| 2012/0039898 A1 | 2/2012 | Throsby et al. |
| 2012/0039899 A1 | 2/2012 | Olsen et al. |
| 2012/0058124 A1 | 3/2012 | Kurosawa et al. |
| 2012/0093823 A1 | 4/2012 | Van Den Brink et al. |
| 2012/0093834 A1 | 4/2012 | Horowitz et al. |
| 2012/0100142 A1 | 4/2012 | Crowe, Jr. et al. |
| 2012/0100150 A1 | 4/2012 | Jiang et al. |
| 2012/0107326 A1 | 5/2012 | Horowitz et al. |
| 2012/0114664 A1 | 5/2012 | Lanzavecchia |
| 2012/0128671 A1 | 5/2012 | Horowitz et al. |
| 2012/0128684 A1 | 5/2012 | Marasco et al. |
| 2012/0213819 A1 | 8/2012 | Tharakaraman et al. |
| 2012/0219585 A1 | 8/2012 | Raman et al. |
| 2012/0276115 A1 | 11/2012 | Van Den Brink et al. |
| 2012/0282273 A1 | 11/2012 | Wrammert et al. |
| 2013/0004505 A1 | 1/2013 | Chang et al. |
| 2013/0022608 A1 | 1/2013 | Burioni et al. |
| 2013/0202608 A1 | 8/2013 | Mookkan et al. |
| 2013/0243792 A1 | 9/2013 | Vogels et al. |
| 2013/0280248 A1 | 10/2013 | Ueno et al. |
| 2013/0289246 A1 | 10/2013 | Crowe et al. |
| 2013/0302348 A1 | 11/2013 | Raguram et al. |
| 2013/0302349 A1 | 11/2013 | Shriver et al. |
| 2013/0309248 A1 | 11/2013 | Throsby et al. |
| 2014/0011982 A1 | 1/2014 | Marasco et al. |
| 2014/0046039 A1 | 2/2014 | Ahmed et al. |
| 2014/0148581 A1 | 5/2014 | Shriver et al. |
| 2014/0206603 A1 | 7/2014 | Sasisekharan et al. |
| 2014/0271655 A1 | 9/2014 | Lanzavecchia |
| 2014/0335504 A1 | 11/2014 | Sasisekharan et al. |
| 2015/0037352 A1 | 2/2015 | Shriver et al. |
| 2015/0147329 A1 | 5/2015 | Raman et al. |
| 2016/0257732 A1 | 9/2016 | Benjamin et al. |
| 2016/0266117 A1 | 9/2016 | Jayaraman et al. |
| 2016/0317612 A1 | 11/2016 | Sasisekharan et al. |
| 2017/0137498 A1 | 5/2017 | Wollacott et al. |
| 2017/0204167 A1 | 7/2017 | Lanzavecchia |
| 2017/0240617 A1 | 8/2017 | Sloan et al. |
| 2017/0306003 A1 | 10/2017 | Raguram et al. |
| 2018/0009850 A1 | 1/2018 | Raman et al. |
| 2018/0099040 A1 | 4/2018 | Marasco |
| 2019/0002536 A1 | 1/2019 | Shriver et al. |
| 2019/0062407 A1 | 2/2019 | Raguram et al. |
| 2019/0142931 A1 | 5/2019 | Tharakaraman et al. |
| 2020/0181243 A1 | 6/2020 | Sloan et al. |
| 2020/0231657 A1 | 7/2020 | Wollacott et al. |
| 2020/0308257 A1 | 10/2020 | Narayan et al. |
| 2021/0054053 A1 | 2/2021 | Sloan et al. |

FOREIGN PATENT DOCUMENTS

| | | |
|---|---|---|
| EP | 0044710 A1 | 1/1982 |
| EP | 0417191 B1 | 3/1993 |
| EP | 2363415 A2 | 9/2011 |
| EP | 2846832 A1 | 3/2015 |
| EP | 3391888 A1 | 10/2018 |
| JP | 62-051700 | 3/1987 |
| JP | 2008104450 A | 5/2008 |
| JP | 2011160681 A | 8/2011 |
| JP | 2011528901 A | 12/2011 |
| JP | 2015519052 A | 7/2015 |
| JP | 6363066 B2 | 7/2018 |
| WO | 198400687 A1 | 3/1984 |
| WO | 200246235 A1 | 6/2002 |
| WO | 2004029207 A2 | 4/2004 |
| WO | 2007089753 A2 | 8/2007 |
| WO | 2007134327 A2 | 11/2007 |
| WO | 2007149715 A2 | 12/2007 |
| WO | 2008028946 A2 | 3/2008 |
| WO | 2008033105 A1 | 3/2008 |
| WO | 2008073161 A2 | 7/2008 |
| WO | 2008091657 A1 | 7/2008 |
| WO | 2008110937 A2 | 9/2008 |
| WO | 2008118970 A2 | 10/2008 |
| WO | 2008140415 A1 | 11/2008 |
| WO | 2008143954 A2 | 11/2008 |
| WO | 2008154813 A1 | 12/2008 |
| WO | 2009035412 A1 | 3/2009 |
| WO | 2009035420 A1 | 3/2009 |
| WO | 2009073163 A1 | 6/2009 |
| WO | 2009073330 A2 | 6/2009 |
| WO | 2009079259 A2 | 6/2009 |
| WO | 2009099394 A1 | 8/2009 |
| WO | 2009111865 A1 | 9/2009 |
| WO | 2009115972 A1 | 9/2009 |
| WO | 2009119722 A1 | 10/2009 |
| WO | 2009121004 A2 | 10/2009 |
| WO | 2009133249 A1 | 11/2009 |
| WO | 2009144667 A1 | 12/2009 |
| WO | 2009147248 A2 | 12/2009 |
| WO | 2010006144 A2 | 1/2010 |
| WO | 2010010466 A2 | 1/2010 |
| WO | 2010010467 A2 | 1/2010 |
| WO | 2010027818 A2 | 3/2010 |
| WO | 2010040281 A1 | 4/2010 |
| WO | 2010040572 A2 | 4/2010 |
| WO | 2010046775 A2 | 4/2010 |
| WO | 2010073647 A1 | 7/2010 |
| WO | 2010074656 A1 | 7/2010 |
| WO | 2010127252 A2 | 11/2010 |
| WO | 2010130636 A1 | 11/2010 |
| WO | 2010132604 A2 | 11/2010 |
| WO | 2010140114 A1 | 12/2010 |
| WO | 2011003100 A2 | 1/2011 |
| WO | 2011041391 A1 | 4/2011 |
| WO | 2011044570 A2 | 4/2011 |
| WO | 2011068143 A1 | 6/2011 |
| WO | 2011087092 A1 | 7/2011 |
| WO | 2011093217 A1 | 8/2011 |
| WO | 2011094445 A1 | 8/2011 |
| WO | 2011096302 A1 | 8/2011 |
| WO | 2011117848 A1 | 9/2011 |
| WO | 2011160083 A1 | 12/2011 |
| WO | 2012021786 A2 | 2/2012 |

(56) References Cited

FOREIGN PATENT DOCUMENTS

| | | |
|---|---|---|
| WO | 2012026878 A1 | 3/2012 |
| WO | 2012029997 A1 | 3/2012 |
| WO | 2012040406 A2 | 3/2012 |
| WO | 2012045001 A2 | 4/2012 |
| WO | 2012047941 A2 | 4/2012 |
| WO | 2012054745 A1 | 4/2012 |
| WO | 2012072788 A1 | 6/2012 |
| WO | 2012096994 A2 | 7/2012 |
| WO | 2013007770 A1 | 1/2013 |
| WO | 2013011347 A1 | 1/2013 |
| WO | 2013020074 A2 | 2/2013 |
| WO | 2013030604 A1 | 3/2013 |
| WO | 2013044840 A1 | 4/2013 |
| WO | 2013048153 A2 | 4/2013 |
| WO | 2013059524 A2 | 4/2013 |
| WO | 2013081371 A1 | 6/2013 |
| WO | 2013081463 A2 | 6/2013 |
| WO | 2013086052 A2 | 6/2013 |
| WO | 2013089496 A1 | 6/2013 |
| WO | 2013114885 A1 | 8/2013 |
| WO | 2013132007 A1 | 9/2013 |
| WO | 2013169377 A1 | 11/2013 |
| WO | 2013170139 A1 | 11/2013 |
| WO | WO2013170139 * | 11/2013 |
| WO | 2014124319 A2 | 8/2014 |
| WO | 2015051010 A1 | 4/2015 |
| WO | 2015112994 A1 | 7/2015 |
| WO | 2017083627 A1 | 5/2017 |
| WO | 2017147248 A1 | 8/2017 |
| WO | 2020198329 A1 | 10/2020 |
| WO | 2021/119467 A1 | 6/2021 |

OTHER PUBLICATIONS

Rogers et al. "Single amino acid substitutions in influenza haemagglutinin change receptor binding specificity" Nature. 304(5921):76-78 (1983).
Rudikoff et al., "Single Amino Acid Substitution Altering Antigen-Binding Specificity", Proc. Natl. Acad. Sci., vol. 79, pp. 1979-1983, Mar. 1982.
Saelens "One Against All: A Broadly Influenza Neutralizing Manmade Monoclonal Antibody Passes Phase I" EBioMedicine 5 (2016) pp. 16-17.
Sauter et al. "Binding of influenza virus hemagglutinin to analogs of its cell-surface receptor, sialic acid: analysis by proton nuclear magnetic resonance spectroscopy and X-ray crystallography" Biochemistry. 31(40):9609-9621 (1992).
Shaman et al., "Forecasting season outbreaks of influenza," PNAS (2012) vol. 109, No. 50, pp. 20425-20430.
Shaman et al., "Real-time influenza forecasts during the 2012-2013 season," Nature Communications (2013) vol. 4, Article 2837, 10 pages.
Shriver and Viswanathan, "Design of a Broadly Neutralizing Antibody Targeting Influenza A" Visterra Inc. (2012) Retrieved from the Internet Aug. 8, 2013; www.visterrainc.com/pdf/ICAAC-VIS410-Presentation-Final-10Sept2012.pdf.
Shriver et al. "Antibody-based strategies to preventand treat influenza" Frontiers in Immunology (2015) vol. 6, Article 315, 6 pages.
Skehel and Wiley "Receptor binding and membrane fusion in virus entry: the influenza hemagglutinin" Annu Rev Biochem. 69:531-569 (2000).
Sloan et al., "Clinical and virological responses to a broad-spectrum human monoclonal antibody in an influenza virus challenge study," Antiviral Research (2020) vol. 6, Article 104763.
Smee et al., "Treatment of Oseltamivir-Resistant Influenza A (H1N1) Virus Infections in Mice With Antiviral Agents," Antiviral Res (2012) vol. 96, No. 1, pp. 13-20.
Smith, G.P., "Filamentous Fusion Phage: Novel Expression Vectors That Display Cloned Antigens on the Virion Surface", Science, 14:228(4705), pp. 1315-1317, 1985.
Soema et al., "Current and next generation influenza vaccines: Formulation and prouction strategies," Eur J Pharm Biopharm (2015) vol. 94, pp. 251-263.
Song et al., "Evaluation of a fully human monoclonal antibody against multiple influenza A viral strains in mice and a pandemic H1N1 strain in nonhuman primates," Antiviral Research (2014) vol. 111, pp. 60-68.
Soundararajan et al. "Networks link antigenic and receptor-binding sites of influenza hemagglutinin: Mechanistic insight into fitter strain propagation", Scientific Reports, vol. 1, Dec. 2011, pp. 1-7.
Sui et al., "Structural and functional bases for broad-spectrum neutralization of avian and human influenza A viruses" Nature Structural & Molecular Biology (2009) vol. 16, No. 3, pp. 265-273.
Sui et al., "Wide prevalence of heterosubtypic broadly neutralizing human anti-influenza A antibodies" Clin Infect Dis. 62(8):1003-1009 (2011).
Tan et al., "A pan-H1 anti-hemagglutinin monoclonal antibody with potent broad-spectrum efficacy in vivo" J Virol. 86 (11):6179-6188 (2012).
Ter Meulen, "Monoclonal antibodies for prophylaxis and therapy of infectious diseases," Expert Opin Emerging Drugs (2007) vol. 12, No. 4, pp. 525-540.
Tharakaraman et al. "A broadly neutralizing human monoclonal antibody is effective against H7N9" PNAS (2015) vol. 112, No. 35, pp. 10890-10895.
Throsby et al., "Heterosubtypic Neutralizing Monoclonal Antibodies Cross-Protective Against H5N1 and H1N1 Recovered From Human IgM+ Memory B Cells," (2008) PLoS One, vol. 3, Issue 12, Article e3942, 15 pages.
Urlaub and Chasin "Isolation of Chinese Hamster Cell Mutants Deficient in Dihydrofolate Reductase Activity," Proc Natl Acad Sci USA (1980) vol. 77, pp. 4216-4220.
Van Den Dool et al. "The Effects of Influenza Vaccination of Health Care Workers in Nursing Homes: Insights from a Mathematical Model," PLoS Medicine (2008) vol. 5, Issue 10, pp. 1453-1460.
Vasquez et al., "Connecting the sequence dots: shedding light on the genesis of antibodies reported to be designed in slim," MABS (2019) vol. 11, No. 5, pp. 803-808.
Wang et al., "Antibody Structure, Instability, and Formulation," Journal of Pharmaceutical Sciences (2007) vol. 96, No. 1, pp. 1-26.
Wang et al., "Broadly protective monoclonal antibodies against H3 influenza viruses following sequential immunization with different hemagglutinins" PLoS Pathog. 6(2):e1000796 (2010).
Wang, "Instability, stabilization, and formulation of liquid protein pharmaceuticals," International Journal of Pharmaceutics (1999) vol. 185, pp. 129-188.
Ward et al., "Binding activities of a repertoire of single immunoglobulin variable domains secreted from *Escherichia coli*", Nature, 1989, vol. 341, pp. 544-546.
Warne et al., "Development of high concentration protein biopharmaceuticals: The use of platform approaches in formulation development," European Journal of Pharmaceutics and Biopharmaceutics (2011), vol. 78, No. 2, pp. 208-212.
Whittle et al. "Broadly neutralizing human antibody that recognizes the receptor-binding pocket of influenza virus hemagglutinin", National Academy of Sciences Proceedings, vol. 108, No. 34, Aug. 23, 2011, pp. 14216-14221.
Williams and Barclay, "The Immunoglobulin Superfamily—Domains for Cell Surface Recognition," Ann Rev Immunol (1988) vol. 6, pp. 381-405.
Wollacott et al., "Safety and Upper Respiratory Pharmacokinetics of the Hemagglutinin Stalk-Binding Antibody VIS410 Support Treatment and Prophylaxis Based on Population Modeling of Seasonal Influenza A Outbreaks," EBioMedicine (2016) vol. 5, pp. 147-155.
Wrammert et al., "Broadly cross-reactive antibodies dominate the human B cell response against 2009 pandemic H1N1 influenza virus infection" J Exp Med. 208(1):181-193 (2011).
Wu et al., "Logistical feasibility and potential benefits of a population-wide passive immunotherapy program during an influenza pandemic," Influenza Other Respi Viruses (2011) vol. 5, Supp. 1, pp. 226-229.

(56) References Cited

OTHER PUBLICATIONS

Wu et al., "Logistical feasibility and potential benefits of a population-wide passive-immunotherapy program during an influenza pandemic," PNAS (2010) vol. 107, No. 7, pp. 3269-3274.
Arnold et al., "The Swiss-Model Workspace: A web-based environment for protein structure homology modelling," Bioinformatics (2006) vol. 22, pp. 195-201.
Balazs et al., "Antibody-based Protection Against HIV Infection by Vectored Immunoprophylaxis," Nature (2011) vol. 481, pp. 81-84.
Baranovich et al. "The Hemagglutinin Stem-Binding Monoclonal Antibody VIS410 Controls Influenza Virus-Induced Acute Respiratory Distress Syndrome" Antimicrobial Agents and Chemotherapy (2016) vol. 60, No. 4, pp. 2118-2131.
Berg, J. K. A Study of VIS410 to Assess Safety and Pharmacokinetics. ClinicalTrials.gov Identifier: NCT02045472. Posted Jan. 24, 2014; Last updated May 14, 2015.
Berry, C.M., et al., "Passive Broad-Spectrum Influenza Immunoprophylaxis", Influenza Research and Treatment, vol. 2014, Article ID 267594, pp. 1-9; Published Sep. 22, 2014.
Bird et al., "Single-chain antigen-binding proteins", Science, 1988, vol. 242, pp. 423-426.
Boni et al., "Virulence attenuation during an influenza A/H5N1 pandemic," Phil Trans R Soc B (2012) 368(1614), 12 pages.
Carr et al., "Influenza hemagglutinin is spring-loaded by a metastable native conformation," Proc Natl Acad Sci USA (1997) vol. 94, pp. 14306-14313.
Chen et al "Humanized antibodies with broad-spectrum neutralization to avian influenza virus H5N1", Antiviral Research, vol. 87, No. 1, Jul. 1, 2010 pp. 81-84.
Chothia et al., "Canonical structures for the hypervariable regions of immunoglobulins", J. Mol. Biol., 1987, vol. 196, pp. 901-917.
Clementi et al. "Broad-range neutralizing anti-influenza A human monoclonal antibodies: new perspectives in therapy and prophylaxis" New Microbiologica (2012) vol. 35, pp. 399-406.
ClinicalTrials.gov Identifier: NCT02045472, "A Study of VIS410 to Assess Safety and Pharmacokinetics," ClinicalTrial.gov updated May 13, 2015, clinicaltrials.gov/ct2/show/record/NCT02045472.
ClinicalTrials.gov Identifier: NCT02468115, "Influenza Challenge Study of VIS410 in Healthy Volunteers," ClinicalTrial.gov updated Apr. 4, 2016, clinicaltrials.gov/ct2/show/record/NCT02468115.
Communication Made to Inventors Prior to Mar. 14, 2013.
Corti et al. "A Neutralizing Antibody Selected from Plasma Cells that Binds to Group 1 and Group 2 Influenza A Hemagglutinins", Science vol. 333, No. 6044, Aug. 2011, pp. 850-856.
Dreyfus et al. "Highly Conserved Protective Epitopes on Influenza B Viruses" Science (2012) vol. 337, pp. 1343-1348.
Ekiert et al, "A Highly Conserved Neutralizing Epitope on Group 2 Influenza A Viruses", Science, vol. 333, No. 6044, Aug. 2011 pp. 843-850.
Ekiert et al."Broadly neutralizing antibodies against influenza virus and prospects for universal therapeies", Current Opinion in Virology, vol. 2, No. 2, Apr. 2012, pp. 134-141.
Ekiert et al., "Antibody recognition of a highly conserved influenza virus epitope" Science 324(5924):246-251 (2009).
Falconer et al., "Stabilization of a monoclonal antibody during purification and formulation by addition of basic amino acid excipients," J Chem Technol Biotechnol (2011) vol. 86, pp. 942-948.
Ferguson et al., "Strategiesfor containing an emerging influenza pandemic in Southeast Asia," Nature (2005) vol. 437(7056), pp. 209-214.
Gamblin and Skehel, "Influenza hemagglutinin and neuraminidase membrane glycoproteins." J Biol Chem (2010) vol. 285, No. 37, pp. 28403-9.
Germann et al., "Mitigation strategies for pandemic influenza in the United States," PNAS (2006) vol. 103, No. 15, pp. 5935-5940.
Gershoni et al., "Epitope Mapping: The First Step in Developing Epitope-Based Vaccines," Biodrugs (2007) vol. 21, No. 3, pp. 145-156.

Gronvall et al., "Next-Generation Monoclonal Antibodies: Challenges and Opportunities," Center for Biosecurity of UPMC Final Report (2013) pp. 1-53.
He et al., "Broadly Neutralizing Anti-Influenza Virus Antibodies: Enhancement of Neutralizing Potency in Polyclonal Mixtures and IgA Backbones," J Virol (2015) vol. 89, No. 7, pp. 3610-3618.
Hershberger et al., "Safety and efficacy of monocolonal antibody VIS410 in adults with uncomplicated influenza A infection: Results from a randomized, double-blind, phase-2, placebo-controlled study," EBioMedicine (2019) vol. 40, pp. 574-582.
Huston et al., "Protein Engineering of Antibody Binding Sites: Recovery of Specific Activity in an Anti-Digoxin Single-Chain Fv Analogue Produced in *Escherichia coli*," Proc Natl Acad Sci USA (1988) vol. 85, pp. 5879-5883.
International Search Report and Written Opinion for International Application No. PCT/US2016/061501 dated Feb. 8, 2017.
International Search Report and Written Opinion for PCT/US2013/040534 dated Sep. 2, 2013.
International Search Report and Written Opinion issued in International Application No. PCT/US2017/019053, dated Jun. 13, 2017.
Jefferson et al., "Oseltamivir for influenza in adults and children: systematic review of clinical study reports and summary of regulatory comments," BMJ (2014) vol. 348, Article g2545, 18 pages.
Jorgensen et al., "Recent trends in stabilising peptides and proteins in pharmaceutical formulation—considerations in the choice of excipients," Expert Opinion on Drug Delivery (2009) vol. 6, No. 11, pp. 1219-1230.
Joshi et al., "Aggregation of Monoclonal Antibody Products: Formation and Removal," Biopharm International (2013) vol. 26, Issue 3, 5 pages.
Joshi et al., "Avoiding antibody aggregation during processing: Establishing hold times," Biotechnol J (2014) vol. 9, pp. 1195-1205.
Kalenik et al., "Influenza prevention and treatment by passive immunization," Acta Biochim Pol (2014) vol. 61, No. 3, pp. 573-87.
Kemble et al., "Intermonomer Disulfide Bonds Impair the Fusion Activity of Influenza Virus Hemagglutinin," J Virol (1992) vol. 66, pp. 4940-4950.
Kiefer et al., "The Swiss-Model Repository and associated resources," Nucleic Acids Research (2009) vol. 37, Database Issue, pp. D387-D392.
Krause et al. "A Broadly Neutralizing Human Monoclonal Antibody That Recognizes a Conserved, Novel Epitope on the Globular Head of the Influenza H1N1 Virus Hemagglutinin", Journal of Virology, vol. 85, No. 20, Oct. 15, 2011, pp. 10905-10908.
Kubota-Koketsu et al "Broad neutralizing human monoclonal antibodies against influenza virus from vaccinated healthy donors", Biochemical and Biophysical Research Communications, vol. 387, No. 1, Sep. 11, 2009 pp. 180-185.
Lachmann, P.J., "The Use of Antibodies in the Prophylaxis and Treatment of Infections", Emerging Microbes and Infections, Published Aug. 8, 2012, 1, e11, pp. 1-5.
Lambert et al., "Influenza Vaccines for the Future," N Engl J Med (2010) vol. 363, No. 21, pp. 2036-2044.
Laursen et al. "Broadly neutralizing antibodies against influenza viruses", Antiviral Research, vol. 98, No. 3, Jun. 2013, pp. 476-483.
Longini et al., "Containing Pandemic Influenza at the Source" Science (2005) vol. 39, pp. 1083-1087.
MacKenzie and Charlson, "Standards for the Use of Ordinal Scales in Clinical Trials," Br Med J (1986) vol. 292, pp. 40-43.
Oh et al., "An Antibody against a Novel and Conserved Epitope in the Hemagglutinin 1 Subunit Neutralizes Numerous H5N1 Influenza Viruses," J Virol (2010) vol. 84, No. 16. pp. 8275-8286.
Okuno et al., "A common neutralizing epitope conserved between the hemagglutinins of influenza A virus H1 and H2 strains." J Virol. 67(5)2552-2558 (1993).
Opposition paper filed in Chilean Application 3051-2014 by AG Pharmaceutical Labs Industrial Association, dated Sep. 9, 2015.
Pedotti et al., "Computational Docking of Antibody-Antigen Complexes, Opportunities and Pitfalls Illustrated by Influenza Hemagglutinin," Int J Mol Sci (2011), vol. 12, pp. 226-251.
Pierce et al., "Accelerating Protein Docking in ZDOCK Using an Advanced 3D Convolution Library," PLoS One (2011) vol. 6, No. 99, Article e24657, 6 pages.

(56) References Cited

OTHER PUBLICATIONS

Extended European Search Report issued in EP Application No. 19217944.8, dated Jun. 25, 2020, 12 pages.
Maggio, "Use of excipients to control aggregation in peptide and protein formulations," J Excipients and Food Chem (2010) vol. 1(2), pp. 40-49.
Harper et al., "Seasonal Influenza in Adults and Children—Diagnosis, Treatment, Chemoprophylaxis, and Institutional Outbreak Management: Clinical Practice Guidelines of the Infection Diseases Society of America," Clin Infect Dis (2009) vol. 48, No. 8, pp. 1003-1032.
Nixon et al., "Fully human monoclonal antibody inhibitors of the neonatal Fc receptor reduce circulating IgG in non-human primates," Frontiers in Immunology (2015) vol. 6, Article 176, 13 pages.
International Search Report and Written Opinion issued in PCT/US2020/064573 dated Mar. 16, 2021,.
Booth et al., "Extending human IgG half-life using structure-guided design," MABS (2018) vol. 10, No. 7, pp. 1098-1110.
Fukao et al., "Combination treatment with the cap-dependent endonuclease inhibitor baloxavir marboxil and a neuraminidase inhibitor in a mouse model of influenza A virus infection," J Antimicrob Chemother (2019) vol. 74, pp. 654-662.
Takashita et al., "Susceptibililty of Influenza Viruses to the Novel Cap-Dependent Endonuclease Inhibitor Baloxavir Marboxil," Frontiers in Microbiology (2018) vol. 9, Article 3026, 7 pages.
International Search Report and Written Opinion issued in PCT/US2020/024664 dated Aug. 7, 2020, 19 Pages.

\* cited by examiner

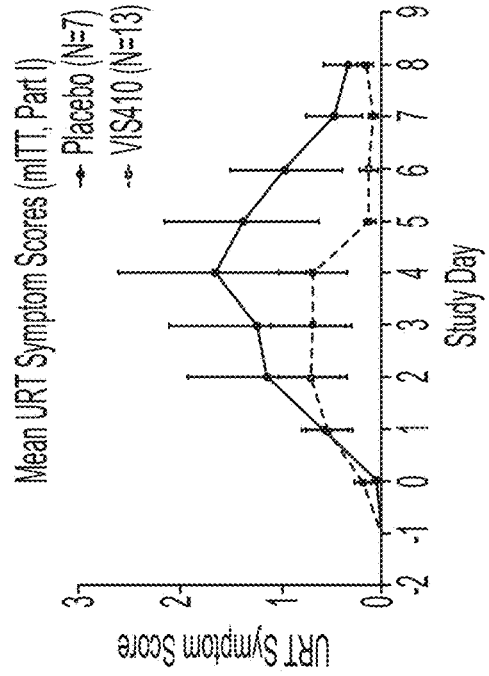
FIG. 25A
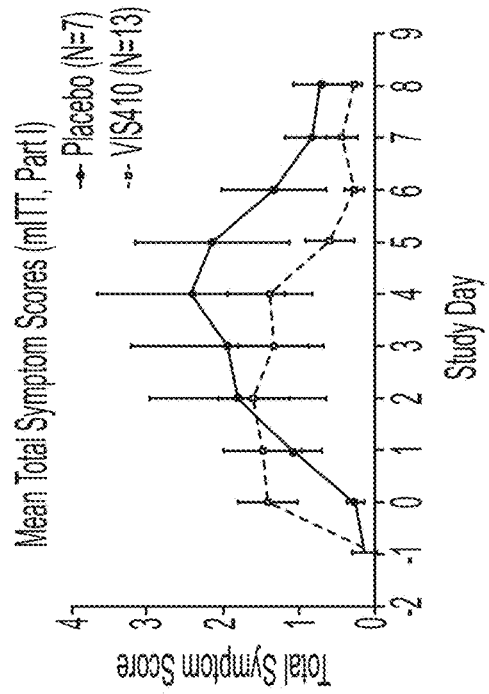
FIG. 25B
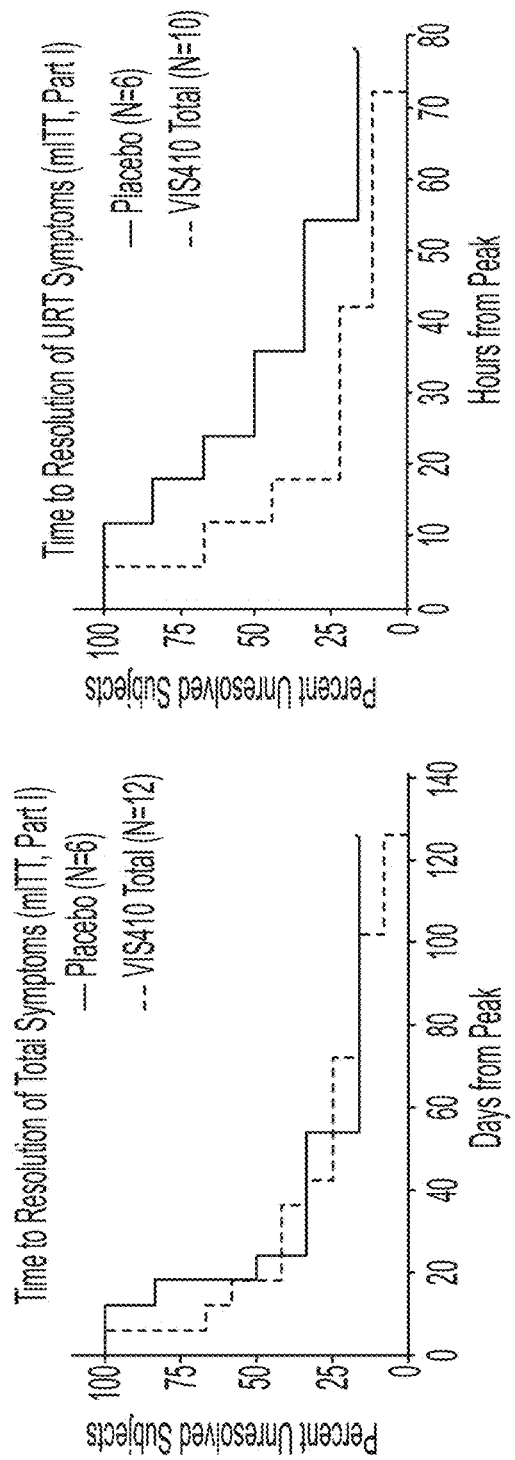
FIG. 25C
FIG. 25D

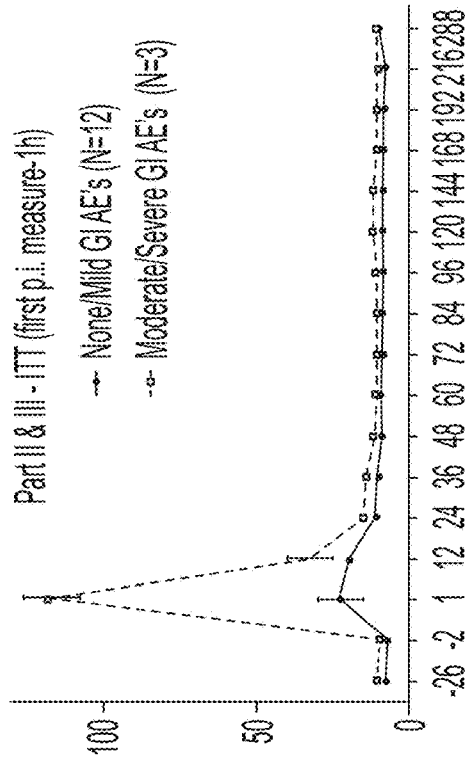
FIG. 27A
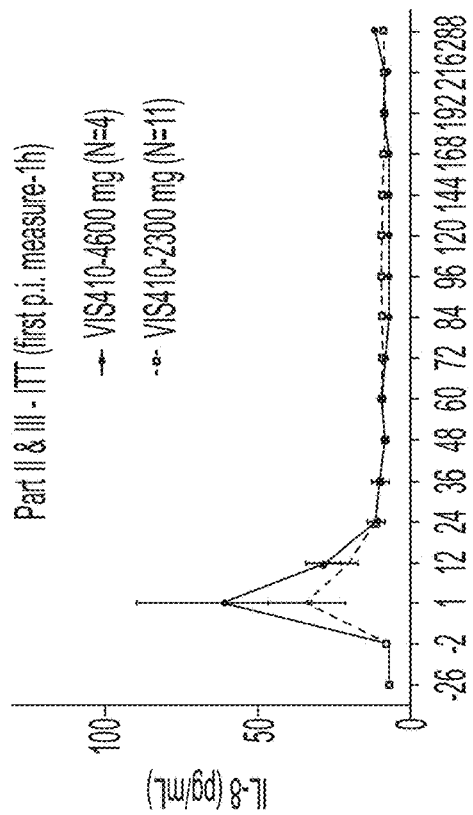
FIG. 27C
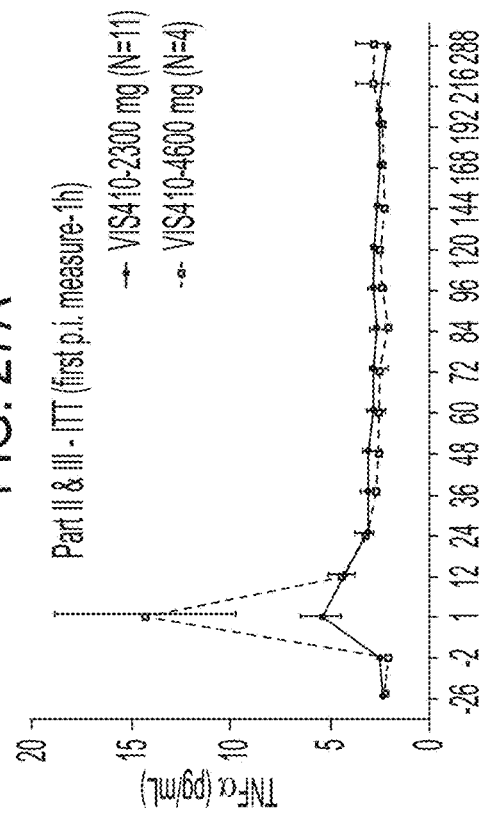
FIG. 27B
FIG. 27D

SEQUENCE LISTING

<160> NUMBER OF SEQ ID NOS: 189

<210> SEQ ID NO 1
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (3)..(3)
<223> OTHER INFORMATION: Ala or Gly

<400> SEQUENCE: 1

Xaa Tyr Xaa Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile, Val or Leu
<220> FEATURE:
<221> NAME/KEY: MOD_RES
<222> LOCATION: (4)..(4)
<223> OTHER INFORMATION: Tyr or Phe
<220> FEATURE:
<221> NAME/KEY: MOD_RES
<222> LOCATION: (7)..(7)
<223> OTHER INFORMATION: Ser or Asn
<220> FEATURE:
<221> NAME/KEY: MOD_RES
<222> LOCATION: (8)..(8)
<223> OTHER INFORMATION: Tyr or Asn
<220> FEATURE:
<221> NAME/KEY: MOD_RES
<222> LOCATION: (9)..(9)
<223> OTHER INFORMATION: Lys or Arg

<400> SEQUENCE: 2

Val Xaa Ser Xaa Asp Gly Xaa Xaa Xaa Tyr Tyr Ala Asp Ser Val Gln
1               5                   10                  15
Gly

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Arg, Lys or Gln
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (15)..(15)
<223> OTHER INFORMATION: Gln or Ser
<220> FEATURE:
<221> NAME/KEY: MOD_RES
<222> LOCATION: (17)..(17)
```

```
<223> OTHER INFORMATION: Tyr, Leu or Val
<220> FEATURE:
<221> NAME/KEY: MOD_RES
<222> LOCATION: (18)..(18)
<223> OTHER INFORMATION: Phe or Leu
<220> FEATURE:
<221> NAME/KEY: MOD_RES
<222> LOCATION: (19)..(19)
<223> OTHER INFORMATION: Asn or Asp
<220> FEATURE:
<221> NAME/KEY: MOD_RES
<222> LOCATION: (20)..(20)
<223> OTHER INFORMATION: Pro or Tyr

<400> SEQUENCE: 3

Asp Xaa Xaa Leu Arg Xaa Leu Leu Tyr Phe Glu Trp Leu Ser Xaa Gly
1               5                   10                  15

Xaa Xaa Xaa Xaa
            20

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Val, Leu or Ile
<220> FEATURE:
<221> NAME/KEY: MOD_RES
<222> LOCATION: (4)..(4)
<223> OTHER INFORMATION: Thr or Ser
<220> FEATURE:
<221> NAME/KEY: MOD_RES
<222> LOCATION: (5)..(5)
<223> OTHER INFORMATION: Tyr, Phe or Trp
<220> FEATURE:
<221> NAME/KEY: MOD_RES
<222> LOCATION: (6)..(6)
<223> OTHER INFORMATION: Asn, Ser or Asp

<400> SEQUENCE: 4

Gln Xaa Xaa Xaa Xaa Xaa Tyr Lys Asn Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (4)..(4)
<223> OTHER INFORMATION: Thr, Ala, Tyr, His, Lys or Asp
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (7)..(7)
```

```
<223> OTHER INFORMATION: Ser or Thr

<400> SEQUENCE: 5

Trp Xaa Ser Xaa Xaa Glu Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or His
<220> FEATURE:
<221> NAME/KEY: MOD_RES
<222> LOCATION: (9)..(9)
<223> OTHER INFORMATION: Thr or Ser

<400> SEQUENCE: 6

Gln Gln Xaa Tyr Arg Thr Pro Pro Xaa
1               5

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (30)..(30)
<223> OTHER INFORMATION: Ser or Thr

<400> SEQUENCE: 7

Xaa Val Gln Leu Leu Glu Xaa Gly Gly Gly Leu Val Lys Pro Gly Gln
1               5                   10                  15

Ser Leu Lys Leu Ser Cys Ala Ala Ser Gly Phe Thr Phe Xaa
            20                  25                  30

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Val Arg Gln Pro Pro Gly Lys Gly Leu Glu Trp Val Ala
1               5                   10

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
```

```
            polypeptide

<400> SEQUENCE: 9

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala or Gln
<220> FEATURE:
<221> NAME/KEY: MOD_RES
<222> LOCATION: (5)..(5)
<223> OTHER INFORMATION: Thr or Ala
<220> FEATURE:
<221> NAME/KEY: MOD_RES
<222> LOCATION: (6)..(6)
<223> OTHER INFORMATION: Thr or Met
<220> FEATURE:
<221> NAME/KEY: MOD_RES
<222> LOCATION: (7)..(7)
<223> OTHER INFORMATION: Leu or Val

<400> SEQUENCE: 10

Trp Gly Xaa Gly Xaa Xaa Xaa Thr Val Ser Ser
1               5                   10

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (3)..(3)
<223> OTHER INFORMATION: Val or Gln
<220> FEATURE:
<221> NAME/KEY: MOD_RES
<222> LOCATION: (9)..(9)
<223> OTHER INFORMATION: Asp or Ser
<220> FEATURE:
<221> NAME/KEY: MOD_RES
<222> LOCATION: (10)..(10)
<223> OTHER INFORMATION: Ser or Thr
<220> FEATURE:
<221> NAME/KEY: MOD_RES
<222> LOCATION: (11)..(11)
<223> OTHER INFORMATION: Leu or Val
<220> FEATURE:
<221> NAME/KEY: MOD_RES
<222> LOCATION: (12)..(12)
<223> OTHER INFORMATION: Ala or Ser
<220> FEATURE:
<221> NAME/KEY: MOD_RES
<222> LOCATION: (13)..(13)
<223> OTHER INFORMATION: Val or Ala
<220> FEATURE:
<221> NAME/KEY: MOD_RES
<222> LOCATION: (14)..(14)
```

```
<223> OTHER INFORMATION: Ser or Thr
<220> FEATURE:
<221> NAME/KEY: MOD_RES
<222> LOCATION: (15)..(15)
<223> OTHER INFORMATION: Leu, Val or Arg
<220> FEATURE:
<221> NAME/KEY: MOD_RES
<222> LOCATION: (17)..(17)
<223> OTHER INFORMATION: Glu or Asp
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (20)..(20)
<223> OTHER INFORMATION: Thr or Ser
<220> FEATURE:
<221> NAME/KEY: MOD_RES
<222> LOCATION: (22)..(22)
<223> OTHER INFORMATION: Asn, Thr, Gln, Asp or Arg
<220> FEATURE:
<221> NAME/KEY: MOD_RES
<222> LOCATION: (24)..(24)
<223> OTHER INFORMATION: Lys or Arg

<400> SEQUENCE: 11

Xaa Ile Xaa Met Thr Gln Ser Pro Xaa Xaa Xaa Xaa Xaa Xaa Xaa Gly
1               5                   10                  15

Xaa Arg Xaa Xaa Ile Xaa Cys Xaa Ser Ser
            20                  25

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Gln or Lys
<220> FEATURE:
<221> NAME/KEY: MOD_RES
<222> LOCATION: (9)..(9)
<223> OTHER INFORMATION: Pro or Ala

<400> SEQUENCE: 12

Trp Tyr Gln Gln Lys Pro Gly Xaa Xaa Pro Lys Leu Leu Ile Tyr
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Asp, Glu or Ser
<220> FEATURE:
<221> NAME/KEY: MOD_RES
<222> LOCATION: (24)..(24)
<223> OTHER INFORMATION: Ala or Pro
<220> FEATURE:
<221> NAME/KEY: MOD_RES
<222> LOCATION: (27)..(27)
<223> OTHER INFORMATION: Val, Phe, Lys or Asp
<220> FEATURE:
<221> NAME/KEY: MOD_RES
<222> LOCATION: (29)..(29)
```

<223> OTHER INFORMATION: Val or Thr

<400> SEQUENCE: 13

Gly Val Pro Xaa Arg Phe Ser Gly Ser Gly Ser Gly Thr Asp Phe Thr
1               5                   10                  15

Leu Thr Ile Ser Ser Leu Gln Xaa Glu Asp Xaa Ala Xaa Tyr Tyr Cys
            20                  25                  30

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly, Gln, Thr, Ser or Asn
<220> FEATURE:
<221> NAME/KEY: MOD_RES
<222> LOCATION: (7)..(7)
<223> OTHER INFORMATION: Leu or Val
<220> FEATURE:
<221> NAME/KEY: MOD_RES
<222> LOCATION: (8)..(8)
<223> OTHER INFORMATION: Asp or Glu

<400> SEQUENCE: 14

Phe Gly Xaa Gly Thr Lys Xaa Xaa Ile Lys
1               5                   10

<210> SEQ ID NO 15
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Ile Ser Tyr Asp Gly Ser Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser

<210> SEQ ID NO 16
<211> LENGTH: 129
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 16

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Thr Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser

<210> SEQ ID NO 17
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser

<210> SEQ ID NO 18
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Leu Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser

<210> SEQ ID NO 19
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Thr Tyr
            20                  25                  30

Ala Met His Trp Val Arg Gln Pro Pro Gly Lys Gly Leu Glu Trp Val
        35                  40                  45

Ala Val Leu Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser

<210> SEQ ID NO 20
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Thr Tyr
            20                  25                  30

```
Ala Met His Trp Val Arg Gln Pro Pro Gly Lys Gly Leu Glu Trp Val
        35                  40                  45

Ala Val Val Ser Phe Asp Gly Asn Asn Arg Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Ser Gly Val Leu Asp Tyr Trp Gly Gln Gly Ala Met Val Thr Val Ser
        115                 120                 125

Ser

<210> SEQ ID NO 21
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Asn Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser

<210> SEQ ID NO 22
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Thr Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Asn Lys Tyr Tyr Ala Asp Ser Val
```

```
                    50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Asp Ser Lys Leu Arg Ser Leu Leu Tyr Phe Glu Trp Leu Ser
                100                 105                 110

Ser Gly Leu Leu Asp Tyr Trp Gly Gln Gly Ala Met Val Thr Val Ser
            115                 120                 125

Ser

<210> SEQ ID NO 23
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Leu Glu Ser Gly Gly Gly Leu Val Lys Pro Gly Gln
  1               5                  10                  15

Ser Leu Lys Leu Ser Cys Ala Ala Ser Gly Phe Thr Phe Thr Ser Tyr
                 20                  25                  30

Gly Met His Trp Val Arg Gln Pro Pro Gly Lys Gly Leu Glu Trp Val
             35                  40                  45

Ala Val Val Ser Tyr Asp Gly Asn Tyr Lys Tyr Tyr Ala Asp Ser Val
         50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Asp Ser Lys Leu Arg Ser Leu Leu Tyr Phe Glu Trp Leu Ser
                100                 105                 110

Gln Gly Tyr Phe Asn Pro Trp Gly Ala Gly Thr Thr Leu Thr Val Ser
            115                 120                 125

Ser

<210> SEQ ID NO 24
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Leu Glu Ser Gly Gly Gly Leu Val Lys Pro Gly Gln
  1               5                  10                  15

Ser Leu Lys Leu Ser Cys Ala Ala Ser Gly Phe Thr Phe Thr Ser Tyr
                 20                  25                  30

Ala Met His Trp Val Arg Gln Pro Pro Gly Lys Gly Leu Glu Trp Val
             35                  40                  45

Ala Val Val Ser Tyr Asp Gly Asn Tyr Lys Tyr Tyr Ala Asp Ser Val
         50                  55                  60

Gln Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                 85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser
```

```
<210> SEQ ID NO 25
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Leu Glu Thr Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser
```

```
<210> SEQ ID NO 26
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Lys Asp Ser Gln Leu Arg Thr Leu Leu Tyr Phe Glu Trp Leu Ser
            100                 105                 110
```

```
Gln Gly Tyr Phe Asn Pro Trp Gly Gln Gly Thr Thr Leu Thr Val Ser
        115                 120                 125
Ser

<210> SEQ ID NO 27
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Thr Leu Leu Tyr Phe Glu Trp Leu Ser
            100                 105                 110

Gln Gly Tyr Phe Asp Pro Trp Gly Gln Gly Thr Thr Leu Thr Val Ser
        115                 120                 125
Ser

<210> SEQ ID NO 28
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Tyr Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
            100                 105                 110

<210> SEQ ID NO 29
<211> LENGTH: 111
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 29

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Ser
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
            100                 105                 110

<210> SEQ ID NO 30
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asp
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
            100                 105                 110

<210> SEQ ID NO 31
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45
```

Lys Leu Leu Ile Tyr Trp Ala Ser Thr Arg Glu Ser Gly Val Pro Asp
            50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Ser Phe Gly Gly Gly Thr Lys Leu Asp Ile Lys
            100                 105                 110

<210> SEQ ID NO 32
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Thr Leu Ser Phe Asn
                20                  25                  30

Tyr Lys Asn Tyr Leu Ala Trp Tyr Gln Gln Lys Pro Gly Gln Pro Pro
             35                  40                  45

Lys Leu Leu Ile Tyr Trp Ala Ser Thr Arg Glu Ser Gly Val Pro Asp
            50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Ser Phe Gly Gly Gly Thr Lys Leu Asp Ile Lys
            100                 105                 110

<210> SEQ ID NO 33
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Thr Val Thr Phe Asn
                20                  25                  30

Tyr Lys Asn Tyr Leu Ala Trp Tyr Gln Gln Lys Pro Gly Gln Pro Pro
             35                  40                  45

Lys Leu Leu Ile Tyr Phe Ala Ser Thr Arg Glu Ser Gly Val Pro Asp
            50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Ser Phe Gly Gly Gly Thr Lys Leu Asp Ile Lys
            100                 105                 110

<210> SEQ ID NO 34

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Phe Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gly Gly Thr Lys Leu Asp Ile Lys
            100                 105                 110

<210> SEQ ID NO 35
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Trp Ser
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
            100                 105                 110

<210> SEQ ID NO 36
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ile Val Met Ser Gln Ser Pro Asp Thr Leu Ala Val Thr Leu Gly
1               5                   10                  15

Glu Arg Ala Ser Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
             35                  40                  45

Lys Val Leu Ile Tyr Trp Ala Ser Ala Arg Glu Thr Gly Val Pro Glu
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Ser Phe Gly Gln Gly Thr Lys Leu Glu Ile Lys
            100                 105                 110

<210> SEQ ID NO 37
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Thr Val Thr Phe Asn
                 20                  25                  30

Tyr Lys Asn Tyr Leu Ala Trp Tyr Gln Gln Lys Pro Gly Gln Pro Pro
             35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Ser Phe Gly Thr Gly Thr Lys Leu Asp Ile Lys
            100                 105                 110

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Thr Val Thr Phe Asn
                 20                  25                  30

Tyr Lys Asn Tyr Leu Ala Trp Tyr Gln Gln Lys Pro Gly Gln Pro Pro
             35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Ser Phe Gly Ser Gly Thr Lys Leu Asp Ile Lys
            100                 105                 110

<210> SEQ ID NO 39
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Asn Gly Thr Lys Leu Asp Ile Lys
            100                 105                 110

<210> SEQ ID NO 41
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn

```
                20                  25                  30

Tyr Lys Asn Tyr Leu Ala Trp Tyr Gln Gln Lys Pro Gly Gln Pro Pro
             35                  40                  45

Lys Leu Leu Ile Tyr Trp Ala Ser Thr Arg Glu Ser Gly Val Pro Asp
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Ser Phe Gly Thr Gly Thr Lys Leu Asp Ile Lys
                100                 105                 110

<210> SEQ ID NO 42
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Ile Val Met Thr Gln Ser Pro Asp Ser Leu Ala Val Ser Leu Gly
  1               5                  10                  15

Glu Arg Ala Thr Ile Asn Cys Lys Ser Ser Gln Thr Leu Ser Phe Asn
             20                  25                  30

Tyr Lys Asn Tyr Leu Ala Trp Tyr Gln Gln Lys Pro Gly Gln Pro Pro
         35                      40                  45

Lys Leu Leu Ile Tyr Trp Ala Ser Thr Arg Glu Ser Gly Val Pro Asp
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Ser Phe Gly Ser Gly Thr Lys Leu Asp Ile Lys
                100                 105                 110

<210> SEQ ID NO 43
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Ile Val Met Thr Gln Ser Pro Asp Ser Leu Ala Val Ser Leu Gly
  1               5                  10                  15

Glu Arg Ala Thr Ile Asn Cys Lys Ser Ser Gln Thr Leu Ser Phe Asn
             20                  25                  30

Tyr Lys Asn Tyr Leu Ala Trp Tyr Gln Gln Lys Pro Gly Gln Pro Pro
         35                      40                  45

Lys Leu Leu Ile Tyr Trp Ala Ser Thr Arg Glu Ser Gly Val Pro Asp
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Ser Phe Gly Gln Gly Thr Lys Leu Asp Ile Lys
```

<210> SEQ ID NO 44
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Asn Gly Thr Lys Leu Asp Ile Lys
            100                 105                 110

<210> SEQ ID NO 45
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 46
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Ser Leu Ser Ala Ser Val Gly
1               5                   10                  15

```
Asp Arg Val Thr Ile Thr Cys Arg Ser Ser Gln Ser Ile Thr Phe Asn
            20                  25                  30

Tyr Lys Asn Tyr Leu Gly Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110
```

<210> SEQ ID NO 47
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Asp Ile Val Met Thr Gln Ser Pro Asp Thr Leu Ala Val Thr Leu Gly
1               5                   10                  15

Glu Arg Ala Thr Ile Gln Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Thr
 65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110
```

<210> SEQ ID NO 48
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Asp Ile Val Met Thr Gln Ser Pro Asp Thr Val Ala Val Thr Val Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                85                  90                  95
```

```
Arg Thr Pro Pro Ser Phe Gly Gln Gly Thr Lys Leu Asp Ile Lys
            100                 105                 110
```

<210> SEQ ID NO 49
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Asp Ile Val Met Thr Gln Ser Pro Asp Thr Val Ala Val Thr Leu Gly
1               5                   10                  15

Glu Arg Ala Thr Ile Asp Cys Lys Ser Ser Gln Thr Val Thr Phe Asn
                20                  25                  30

Tyr Lys Asn Tyr Leu Ala Trp Tyr Gln Gln Lys Pro Gly Gln Pro Pro
            35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110
```

<210> SEQ ID NO 50
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Asp Ile Val Met Thr Gln Ser Pro Asp Thr Leu Ala Val Thr Val Gly
1               5                   10                  15

Glu Arg Ala Thr Ile Arg Cys Lys Ser Ser Gln Thr Val Thr Phe Asn
                20                  25                  30

Tyr Lys Asn Tyr Leu Ala Trp Tyr Gln Gln Lys Pro Gly Gln Pro Pro
            35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110
```

<210> SEQ ID NO 51
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Asp Ile Val Met Thr Gln Ser Pro Asp Thr Leu Ala Val Ser Arg Gly
1               5                   10                  15

Glu Arg Ala Thr Ile Asp Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Glu Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110
```

<210> SEQ ID NO 52
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asp
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110
```

<210> SEQ ID NO 53
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Thr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80
```

```
Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110
```

<210> SEQ ID NO 54
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser His Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110
```

<210> SEQ ID NO 55
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Lys Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110
```

<210> SEQ ID NO 56
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide -continued

```
<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Asp Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 57
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 58
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
```

```
                65                  70                  75                  80
Ser Leu Gln Pro Glu Asp Lys Ala Thr Tyr Tyr Cys Gln Gln His Tyr
                    85                  90                  95

Arg Thr Pro Pro Ser Phe Gly Gln Gly Thr Lys Val Glu Ile Lys
                100                 105                 110

<210> SEQ ID NO 59
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
                20                  25                  30

Tyr Lys Asn Tyr Leu Ala Trp Tyr Gln Gln Lys Pro Gly Lys Ala Pro
            35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Asp Ala Thr Tyr Tyr Cys Gln Gln His Tyr
                    85                  90                  95

Arg Thr Pro Pro Ser Phe Gly Gln Gly Thr Lys Val Glu Ile Lys
                100                 105                 110

<210> SEQ ID NO 60
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
                20                  25                  30

Tyr Lys Asn Tyr Leu Ala Trp Tyr Gln Gln Lys Pro Gly Lys Ala Pro
            35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Tyr
                    85                  90                  95

Arg Thr Pro Pro Ser Phe Gly Gln Gly Thr Lys Val Glu Ile Lys
                100                 105                 110

<210> SEQ ID NO 61
<211> LENGTH: 111
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Thr Arg Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 63
<211> LENGTH: 405
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 63
gaggtacagc tcctcgaatc gggagggga ctggtcaaac ccggtcaatc gctcaaactc      60
tcgtgtgcag cgtcaggttt tacgttcagc tcatatggga tgcactgggt ccgccagcct    120
ccgggaaagg gactggagtg ggtggcagtc gtgtcgtatg acgggagcaa taagtactac    180
gccgattcag tgcaaggtcg gtttaccatt tcgagggata acagcaagaa cacgctctac    240
ttgcagatga actcacttag agcggaagat acggctgtgt actattgcgc caaagacaca    300
aagctgcgat ccctgttgta cttcgaatgg ttgtcctcgg gcttgcttga ctattggggg    360
cagggcgcca tggtcacagt atccagcgcg tcgactaagg ggccc           405

<210> SEQ ID NO 64
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gagatcgtga tgacgcagag ccccgatagc ctcgctgtct cattggggga acgggccacg    60
attaactgca aatcctcaca gtcggtgact ttcagctata agaattacct ggcatggtat   120
cagcagaagc cgggtcaacc cccaaaactg ttgatctact gggcctccac acgcgagtcg   180
ggagtcccgg accgattttc gggttcaggg tccggcactg actttaccct cacaatttca   240
tcgcttcaag cggaggatgt agcagtgtac tattgtcagc agtattacag aacacctccc   300
accttcggag ggggaacgaa acttgacatc aagggatcc                          339

<210> SEQ ID NO 65
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gagatcgtga tgacgcagag ccccgatagc ctcgctgtct cattggggga acgggccacg    60
attaactgca aatcctcaca gtcggtgact ttcgactata agaattacct ggcatggtat   120
cagcagaagc cgggtcaacc cccaaaactg ttgatctact gggcctccac acgcgagtcg   180
ggagtcccgg accgattttc gggttcaggg tccggcactg actttaccct cacaatttca   240
tcgcttcaag cggaggatgt agcagtgtac tattgtcagc agtattacag aacacctccc   300
accttcggag ggggaacgaa acttgacatc aagggatcc                          339

<210> SEQ ID NO 66
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gaagtgcaac tcctcgagtc aggaggaggt ttggtgaaac cgggtcagtc cttgaaactg    60
agctgtgcag caagcgggtt cacgtttacg tcgtacggca tgcactgggt acggcagcct   120
cccgggaagg gacttgaatg ggtcgccgtc atctcatacg acgggtcgta caaatactat   180
gcggatagcg tgcaaggtcg cttcacaatt tcccgggaca attcgaagaa tacactgtat   240
cttcagatga actcgctcag ggctgaggac acggcggtct attactgcgc gaaggattcg   300
cgactcagat ccctttttgta ctttgagtgg ctgtcgcagg ggtatttcaa cccatgggga   360
gccggaacca ctttgaccgt atcaagcgcg tcaacaaagg ggccc                   405

<210> SEQ ID NO 67
<211> LENGTH: 654
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 67
gaaattgtaa tgacgcagag ccctgatagc cttgccgtgt ccctgggtga gagggcgaca      60
atcaattgta agtcatcaca gtcggtcacg tacaactaca agaactacct ggcgtggtat     120
caacagaaac ccgggcagcc gcccaaattg ctcatctatt gggcttcgac acgggagtcg     180
ggtgtgccag accgcttctc cgggtcagga tcgggaactg acttcacgtt gactatttcg     240
tccctccagg cagaagatgt agccgtctac tattgccaac agtattacag aacgccgcct     300
acatttggag gcgggaccaa acttgacatc aagggatccg tggccgcccc cagcgtcttc     360
atcttcccgc ccagcgacga gcagctgaag tcgggcacgg ccagcgtggt gtgcctcctg     420
aacaacttct accccgcga ggcgaaggtc cagtggaagg tggacaacgc cctgcagagc     480
gggaacagcc aggagagcgt gaccgagcag gactcgaagg acagcaccta cagcctcagc     540
agcaccctga cgctgagcaa ggccgactac gagaagcaca aggtctacgc ctgcgaggtg     600
acccaccagg ggctctcgag ccccgtgacc aagagcttca ccggggcga gtgc            654

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Tyr Ala Met His
1               5

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Val Ser Tyr Asp Gly Asn Tyr Lys Tyr Tyr Ala Asp Ser Val Gln
1               5                   10                  15

Gly

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Ser Arg Leu Arg Ser Leu Leu Tyr Phe Glu Trp Leu Ser Gln Gly
1               5                   10                  15

Tyr Phe Asn Pro
            20

<210> SEQ ID NO 71
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 71

Gln Ser Ile Thr Phe Asn Tyr Lys Asn Tyr Leu Ala
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Gly Ser Tyr Leu Glu Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Gln His Tyr Arg Thr Pro Pro Ser
1               5

<210> SEQ ID NO 74
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Leu Glu Thr Gly Gly Gly Leu Val Lys Pro Gly Gln
1               5                   10                  15

Ser Leu Lys Leu Ser Cys Ala Ala Ser Gly Phe Thr Phe Thr
            20                  25                  30

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Val Arg Gln Pro Pro Gly Lys Gly Leu Glu Trp Val Ala
1               5                   10

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76
```

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Trp Gly Gln Gly Thr Thr Leu Thr Val Ser Ser
1               5                   10

<210> SEQ ID NO 78
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ser Ser
            20                  25

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Tyr Gln Gln Lys Pro Gly Lys Ala Pro Lys Leu Leu Ile Tyr
1               5                   10                  15

<210> SEQ ID NO 80
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81
```

```
Phe Gly Gln Gly Thr Lys Val Glu Ile Lys
1               5                   10

<210> SEQ ID NO 82
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Leu Glu Ser Gly Gly Leu Val Lys Pro Gly Gln
1               5                   10                  15

Ser Leu Lys Leu Ser Cys Ala Ala Ser Gly Phe Thr Phe Thr
                20                  25                  30

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Lys Ser Ser Gln Ser Val Thr Tyr Asn Tyr Lys Asn Tyr Leu Ala
1               5                   10                  15

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Trp Ala Ser Thr Arg Glu Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Gln Tyr Tyr Arg Thr Pro Pro Thr
1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Tyr Gly Met His
1               5

<210> SEQ ID NO 87
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Ile Ser Tyr Asp Gly Ser Tyr Lys Tyr Tyr Ala Asp Ser Val Gln
1               5                   10                  15

Gly

<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Ser Glu Leu Arg Ser Leu Leu Tyr Phe Glu Trp Leu Ser Gln Gly
1               5                   10                  15

Tyr Phe Asn Pro
            20

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Trp Gly Ala Gly Thr Thr Leu Thr Val Ser Ser
1               5                   10

<210> SEQ ID NO 90
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Trp Tyr Gln Gln Lys Pro Gly Gln Pro Pro Lys Leu Leu Ile Tyr
1               5                   10                  15

<210> SEQ ID NO 92
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Phe Gly Gly Gly Thr Lys Leu Asp Ile Lys
1               5                   10

<210> SEQ ID NO 94
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Ile Ser Tyr Asp Gly Ser Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
```

```
            210                 215                 220

Lys Lys Val Glu Pro Pro Lys Ser Cys Asp Lys Thr His Thr Cys Pro
225                 230                 235                 240

Pro Cys Pro Gly Thr Glu Leu Leu Gly Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Lys Phe
                275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
                340                 345                 350

Lys Gly Gln Pro Arg Glu Pro Gln Val Tyr Thr Leu Pro Pro Ser Arg
                355                 360                 365

Asp Glu Leu Thr Lys Asn Gln Val Ser Leu Thr Cys Leu Val Lys Gly
                370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
                435                 440                 445

Tyr Thr Gln Lys Ser Leu Ser Leu Ser Pro Gly Lys
    450                 455                 460

<210> SEQ ID NO 95
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Tyr Asn
                20                  25                  30

Tyr Lys Asn Tyr Leu Ala Trp Tyr Gln Gln Lys Pro Gly Gln Pro Pro
            35                  40                  45

Lys Leu Leu Ile Tyr Trp Ala Ser Thr Arg Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys Gly
                100                 105                 110
```

```
Ser Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 96
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Gly Met His Trp Val Arg Gln Pro Pro Gly Lys Gly Leu Glu
        35                  40                  45

Trp Val Ala Val Ile Ser Tyr Asp Gly Ser Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Ala Gly Thr Thr Leu Thr
        115                 120                 125

Val Ser Ser
    130

<210> SEQ ID NO 97
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Ser
            20                  25                  30

Ser Tyr Gly Met His Trp Val Arg Gln Pro Pro Gly Lys Gly Leu Glu
        35                  40                  45
```

Trp Val Ala Val Val Ser Tyr Asp Gly Ser Asn Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Thr Lys Leu Arg Ser Leu Leu Tyr Phe Glu Trp
                100                 105                 110

Leu Ser Ser Gly Leu Leu Asp Tyr Trp Gly Gln Gly Ala Met Val Thr
                115                 120                 125

Val Ser Ser
    130

<210> SEQ ID NO 98
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
                20                  25                  30

Ser Tyr Gly Met His Trp Val Arg Gln Pro Pro Gly Lys Gly Leu Glu
            35                  40                  45

Trp Val Ala Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
                100                 105                 110

Leu Ser Gln Gly Tyr Phe Asn Pro Trp Gly Ala Gly Thr Thr Leu Thr
                115                 120                 125

Val Ser Ser
    130

<210> SEQ ID NO 99
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
                20                  25                  30

Ser Tyr Gly Met His Trp Val Arg Gln Pro Pro Gly Lys Gly Leu Glu
            35                  40                  45

Trp Val Ala Val Leu Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
                100                 105                 110

Leu Ser Gln Gly Tyr Phe Asn Pro Trp Gly Ala Gly Thr Thr Leu Thr
            115                 120                 125

Val Ser Ser
    130

<210> SEQ ID NO 100
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
                20                  25                  30

Thr Tyr Ala Met His Trp Val Arg Gln Pro Pro Gly Lys Gly Leu Glu
            35                  40                  45

Trp Val Ala Val Leu Ser Tyr Asp Gly Asn Tyr Lys Tyr Tyr Ala Asp
        50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
                100                 105                 110

Leu Ser Gln Gly Tyr Phe Asn Pro Trp Gly Ala Gly Thr Thr Leu Thr
            115                 120                 125

Val Ser Ser
    130

<210> SEQ ID NO 101
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Ser
                20                  25                  30

Ser Tyr Gly Met His Trp Val Arg Gln Pro Pro Gly Lys Gly Leu Glu
            35                  40                  45

Trp Val Ala Val Ser Tyr Asp Gly Asn Asn Lys Tyr Tyr Ala Asp
        50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Lys Asp Ser Lys Leu Arg Ser Leu Leu Tyr Phe Glu Trp
            100                 105                 110

Leu Ser Ser Gly Leu Leu Asp Tyr Trp Gly Gln Gly Ala Met Val Thr
            115                 120                 125

Val Ser Ser
    130

<210> SEQ ID NO 102
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Thr Tyr Ala Met His Trp Val Arg Gln Pro Pro Gly Lys Gly Leu Glu
            35                  40                  45

Trp Val Ala Val Ser Tyr Asp Gly Asn Asn Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Lys Asp Ser Lys Leu Arg Ser Leu Leu Tyr Phe Glu Trp
            100                 105                 110

Leu Ser Ser Gly Leu Leu Asp Tyr Trp Gly Gln Gly Ala Met Val Thr
            115                 120                 125

Val Ser Ser
    130

<210> SEQ ID NO 103
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Thr Tyr Ala Met His Trp Val Arg Gln Pro Pro Gly Lys Gly Leu Glu
            35                  40                  45

Trp Val Ala Val Ser Phe Asp Gly Asn Asn Arg Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
            85                  90                  95

```
Tyr Cys Ala Lys Asp Ser Gln Leu Arg Ser Leu Leu Tyr Phe Glu Trp
                100                 105                 110

Leu Ser Ser Gly Val Leu Asp Tyr Trp Gly Gln Gly Ala Met Val Thr
        115                 120                 125

Val Ser Ser
    130

<210> SEQ ID NO 104
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Gly Met His Trp Val Arg Gln Pro Pro Gly Lys Gly Leu Glu
        35                  40                  45

Trp Val Ala Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Lys Leu Arg Ser Leu Leu Tyr Phe Glu Trp
                100                 105                 110

Leu Ser Gln Gly Tyr Phe Asn Pro Trp Gly Ala Gly Thr Thr Leu Thr
        115                 120                 125

Val Ser Ser
    130

<210> SEQ ID NO 105
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Ala Met His Trp Val Arg Gln Pro Pro Gly Lys Gly Leu Glu
        35                  40                  45

Trp Val Ala Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
                100                 105                 110
```

Leu Ser Gln Gly Tyr Phe Asn Pro Trp Gly Gln Gly Thr Thr Leu Thr
            115                 120                 125

Val Ser Ser
    130

<210> SEQ ID NO 106
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Ile Asp Gln Val Gln Leu Leu Glu Thr Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Ala Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Gln Gly Thr Thr Leu Thr
            115                 120                 125

Val Ser Ser
    130

<210> SEQ ID NO 107
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Ala Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Gln Leu Arg Thr Leu Leu Tyr Phe Glu Trp
            100                 105                 110

Leu Ser Gln Gly Tyr Phe Asn Pro Trp Gly Gln Gly Thr Thr Leu Thr
            115                 120                 125

Val Ser Ser
    130

<210> SEQ ID NO 108
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Ala Met His Trp Val Arg Gln Pro Pro Gly Lys Gly Leu Glu
        35                  40                  45

Trp Val Ala Val Ser Tyr Asp Gly Asn Tyr Lys Tyr Tyr Ala Asp
50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Thr Leu Leu Tyr Phe Glu Trp
                100                 105                 110

Leu Ser Gln Gly Tyr Phe Asp Pro Trp Gly Gln Gly Thr Thr Leu Thr
            115                 120                 125

Val Ser Ser
    130

<210> SEQ ID NO 109
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Ser
            20                  25                  30

Ser Tyr Gly Met His Trp Val Arg Gln Pro Pro Gly Lys Gly Leu Glu
        35                  40                  45

Trp Val Ala Val Ser Tyr Asp Gly Ser Asn Lys Tyr Tyr Ala Asp
50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Lys Leu Arg Ser Leu Leu Tyr Phe Glu Trp
                100                 105                 110

Leu Ser Ser Gly Leu Leu Asp Tyr Trp Gly Gln Gly Ala Met Val Thr
            115                 120                 125

Val Ser Ser
    130

<210> SEQ ID NO 110
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Thr
            20                  25                  30

Tyr Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Pro Thr Phe Gly Gly Gly Thr Lys Leu Asp Ile
            100                 105                 110

Lys

<210> SEQ ID NO 111
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Thr
            20                  25                  30

Phe Ser Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Pro Thr Phe Gly Gly Gly Thr Lys Leu Asp Ile
            100                 105                 110

Lys

<210> SEQ ID NO 112
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Thr
            20                  25                  30

Phe Asp Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Pro Thr Phe Gly Gly Gly Thr Lys Leu Asp Ile
            100                 105                 110

Lys

<210> SEQ ID NO 113
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Thr
            20                  25                  30

Trp Ser Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Pro Thr Phe Gly Gly Gly Thr Lys Leu Asp Ile
            100                 105                 110

Lys

<210> SEQ ID NO 114
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Gly Gly Thr Lys Leu Asp Ile
                100                 105                 110

Lys

<210> SEQ ID NO 115
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Ile Asp Glu Ile Val Met Thr Gln Ser Pro Asp Ser Leu Ala Val Ser
 1               5                  10                  15

Leu Gly Glu Arg Ala Thr Ile Asn Cys Lys Ser Ser Gln Thr Leu Ser
                 20                  25                  30

Phe Asn Tyr Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Gly Gly Thr Lys Leu Asp Ile
                100                 105                 110

Lys

<210> SEQ ID NO 116
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ile Asp Glu Ile Val Met Thr Gln Ser Pro Asp Ser Leu Ala Val Ser
 1               5                  10                  15

Leu Gly Glu Arg Ala Thr Ile Asn Cys Lys Ser Ser Gln Thr Val Thr
                 20                  25                  30

Phe Asn Tyr Lys Asn Tyr Leu Ala Trp Tyr Gln Gln Lys Pro Gly Gln
             35                  40                  45

Pro Pro Lys Leu Leu Ile Tyr Phe Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Gly Gly Thr Lys Leu Asp Ile
                100                 105                 110

Lys
```

<210> SEQ ID NO 117
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gly Gly Thr Lys Leu Asp Ile
            100                 105                 110

Lys

<210> SEQ ID NO 118
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ile Asp Glu Ile Val Met Ser Gln Ser Pro Asp Thr Leu Ala Val Thr
1               5                   10                  15

Leu Gly Glu Arg Ala Ser Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Val Leu Ile Tyr Trp Ala Ser Ala Arg Glu Thr Gly Val
    50                  55                  60

Pro Glu Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Glu Ile
            100                 105                 110

Lys

<210> SEQ ID NO 119
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
            35                  40                  45

Ala Pro Lys Leu Leu Ile Tyr Trp Gly Ser Tyr Leu Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys
```

<210> SEQ ID NO 120
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Gly Trp Tyr Gln Gln Lys Pro Gly Lys
            35                  40                  45

Ala Pro Lys Leu Leu Ile Tyr Trp Gly Ser Tyr Leu Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys
```

<210> SEQ ID NO 121
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
```

```
                    50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Thr Gly Thr Lys Leu Asp Ile
            100                 105                 110

Lys

<210> SEQ ID NO 122
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ile Asp Glu Ile Val Met Thr Gln Ser Pro Asp Ser Leu Ala Val Ser
 1                5                  10                  15

Leu Gly Glu Arg Ala Thr Ile Asn Cys Lys Ser Ser Gln Thr Val Thr
                 20                  25                  30

Phe Asn Tyr Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Ser Gly Thr Lys Leu Asp Ile
            100                 105                 110

Lys

<210> SEQ ID NO 123
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ile Asp Glu Ile Val Met Thr Gln Ser Pro Asp Ser Leu Ala Val Ser
 1                5                  10                  15

Leu Gly Glu Arg Ala Thr Ile Asn Cys Lys Ser Ser Gln Thr Val Thr
                 20                  25                  30

Phe Asn Tyr Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Gln Gly Thr Lys Leu Asp Ile
            100                 105                 110
```

Lys

<210> SEQ ID NO 124
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val
            20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Asn Gly Thr Lys Leu Asp Ile
            100                 105                 110

Lys

<210> SEQ ID NO 125
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Thr Gly Thr Lys Leu Asp Ile
            100                 105                 110

Lys

<210> SEQ ID NO 126
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Ser Gly Thr Lys Leu Asp Ile
            100                 105                 110

Lys

<210> SEQ ID NO 127
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 128
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

```
Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Asn Gly Thr Lys Leu Asp Ile
            100                 105                 110

Lys

<210> SEQ ID NO 129
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ile Asp Asp Ile Val Met Thr Gln Ser Pro Asp Thr Leu Ala Val Thr
1               5                   10                  15

Leu Gly Glu Arg Ala Thr Ile Gln Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Thr Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 130
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ile Asp Asp Ile Val Met Thr Gln Ser Pro Asp Thr Val Ala Val Thr
1               5                   10                  15

Val Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
            100                 105                 110
```

Lys

<210> SEQ ID NO 131
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Ile Asp Asp Ile Val Met Thr Gln Ser Pro Asp Thr Val Ala Val Thr
1               5                   10                  15

Leu Gly Glu Arg Ala Thr Ile Asp Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Thr Pro Pro Ser Phe Gly Gln Gly Thr Lys Leu Asp Ile
            100                 105                 110

Lys

<210> SEQ ID NO 132
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Ile Asp Asp Ile Val Met Thr Gln Ser Pro Asp Thr Leu Ala Val Thr
1               5                   10                  15

Val Gly Glu Arg Ala Thr Ile Arg Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Thr Pro Pro Ser Phe Gly Gln Gly Thr Lys Leu Asp Ile
            100                 105                 110

Lys

<210> SEQ ID NO 133
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Ile Asp Asp Ile Val Met Thr Gln Ser Pro Asp Thr Leu Ala Val Ser
1               5                   10                  15

Arg Gly Glu Arg Ala Thr Ile Asp Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Glu Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 134
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asp Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 135
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Thr Leu Glu Ser Gly Val
            50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 136
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ile Asp Asp Ile Gln Met Thr Gln Ser Pro Ser Ser Leu Ser Ala Ser
 1               5                  10                  15

Val Gly Asp Arg Val Thr Ile Thr Cys Arg Ser Ser Gln Ser Ile Thr
                20                  25                  30

Phe Asn Tyr Lys Asn Tyr Leu Ala Trp Tyr Gln Gln Lys Pro Gly Lys
            35                  40                  45

Ala Pro Lys Leu Leu Ile Tyr Trp Gly Ser His Leu Glu Ser Gly Val
            50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 137
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ile Asp Asp Ile Gln Met Thr Gln Ser Pro Ser Ser Leu Ser Ala Ser
 1               5                  10                  15

Val Gly Asp Arg Val Thr Ile Thr Cys Arg Ser Ser Gln Ser Ile Thr
                20                  25                  30

Phe Asn Tyr Lys Asn Tyr Leu Ala Trp Tyr Gln Gln Lys Pro Gly Lys
            35                  40                  45

Ala Pro Lys Leu Leu Ile Tyr Trp Gly Ser Lys Leu Glu Ser Gly Val
            50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile

Lys

<210> SEQ ID NO 138
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Asp Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110
```

Lys

<210> SEQ ID NO 139
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Gln
                85                  90                  95

His Tyr Arg Thr Pro Pro Ser Phe Gly Gln Gly Thr Lys Val Glu Ile
            100                 105                 110
```

Lys

<210> SEQ ID NO 140
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 140

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Lys Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 141
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Asp Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 142
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys

```
                 35                  40                  45

Ala Pro Lys Leu Leu Ile Tyr Trp Gly Ser Tyr Leu Glu Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Arg Thr Pro Pro Ser Phe Gly Gln Gly Thr Lys Val Glu Ile
                100                 105                 110

Lys

<210> SEQ ID NO 143
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ile Asp Asp Ile Gln Met Thr Gln Ser Pro Ser Ser Leu Ser Ala Ser
 1               5                  10                  15

Val Gly Asp Arg Val Thr Ile Thr Cys Arg Ser Ser Gln Ser Ile Thr
                 20                  25                  30

Phe Asn Tyr Lys Asn Tyr Leu Ala Trp Tyr Gln Gln Lys Pro Gly Lys
                 35                  40                  45

Ala Pro Lys Leu Leu Ile Tyr Trp Gly Ser Thr Arg Glu Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

His Tyr Arg Thr Pro Pro Ser Phe Gly Gln Gly Thr Lys Val Glu Ile
                100                 105                 110

Lys

<210> SEQ ID NO 144
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ile Asp Asp Ile Gln Met Thr Gln Ser Pro Ser Ser Leu Ser Ala Ser
 1               5                  10                  15

Val Gly Asp Arg Val Thr Ile Thr Cys Arg Ser Ser Gln Ser Ile Thr
                 20                  25                  30

Phe Asn Tyr Lys Asn Tyr Leu Ala Trp Tyr Gln Gln Lys Pro Gly Lys
                 35                  40                  45

Ala Pro Lys Leu Leu Ile Tyr Trp Gly Ser Tyr Leu Glu Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95
```

His Tyr Arg Thr Pro Pro Ser Phe Gly Gln Gly Thr Lys Val Glu Ile
            100                 105                 110
Lys

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Ser Ile Thr Phe Asp Tyr Lys Asn Tyr Leu Ala
1               5                   10

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Lys Ser Ser Gln Ser Val Thr Phe Asn Tyr Lys Asn Tyr Leu Ala
1               5                   10                  15

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Trp Ala Ser Ala Arg Glu Ser
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gln Gln His Tyr Arg Thr Pro Pro Thr
1               5

<210> SEQ ID NO 149
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149
gacattcaga tgactcagtc gccttcgtca ttgtccgcct ccgtgggtga tagggtcacg      60
atcacgtgcc ggagcagcca gtccatcacc ttcaattaca aaaactatttg gcatggtat     120 caacagaaac ccggaaaggc gccgaagctc ctgatctact ggggttcata tcttgagtcg    180
ggggtgccgt cgagattttc gggcagcgga tcagggacgg atttcacgct gaccatttcg    240

| | |
|---|---|
| tcactccagc ccgaggactt tgcgacatat tactgtcaac agcactacag gacaccccca | 300 |
| tctttcggac aggggactaa agtagaaatc aagggatccg tggccgcccc cagcgtcttc | 360 |
| atcttcccgc ccagcgacga gcagctgaag tcgggcacgg ccagcgtggt gtgcctcctg | 420 |
| aacaacttct accccgcga ggcgaaggtc cagtggaagg tggacaacgc cctgcagagc | 480 |
| gggaacagcc aggagagcgt gaccgagcag gactcgaagg acagcaccta cagcctcagc | 540 |
| agcaccctga cgctgagcaa ggccgactac gagaagcaca aggtctacgc ctgcgaggtg | 600 |
| acccaccagg ggctctcgag ccccgtgacc aagagcttca accggggcga gtgctga | 657 |

<210> SEQ ID NO 150
<211> LENGTH: 663
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 150

| | |
|---|---|
| gacattcaga tgactcagtc gccttcgtca ttgtccgcct ccgtgggtga tagggtcacg | 60 |
| atcacgtgcc ggagcagcca gtccatcacc ttcaattaca aaaactattt ggcatggtat | 120 |
| caacagaaac ccggaaaggc gccgaagctc ctgatctact ggggttcata tcttgagtcg | 180 |
| ggggtgccgt cgagattttc gggcagcgga tcagggacgg attcacgct gaccatttcg | 240 |
| tcactccagc ccgaggactt tgcgacatat tactgtcaac agcactacag gacaccccca | 300 |
| tctttcggac aggggactaa agtagaaatc aagggatccg tggccgcccc cagcgtcttc | 360 |
| atcttcccgc ccagcgacga gcagctgaag tcgggcacgg ccagcgtggt gtgcctcctg | 420 |
| aacaacttct accccgcga ggcgaaggtc cagtggaagg tggacaacgc cctgcagagc | 480 |
| gggaacagcc aggagagcgt gaccgagcag gactcgaagg acagcaccta cagcctcagc | 540 |
| agcaccctga cgctgagcaa ggccgactac gagaagcaca aggtctacgc ctgcgaggtg | 600 |
| acccaccagg ggctctcgag ccccgtgacc aagagcttca accggggcga gtgctgagaa | 660 |
| ttc | 663 |

<210> SEQ ID NO 151
<211> LENGTH: 1383
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 151

| | |
|---|---|
| caggtacaat tgcttgagac aggtggagga ctcgtgaagc caggtcagtc attgaaactg | 60 |
| agctgtgccg catccgggtt cacattcact tcctacgcga tgcactgggt ccgccagcct | 120 |
| cccggaaagg gacttgagtg gtcgctgtg gtatcgtatg atgggaatta caaatactat | 180 |
| gcagactccg tgcaaggccg gtttacgatt agcagggaca actcgaagaa taccctttac | 240 |
| ctccaaatga actcgctccg agcggaggac acggcggtgt attactgcgc gaaggattca | 300 |
| cggttgagat cgctgctcta ttttgaatgg ttgtcacagg ggtacttcaa cccgtggggt | 360 |
| cagggaacaa cactgaccgt cagctcagcc tcgactaaag gcccagcgt gttcccgctg | 420 |
| gcccccagca gcaagagcac cagcggcggg accgccgccc tggctgcct cgtcaaggac | 480 |
| tacttccccg agcccgtgac cgtgtcgtgg aacagcggcg cgctgacgag cggggtccac | 540 |

```
accttcccgg ccgtgctgca gagcagcggc ctctactcgc tgagcagcgt ggtcaccgtg      600
cccagcagca gcctggggac ccagacgtac atctgcaacg tgaaccacaa gccctcgaac      660
accaaggtcg acaagaaggt ggagcccccg aagagctgcg acaaaactca cacatgccca      720
ccgtgcccag gtactgaact cctgggggga ccgtcagtct tcctcttccc cccaaaaccc      780
aaggacaccc tcatgatctc ccggacccct gaggtcacat gcgtggtggt ggacgtgagc      840
cacgaagacc ctgaggtcaa gttcaactgg tacgtggacg gcgtggaggt gcataatgcc      900
aagacaaagc cgcgggagga gcagtacaac agcacgtacc gtgtggtcag cgtcctcacc      960
gtcctgcacc aggactggct gaatggcaag gagtacaagt gcaaggtctc caacaaagcc     1020
ctcccagccc ccatcgagaa aaccatctcc aaagccaaag gtgagccccg agaaccacag     1080
gtgtacaccc tgcccccatc ccgggatgag ctgaccaaga accaggtcag cctgacctgc     1140
ctggtcaaag gcttctatcc cagcgacatc gccgtggagt gggagagcaa tgggcagccg     1200
gagaacaact acaagaccac gcctcccgtg ctggactccg acggctcctt cttcctctac     1260
agcaagctca ccgtggacaa gagcaggtgg cagcagggga acgtcttctc atgctccgtg     1320
atgcatgagg ctctgcacaa ccactacacg cagaagagcc tctccctgtc tccgggtaaa     1380
tga                                                                   1383
```

<210> SEQ ID NO 152
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152

```
gaagtacaat tgcttgagtc gggtggagga ctcgtgaagc caggtcagtc attgaaactg       60
agctgtgccg catccgggtt cacattcact tcctacgcga tgcactgggt ccgccagcct      120
cccggaaagg gacttgagtg ggtcgctgtg gtatcgtatg atgggaatta caaatactat      180
gcagactccg tgcaaggccg gtttacgatt agcagggaca actcgaagaa taccctttac      240
ctccaaatga actcgctccg agcggaggac acggcgtgt attactgcgc gaaggattca      300
cggttgagat cgctgctcta tttgaatgg ttgtcacagg ggtacttcaa cccgtggggt      360
cagggaacaa cactgaccgt cagctcagcc tcgactaaag gcccagcgt gttcccgctg      420 gcccccagca gcaagagcac cagcggcggg accgccgccc tgggctgcct cgtcaaggac      480
tacttccccg agcccgtgac cgtgtcgtgg aacagcggcg cgctgacgag cggggtccac      540
accttcccgg ccgtgctgca gagcagcggc ctctactcgc tgagcagcgt ggtcaccgtg      600
cccagcagca gcctggggac ccagacgtac atctgcaacg tgaaccacaa gccctcgaac      660
accaaggtcg acaagaaggt ggagcccccg aagagctgcg acgtaccca cacatgccca      720 ccgtgcccag gtactgaact cctgggggga ccgtcagtct tcctcttccc cccaaaaccc      780
aaggacaccc tcatgatctc ccggacccct gaggtcacat gcgtggtggt ggacgtgagc      840
cacgaagacc ctgaggtcaa gttcaactgg tacgtggacg gcgtggaggt gcataatgcc      900
aagacaaagc cgcgggagga gcagtacaac agcacgtacc gtgtggtcag cgtcctcacc      960
gtcctgcacc aggactggct gaatggcaag gagtacaagt gcaaggtctc caacaaagcc     1020
ctcccagccc ccatcgagaa aaccatctcc aaagccaaag gtgagccccg agaaccacag     1080
gtgtacaccc tgcccccatc ccgggatgag ctgaccaaga accaggtcag cctgacctgc     1140
```

```
ctggtcaaag gcttctatcc cagcgacatc gccgtggagt gggagagcaa tgggcagccg    1200
gagaacaact acaagaccac gcctcccgtg ctggactccg acggctcctt cttcctctac    1260
agcaagctca ccgtggacaa gagcaggtgg cagcagggga acgtcttctc atgctccgtg    1320
atgcatgagg ctctgcacaa ccactacacg cagaagagcc tctccctgtc tccgggtaaa    1380
tga                                                                  1383
```

<210> SEQ ID NO 153
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Gln
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110
```

<210> SEQ ID NO 154
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Arg
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110
```

<210> SEQ ID NO 155
<211> LENGTH: 111
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Glu
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 156
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asp
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Thr Arg Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 157
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Gln Tyr Lys Asn Tyr Leu Ala Trp Tyr Gln Gln Lys Pro Gly Lys
        35                  40                  45
```

Ala Pro Lys Leu Leu Ile Tyr Trp Gly Ser Tyr Leu Glu Ser Gly Val
            50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 158
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Arg Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
            50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 159
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Glu Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
            50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 160
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 160

```
Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asp Tyr Lys Asn Tyr Leu Ala Trp Tyr Gln Gln Lys Pro Gly Lys
        35                  40                  45

Ala Pro Lys Leu Leu Ile Tyr Trp Gly Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110
```

Lys

<210> SEQ ID NO 161
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 161

```
Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125
```

Ser

<210> SEQ ID NO 162
<211> LENGTH: 129
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 162

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Ser Phe Ser Thr Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Ala Asp Thr Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser

<210> SEQ ID NO 163
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Leu Glu Ser Gly Gly Gly Leu Arg Lys Pro Gly Gln
1               5                   10                  15

Ser Leu Lys Leu Ser Cys Ala Ala Ser Gly Phe Ser Phe Ser Thr Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser

<210> SEQ ID NO 164
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164
```

Gln Val Gln Leu Leu Glu Thr Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Val Thr Val Ser
        115                 120                 125

Ser

<210> SEQ ID NO 165
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 166
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Asp
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
            100                 105                 110

<210> SEQ ID NO 167
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Trp Gln
             20                  25                  30

Tyr Lys Asn Tyr Leu Ala Trp Tyr Gln Gln Lys Pro Gly Lys Ala Pro
         35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
            100                 105                 110

<210> SEQ ID NO 168
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Trp Arg
             20                  25                  30

Tyr Lys Asn Tyr Leu Ala Trp Tyr Gln Gln Lys Pro Gly Lys Ala Pro
         35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
            100                 105                 110

<210> SEQ ID NO 169
<211> LENGTH: 111

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Glu
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Val, Leu or Ile
<220> FEATURE:
<221> NAME/KEY: MOD_RES
<222> LOCATION: (4)..(4)
<223> OTHER INFORMATION: Thr or Ser
<220> FEATURE:
<221> NAME/KEY: MOD_RES
<222> LOCATION: (5)..(5)
<223> OTHER INFORMATION: Tyr, Phe or Trp
<220> FEATURE:
<221> NAME/KEY: MOD_RES
<222> LOCATION: (6)..(6)
<223> OTHER INFORMATION: Asn, Ser, Asp, Gln, Arg or Glu

<400> SEQUENCE: 170

Gln Xaa Xaa Xaa Xaa Xaa Tyr Lys Asn Tyr Leu Ala
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Trp Gly Gln Gly Thr Thr Val Thr Val Ser Ser
1               5                   10

<210> SEQ ID NO 172
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gln Ser Ile Thr Phe Glu Tyr Lys Asn Tyr Leu Ala
1               5                   10

<210> SEQ ID NO 173
<211> LENGTH: 329
<212> TYPE: PRT
<213> ORGANISM: Influenza A virus

<400> SEQUENCE: 173

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Thr Glu Gly Phe Thr Trp Thr
        115                 120                 125

Gly Val Thr Gln Asn Gly Gly Ser Asn Ala Cys Lys Arg Gly Pro Gly
    130                 135                 140

Ser Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Ile His His Pro Ser Thr Asn Gln Glu Gln Thr
            180                 185                 190

Ser Leu Tyr Val Gln Ala Ser Gly Arg Val Thr Val Ser Thr Arg Arg
        195                 200                 205

Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Asp Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320
```

```
Arg Asn Val Pro Glu Lys Gln Thr Arg
                325

<210> SEQ ID NO 174
<211> LENGTH: 175
<212> TYPE: PRT
<213> ORGANISM: Influenza A virus

<400> SEQUENCE: 174

Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
        115                 120                 125

Asn Ala Glu Glu Met Gly Asn Gly Cys Phe Lys Ile Tyr His Lys Cys
    130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly
                165                 170                 175

<210> SEQ ID NO 175
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Thr Tyr
            20                  25                  30

Ala Met His Trp Val Arg Gln Ala Pro Gly Arg Gly Leu Glu Trp Val
        35                  40                  45

Ala Val Ile Ser Tyr Asp Gly Asn Tyr Lys Tyr Tyr Ala Asp Ser Val
    50                  55                  60

Lys Gly Arg Phe Ser Ile Ser Arg Asp Asn Ser Asn Thr Leu His
65                  70                  75                  80

Leu Glu Met Asn Thr Leu Arg Thr Glu Asp Thr Ala Leu Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Pro Trp Gly Gln Gly Thr Leu Val Thr Val Thr
        115                 120                 125
```

Ser

<210> SEQ ID NO 176
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

```
Gln Val Gln Leu Val Gln Ser Gly Gly Gly Val Val Pro Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Tyr Lys Tyr Tyr Ala Asp Ser Val
    50                  55                  60

Arg Gly Arg Phe Thr Ile Ser Arg Asp Asn Ser Lys Asn Thr Leu Asn
65                  70                  75                  80

Leu Asp Met Asn Ser Leu Arg Thr Glu Asp Thr Ala Leu Tyr Tyr Cys
                85                  90                  95

Ala Lys Asp Ser Gln Leu Arg Ser Leu Leu Tyr Phe Asp Trp Leu Ser
            100                 105                 110

Gln Gly Tyr Phe Asp His Trp Gly Gln Gly Thr Leu Val Thr Val Ser
        115                 120                 125

Ser
```

<210> SEQ ID NO 177
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Asp Trp Leu Ser
            100                 105                 110

Gln Gly Tyr Phe Asp Tyr Trp Gly Gln Gly Thr Leu Val Thr Val Ser
        115                 120                 125

Ser
```

<210> SEQ ID NO 178

<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 179
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Thr Glu Asp Thr Ala Leu Tyr Tyr Cys
                85                  90                  95

Ala Lys Asp Ser Gln Leu Arg Ser Leu Leu Tyr Phe Asp Trp Leu Ser
            100                 105                 110

Gln Gly Tyr Phe Asp His Trp Gly Gln Gly Thr Leu Val Thr Val Ser
        115                 120                 125

Ser

<210> SEQ ID NO 180
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

Asp Ile Gln Met Thr Ser Gln Pro Asp Ser Leu Ala Val Ser Leu Gly
1               5                   10                  15

Ala Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Val Leu Ile Tyr Trp Ala Ser Ala Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys
            100                 105                 110

<210> SEQ ID NO 181
<211> LENGTH: 329
<212> TYPE: PRT
<213> ORGANISM: Influenza A virus

<400> SEQUENCE: 181

Thr Asn Ala Asp Thr Ile Cys Ile Gly Tyr His Ala Asn Asn Ser Thr
1               5                   10                  15

Asp Thr Val Asp Thr Val Leu Glu Lys Asn Val Thr Val Thr His Ser
            20                  25                  30

Val Asn Leu Leu Glu Asp Ser His Asn Gly Lys Leu Cys Lys Leu Lys
        35                  40                  45

Gly Ile Ala Pro Leu Gln Leu Gly Lys Cys Asn Ile Ala Gly Trp Leu
    50                  55                  60

Leu Gly Asn Pro Glu Cys Asp Leu Leu Leu Thr Ala Ser Ser Trp Ser
65                  70                  75                  80

Tyr Ile Val Glu Thr Ser Asn Ser Glu Asn Gly Thr Cys Tyr Pro Gly
                85                  90                  95

Asp Phe Ile Asp Tyr Glu Glu Leu Arg Glu Gln Leu Ser Ser Val Ser
            100                 105                 110

Ser Phe Glu Lys Phe Glu Ile Phe Pro Lys Thr Ser Ser Trp Pro Asn
        115                 120                 125

His Glu Thr Thr Lys Gly Val Thr Ala Ala Cys Ser Tyr Ala Gly Ala
    130                 135                 140

Ser Ser Phe Tyr Arg Asn Leu Leu Trp Leu Thr Lys Lys Gly Ser Ser
145                 150                 155                 160

Tyr Pro Lys Leu Ser Lys Ser Tyr Val Asn Asn Lys Gly Lys Glu Val
                165                 170                 175

Leu Val Leu Trp Gly Val His His Pro Pro Thr Gly Thr Asp Gln Gln
            180                 185                 190

Ser Leu Tyr Gln Asn Ala Asp Ala Tyr Val Ser Val Gly Ser Ser Lys
        195                 200                 205

Tyr Asn Arg Arg Phe Thr Pro Glu Ile Ala Ala Arg Pro Lys Val Arg
    210                 215                 220

Asp Gln Ala Gly Arg Met Asn Tyr Tyr Trp Thr Leu Leu Glu Pro Gly
225                 230                 235                 240

Asp Thr Ile Thr Phe Glu Ala Thr Gly Asn Leu Ile Ala Pro Trp Tyr

```
                    245                 250                 255
Ala Phe Ala Leu Asn Arg Gly Ser Gly Ser Gly Ile Ile Thr Ser Asp
            260                 265                 270

Ala Pro Val His Asp Cys Asn Thr Lys Cys Gln Thr Pro His Gly Ala
            275                 280                 285

Ile Asn Ser Ser Leu Pro Phe Gln Asn Ile His Pro Val Thr Ile Gly
            290                 295                 300

Glu Cys Pro Lys Tyr Val Arg Ser Thr Lys Leu Arg Met Ala Thr Gly
305                 310                 315                 320

Leu Arg Asn Ile Pro Ser Ile Gln Ser
                325

<210> SEQ ID NO 182
<211> LENGTH: 222
<212> TYPE: PRT
<213> ORGANISM: Influenza A virus

<400> SEQUENCE: 182

Gly Leu Phe Gly Ala Ile Ala Gly Phe Ile Glu Gly Gly Trp Thr Gly
1               5                   10                  15

Met Ile Asp Gly Trp Tyr Gly Tyr His His Gln Asn Glu Gln Gly Ser
            20                  25                  30

Gly Tyr Ala Ala Asp Gln Lys Ser Thr Gln Asn Ala Ile Asp Gly Ile
        35                  40                  45

Thr Asn Lys Val Asn Ser Val Ile Glu Lys Met Asn Thr Gln Phe Thr
    50                  55                  60

Ala Val Gly Lys Glu Phe Asn Asn Leu Glu Arg Ile Glu Asn Leu
65                  70                  75                  80

Asn Lys Lys Val Asp Asp Gly Phe Leu Asp Ile Trp Thr Tyr Asn Ala
                85                  90                  95

Glu Leu Leu Val Leu Leu Glu Asn Glu Arg Thr Leu Asp Phe His Asp
            100                 105                 110

Ser Asn Val Arg Asn Leu Tyr Glu Lys Val Lys Ser Gln Leu Lys Asn
        115                 120                 125

Asn Ala Lys Glu Ile Gly Asn Gly Cys Phe Glu Phe Tyr His Lys Cys
    130                 135                 140

Asp Asp Ala Cys Met Glu Ser Val Arg Asn Gly Thr Tyr Asp Tyr Pro
145                 150                 155                 160

Lys Tyr Ser Glu Glu Ser Lys Leu Asn Arg Glu Glu Ile Asp Gly Val
                165                 170                 175

Lys Leu Glu Ser Met Gly Val Tyr Gln Ile Leu Ala Ile Tyr Ser Thr
            180                 185                 190

Val Ala Ser Ser Leu Val Leu Val Ser Leu Gly Ala Ile Ser Phe
        195                 200                 205

Trp Met Cys Ser Asn Gly Ser Leu Gln Cys Arg Ile Cys Ile
210                 215                 220

<210> SEQ ID NO 183
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Glu Val Gln Leu Leu Glu Ser Gly Gly Gly Leu Val Lys Pro Gly Gln
```

```
                1               5                   10                  15

Ser Leu Lys Leu Ser Cys Ala Ala Ser Gly Phe Thr Phe Thr
                20                  25                  30

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Ser or Thr
<220> FEATURE:
<221> NAME/KEY: MOD_RES
<222> LOCATION: (8)..(8)
<223> OTHER INFORMATION: Ala or Gly

<400> SEQUENCE: 184

Gly Phe Thr Phe Xaa Xaa Tyr Xaa Met His
1               5                   10

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Val, Leu or Ile
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Tyr, Phe or Trp
<220> FEATURE:
<221> NAME/KEY: MOD_RES
<222> LOCATION: (9)..(9)
<223> OTHER INFORMATION: Asn, Ser or Asp

<400> SEQUENCE: 185

Xaa Ser Ser Gln Xaa Xaa Xaa Xaa Xaa Tyr Lys Asn Tyr Leu Ala
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
```

```
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Val, Leu or Ile
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Tyr, Phe or Trp
<220> FEATURE:
<221> NAME/KEY: MOD_RES
<222> LOCATION: (9)..(9)
<223> OTHER INFORMATION: Asn, Ser, Asp, Gln, Arg or Glu

<400> SEQUENCE: 186

Xaa Ser Ser Gln Xaa Xaa Xaa Xaa Xaa Tyr Lys Asn Tyr Leu Ala
 1               5                  10                  15

<210> SEQ ID NO 187
<211> LENGTH: 653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
gaaattgtaa tgacgcagag ccctgatagc cttgccgtgt ccctgggtga gagggcgaca      60
atcaattgta agtcatcaca gtcggtcacg tacaactaca gaactacct ggcgtggtat      120 caacagaaac ccgggcagcc gcccaaattg ctcatctatt gggcttcgac acgggagtcg     180
ggtgtgccag accgcttctc cgggtcagga tcgggaactg acttcacgtt gactatttcg     240
tccctccagg cagaagatgt agccgtctac tattgccaac agtattacag aacgccgcct     300
acatttggag gcgggaccaa acttgacatc aagggatccg tggccgcccc cagcgtcttc     360
atcttcccgc cagcgacga gcagctgaag tcgggcacgg ccagcgtggt gtgcctcctg     420
aacaacttct accccgcga ggcgaaggtc cagtggaagg tggacaacgc cctgcagagc     480
gggaacagcc aggagagcgt gaccgagcag gactcgaagg acagcaccta cagcctcagc     540
agcaccctga cgctgagcaa ggccgactac gagaagcaca aggtctacgc ctgcgaggtg     600
acccaccagg ggctctcgag ccccgtgacc aagagcttca ccggggcga gtg            653

<210> SEQ ID NO 188
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Thr Tyr Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60
```

```
Arg Phe Ser Gly Ser Gly Ser Gly Thr Asp Phe Thr Leu Thr Ile Ser
 65                 70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys Gly
            100                 105                 110

Ser Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu
    210                 215
```

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Val, Leu or Ile
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Tyr, Phe or Trp
<220> FEATURE:
<221> NAME/KEY: MOD_RES
<222> LOCATION: (9)..(9)
<223> OTHER INFORMATION: Asn, Ser, Asp or Glu

<400> SEQUENCE: 189

```
Xaa Ser Ser Gln Xaa Xaa Xaa Xaa Xaa Tyr Lys Asn Tyr Leu Ala
 1               5                  10                  15
```

COMPOSITIONS AND METHODS FOR TREATING AND PREVENTING INFLUENZA

CROSS REFERENCE TO RELATED APPLICATIONS

This application claims the benefit of U.S. Provisional Application No. 62/823,426, filed Mar. 25, 2019, U.S. Provisional Application No. 62/873,401, filed Jul. 12, 2019, and U.S. Provisional Application No. 62/890,938, filed Aug. 23, 2019. The contents of the aforementioned applications are hereby incorporated by reference in their entirety.

SEQUENCE LISTING

The instant application contains a Sequence Listing which has been filed electronically in ASCII format and is hereby incorporated by reference in its entirety. Said ASCII copy, created on Mar. 23, 2020, is named P2029-703010_SL.txt and is 187,019 bytes in size.

BACKGROUND

Influenza is an infectious disease caused by RNA viruses of the family Orthomyxoviridae (the influenza viruses). Influenza viruses are classified based on core protein into three genera A, B and C that are further divided into subtypes determined by the viral envelope glycoproteins haemagglutinin (HA) and neuraminidase (NA). Influenza A viruses infect a range of mammalian and avian species, whereas type B and C infections are largely restricted to humans. Only types A and B cause human disease of any concern.

High mutation rates and frequent genetic reassortments of the influenza viruses contribute to great variability of the HA and NA antigens. Minor point mutations causing small changes ("antigenic drift") occur relatively often. Antigenic drift enables the virus to evade immune recognition, resulting in repeated influenza outbreaks during interpandemic years. Major changes in the HA antigen ("antigenic shift") are caused by reassortment of genetic material from different influenza A subtypes. Antigenic shifts resulting in new pandemic strains are rare events, occurring through reassortment between animal and human subtypes, for example in co-infected pigs.

Influenza A spreads around the world in seasonal epidemics, resulting in the deaths of between 250,000 and 500,000 people every year, and up to millions in some pandemic years. On average 41,400 people died each year in the United States between 1979 and 2001 from influenza.

SUMMARY

The disclosure is based, at least in part, on the discovery of human anti-HA antibodies comprising functional and structural properties disclosed herein, e.g., antibodies that bind a conserved region or epitope on influenza virus and uses thereof.

Accordingly, the disclosure features binding agents, e.g., antibody molecules, or preparations, or isolated preparations thereof, that bind hemagglutinin (HA) from influenza viruses. In an embodiment, a binding agent, e.g., an antibody molecule, is broad spectrum, and binds more than one HA, e.g., an HA from one or both of Group 1 or Group 2 strains of influenza A viruses. Therefore, in some embodiments, a binding agent, e.g., an antibody molecule, featured in the disclosure can treat or prevent infection by a Group 1 influenza virus and a Group 2 influenza virus. In certain embodiments, the binding agent (e.g., an antibody molecule described herein) is effective at treating or preventing infection by a plurality of influenza virus strains (e.g., H1N1 and H7N9). In other embodiments, a binding agent, e.g., an antibody molecule, featured in the disclosure can treat or prevent infection by an influenza A virus and/or an influenza B virus. The binding agents, e.g., antibody molecules, share sufficient structural similarity with antibodies or variable regions disclosed herein such that they possess functional attributes of the antibodies disclosed herein. In some embodiments, the structural similarity can be in terms of three-dimensional structure, or linear amino acid sequence, or both. Without wishing to be bound by theory, it is believed that in an embodiment, the antibody molecules described herein can be used, as a single agent or combination therapy, to treat or prevent influenza in patients exhibiting severe symptoms and/or infected with drug resistant strains.

In an aspect, the disclosure features a method of treating or preventing an influenza virus infection, or a symptom thereof, in a subject, comprising administering to the subject an effective amount of a combination of an anti-HA antibody molecule described herein, e.g., VIS410 (also known as Ab 044 herein), and one or more (e.g., two, three, or four) anti-viral agents.

In an embodiment, the one or more anti-viral agents comprise a neuraminidase inhibitor. In an embodiment, the one or more anti-viral agents do not comprise a neuraminidase inhibitor. In an embodiment, the neuraminidase inhibitor comprises one, two, or all of oseltamivir, peramivir, or zanamivir.

In an embodiment, the one or more anti-viral agents comprise an endonuclease inhibitor (e.g., a cap-dependent endonuclease inhibitor). In an embodiment, the one or more anti-viral agents do not comprise an endonuclease inhibitor (e.g., a cap-dependent endonuclease inhibitor). In an embodiment, the endonuclease inhibitor (e.g., the cap-dependent endonuclease inhibitor) comprises baloxavir marboxil.

In an embodiment, the one or more anti-viral agents comprise a polymerase basic protein 2 (PB2) inhibitor. In an embodiment, the one or more anti-viral agents do not comprise a PB2 inhibitor. In an embodiment, the PB2 inhibitor comprises pimodivir.

In an embodiment, the one or more anti-viral agents comprise one, two, three, four, or all of oseltamivir, peramivir, zanamivir, baloxavir marboxil, or pimodivir. In an embodiment, the one or more anti-viral agents comprise oseltamivir. In an embodiment, the one or more anti-viral agents comprise pimodivir. In an embodiment, the one or more anti-viral agents comprise peramivir. In an embodiment, the one or more anti-viral agents comprise zanamivir. In an embodiment, the one or more anti-viral agents comprise baloxavir marboxil. In an embodiment, the one or more anti-viral agents comprise pimodivir.

In an embodiment, the one or more anti-viral agents comprise a neuraminidase inhibitor and an endonuclease inhibitor (e.g., a cap-dependent endonuclease inhibitor). In an embodiment, the one or more anti-viral agents comprise (a) one, two, or all of oseltamivir, peramivir, or zanamivir, and (b) baloxavir marboxil.

In an embodiment, the one or more anti-viral agents comprise a neuraminidase inhibitor and an PB2 inhibitor. In an embodiment, the one or more anti-viral agents comprise (a) one, two, or all of oseltamivir, peramivir, or zanamivir, and (b) pimodivir.

In an embodiment, the one or more anti-viral agents comprise an endonuclease inhibitor (e.g., a cap-dependent endonuclease inhibitor) and an PB2 inhibitor. In an embodiment, the one or more anti-viral agents comprise baloxavir and pimodivir.

In an embodiment, the one or more anti-viral agents comprise a neuraminidase inhibitor, an endonuclease inhibitor (e.g., a cap-dependent endonuclease inhibitor), and a PB2 inhibitor. In an embodiment, the one or more anti-viral agents comprise (a) one, two, or all of oseltamivir, peramivir, or zanamivir, (b) baloxavir marboxil, and (c) pimodivir.

In an embodiment, the anti-HA antibody molecule (e.g., VIS410) is administered prior to, concurrently with, or subsequent to, the one or more anti-viral agents. In an embodiment, the anti-HA antibody molecule (e.g., VIS410) is administered before any of the one or more antiviral agents. In an embodiment, the anti-HA antibody molecule (e.g., VIS410) is administered after any of the one or more antiviral agents. In an embodiment, the anti-HA antibody molecule (e.g., VIS410) is administered before at least one of the one or more antiviral agents and after at least one of the one or more antiviral agents.

In an embodiment, the anti-HA antibody molecule (e.g., VIS410) is administered, e.g., intravenously, at a dose of between 500 mg and 5000 mg, e.g., between 500 mg and 4500 mg, between 500 mg and 4000 mg, between 500 mg and 3500 mg, between 500 mg and 3000 mg, between 500 mg and 2500 mg, between 500 mg and 2000 mg, between 500 mg and 1500 mg, between 500 mg and 1000 mg, between 1000 mg and 5000 mg, between 1500 mg and 5000 mg, between 2000 mg and 5000 mg, between 2500 mg and 5000 mg, between 3000 mg and 5000 mg, between 3500 mg and 5000 mg, between 4000 mg and 5000 mg, between 4500 mg and 5000 mg, between 1000 mg and 4500 mg, between 1500 mg and 4000 mg, between 2000 mg and 3500 mg, between 2500 mg and 3000 mg, between 500 mg and 1500 mg, between 1000 mg and 2000 mg, between 1500 mg and 2500 mg, between 2000 mg and 3000 mg, between 2500 mg and 3500 mg, between 3000 mg and 4000 mg, between 4000 mg and 5000 mg, e.g., about 500 mg, 1000 mg, 1500 mg, 2000 mg, 2500 mg, 3000 mg, 3500 mg, 4000 mg, 4500 mg, or 5000 mg, e.g., as a single dose.

In an embodiment, the anti-HA antibody molecule (e.g., VIS410) is administered, e.g., intravenously, at a dose of between 1500 mg and 2500 mg (e.g., about 2000 mg) or between 3500 mg and 4500 mg (e.g., about 4000 mg), e.g., as a single dose.

In an embodiment, the one or more anti-viral agents (e.g., oseltamivir) is administered, e.g., orally, at a dose of between 25 mg and 150 mg, e.g., between 25 mg and 125 mg, between 25 and 100 mg, between 25 mg and 75 mg, between 25 mg and 50 mg, between 50 mg and 150 mg, between 75 mg and 150 mg, between 100 mg and 150 mg, between 125 mg and 150 mg, between 125 mg and 150 mg, between 50 mg and 125 mg, between 75 mg and 100 mg, between 50 mg and 100 mg, between 75 mg and 125 mg, e.g., about 25 mg, 50 mg, 75 mg, 100 mg, 125 mg, or 150 mg, e.g., twice a day (e.g., once every twelve hours), once every day, once every two days, or once every three days, e.g., for at least 1, 2, 3, 4, 5, 6, 7, 8, 9, 10, 11, 12, 13, or 14 days.

In an embodiment, the one or more anti-viral agents comprises oseltamivir, and wherein oseltamivir is administered, e.g., orally, at a dose between 50 mg and 100 mg (e.g., about 75 mg), twice a day (e.g., once every twelve hours) or once every day, e.g., for 5 to 10 days.

In an embodiment, the one or more anti-viral agents (e.g., peramivir) is administered, e.g., intravenously (e.g., over 10-60 minutes, e.g., 15-30 minutes), at a dose of between 100 mg and 1000 mg, e.g., between 100 mg and 900 mg, between 100 and 800 mg, between 100 and 700 mg, between 100 and 600 mg, between 100 and 500 mg, between 100 and 400 mg, between 100 and 300 mg, between 100 and 200 mg, between 200 mg and 1000 mg, between 300 mg and 1000 mg, between 400 mg and 1000 mg, between 500 mg and 1000 mg, between 600 mg and 1000 mg, between 700 mg and 1000 mg, between 800 mg and 1000 mg, between 900 mg and 1000 mg, between 200 mg and 900 mg, between 300 mg and 800 mg, between 400 mg and 700 mg, between 500 mg and 600 mg, between 100 mg and 300 mg, between 200 mg and 400 mg, between 300 mg and 500 mg, between 400 mg and 600 mg, between 500 mg and 700 mg, between 600 mg and 800 mg, between 700 mg and 900 mg, or between 800 mg and 1000 mg, e.g., about 100 mg, 200 mg, 300 mg, 400 mg, 500 mg, 600 mg, 700 mg, 800 mg, 900 mg, or 1000 mg, e.g., as a single dose.

In an embodiment, the one or more anti-viral agents comprises peramivir, and wherein peramivir is administered, e.g., intravenously, at a dose between 400 mg and 800 mg (e.g., about 600 mg), e.g., as a single dose.

In an embodiment, the one or more anti-viral agents (e.g., zanamivir) is administered, e.g., by inhalation, at a dose of between 1 mg and 50 mg, e.g., between 1 mg and 40 mg, between 1 mg and 30 mg, between 1 mg and 20 mg, between 1 mg and 10 mg, between 1 mg and 5 mg, between 1 mg and 2 mg, between 2 mg and 50 mg, between 5 mg and 50 mg, between 10 mg and 50 mg, between 20 mg and 50 mg, between 30 mg and 50 mg, between 40 mg and 50 mg, between 2 mg and 40 mg, between 5 mg and 30 mg, between 10 mg and 20 mg, between 1 mg and 5 mg, between 2 mg and 10 mg, between 5 mg and 20 mg, between 10 mg and 30 mg, between 20 mg and 40 mg, between 30 mg and 50 mg, e.g., about 1 mg, 2 mg, 5 mg, 10 mg, 20 mg, 30 mg, 40 mg, or 50 mg, e.g., twice a day (e.g., once every twelve hours), once every day, once every two days, or once every three days, e.g., for at least 1, 2, 3, 4, 5, 6, 7, 8, 9, 10, 11, 12, 13, 14, 15, 16, 17, 18, 19, 20, 21, 22, 23, 24, 25, 26, 27, or 28 days.

In an embodiment, the one or more anti-viral agents comprises zanamivir, and wherein zanamivir is administered, e.g., by inhalation, at a dose of between 5 mg and 15 mg (e.g., about 10 mg), once every twelve hours or once a day, e.g., for 5-10 days.

In an embodiment, the one or more anti-viral agents (e.g., baloxavir marboxil) is administered, e.g., orally, at a dose of between 10 mg and 200 mg, e.g., between 10 mg and 180 mg, between 10 mg and 160 mg, between 10 mg and 140 mg, between 10 mg and 120 mg, between 10 mg and 100 mg, between 10 mg and 80 mg, between 10 mg and 60 mg, between 10 mg and 40 mg, between 10 mg and 20 mg, between 20 mg and 200 mg, between 40 mg and 200 mg, between 60 mg and 200 mg, between 80 mg and 200 mg, between 100 mg and 200 mg, between 120 mg and 200 mg, between 140 mg and 200 mg, between 160 mg and 200 mg, between 180 mg and 200 mg, between 20 mg and 180 mg, between 40 mg and 160 mg, between 60 mg and 140 mg, between 80 mg and 120 mg, between 10 mg and 30 mg, between 20 mg and 40 mg, between 30 mg and 50 mg, between 40 mg and 60 mg, between 50 mg and 70 mg, between 60 mg and 80 mg, between 70 mg and 90 mg, between 80 mg and 100 mg, between 90 mg and 110 mg, between 100 mg and 120 mg, between 110 mg and 130 mg, between 120 mg and 140 mg, between 130 mg and 150 mg, between 140 mg and 160 mg, between 150 mg and 170 mg, between 160 mg and 180 mg, between 170 mg and 190 mg, e.g., about 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, or 200 mg, e.g., as a single dose.

In an embodiment, the one or more anti-viral agents comprises baloxavir marboxil, and wherein baloxavir marboxil is administered, e.g., orally, at a dose of between 20 mg to 60 mg (e.g., about 40 mg), e.g., for a subject having a weight of less than 80 kg, or between 60 mg and 100 mg (e.g., about 80 mg), e.g., for a subject having a weight of 80 kg or more, e.g., as a single dose.

In an embodiment, the one or more anti-viral agents (e.g., pimodivir) is administered, e.g., orally, at a dose of between 100 mg and 1000 mg, e.g., between 100 mg and 900 mg, between 100 mg and 800 mg, between 100 mg and 700 mg, between 100 mg and 600 mg, between 100 mg and 500 mg, between 100 mg and 400 mg, between 100 mg and 300 mg, between 100 mg and 200 mg, between 200 mg and 1000 mg, between 300 mg and 1000 mg, between 400 mg and 1000 mg, between 500 mg and 1000 mg, between 600 mg and 1000 mg, between 700 mg and 1000 mg, between 800 mg and 1000 mg, between 900 mg and 1000 mg, between 200 mg and 900 mg, between 300 mg and 800 mg, between 400 mg and 700 mg, between 500 mg and 600 mg, between 100 mg and 300 mg, between 200 mg and 400 mg, between 300 mg and 500 mg, between 400 mg and 600 mg, between 500 mg and 700 mg, between 600 mg and 800 mg, between 700 mg and 900 mg, between 800 mg and 1000 mg, e.g., about 100 mg, 200 mg, 300 mg, 400 mg, 500 mg, 600 mg, 700 mg, 800 mg, 900 mg, or 1000 mg, e.g., twice a day, once a day, once every two days, or once every three days.

In an embodiment, the one or more anti-viral agents comprises pimodivir, and wherein pimodivir is administered, e.g., orally, at a dose of between 200 mg to 400 mg (e.g., about 300 mg), e.g., twice a day. In an embodiment, the one or more anti-viral agents comprises pimodivir, and wherein pimodivir is administered, e.g., orally, at a dose of between 500 mg to 700 mg (e.g., about 600 mg), e.g., twice a day.

In an embodiment, the one or more anti-viral agents is administered within 12, 24, 36, 48, 60, or 72 hours of onset of an influenza symptom. In an embodiment, the one or more anti-viral agents is administered within 1, 2, 3, 4, 5, 6, 7, 8, 9, 10, 11, 12, 13, or 14 days of exposure to an influenza virus or an influenza infection (e.g., latent or acute). In certain embodiments, the one or more anti-viral agents is administered within 1, 2, 3, 4, 5, 6, 7, 8, 9, 10, 11, 12, 13, or 14 days of an influenza outbreak.

In an embodiment, the subject is infected with, or is at risk of being infected with, an influenza virus A, an influenza virus B, an influenza virus C, an influenza virus D, or combination thereof. In an embodiment, the subject is infected with, or is at risk of being infected with, an influenza virus A. In an embodiment, the subject is infected with, or is at risk of being infected with, a Group 1 influenza virus (e.g., an H1, H2, H5, H6, H8, H9, H11, H12, H13, or H16 influenza virus, or a combination thereof). In an embodiment, the subject is infected with, or is at risk of being infected with, a Group 2 influenza virus (e.g., an H3, H4, H7, H10, H14, or H15 influenza virus, or a combination thereof). In an embodiment, the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof. In an embodiment, the subject is infected with, or is at risk of being infected with, an H1N1 or H3N2 influenza virus, or a combination thereof. In an embodiment, the subject is infected with, or is at risk of being infected with, an H1N1 or H7N9 influenza virus, or a combination thereof.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, an influenza virus that is resistant to oseltamivir. In an embodiment, the antibody molecule, exhibits anti-viral activity against, e.g., inhibits replication of, an influenza virus that is resistant to oseltamivir, e.g., with an $EC_{50}$ of between 0.01-30 µg/mL (e.g., 0.05-25 µg/mL, 0.06-25 µg/mL, 0.07-25 µg/mL, 0.05-24 µg/mL, 0.05-23 µg/mL, 0.05-22 µg/mL, 0.06-24 µg/mL, 0.06-23 µg/mL, 0.06-22 µg/mL, 0.07-24 µg/mL, 0.07-23 µg/mL, 0.07-22 µg/mL, or 0.071-22 µg/mL). In an embodiment, the subject is infected with, or is at risk of being infected with, an influenza virus that is resistant to peramivir. In an embodiment, the subject is infected with, or is at risk of being infected with, an influenza virus that is resistant to zanamivir. In an embodiment, the subject is infected with, or is at risk of being infected with, an influenza virus that is resistant to baloxavir marboxil. In an embodiment, the subject is infected with, or is at risk of being infected with, an influenza virus that is resistant to pimodivir.

In an embodiment, the subject is infected with, or is at risk of being infected with, a secondary bacterial infection.

In an embodiment, the combination results in an enhanced antiviral activity, in vitro or in vivo, e.g., as determined by an assay described (e.g., an in vitro antiviral assay, e.g., NP ELISA or CPE assay). In an embodiment, the combination results in a synergistic antiviral activity, in vitro or in vivo, e.g., as determined by an assay described herein (e.g., MacSnyergy II analysis). In an embodiment, the combination results in an additive antiviral activity, in vitro or in vivo, e.g., as determined by an assay described herein (e.g., MacSnyergy II analysis).

In an embodiment, the antibody molecule comprises:

```
(a) a heavy chain immunoglobulin variable region
segment comprising: a CDR1 comprising the sequence
                                         (SEQ ID NO: 68)
S-Y-A-M-H;

a CDR2 comprising the sequence
                                         (SEQ ID NO: 69)
V-V-S-Y-D-G-N-Y-K-Y-Y-A-D-S-V-Q-G;
and a CDR3 comprising the sequence
                                         (SEQ ID NO: 70)
D-S-R-L-R-S-L-L-Y-F-E-W-L-S-Q-G-Y-F-N-P;
and (b) a light chain immunoglobulin variable region
segment comprising: a CDR1 comprising the sequence
                                        (SEQ ID NO: 145)
Q-S-I-T-F-D-Y-K-N-Y-L-A;

a CDR2 comprising the sequence
                                         (SEQ ID NO: 72)
W-G-S-Y-L-E-S;
and a CDR3 comprising the sequence
                                         (SEQ ID NO: 73)
Q-Q-H-Y-R-T-P-P-S.
```

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')$_2$ fragment, a Fab fragment, or an Fd fragment.

In an aspect, the disclosure features a method of treating or preventing an influenza virus infection, or a symptom thereof, in a subject, comprising administering to the subject an effective amount of an anti-HA antibody molecule described herein, e.g., VIS410, wherein the subject is infected with, or is at risk of being infected with, an influenza virus that is resistant to an antiviral agent described herein.

In an embodiment, the method further comprises acquiring knowledge that an influenza virus that is resistant to the antiviral agent is present in the subject. In an embodiment, the method further comprises determining the presence of an influenza virus that is resistant to the antiviral agent in a sample from the subject, e.g., by an assay described herein. In an embodiment, the antibody molecule is administered or used responsive to a determination of the presence of an influenza virus that is resistant to the antiviral agent. In an embodiment, the method further comprises evaluating a subject who is infected with, or is at risk of being infected with, an influenza virus that is resistant to the antiviral agent. In an embodiment, the method further comprises selecting a subject who is infected with, or is at risk of being infected with, an influenza virus that is resistant to the antiviral agent.

In an embodiment, the subject is undergoing or has undergone a treatment comprising the antiviral agent. In an embodiment, responsive to a determination of the presence of an influenza virus that is resistant to the antiviral agent, the antiviral agent is discontinued. In an embodiment, the antibody molecule is administered or used after cessation of the antiviral agent.

In an embodiment, the antibody molecule is administered or used as a single agent. In an embodiment, the antibody molecule is administered or used in combination with a second antiviral agent, e.g., an antiviral agent described herein.

In an embodiment, the anti-HA antibody molecule (e.g., VIS410) is administered, e.g., intravenously, at a dose of between 500 mg and 5000 mg, e.g., between 500 mg and 4500 mg, between 500 mg and 4000 mg, between 500 mg and 3500 mg, between 500 mg and 3000 mg, between 500 mg and 2500 mg, between 500 mg and 2000 mg, between 500 mg and 1500 mg, between 500 mg and 1000 mg, between 1000 mg and 5000 mg, between 1500 mg and 5000 mg, between 2000 mg and 5000 mg, between 2500 mg and 5000 mg, between 3000 mg and 5000 mg, between 3500 mg and 5000 mg, between 4000 mg and 5000 mg, between 4500 mg and 5000 mg, between 1000 mg and 4500 mg, between 1500 mg and 4000 mg, between 2000 mg and 3500 mg, between 2500 mg and 3000 mg, between 500 mg and 1500 mg, between 1000 mg and 2000 mg, between 1500 mg and 2500 mg, between 2000 mg and 3000 mg, between 2500 mg and 3500 mg, between 3000 mg and 4000 mg, between 4000 mg and 5000 mg, e.g., about 500 mg, 1000 mg, 1500 mg, 2000 mg, 2500 mg, 3000 mg, 3500 mg, 4000 mg, 4500 mg, or 5000 mg, e.g., as a single dose.

In an embodiment, the anti-HA antibody molecule (e.g., VIS410) is administered, e.g., intravenously, at a dose of between 1500 mg and 2500 mg (e.g., about 2000 mg) or between 3500 mg and 4500 mg (e.g., about 4000 mg), e.g., as a single dose.

In an embodiment, the antiviral agent comprises an endonuclease inhibitor (e.g., a cap-dependent endonuclease inhibitor). In an embodiment, the endonuclease inhibitor comprises baloxavir marboxil. In an embodiment, the antiviral agent comprises a neuraminidase inhibitor. In an embodiment, the neuraminidase inhibitor comprises oseltamivir, peramivir, or zanamivir, or a combination thereof. In an embodiment, the antiviral agent comprises a PB2 inhibitor. In an embodiment, the PB2 inhibitor comprises pimodivir. In an embodiment, the antiviral agent is administered in accordance with a dosage regimen described herein.

In an embodiment, the influenza virus is an influenza virus A, an influenza virus B, an influenza virus C, an influenza virus D, or combination thereof. In an embodiment, the influenza virus is an influenza virus A. In an embodiment, the influenza virus is a Group 1 influenza virus (e.g., an H1, H2, H5, H6, H8, H9, H11, H12, H13, or H16 influenza virus, or a combination thereof). In an embodiment, the influenza virus is a Group 2 influenza virus (e.g., an H3, H4, H7, H10, H14, or H15 influenza virus, or a combination thereof). In an embodiment, the influenza virus is an H1N1, H1N2, H2N2, H3N2, H5N1, H6N1, H7N2, H7N3, H7N7, H7N9, H9N2, or H10N7 influenza virus, or a combination thereof. In an embodiment, the influenza virus is an H1N1 or H3N2 influenza virus, or a combination thereof. In an embodiment, the subject is infected with, or is at risk of being infected with, an H1N1 or H7N9 influenza virus, or a combination thereof. In an embodiment, the influenza virus has a mutation (e.g., a substitution) at position 38 of the polymerase acidic protein (PA), e.g., an I38T or I38F substitution.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, a secondary bacterial infection.

In an embodiment, the antibody molecule comprises:

```
(a) a heavy chain immunoglobulin variable region
segment comprising: a CDR1 comprising the sequence
                                      (SEQ ID NO: 68)
S-Y-A-M-H;

a CDR2 comprising the sequence
                                      (SEQ ID NO: 69)
V-V-S-Y-D-G-N-Y-K-Y-A-D-S-V-Q-G;
and a CDR3 comprising the sequence
```

-continued

```
                                      (SEQ ID NO: 70)
D-S-R-L-R-S-L-L-Y-F-E-W-L-S-Q-G-Y-F-N-P;
and (b) a light chain immunoglobulin variable region
segment comprising: a CDR1 comprising the sequence
                                      (SEQ ID NO: 145)
Q-S-I-T-F-D-Y-K-N-Y-L-A;

a CDR2 comprising the sequence
                                       (SEQ ID NO: 72)
W-G-S-Y-L-E-S;
and a CDR3 comprising the sequence
                                       (SEQ ID NO: 73)
Q-Q-H-Y-R-T-P-P-S.
```

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')₂ fragment, a Fab fragment, or an Fd fragment.

In an aspect, the disclosure features a method of evaluating a subject, the method comprising: acquiring acknowledge that the subject is infected with, or is at risk of being infected with, an influenza virus that is resistant to an antiviral agent described herein; and selecting the subject for a treatment comprising an anti-HA antibody molecule described herein, e.g., VIS410.

In an embodiment, the subject is infected with, or is at risk of being infected with, an influenza virus A, an influenza virus B, an influenza virus C, an influenza virus D, or combination thereof. In an embodiment, the subject is infected with, or is at risk of being infected with, an influenza virus A. In an embodiment, the subject is infected with, or is at risk of being infected with, a Group 1 influenza virus (e.g., an H1, H2, H5, H6, H8, H9, H11, H12, H13, or H16 influenza virus, or a combination thereof). In an embodiment, the subject is infected with, or is at risk of being infected with, a Group 2 influenza virus (e.g., an H3, H4, H7, H10, H14, or H15 influenza virus, or a combination thereof). In an embodiment, the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof. In an embodiment, the subject is infected with, or is at risk of being infected with, an H1N1 or H3N2 influenza virus, or a combination thereof. In an embodiment, the subject is infected with, or is at risk of being infected with, an H1N1 or H7N9 influenza virus, or a combination thereof. In an embodiment, the influenza virus has a mutation (e.g., a substitution) at position 38 of the polymerase acidic protein (PA), e.g., an I38T or I38F substitution.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, a secondary bacterial infection.

In an embodiment, the antibody molecule comprises:

```
(a) a heavy chain immunoglobulin variable region
segment comprising: a CDR1 comprising the sequence
                                       (SEQ ID NO: 68)
S-Y-A-M-H;

a CDR2 comprising the sequence
                                       (SEQ ID NO: 69)
V-V-S-Y-D-G-N-Y-K-Y-Y-A-D-S-V-Q-G;
and a CDR3 comprising the sequence
                                       (SEQ ID NO: 70)
D-S-R-L-R-S-L-L-Y-F-E-W-L-S-Q-G-Y-F-N-P;
and (b) a light chain immunoglobulin variable region
segment comprising: a CDR1 comprising the sequence
                                      (SEQ ID NO: 145)
Q-S-I-T-F-D-Y-K-N-Y-L-A;

a CDR2 comprising the sequence
                                       (SEQ ID NO: 72)
W-G-S-Y-L-E-S;
and a CDR3 comprising the sequence
                                       (SEQ ID NO: 73)
Q-Q-H-Y-R-T-P-P-S.
```

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')₂ fragment, a Fab fragment, or an Fd fragment.

In an aspect, the disclosure features a method of evaluating a therapy, the method comprising: acquiring acknowledge that a subject is infected with, or is at risk of being infected with, an influenza virus that is resistant to an antiviral agent described herein; and selecting a treatment comprising an anti-HA antibody molecule described herein, e.g., VIS410, for treating or preventing influenza in the subject.

In an embodiment, the subject is infected with, or is at risk of being infected with, an influenza virus A, an influenza virus B, an influenza virus C, an influenza virus D, or combination thereof. In an embodiment, the subject is infected with, or is at risk of being infected with, an influenza virus A. In an embodiment, the subject is infected with, or is at risk of being infected with, a Group 1 influenza virus (e.g., an H1, H2, H5, H6, H8, H9, H11, H12, H13, or H16 influenza virus, or a combination thereof). In an embodiment, the subject is infected with, or is at risk of being infected with, a Group 2 influenza virus (e.g., an H3, H4, H7, H10, H14, or H15 influenza virus, or a combination thereof). In an embodiment, the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof. In an embodiment, the subject is infected with, or is at risk of being infected with, an H1N1 or H3N2 influenza virus, or a combination thereof. In an embodiment, the subject is infected with, or is at risk of being infected with, an H1N1 or H7N9 influenza virus, or a combination thereof. In an embodiment, the influenza virus has a mutation (e.g., a substitution) at position 38 of the polymerase acidic protein (PA), e.g., an I38T or I38F substitution.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, a secondary bacterial infection.

In an embodiment, the antibody molecule comprises:

```
(a) a heavy chain immunoglobulin variable region
segment comprising: a CDR1 comprising the sequence
                                        (SEQ ID NO: 68)
S-Y-A-M-H;

a CDR2 comprising the sequence
                                        (SEQ ID NO: 69)
V-V-S-Y-D-G-N-Y-K-Y-Y-A-D-S-V-Q-G;
and a CDR3 comprising the sequence
                                        (SEQ ID NO: 70)
D-S-R-L-R-S-L-L-Y-F-E-W-L-S-Q-G-Y-F-N-P;
and (b) a light chain immunoglobulin variable region
segment comprising: a CDR1 comprising the sequence
                                       (SEQ ID NO: 145)
Q-S-I-T-F-D-Y-K-N-Y-L-A;

a CDR2 comprising the sequence
                                        (SEQ ID NO: 72)
W-G-S-Y-L-E-S;
and a CDR3 comprising the sequence
                                        (SEQ ID NO: 73)
Q-Q-H-Y-R-T-P-P-S.
```

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')$_2$ fragment, a Fab fragment, or an Fd fragment.

In an aspect, the disclosure features a method of treating or preventing an influenza virus infection, or a symptom thereof, in a subject, comprising administering (e.g., the administration is continued, or the dosage is maintained) to the subject an anti-HA antibody molecule described herein, e.g., VIS410, responsive to a change in the level of one or more (e.g., 2, 3, 4, 5, 6, or more) cytokines in the subject.

In an embodiment, a change in the level of the one or more cytokines is indicative that the subject is responsive, or partial responsive, to the anti-HA antibody molecule. In an embodiment, responsive to a change in the level of one or more cytokines, the administration of VIS410 is continued.

In an embodiment, a change in the level of one or more cytokines is indicative that the subject experiences, has experienced, or is likely to experience an adverse event, e.g., an adverse event described herein, e.g., a gastrointestinal adverse event (e.g., diarrhea, nausea, vomiting, and/or abdominal pain). In an embodiment, responsive to a change in the level of one or more cytokines, the administration of VIS410 is reduced (e.g., reduced dose) or discontinued.

In an embodiment, the method further comprises acquiring acknowledge that the level of one or more cytokines is changed. In an embodiment, the method further comprises determining that the level of one or more cytokines is changed. In an embodiment, the level of one or more cytokines is determined periodically, e.g., every week, every two weeks, every three weeks, every four weeks, every six weeks, or every eight weeks.

In an embodiment, the level of one or more cytokines is increased, decreased, or increased then decreased.

In an embodiment, the level of one or more cytokines is changed (e.g., increased or decreased) by at least 10%, 20%, 30%, 40%, 50%, 60%, 70%, 80%, 90%, or 100%, or at least 2, 3, 4, 5, 6, 7, 8, 9, or 10-fold, compared to the level prior to administration of the anti-HA antibody molecule. In an embodiment, the level of one or more cytokines is increased within about 24 hours (e.g., within about 1, 2, 3, 4, 5, 6, 7, 8, 9, 10, 11, 12, 13, 14, 16, 17, 18, 19, 20, 21, 22, or 23 hours) after administration of the anti-HA antibody molecule. In an embodiment, the level of one or more cytokines is increased within about 1 hour after administration of the anti-HA antibody molecule.

In an embodiment, the level of one or more cytokines is further decreased within about 36 hours (e.g., within about 12, 13, 14, 15, 16, 17, 18, 19, 20, 21, 22, 23, 24, 25, 26, 27, 28, 29, 30, 31, 32, 33, 34, or 35 hours), e.g., returned to about the same level (e.g., within about ±25%, ±20%, ±15%, ±10%, or ±5%) prior to administration of the anti-HA molecules.

In an embodiment, the one or more cytokines comprise one, two, three, four, five, or all of IL-6, IL-8, IL-10, IFN-γ, TNF-α, or IL-33. In an embodiment, the one or more cytokines comprise one, two, three, or all of IL-8, IFN-γ, IL-6, or TNF-α. In an embodiment, the one or more cytokines comprises one, two, or all of IL-8, IFN-γ, or IL-6. In an embodiment, the one or more cytokines comprise one, two, or all of IL-8, IFN-γ, or TNF-α. In an embodiment, the one or more cytokines comprise IL-8. In an embodiment, the one or more cytokines further comprise IFN-γ, TNF-α, or both. In an embodiment, the one or more cytokines comprise TNF-α. In an embodiment, the one or more cytokines comprise IL-6. In an embodiment, the one or more cytokines comprise one, two, three, four, or all of IL-6, IL-8, IL-10, IFN-γ, or TNF-α. In an embodiment, the one or more cytokines comprise IL-8, IFN-γ, or TNF-α, and optionally IL-6. In an embodiment, the one or more cytokines do not comprise IL-10.

In an embodiment, the method further comprises administering a therapeutic agent or modality to treat or prevent an adverse event in the subject, e.g., to reduce the severity of the adverse event. In an embodiment, the therapeutic agent or modality is administered prior to, concurrently with, or after administration of the anti-HA antibody molecule. In an embodiment, the therapeutic agent or modality is administered prior to administration of the anti-HA antibody molecule, e.g., at least 1, 2, 3, 4, 5, 6, 7, 8, 9, 10, 12, 15, 18, 21, 24, 27, 30, 33, or 36 hours, or within 1, 2, 3, 4, 5, 6, 7, 8, 9, 10, 12, 15, 18, 21, 24, 27, 30, 33, or 36 hours, prior to administration of the anti-HA antibody molecule. In an embodiment, the therapeutic agent or modality comprises one, two, three, four, or all the following: (a) diphenhydramine (e.g., one dose of diphenhydramine, e.g., about 25 mg to about 100 mg, e.g., about 50 mg, of diphenhydramine), (b) ibuprofen (e.g., one dose of ibuprofen, e.g., about 300 mg to about 1000 mg ibuprofen, e.g., about 600 mg, of ibuprofen), (c) aspirin (e.g., one dose of aspirin), (d) montelukast (e.g., one dose of montelukast, e.g., about 5 mg to about 25 mg, e.g., 10 mg, of montelukast), or (e) ranitidine (e.g., oral ranitidine, e.g., one dose of ranitidine, e.g., about 100 mg to about 200 mg, e.g., about 150 mg, of ranitidine). In an embodiment, the therapeutic agent or modality comprises (a). In an embodiment, the therapeutic agent or modality comprises (b). In an embodiment, the therapeutic agent or modality comprises (c). In an embodiment, the therapeutic agent or modality comprises (d). In an embodiment, the therapeutic agent or modality comprises (e). In an embodiment, the therapeutic agent or modality comprises (a) and (b), (a) and (c), (a) and (d), (a) and (e), (b) and (c), (b) and (d), (b) and (e), (c) and (d), (c) and (e), or (d) and (e). In an embodiment, the therapeutic agent or modality comprises one, two, or all of (a), (b), or (c).

In an embodiment, the subject is infected with, or is at risk of being infected with, an influenza virus A, an influenza virus B, an influenza virus C, an influenza virus D, or combination thereof. In an embodiment, the subject is infected with, or is at risk of being infected with, an influenza virus A. In an embodiment, the subject is infected with, or is at risk of being infected with, a Group 1 influenza virus (e.g., an H1, H2, H5, H6, H8, H9, H11, H12, H13, or H16 influenza virus, or a combination thereof). In an embodiment, the subject is infected with, or is at risk of being infected with, a Group 2 influenza virus (e.g., an H3, H4, H7, H10, H14, or H15 influenza virus, or a combination thereof). In an embodiment, the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof. In an embodiment, the subject is infected with, or is at risk of being infected with, an H1N1 or H3N2 influenza virus, or a combination thereof. In an embodiment, the subject is infected with, or is at risk of being infected with, an H1N1 or H7N9 influenza virus, or a combination thereof. In an embodiment, the influenza virus has a mutation (e.g., a substitution) at position 38 of the polymerase acidic protein (PA), e.g., an I38T or I38F substitution.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, a secondary bacterial infection.

In an embodiment, the antibody molecule comprises:

(a) a heavy chain immunoglobulin variable region
segment comprising: a CDR1 comprising the sequence
                                          (SEQ ID NO: 68)
S-Y-A-M-H;

a CDR2 comprising the sequence
                                          (SEQ ID NO: 69)
V-V-S-Y-D-G-N-Y-K-Y-Y-A-D-S-V-Q-G;
and a CDR3 comprising the sequence
                                          (SEQ ID NO: 70)
D-S-R-L-R-S-L-L-Y-F-E-W-L-S-Q-G-Y-F-N-P;
and (b) a light chain immunoglobulin variable region
segment comprising: a CDR1 comprising the sequence
                                          (SEQ ID NO: 145)
Q-S-I-T-F-D-Y-K-N-Y-L-A;

a CDR2 comprising the sequence
                                          (SEQ ID NO: 72)
W-G-S-Y-L-E-S;
and a CDR3 comprising the sequence
                                          (SEQ ID NO: 73)
Q-Q-H-Y-R-T-P-P-S.

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')$_2$ fragment, a Fab fragment, or an Fd fragment.

In an aspect, the disclosure features a method of treating or preventing an influenza virus infection, or a symptom thereof, in a subject, comprising modifying the administration of an anti-HA antibody molecule described herein, e.g., VIS410, to the subject, responsive to a change in the level of one or more (e.g., 2, 3, 4, 5, 6, or more) cytokines in the subject.

In an embodiment, a change in the level of one or more cytokines is indicative that the subject experiences, has experienced, or is likely to experience an adverse event, e.g., an adverse event described herein, e.g., a gastrointestinal adverse event (e.g., diarrhea, nausea, vomiting, and/or abdominal pain). In an embodiment, responsive to a change in the level of one or more cytokines, the administration of VIS410 is reduced (e.g., reduced dose) or discontinued.

In an embodiment, the method further comprises acquiring acknowledge that the level of one or more cytokines is changed. In an embodiment, the method further comprises determining that the level of one or more cytokines is changed. In an embodiment, the level of one or more cytokines is determined periodically, e.g., every week, every two weeks, every three weeks, every four weeks, every six weeks, or every eight weeks.

In an embodiment, the level of one or more cytokines is increased, decreased, or increased then decreased.

In an embodiment, the level of one or more cytokines is changed (e.g., increased or decreased) by at least 10%, 20%, 30%, 40%, 50%, 60%, 70%, 80%, 90%, or 100%, or at least 2, 3, 4, 5, 6, 7, 8, 9, or 10-fold, compared to the level prior to administration of the anti-HA antibody molecule. In an embodiment, the level of one or more cytokines is increased within about 24 hours (e.g., within about 1, 2, 3, 4, 5, 6, 7, 8, 9, 10, 11, 12, 13, 14, 16, 17, 18, 19, 20, 21, 22, or 23 hours) after administration of the anti-HA antibody molecule. In an embodiment, the level of one or more cytokines is increased within about 1 hour after administration of the anti-HA antibody molecule.

In an embodiment, the level of one or more cytokines is further decreased within about 36 hours (e.g., within about 12, 13, 14, 15, 16, 17, 18, 19, 20, 21, 22, 23, 24, 25, 26, 27, 28, 29, 30, 31, 32, 33, 34, or 35 hours), e.g., returned to about the same level (e.g., within about ±25%, ±20%, ±15%, ±10%, or ±5%) prior to administration of the anti-HA molecules.

In an embodiment, the one or more cytokines comprise one, two, three, four, five, or all of IL-6, IL-8, IL-10, IFN-γ, TNF-α, or IL-33. In an embodiment, the one or more cytokines comprise one, two, three, or all of IL-8, IFN-γ, IL-6, or TNF-α. In an embodiment, the one or more cytokines comprises one, two, or all of IL-8, IFN-γ, or IL-6. In an embodiment, the one or more cytokines comprise one, two, or all of IL-8, IFN-γ, or TNF-α. In an embodiment, the one or more cytokines comprise IL-8. In an embodiment, the one or more cytokines further comprise IFN-γ, TNF-α, or both. In an embodiment, the one or more cytokines comprise TNF-α. In an embodiment, the one or more cytokines comprise IL-6. In an embodiment, the one or more cytokines comprise one, two, three, four, or all of IL-6, IL-8, IL-10, IFN-γ, or TNF-α. In an embodiment, the one or more cytokines comprise IL-8, IFN-γ, or TNF-α, and optionally IL-6. In an embodiment, the one or more cytokines do not comprise IL-10.

In an embodiment, the method further comprises administering a therapeutic agent or modality to treat or prevent an adverse event in the subject, e.g., to reduce the severity of the adverse event. In an embodiment, the therapeutic agent or modality is administered prior to, concurrently with, or after administration of the anti-HA antibody molecule. In an embodiment, the therapeutic agent or modality is administered prior to administration of the anti-HA antibody molecule, e.g., at least 1, 2, 3, 4, 5, 6, 7, 8, 9, 10, 12, 15, 18, 21, 24, 27, 30, 33, or 36 hours, or within 1, 2, 3, 4, 5, 6, 7, 8, 9, 10, 12, 15, 18, 21, 24, 27, 30, 33, or 36 hours, prior to administration of the anti-HA antibody molecule. In an embodiment, the therapeutic agent or modality comprises one, two, or all the following: (a) diphenhydramine (e.g., one dose of diphenhydramine, e.g., about 25 mg to about 100 mg, e.g., about 50 mg, of diphenhydramine), (b) ibuprofen (e.g., one dose of ibuprofen, e.g., about 300 mg to about 1000 mg ibuprofen, e.g., about 600 mg, of ibuprofen), (c) aspirin (e.g., one dose of aspirin), (d) montelukast (e.g., one dose of montelukast, e.g., about 5 mg to about 25 mg, e.g., 10 mg, of montelukast), or (e) ranitidine (e.g., oral ranitidine, e.g., one dose of ranitidine, e.g., about 100 mg to about 200 mg, e.g., about 150 mg, of ranitidine). In an embodiment, the therapeutic agent or modality comprises (a). In an embodiment, the therapeutic agent or modality comprises (b). In an embodiment, the therapeutic agent or modality comprises (c). In an embodiment, the therapeutic agent or modality comprises (d). In an embodiment, the therapeutic agent or modality comprises (e). In an embodiment, the therapeutic agent or modality comprises (a) and (b), (a) and (c), (a) and (d), (a) and (e), (b) and (c), (b) and (d), (b) and (e), (c) and (d), (c) and (e), or (d) and (e). In an embodiment, the therapeutic agent or modality comprises one, two, or all of (a), (b), or (c).

In an embodiment, the subject is infected with, or is at risk of being infected with, an influenza virus A, an influenza virus B, an influenza virus C, an influenza virus D, or combination thereof. In an embodiment, the subject is infected with, or is at risk of being infected with, an influenza virus A. In an embodiment, the subject is infected with, or is at risk of being infected with, a Group 1 influenza virus (e.g., an H1, H2, H5, H6, H8, H9, H11, H12, H13, or H16 influenza virus, or a combination thereof). In an embodiment, the subject is infected with, or is at risk of being infected with, a Group 2 influenza virus (e.g., an H3, H4, H7, H10, H14, or H15 influenza virus, or a combination thereof). In an embodiment, the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof. In an embodiment, the subject is infected with, or is at risk of being infected with, an H1N1 or H3N2 influenza virus, or a combination thereof. In an embodiment, the subject is infected with, or is at risk of being infected with, an H1N1 or H7N9 influenza virus, or a combination thereof. In an embodiment, the influenza virus has a mutation (e.g., a substitution) at position 38 of the polymerase acidic protein (PA), e.g., an I38T or I38F substitution.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, a secondary bacterial infection.

In an embodiment, the antibody molecule comprises:

```
(a) a heavy chain immunoglobulin variable region
segment comprising: a CDR1 comprising the sequence
                                    (SEQ ID NO: 68)
S-Y-A-M-H;

a CDR2 comprising the sequence
                                    (SEQ ID NO: 69)
V-V-S-Y-D-G-N-Y-K-Y-A-D-S-V-Q-G;
and a CDR3 comprising the sequence
                                    (SEQ ID NO: 70)
D-S-R-L-R-S-L-L-Y-F-E-W-L-S-Q-G-Y-F-N-P;
and
```

(b) a light chain immunoglobulin variable region
segment comprising: a CDR1 comprising the sequence
(SEQ ID NO: 145)
Q-S-I-T-F-D-Y-K-N-Y-L-A;

a CDR2 comprising the sequence
(SEQ ID NO: 72)
W-G-S-Y-L-E-S;
and a CDR3 comprising the sequence
(SEQ ID NO: 73)
Q-Q-H-Y-R-T-P-P-S.

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')₂ fragment, a Fab fragment, or an Fd fragment.

In an aspect, the disclosure features a method of evaluating an influenza therapy, the method comprising: acquiring acknowledge that the level of one or more cytokines is elevated in a subject after administration of an anti-HA antibody molecule described herein, e.g., VIS410, wherein an elevated level of one or more cytokines is indicative that the anti-HA antibody molecule is effective in treating or preventing an influenza infection, or a symptom thereof.

In an embodiment, the method further comprises determining that the level of one or more cytokines is increased. In an embodiment, the level of one or more cytokines is determined periodically, e.g., every week, every two weeks, every three weeks, every four weeks, every six weeks, or every eight weeks.

In an embodiment, the level of one or more cytokines is increased by at least 10%, 20%, 30%, 40%, 50%, 60%, 70%, 80%, 90%, or 100%, or at least 2, 3, 4, 5, 6, 7, 8, 9, or 10-fold, compared to the level prior to administration of the anti-HA antibody molecule. In an embodiment, the level of one or more cytokines is increased within about 24 hours (e.g., within about 1, 2, 3, 4, 5, 6, 7, 8, 9, 10, 11, 12, 13, 14, 16, 17, 18, 19, 20, 21, 22, or 23 hours) after administration of the anti-HA antibody molecule. In an embodiment, the level of one or more cytokines is increased within about 1 hour after administration of the anti-HA antibody molecule.

In an embodiment, the level of one or more cytokines is further decreased within about 36 hours (e.g., within about 12, 13, 14, 15, 16, 17, 18, 19, 20, 21, 22, 23, 24, 25, 26, 27, 28, 29, 30, 31, 32, 33, 34, or 35 hours), e.g., returned to about the same level (e.g., within about ±25%, ±20%, ±15%, ±10%, or ±5%) prior to administration of the anti-HA molecules.

In an embodiment, the one or more cytokines comprise one, two, three, four, five, or all of IL-6, IL-8, IL-10, IFN-γ, TNF-α, or IL-33. In an embodiment, the one or more cytokines comprise one, two, three, or all of IL-8, IFN-γ, IL-6, or TNF-α. In an embodiment, the one or more cytokines comprises one, two, or all of IL-8, IFN-γ, or IL-6. In an embodiment, the one or more cytokines comprise one, two, or all of IL-8, IFN-γ, or TNF-α. In an embodiment, the one or more cytokines comprise IL-8. In an embodiment, the one or more cytokines further comprise IFN-γ, TNF-α, or both. In an embodiment, the one or more cytokines comprise TNF-α. In an embodiment, the one or more cytokines comprise IL-6. In an embodiment, the one or more cytokines comprise one, two, three, four, or all of IL-6, IL-8, IL-10, IFN-γ, or TNF-α. In an embodiment, the one or more cytokines comprise IL-8, IFN-γ, or TNF-α, and optionally IL-6. In an embodiment, the one or more cytokines do not comprise IL-10.

In an embodiment, the subject is infected with, or is at risk of being infected with, an influenza virus A, an influenza virus B, an influenza virus C, an influenza virus D, or combination thereof. In an embodiment, the subject is infected with, or is at risk of being infected with, an influenza virus A. In an embodiment, the subject is infected with, or is at risk of being infected with, a Group 1 influenza virus (e.g., an H1, H2, H5, H6, H8, H9, H11, H12, H13, or H16 influenza virus, or a combination thereof). In an embodiment, the subject is infected with, or is at risk of being infected with, a Group 2 influenza virus (e.g., an H3, H4, H7, H10, H14, or H15 influenza virus, or a combination thereof). In an embodiment, the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof. In an embodiment, the subject is infected with, or is at risk of being infected with, an H1N1 or H3N2 influenza virus, or a combination thereof. In an embodiment, the subject is infected with, or is at risk of being infected with, an H1N1 or H7N9 influenza virus, or a combination thereof. In an embodiment, the influenza virus has a mutation (e.g., a substitution) at position 38 of the polymerase acidic protein (PA), e.g., an I38T or I38F substitution.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, a secondary bacterial infection.

In an embodiment, the antibody molecule comprises:

(a) a heavy chain immunoglobulin variable region
segment comprising: a CDR1 comprising the sequence
(SEQ ID NO: 68)
S-Y-A-M-H;

a CDR2 comprising the sequence
(SEQ ID NO: 69)
V-V-S-Y-D-G-N-Y-K-Y-Y-A-D-S-V-Q-G;
and a CDR3 comprising the sequence
(SEQ ID NO: 70)
D-S-R-L-R-S-L-L-Y-F-E-W-L-S-Q-G-Y-F-N-P;
and -continued
(b) a light chain immunoglobulin variable region
segment comprising: a CDR1 comprising the sequence
(SEQ ID NO: 145)
Q-S-I-T-F-D-Y-K-N-Y-L-A;

a CDR2 comprising the sequence
(SEQ ID NO: 72)
W-G-S-Y-L-E-S;
and a CDR3 comprising the sequence
(SEQ ID NO: 73)
Q-Q-H-Y-R-T-P-P-S.

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')$_2$ fragment, a Fab fragment, or an Fd fragment.

In an aspect, the disclosure features a method of evaluating an influenza therapy, the method comprising:
acquiring acknowledge that the level of one or more cytokines is elevated in a subject after administration of an anti-HA antibody molecule described herein, e.g., VIS410, wherein an elevated level of one or more cytokines is indicative that the anti-HA antibody molecule is capable of causing an adverse event in the subject.

In an embodiment, the method further comprises determining that the level of one or more cytokines is increased. In an embodiment, the level of one or more cytokines is determined periodically, e.g., every week, every two weeks, every three weeks, every four weeks, every six weeks, or every eight weeks.

In an embodiment, the level of one or more cytokines is increased by at least 10%, 20%, 30%, 40%, 50%, 60%, 70%, 80%, 90%, or 100%, or at least 2, 3, 4, 5, 6, 7, 8, 9, or 10-fold, compared to the level prior to administration of the anti-HA antibody molecule. In an embodiment, the level of one or more cytokines is increased within about 24 hours (e.g., within about 1, 2, 3, 4, 5, 6, 7, 8, 9, 10, 11, 12, 13, 14, 16, 17, 18, 19, 20, 21, 22, or 23 hours) after administration of the anti-HA antibody molecule. In an embodiment, the level of one or more cytokines is increased within about 1 hour after administration of the anti-HA antibody molecule.

In an embodiment, the level of one or more cytokines is further decreased within about 36 hours (e.g., within about 12, 13, 14, 15, 16, 17, 18, 19, 20, 21, 22, 23, 24, 25, 26, 27, 28, 29, 30, 31, 32, 33, 34, or 35 hours), e.g., returned to about the same level (e.g., within about ±25%, ±20%, ±15%, ±10%, or ±5%) prior to administration of the anti-HA molecules.

In an embodiment, the one or more cytokines comprise one, two, three, four, five, or all of IL-6, IL-8, IL-10, IFN-γ, TNF-α, or IL-33. In an embodiment, the one or more cytokines comprise one, two, three, or all of IL-8, IFN-γ, IL-6, or TNF-α. In an embodiment, the one or more cytokines comprises one, two, or all of IL-8, IFN-γ, or IL-6. In an embodiment, the one or more cytokines comprise one, two, or all of IL-8, IFN-γ, or TNF-α. In an embodiment, the one or more cytokines comprise IL-8. In an embodiment, the one or more cytokines further comprise IFN-γ, TNF-α, or both. In an embodiment, the one or more cytokines comprise TNF-α. In an embodiment, the one or more cytokines comprise IL-6. In an embodiment, the one or more cytokines comprise one, two, three, four, or all of IL-6, IL-8, IL-10, IFN-γ, or TNF-α. In an embodiment, the one or more cytokines comprise IL-8, IFN-γ, or TNF-α, and optionally IL-6. In an embodiment, the one or more cytokines do not comprise IL-10.

In an embodiment, the subject is infected with, or is at risk of being infected with, an influenza virus A, an influenza virus B, an influenza virus C, an influenza virus D, or combination thereof. In an embodiment, the subject is infected with, or is at risk of being infected with, an influenza virus A. In an embodiment, the subject is infected with, or is at risk of being infected with, a Group 1 influenza virus (e.g., an H1, H2, H5, H6, H8, H9, H11, H12, H13, or H16 influenza virus, or a combination thereof). In an embodiment, the subject is infected with, or is at risk of being infected with, a Group 2 influenza virus (e.g., an H3, H4, H7, H10, H14, or H15 influenza virus, or a combination thereof). In an embodiment, the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof. In an embodiment, the subject is infected with, or is at risk of being infected with, an H1N1 or H3N2 influenza virus, or a combination thereof. In an embodiment, the subject is infected with, or is at risk of being infected with, an H1N1 or H7N9 influenza virus, or a combination thereof. In an embodiment, the influenza virus has a mutation (e.g., a substitution) at position 38 of the polymerase acidic protein (PA), e.g., an I38T or I38F substitution.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, a secondary bacterial infection.

In an embodiment, the antibody molecule comprises:

(a) a heavy chain immunoglobulin variable region segment comprising:
(SEQ ID NO: 68)
a CDR1 comprising the sequence
S-Y-A-M-H;

a CDR2 comprising the sequence
(SEQ ID NO: 69)
V-V-S-Y-D-G-N-Y-K-Y-Y-A-D-S-V-Q-G;
and a CDR3 comprising the sequence
(SEQ ID NO: 70)
D-S-R-L-R-S-L-L-Y-F-E-W-L-S-Q-G-Y-F-N-P;
and (b) a light chain immunoglobulin variable region segment comprising:

```
a CDR1 comprising the sequence                    (SEQ ID NO: 145)
Q-S-I-T-F-D-Y-K-N-Y-L-A;

a CDR2 comprising the sequence                    (SEQ ID NO: 72)
W-G-S-Y-L-E-S;
and a CDR3 comprising the sequence
                                                  (SEQ ID NO: 73)
Q-Q-H-Y-R-T-P-P-S.
```

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')$_2$ fragment, a Fab fragment, or an Fd fragment.

In an aspect, the disclosure features a method of evaluating a subject, the method comprising: acquiring acknowledge that the level of one or more cytokines is elevated in a subject after administration of an anti-HA antibody molecule described herein, e.g., VIS410; and selecting the subject as suitable for continued administration of the anti-HA antibody molecule.

In an embodiment, the method further comprises determining that the level of one or more cytokines is increased. In an embodiment, the level of one or more cytokines is determined periodically, e.g., every week, every two weeks, every three weeks, every four weeks, every six weeks, or every eight weeks.

In an embodiment, the level of one or more cytokines is increased by at least 10%, 20%, 30%, 40%, 50%, 60%, 70%, 80%, 90%, or 100%, or at least 2, 3, 4, 5, 6, 7, 8, 9, or 10-fold, compared to the level prior to administration of the anti-HA antibody molecule. In an embodiment, the level of one or more cytokines is increased within about 24 hours (e.g., within about 1, 2, 3, 4, 5, 6, 7, 8, 9, 10, 11, 12, 13, 14, 16, 17, 18, 19, 20, 21, 22, or 23 hours) after administration of the anti-HA antibody molecule. In an embodiment, the level of one or more cytokines is increased within about 1 hour after administration of the anti-HA antibody molecule.

In an embodiment, the level of one or more cytokines is further decreased within about 36 hours (e.g., within about 12, 13, 14, 15, 16, 17, 18, 19, 20, 21, 22, 23, 24, 25, 26, 27, 28, 29, 30, 31, 32, 33, 34, or 35 hours), e.g., returned to about the same level (e.g., within about ±25%, ±20%, ±15%, ±10%, or ±5%) prior to administration of the anti-HA molecules.

In an embodiment, the one or more cytokines comprise one, two, three, four, five, or all of IL-6, IL-8, IL-10, IFN-γ, TNF-α, or IL-33. In an embodiment, the one or more cytokines comprise one, two, three, or all of IL-8, IFN-γ, IL-6, or TNF-α. In an embodiment, the one or more cytokines comprises one, two, or all of IL-8, IFN-γ, or IL-6. In an embodiment, the one or more cytokines comprise one, two, or all of IL-8, IFN-γ, or TNF-α. In an embodiment, the one or more cytokines comprise IL-8. In an embodiment, the one or more cytokines further comprise IFN-γ, TNF-α, or both. In an embodiment, the one or more cytokines comprise TNF-α. In an embodiment, the one or more cytokines comprise IL-6. In an embodiment, the one or more cytokines comprise one, two, three, four, or all of IL-6, IL-8, IL-10, IFN-γ, or TNF-α. In an embodiment, the one or more cytokines comprise IL-8, IFN-γ, or TNF-α, and optionally IL-6. In an embodiment, the one or more cytokines do not comprise IL-10.

In an embodiment, the method further comprises administering a therapeutic agent or modality to treat or prevent an adverse event in the subject, e.g., to reduce the severity of the adverse event. In an embodiment, the therapeutic agent or modality is administered prior to, concurrently with, or after administration of the anti-HA antibody molecule. In an embodiment, the therapeutic agent or modality is administered prior to administration of the anti-HA antibody molecule, e.g., at least 1, 2, 3, 4, 5, 6, 7, 8, 9, 10, 12, 15, 18, 21, 24, 27, 30, 33, or 36 hours, or within 1, 2, 3, 4, 5, 6, 7, 8, 9, 10, 12, 15, 18, 21, 24, 27, 30, 33, or 36 hours, prior to administration of the anti-HA antibody molecule. In an embodiment, the therapeutic agent or modality comprises one, two, or all the following: (a) diphenhydramine (e.g., one dose of diphenhydramine, e.g., about 25 mg to about 100 mg, e.g., about 50 mg, of diphenhydramine), (b) ibuprofen (e.g., one dose of ibuprofen, e.g., about 300 mg to about 1000 mg ibuprofen, e.g., about 600 mg, of ibuprofen), (c) aspirin (e.g., one dose of aspirin), (d) montelukast (e.g., one dose of montelukast, e.g., about 5 mg to about 25 mg, e.g., 10 mg, of montelukast), or (e) ranitidine (e.g., oral ranitidine, e.g., one dose of ranitidine, e.g., about 100 mg to about 200 mg, e.g., about 150 mg, of ranitidine). In an embodiment, the therapeutic agent or modality comprises (a). In an embodiment, the therapeutic agent or modality comprises (b). In an embodiment, the therapeutic agent or modality comprises (c). In an embodiment, the therapeutic agent or modality comprises (d). In an embodiment, the therapeutic agent or modality comprises (e). In an embodiment, the therapeutic agent or modality comprises (a) and (b), (a) and (c), (a) and (d), (a) and (e), (b) and (c), (b) and (d), (b) and (e), (c) and (d), (c) and (e), or (d) and (e). In an embodiment, the therapeutic agent or modality comprises one, two, or all of (a), (b), or (c).

In an embodiment, the subject is infected with, or is at risk of being infected with, an influenza virus A, an influenza virus B, an influenza virus C, an influenza virus D, or combination thereof. In an embodiment, the subject is infected with, or is at risk of being infected with, an influenza virus A. In an embodiment, the subject is infected with, or is at risk of being infected with, a Group 1 influenza virus (e.g., an H1, H2, H5, H6, H8, H9, H11, H12, H13, or H16 influenza virus, or a combination thereof). In an embodiment, the subject is infected with, or is at risk of being infected with, a Group 2 influenza virus (e.g., an H3, H4, H7, H10, H14, or H15 influenza virus, or a combination thereof). In an embodiment, the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof. In an embodiment, the subject is infected with, or is at risk of being infected with, an H1N1 or H3N2 influenza virus, or a combination thereof. In an embodiment, the subject is infected with, or is at risk of being infected with, an H1N1 or H7N9 influenza virus, or a combination thereof. In an embodiment, the influenza virus has a mutation (e.g., a substitution) at position 38 of the polymerase acidic protein (PA), e.g., an I38T or I38F substitution.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, a secondary bacterial infection.

In an embodiment, the antibody molecule comprises:

(a) a heavy chain immunoglobulin variable region segment comprising:
a CDR1 comprising the sequence (SEQ ID NO: 68)
S-Y-A-M-H;

a CDR2 comprising the sequence (SEQ ID NO: 69)
V-V-S-Y-D-G-N-Y-K-Y-Y-A-D-S-V-Q-G; and a CDR3 comprising the sequence (SEQ ID NO: 70)
D-S-R-L-R-S-L-L-Y-F-E-W-L-S-Q-G-Y-F-N-P; and (b) a light chain immunoglobulin variable region segment comprising:
a CDR1 comprisingthe sequence (SEQ ID NO: 145)
Q-S-I-T-F-D-Y-K-N-Y-L-A;

a CDR2 comprising the sequence (SEQ ID NO: 72)
W-G-S-Y-L-E-S; and a CDR3 comprising the sequence (SEQ ID NO: 73)
Q-Q-H-Y-R-T-P-P-S.

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')$_2$ fragment, a Fab fragment, or an Fd fragment.

In an aspect, the disclosure features a method of evaluating a therapy, the method comprising: acquiring acknowledge that the level of one or more cytokines is elevated in a subject after administration of an anti-HA antibody molecule described herein, e.g., VIS410; and selecting the anti-HA antibody molecule as suitable for treating or preventing an influenza infection, or a symptom thereof, in the subject.

In an embodiment, the method further comprises determining that the level of one or more cytokines is increased. In an embodiment, the level of one or more cytokines is determined periodically, e.g., every week, every two weeks, every three weeks, every four weeks, every six weeks, or every eight weeks.

In an embodiment, the level of one or more cytokines is increased by at least 10%, 20%, 30%, 40%, 50%, 60%, 70%, 80%, 90%, or 100%, or at least 2, 3, 4, 5, 6, 7, 8, 9, or 10-fold, compared to the level prior to administration of the anti-HA antibody molecule. In an embodiment, the level of one or more cytokines is increased within about 24 hours (e.g., within about 1, 2, 3, 4, 5, 6, 7, 8, 9, 10, 11, 12, 13, 14, 16, 17, 18, 19, 20, 21, 22, or 23 hours) after administration of the anti-HA antibody molecule. In an embodiment, the level of one or more cytokines is increased within about 1 hour after administration of the anti-HA antibody molecule.

In an embodiment, the level of one or more cytokines is further decreased within about 36 hours (e.g., within about 12, 13, 14, 15, 16, 17, 18, 19, 20, 21, 22, 23, 24, 25, 26, 27, 28, 29, 30, 31, 32, 33, 34, or 35 hours), e.g., returned to about the same level (e.g., within about ±25%, ±20%, ±15%, ±10%, or ±5%) prior to administration of the anti-HA molecules.

In an embodiment, the one or more cytokines comprise one, two, three, four, five, or all of IL-6, IL-8, IL-10, IFN-γ, TNF-α, or IL-33. In an embodiment, the one or more cytokines comprise one, two, three, or all of IL-8, IFN-γ, IL-6, or TNF-α. In an embodiment, the one or more cytokines comprises one, two, or all of IL-8, IFN-γ, or IL-6. In an embodiment, the one or more cytokines comprise one, two, or all of IL-8, IFN-γ, or TNF-α. In an embodiment, the one or more cytokines comprise IL-8. In an embodiment, the one or more cytokines further comprise IFN-γ, TNF-α, or both. In an embodiment, the one or more cytokines comprise TNF-α. In an embodiment, the one or more cytokines comprise IL-6. In an embodiment, the one or more cytokines comprise one, two, three, four, or all of IL-6, IL-8, IL-10, IFN-γ, or TNF-α. In an embodiment, the one or more cytokines comprise IL-8, IFN-γ, or TNF-α, and optionally IL-6. In an embodiment, the one or more cytokines do not comprise IL-10.

In an embodiment, the subject is infected with, or is at risk of being infected with, an influenza virus A, an influenza virus B, an influenza virus C, an influenza virus D, or combination thereof. In an embodiment, the subject is infected with, or is at risk of being infected with, an influenza virus A. In an embodiment, the subject is infected with, or is at risk of being infected with, a Group 1 influenza virus (e.g., an H1, H2, H5, H6, H8, H9, H11, H12, H13, or H16 influenza virus, or a combination thereof). In an embodiment, the subject is infected with, or is at risk of being infected with, a Group 2 influenza virus (e.g., an H3, H4, H7, H10, H14, or H15 influenza virus, or a combination thereof). In an embodiment, the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof. In an embodiment, the subject is infected with, or is at risk of being infected with, an H1N1 or H3N2 influenza virus, or a combination thereof. In an embodiment, the subject is infected with, or is at risk of being infected with, an H1N1 or H7N9 influenza virus, or a combination thereof. In an embodiment, the influenza virus has a mutation (e.g., a substitution) at position 38 of the polymerase acidic protein (PA), e.g., an I38T or I38F substitution.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, a secondary bacterial infection.

In an embodiment, the antibody molecule comprises:

```
(a) a heavy chain immunoglobulin variable region
segment comprising:
                                         (SEQ ID NO: 68)
a CDR1 comprising the sequence
S-Y-A-M-H;

(SEQ ID NO: 69)
a CDR2 comprising the sequence
V-V-S-Y-D-G-N-Y-K-Y-Y-A-D-S-V-Q-G;
and (SEQ ID NO: 70)
a CDR3 comprising the sequence
D-S-R-L-R-S-L-L-Y-F-E-W-L-S-Q-G-Y-F-N-P;
and (b) a light chain immunoglobulin variable region
segment comprising:
a CDR1 comprising the sequence
                                         (SEQ ID NO: 145)
Q-S-I-T-F-D-Y-K-N-Y-L-A;

(SEQ ID NO: 72)
a CDR2 comprising the sequence
W-G-S-Y-L-E-S;
and a CDR3 comprising the sequence
                                         (SEQ ID NO: 73)
Q-Q-H-Y-R-T-P-P-S.
```

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')$_2$ fragment, a Fab fragment, or an Fd fragment.

In an aspect, the disclosure features a method of evaluating a subject, the method comprising: acquiring acknowledge that the level of one or more cytokines is elevated in a subject after administration of an anti-HA antibody molecule described herein, e.g., VIS410; and selecting the subject as not suitable for continued administration of the anti-HA antibody molecule.

In an embodiment, the method further comprises determining that the level of one or more cytokines is increased. In an embodiment, the level of one or more cytokines is determined periodically, e.g., every week, every two weeks, every three weeks, every four weeks, every six weeks, or every eight weeks.

In an embodiment, the level of one or more cytokines is increased by at least 10%, 20%, 30%, 40%, 50%, 60%, 70%, 80%, 90%, or 100%, or at least 2, 3, 4, 5, 6, 7, 8, 9, or 10-fold, compared to the level prior to administration of the anti-HA antibody molecule. In an embodiment, the level of one or more cytokines is increased within about 24 hours (e.g., within about 1, 2, 3, 4, 5, 6, 7, 8, 9, 10, 11, 12, 13, 14, 16, 17, 18, 19, 20, 21, 22, or 23 hours) after administration of the anti-HA antibody molecule. In an embodiment, the level of one or more cytokines is increased within about 1 hour after administration of the anti-HA antibody molecule.

In an embodiment, the level of one or more cytokines is further decreased within about 36 hours (e.g., within about 12, 13, 14, 15, 16, 17, 18, 19, 20, 21, 22, 23, 24, 25, 26, 27, 28, 29, 30, 31, 32, 33, 34, or 35 hours), e.g., returned to about the same level (e.g., within about ±25%, ±20%, ±15%, ±10%, or ±5%) prior to administration of the anti-HA molecules.

In an embodiment, the one or more cytokines comprise one, two, three, four, five, or all of IL-6, IL-8, IL-10, IFN-γ, TNF-α, or IL-33. In an embodiment, the one or more cytokines comprise one, two, three, or all of IL-8, IFN-γ, IL-6, or TNF-α. In an embodiment, the one or more cytokines comprises one, two, or all of IL-8, IFN-γ, or IL-6. In an embodiment, the one or more cytokines comprise one, two, or all of IL-8, IFN-γ, or TNF-α. In an embodiment, the one or more cytokines comprise IL-8. In an embodiment, the one or more cytokines further comprise IFN-γ, TNF-α, or both. In an embodiment, the one or more cytokines comprise TNF-α. In an embodiment, the one or more cytokines comprise IL-6. In an embodiment, the one or more cytokines comprise one, two, three, four, or all of IL-6, IL-8, IL-10, IFN-γ, or TNF-α. In an embodiment, the one or more cytokines comprise IL-8, IFN-γ, or TNF-α, and optionally IL-6. In an embodiment, the one or more cytokines do not comprise IL-10.

In an embodiment, the method further comprises administering a therapeutic agent or modality to treat or prevent an adverse event in the subject, e.g., to reduce the severity of the adverse event. In an embodiment, the therapeutic agent or modality is administered prior to, concurrently with, or after administration of the anti-HA antibody molecule. In an embodiment, the therapeutic agent or modality is administered prior to administration of the anti-HA antibody molecule, e.g., at least 1, 2, 3, 4, 5, 6, 7, 8, 9, 10, 12, 15, 18, 21, 24, 27, 30, 33, or 36 hours, or within 1, 2, 3, 4, 5, 6, 7, 8, 9, 10, 12, 15, 18, 21, 24, 27, 30, 33, or 36 hours, prior to administration of the anti-HA antibody molecule. In an embodiment, the therapeutic agent or modality comprises one, two, or all the following: (a) diphenhydramine (e.g., one dose of diphenhydramine, e.g., about 25 mg to about 100 mg, e.g., about 50 mg, of diphenhydramine), (b) ibuprofen (e.g., one dose of ibuprofen, e.g., about 300 mg to about 1000 mg ibuprofen, e.g., about 600 mg, of ibuprofen), (c) aspirin (e.g., one dose of aspirin), (d) montelukast (e.g., one dose of montelukast, e.g., about 5 mg to about 25 mg, e.g., 10 mg, of montelukast), or (e) ranitidine (e.g., oral ranitidine, e.g., one dose of ranitidine, e.g., about 100 mg to about 200 mg, e.g., about 150 mg, of ranitidine). In an embodiment, the therapeutic agent or modality comprises (a). In an embodiment, the therapeutic agent or modality comprises (b). In an embodiment, the therapeutic agent or modality comprises (c). In an embodiment, the therapeutic agent or modality comprises (d). In an embodiment, the therapeutic agent or modality comprises (e). In an embodiment, the therapeutic agent or modality comprises (a) and (b), (a) and (c), (a) and (d), (a) and (e), (b) and (c), (b) and (d), (b) and (e), (c) and (d), (c) and (e), or (d) and (e). In an embodiment, the therapeutic agent or modality comprises one, two, or all of (a), (b), or (c).

In an embodiment, the subject is infected with, or is at risk of being infected with, an influenza virus A, an influenza virus B, an influenza virus C, an influenza virus D, or combination thereof. In an embodiment, the subject is infected with, or is at risk of being infected with, an influenza virus A. In an embodiment, the subject is infected with, or is at risk of being infected with, a Group 1 influenza virus (e.g., an H1, H2, H5, H6, H8, H9, H11, H12, H13, or H16 influenza virus, or a combination thereof). In an embodiment, the subject is infected with, or is at risk of being infected with, a Group 2 influenza virus (e.g., an H3, H4, H7, H10, H14, or H15 influenza virus, or a combination thereof). In an embodiment, the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof. In an embodiment, the subject is infected with, or is at risk of being infected with, an H1N1 or H3N2 influenza virus, or a combination thereof. In an embodiment, the subject is infected with, or is at risk of being infected with, an H1N1 or H7N9 influenza virus, or a combination thereof. In an embodiment, the influenza virus has a mutation (e.g., a substitution) at position 38 of the polymerase acidic protein (PA), e.g., an I38T or I38F substitution.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, a secondary bacterial infection.

In an embodiment, the antibody molecule comprises:

```
(a) a heavy chain immunoglobulin variable region
segment comprising:
                                         (SEQ ID NO: 68)
a CDR1 comprising the sequence
S-Y-A-M-H;

(SEQ ID NO: 69)
a CDR2 comprising the sequence
V-V-S-Y-D-G-N-Y-K-Y-Y-A-D-S-V-Q-G;
and (SEQ ID NO: 70)
a CDR3 comprising the sequence
D-S-R-L-R-S-L-L-Y-F-E-W-L-S-Q-G-Y-F-N-P;
and (b) a light chain immunoglobulin variable region
segment comprising:
                                        (SEQ ID NO: 145)
a CDR1 comprising the sequence
Q-S-I-T-F-D-Y-K-N-Y-L-A;

(SEQ ID NO: 72)
a CDR2 comprising the sequence
W-G-S-Y-L-E-S;
and
```

```
                                         (SEQ ID NO: 73)
a CDR3 comprising the sequence
Q-Q-H-Y-R-T-P-P-S.
```

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')$_2$ fragment, a Fab fragment, or an Fd fragment.

In an aspect, the disclosure features a method of evaluating a therapy, the method comprising: acquiring acknowledge that the level of one or more cytokines is elevated in a subject after administration of an anti-HA antibody molecule described herein, e.g., VIS410; and selecting the anti-HA antibody molecule as not suitable for treating or preventing an influenza infection, or a symptom thereof, in the subject.

In an embodiment, the method further comprises determining that the level of one or more cytokines is increased. In an embodiment, the level of one or more cytokines is determined periodically, e.g., every week, every two weeks, every three weeks, every four weeks, every six weeks, or every eight weeks.

In an embodiment, the level of one or more cytokines is increased by at least 10%, 20%, 30%, 40%, 50%, 60%, 70%, 80%, 90%, or 100%, or at least 2, 3, 4, 5, 6, 7, 8, 9, or 10-fold, compared to the level prior to administration of the anti-HA antibody molecule. In an embodiment, the level of one or more cytokines is increased within about 24 hours (e.g., within about 1, 2, 3, 4, 5, 6, 7, 8, 9, 10, 11, 12, 13, 14, 16, 17, 18, 19, 20, 21, 22, or 23 hours) after administration of the anti-HA antibody molecule. In an embodiment, the level of one or more cytokines is increased within about 1 hour after administration of the anti-HA antibody molecule.

In an embodiment, the level of one or more cytokines is further decreased within about 36 hours (e.g., within about 12, 13, 14, 15, 16, 17, 18, 19, 20, 21, 22, 23, 24, 25, 26, 27, 28, 29, 30, 31, 32, 33, 34, or 35 hours), e.g., returned to about the same level (e.g., within about ±25%, ±20%, ±15%, ±10%, or ±5%) prior to administration of the anti-HA molecules.

In an embodiment, the one or more cytokines comprise one, two, three, four, five, or all of IL-6, IL-8, IL-10, IFN-γ, TNF-α, or IL-33. In an embodiment, the one or more cytokines comprise one, two, three, or all of IL-8, IFN-γ, IL-6, or TNF-α. In an embodiment, the one or more cytokines comprises one, two, or all of IL-8, IFN-γ, or IL-6. In an embodiment, the one or more cytokines comprise one, two, or all of IL-8, IFN-γ, or TNF-α. In an embodiment, the one or more cytokines comprise IL-8. In an embodiment, the one or more cytokines further comprise IFN-γ, TNF-α, or both. In an embodiment, the one or more cytokines comprise TNF-α. In an embodiment, the one or more cytokines comprise IL-6. In an embodiment, the one or more cytokines comprise one, two, three, four, or all of IL-6, IL-8, IL-10, IFN-γ, or TNF-α. In an embodiment, the one or more cytokines comprise IL-8, IFN-γ, or TNF-α, and optionally IL-6. In an embodiment, the one or more cytokines do not comprise IL-10.

In an embodiment, the subject is infected with, or is at risk of being infected with, an influenza virus A, an influenza virus B, an influenza virus C, an influenza virus D, or combination thereof. In an embodiment, the subject is infected with, or is at risk of being infected with, an influenza virus A. In an embodiment, the subject is infected with, or is at risk of being infected with, a Group 1 influenza virus (e.g., an H1, H2, H5, H6, H8, H9, H11, H12, H13, or H16 influenza virus, or a combination thereof). In an embodiment, the subject is infected with, or is at risk of being infected with, a Group 2 influenza virus (e.g., an H3, H4, H7, H10, H14, or H15 influenza virus, or a combination thereof). In an embodiment, the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof. In an embodiment, the subject is infected with, or is at risk of being infected with, an H1N1 or H3N2 influenza virus, or a combination thereof. In an embodiment, the subject is infected with, or is at risk of being infected with, an H1N1 or H7N9 influenza virus, or a combination thereof. In an embodiment, the influenza virus has a mutation (e.g., a substitution) at position 38 of the polymerase acidic protein (PA), e.g., an I38T or I38F substitution.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, a secondary bacterial infection.

In an embodiment, the antibody molecule comprises:

(a) a heavy chain immunoglobulin variable region
segment comprising:
                                          (SEQ ID NO: 68)
a CDR1 comprising the sequence
S-Y-A-M-H;

(SEQ ID NO: 69)
a CDR2 comprising the sequence
V-V-S-Y-D-G-N-Y-K-Y-Y-A-D-S-V-Q-G;
and (SEQ ID NO: 70)
a CDR3 comprising the sequence
D-S-R-L-R-S-L-L-Y-F-E-W-L-S-Q-G-Y-F-N-P;
and (b) a light chain immunoglobulin variable region
segment comprising:
                                         (SEQ ID NO: 145)
a CDR1 comprising the sequence
Q-S-I-T-F-D-Y-K-N-Y-L-A;

(SEQ ID NO: 72)
a CDR2 comprising the sequence
W-G-S-Y-L-E-S;
and

-continued
                                          (SEQ ID NO: 73)
a CDR3 comprising the sequence
Q-Q-H-Y-R-T-P-P-S.

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')₂ fragment, a Fab fragment, or an Fd fragment.

In an aspect, the disclosure features a method of treating or preventing an influenza virus infection, or a symptom thereof, in a subject, comprising administering to the subject an anti-HA antibody molecule described herein, e.g., VIS410, wherein the subject has one or more (e.g., 2, 3, 4, 5, 6, 7, 8, 9, 10, 11, 12, 13, 14, or all) of the following characteristics:

(a) is at least about 60 years old, e.g., at least about 65, 70, 75, or 80 years old;

(b) has received, or has not received, a second antiviral therapy (e.g., oseltamivir), e.g., within about 1, 2, or 3 days prior to administration of the anti-HA antibody molecule;

(c) has an onset of influenza, at least about 24, 36, 48, 60, 72, or 96 hours (e.g., at least about 60, 61, 62, 63, 64, 65, 66, 67, 68, 69, 70, 71, 72, 73, 74, 75, 76, 77, 78, 79, or 80 hours), or within about 24, 36, 48, 60, 72, 96, or 120 hours, prior to administration of the anti-HA antibody molecule;

(d) has received, or has not received, an influenza vaccine, e.g., within about 1, 2, 3, 4, 5, or 6 months, prior to administration of the anti-HA antibody molecule;

(e) is identified as being infected with an influenza A virus, e.g., within about 12, 24, 36, or 48 hours, prior to administration of the anti-HA antibody molecule;

(f) is infected with, is at risk of being infected with, an H1 influenza virus (e.g., an H1N1 virus), an H3 influenza virus (e.g., an H3N2 virus), or an H7 influenza virus (e.g., an H7N9 virus);

(g) receives, or is more likely to receive, an oxygen therapy, positive pressure ventilation, or a therapy to treat or prevent bacterial pneumonia;

(h) is, or is more likely to be, intubated, or receives, or is more likely to receive mechanical ventilation;

(i) has an ordinal scale score above about 2.0 (e.g., above about 2.0, 2.1, 2.2, 2.25, 2.3, 2.4, or 2.5), e.g., based on one, two, three, four, or five of the ordinal scale described herein;

(j) requires greater intensity of care (e.g., ICU care);

(k) has a clinical response (e.g., as determined by one, two, three, four, or five vital signs described herein, e.g., meeting a specified threshold described herein), within about 24, 36, 48, 60, 72, 84, 96, 108, or 120 hours, after administration of the anti-HA antibody molecule;

(l) has a symptom score (e.g., determined by FluPRO) that is decreased by at least about 10%, 20%, 30%, 40%, 50%, 60%, 70%, 80%, 90%, or more), within 1, 2, 3, 4, 5, 6, 7, 8, 9, 10, 11, 12, 13, or 14 days, after administration of the anti-HA antibody molecule;

(m) has a symptom score (e.g., determined by visual analog score (VAS)) that is increased by at least about 2, 3, 4, 5, 6, 7, 8, 9, or 10-fold), within 1, 2, 3, 4, 5, 6, 7, 8, 9, 10, 11, 12, 13, or 14 days, after administration of the anti-HA antibody molecule;

(n) is negative for viral titer (e.g., determined by TCID50), within 1, 2, 3, 4, 5, 6, 7, 8, 9, 10, 11, 12, 13, or 14 days, after administration of the anti-HA antibody molecule; or (o) does not develop, or develops no more than 1, treatment emergent adverse event (TEAE) described herein (e.g., a serious TEAE described herein).

In an embodiment, the method further comprises knowledge that the subject has one or more (e.g., 2, 3, 4, 5, 6, 7, 8, 9, 10, 11, 12, 13, 14, or all) of the characteristics (a)-(o).

In an embodiment, the method further comprises determining that the subject has one or more (e.g., 2, 3, 4, 5, 6, 7, 8, 9, 10, 11, 12, 13, 14, or all) of the characteristics (a)-(o).

In an embodiment, the anti-HA antibody molecule is administered, responsive to a determination that the subject has one or more (e.g., 2, 3, 4, 5, 6, 7, 8, 9, 10, 11, 12, 13, 14, or all) of the characteristics (a)-(o).

In an embodiment, the subject is infected with, or is at risk of being infected with, an influenza virus A, an influenza virus B, an influenza virus C, an influenza virus D, or combination thereof. In an embodiment, the subject is infected with, or is at risk of being infected with, an influenza virus A. In an embodiment, the subject is infected with, or is at risk of being infected with, a Group 1 influenza virus (e.g., an H1, H2, H5, H6, H8, H9, H11, H12, H13, or H16 influenza virus, or a combination thereof). In an embodiment, the subject is infected with, or is at risk of being infected with, a Group 2 influenza virus (e.g., an H3, H4, H7, H10, H14, or H15 influenza virus, or a combination thereof). In an embodiment, the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof. In an embodiment, the subject is infected with, or is at risk of being infected with, an H1N1 or H3N2 influenza virus, or a combination thereof. In an embodiment, the subject is infected with, or is at risk of being infected with, an H1N1 or H7N9 influenza virus, or a combination thereof. In an embodiment, the influenza virus has a mutation (e.g., a substitution) at position 38 of the polymerase acidic protein (PA), e.g., an I38T or I38F substitution.

In an embodiment, the subject is infected with, or is at risk of being infected with, an influenza virus that is resistant to one, two, three, four, or all of oseltamivir, peramivir, zanamivir, baloxavir marboxil, or pimodivir. In an embodiment, the subject is infected with, or is at risk of being infected with, a secondary bacterial infection.

In an embodiment, the antibody molecule comprises:

```
(a) a heavy chain immunoglobulin variable region
segment comprising:
                                    (SEQ ID NO: 68)
a CDR1 comprising the sequence
S-Y-A-M-H;
```

-continued

```
                                    (SEQ ID NO: 69)
a CDR2 comprising the sequence
V-V-S-Y-D-G-N-Y-K-Y-Y-A-D-S-V-Q-G;
and
                                    (SEQ ID NO: 70)
a CDR3 comprising the sequence
D-S-R-L-R-S-L-L-Y-F-E-W-L-S-Q-G-Y-F-N-P;
and (b) a light chain immunoglobulin variable region
segment comprising:
                                   (SEQ ID NO: 145)
a CDR1 comprising the sequence
Q-S-I-T-F-D-Y-K-N-Y-L-A;
                                    (SEQ ID NO: 72)
a CDR2 comprising the sequence
W-G-S-Y-L-E-S;
and
                                    (SEQ ID NO: 73)
a CDR3 comprising the sequence
Q-Q-H-Y-R-T-P-P-S.
```

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full-length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a $F(ab')_2$ fragment, a Fab fragment, or an Fd fragment.

In an aspect, the disclosure features a combination comprising an anti-HA antibody molecule described herein, e.g., VIS410, and one or more (e.g., two, three, or four) anti-viral agents, for use in treating or preventing an influenza virus infection, or a symptom hereof, in a subject, e.g., in accordance with a method described herein.

In an aspect, the disclosure features an anti-HA antibody molecule described herein, e.g., VIS410, for use in treating or preventing an influenza virus infection, or a symptom hereof (e.g., in a method for treating or preventing an influenza virus infection, or a symptom hereof), in a subject, wherein the subject is infected with, or is at risk of being infected with, an influenza virus that is resistant to an antiviral agent described herein, e.g., in accordance with a method described herein.

In an aspect, the disclosure features an anti-HA antibody molecule described herein, e.g., VIS410, for use in treating or preventing an influenza virus infection, or a symptom hereof, in a subject, wherein the anti-HA antibody molecule is administered (e.g., the administration is continued, or the dosage is maintained), responsive to a change in the level of one or more (e.g., 2, 3, 4, 5, 6, or more) cytokines in the subject, e.g., in accordance with a method described herein.

In an aspect, the disclosure features an anti-HA antibody molecule described herein, e.g., VIS410, for use in treating or preventing an influenza virus infection, or a symptom hereof, in a subject, wherein administration of the anti-HA antibody molecule is modified, responsive to a change in the level of one or more (e.g., 2, 3, 4, 5, 6, or more) cytokines in the subject, e.g., in accordance with a method described herein.

In an aspect, the disclosure features an anti-HA antibody molecule described herein, e.g., VIS410, for use in treating or preventing an influenza virus infection, or a symptom hereof, in a subject, wherein the subject has one or more (e.g., 2, 3, 4, 5, 6, 7, 8, 9, 10, 11, 12, 13, 14, or all) of the following characteristics:

(a) is at least about 60 years old, e.g., at least about 65, 70, 75, or 80 years old;

(b) has received, or has not received, a second antiviral therapy (e.g., oseltamivir), e.g., within about 1, 2, or 3 days prior to administration of the anti-HA antibody molecule;

(c) has an onset of influenza, at least about 24, 36, 48, 60, 72, or 96 hours (e.g., at least about 60, 61, 62, 63, 64, 65, 66, 67, 68, 69, 70, 71, 72, 73, 74, 75, 76, 77, 78, 79, or 80 hours), or within about 24, 36, 48, 60, 72, 96, or 120 hours, prior to administration of the anti-HA antibody molecule;

(d) has received, or has not received, an influenza vaccine, e.g., within about 1, 2, 3, 4, 5, or 6 months, prior to administration of the anti-HA antibody molecule;

(e) is identified as being infected with an influenza A virus, e.g., within about 12, 24, 36, or 48 hours, prior to administration of the anti-HA antibody molecule;

(f) is infected with, is at risk of being infected with, an H1 influenza virus (e.g., an H1N1 virus), an H3 influenza virus (e.g., an H3N2 virus), or an H7 influenza virus (e.g., an H7N9 virus);

(g) receives, or is more likely to receive, an oxygen therapy, positive pressure ventilation, or a therapy to treat or prevent bacterial pneumonia;

(h) is, or is more likely to be, intubated, or receives, or is more likely to receive mechanical ventilation;

(i) has an ordinal scale score above about 2.0 (e.g., above about 2.0, 2.1, 2.2, 2.25, 2.3, 2.4, or 2.5) (e.g., based on one, two, three, four, or five of the ordinal scale described herein, e.g., based on one or more (e.g., all) parameters chosen from death, ICU stay with mechanical ventilation, ICU stay without mechanical ventilation, non-ICU hospitalization, or discharge);

(j) requires greater intensity of care (e.g., ICU care);

(k) has a clinical response (e.g., as determined by one, two, three, four, or five vital signs described herein, e.g., meeting a specified threshold described herein), within about 24, 36, 48, 60, 72, 84, 96, 108, or 120 hours, after administration of the anti-HA antibody molecule;

(l) has a symptom score (e.g., determined by FluPRO) that is decreased by at least about 10%, 20%, 30%, 40%, 50%, 60%, 70%, 80%, 90%, or more), within 1, 2, 3, 4, 5, 6, 7, 8, 9, 10, 11, 12, 13, or 14 days, after administration of the anti-HA antibody molecule;

(m) has a symptom score (e.g., determined by visual analog score (VAS)) that is increased by at least about 2, 3, 4, 5, 6, 7, 8, 9, or 10-fold), within 1, 2, 3, 4, 5, 6, 7, 8, 9, 10, 11, 12, 13, or 14 days, after administration of the anti-HA antibody molecule;

(n) is negative for viral titer (e.g., determined by TCID50), within 1, 2, 3, 4, 5, 6, 7, 8, 9, 10, 11, 12, 13, or 14 days, after administration of the anti-HA antibody molecule; or (o) does not develop, or develops no more than 1, treatment emergent adverse event (TEAE) described herein (e.g., a serious TEAE described herein).

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments featured in the disclosure are set forth in the accompanying drawings and the description below. Other features, objects, and advantages featured in the disclosure will be apparent from the description and drawings, and from the claims.

intravenous diphenhydramine+montelukast, or oral diphenhydramine+oral ibuprofen) over time, including at the 1 hour post-VIS410 infusion time point, in patients from Parts 2 and 3.

Figure 15:
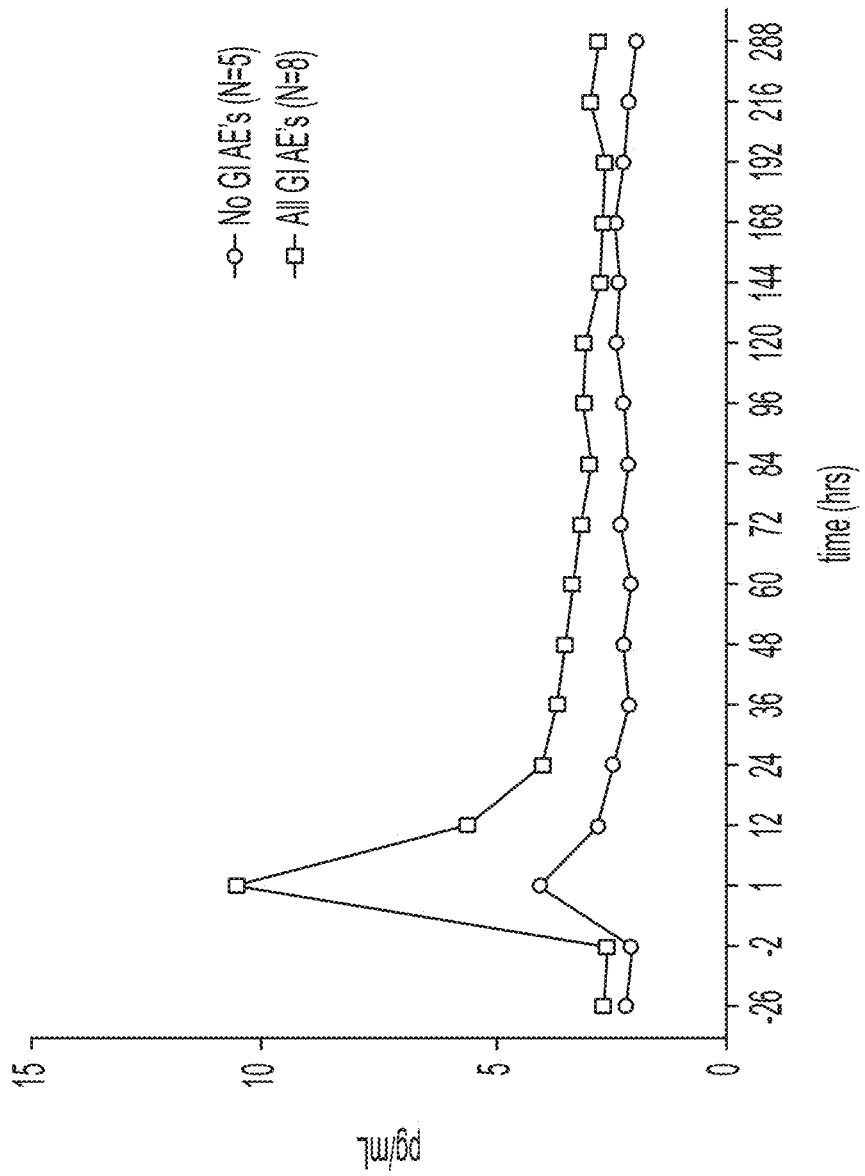

FIG. 15 is a graph showing mean serum TNF-α levels in VIS410-treated patients that either experienced a gastrointestinal adverse event (GI AE) or did not. The patient population shown here included only MITT patients.

Figure 16:
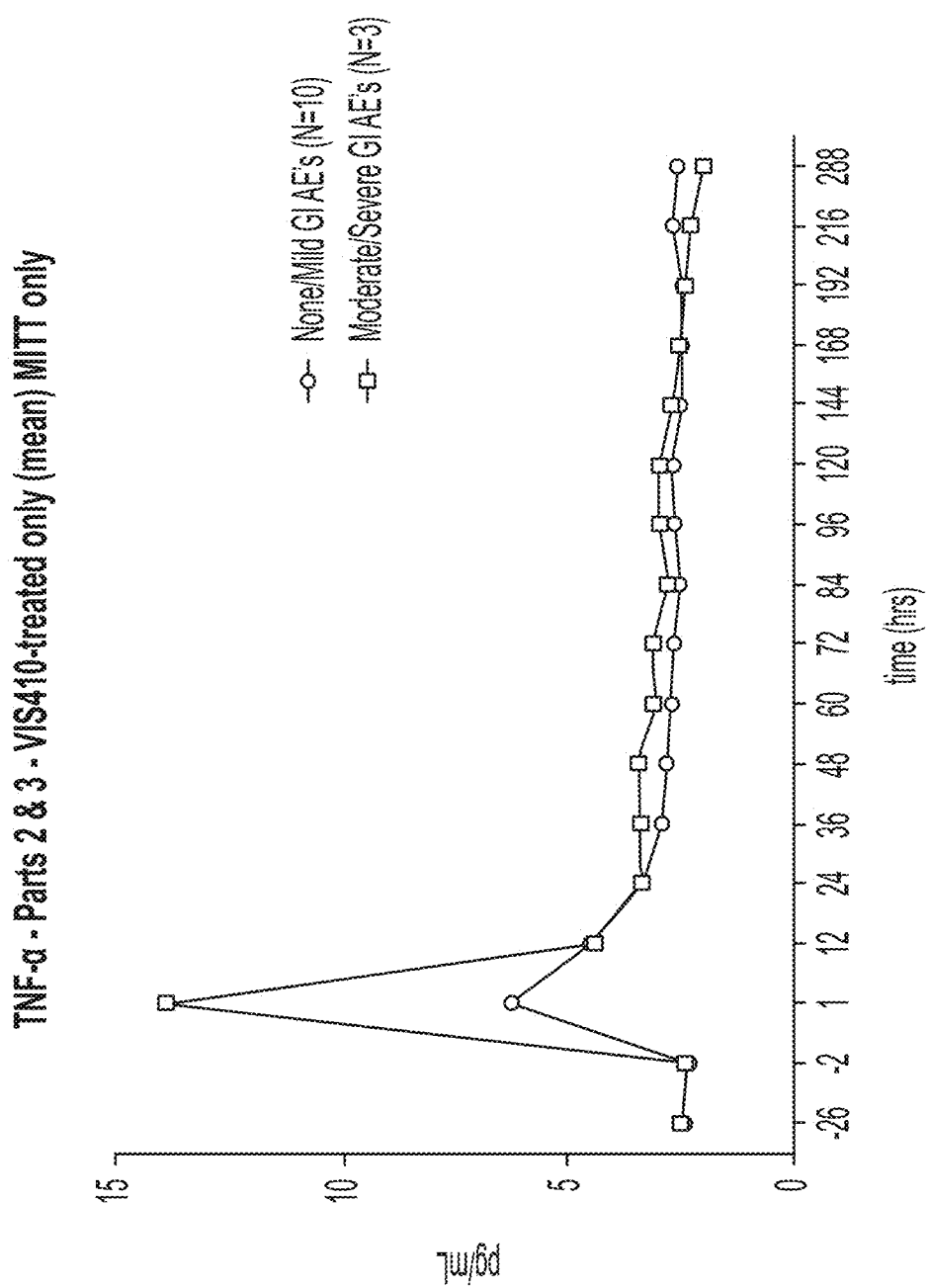

FIG. 16 is a graph showing mean serum TNF-α levels in VIS410-treated patients that either experienced a moderate or severe gastrointestinal adverse event (GI AE), or experienced either a mild GI AE or no GI AE at all. The patient population shown here included only MITT patients.

Figure 17:
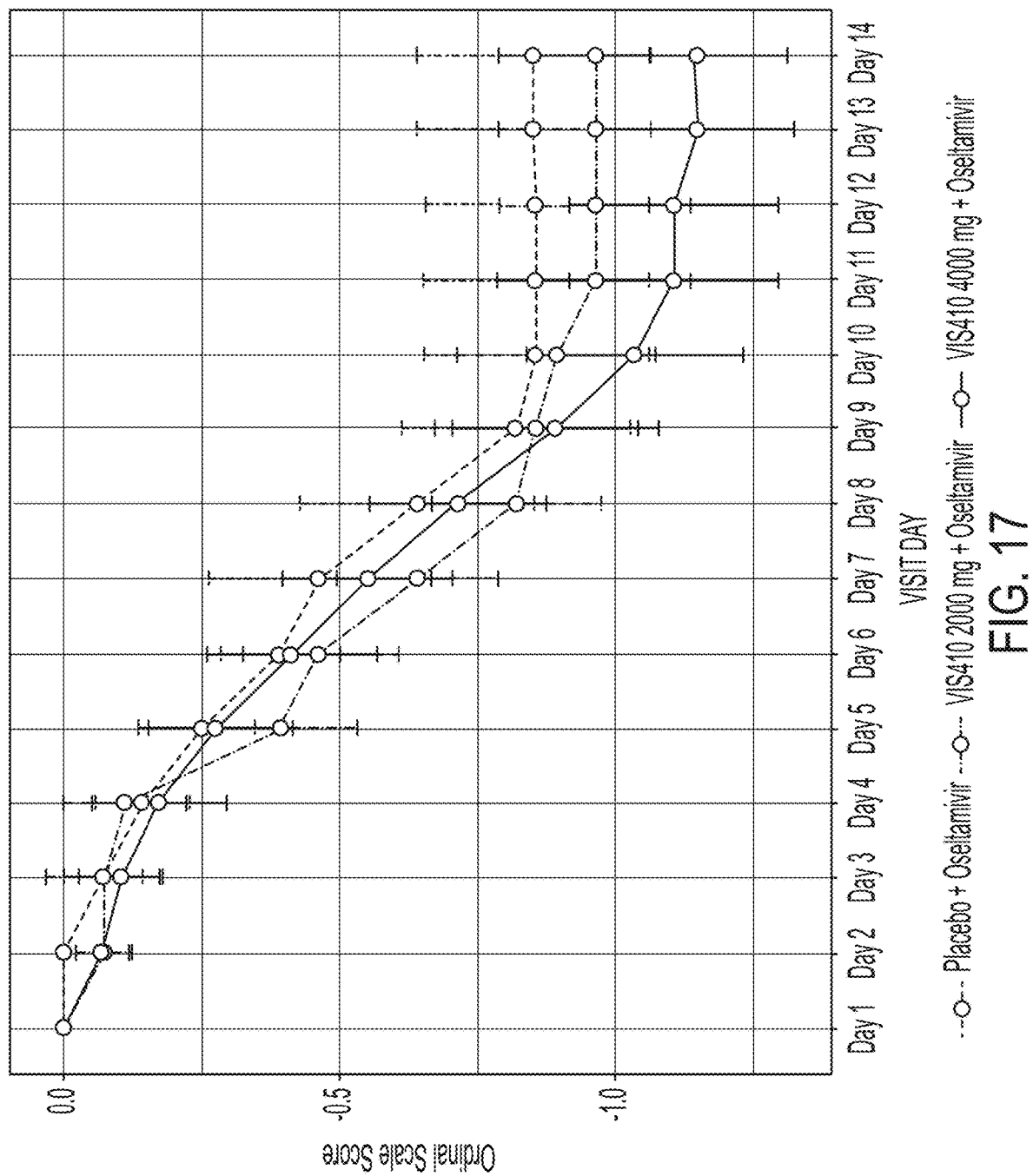

FIG. 17 is a graph showing change in disease severity relative to baseline over time in influenza patients according to a 5-level ordinal scale. Patients received oseltamivir and one of 2000 mg VIS410, 4000 mg VIS410, or a placebo.

Figure 18:
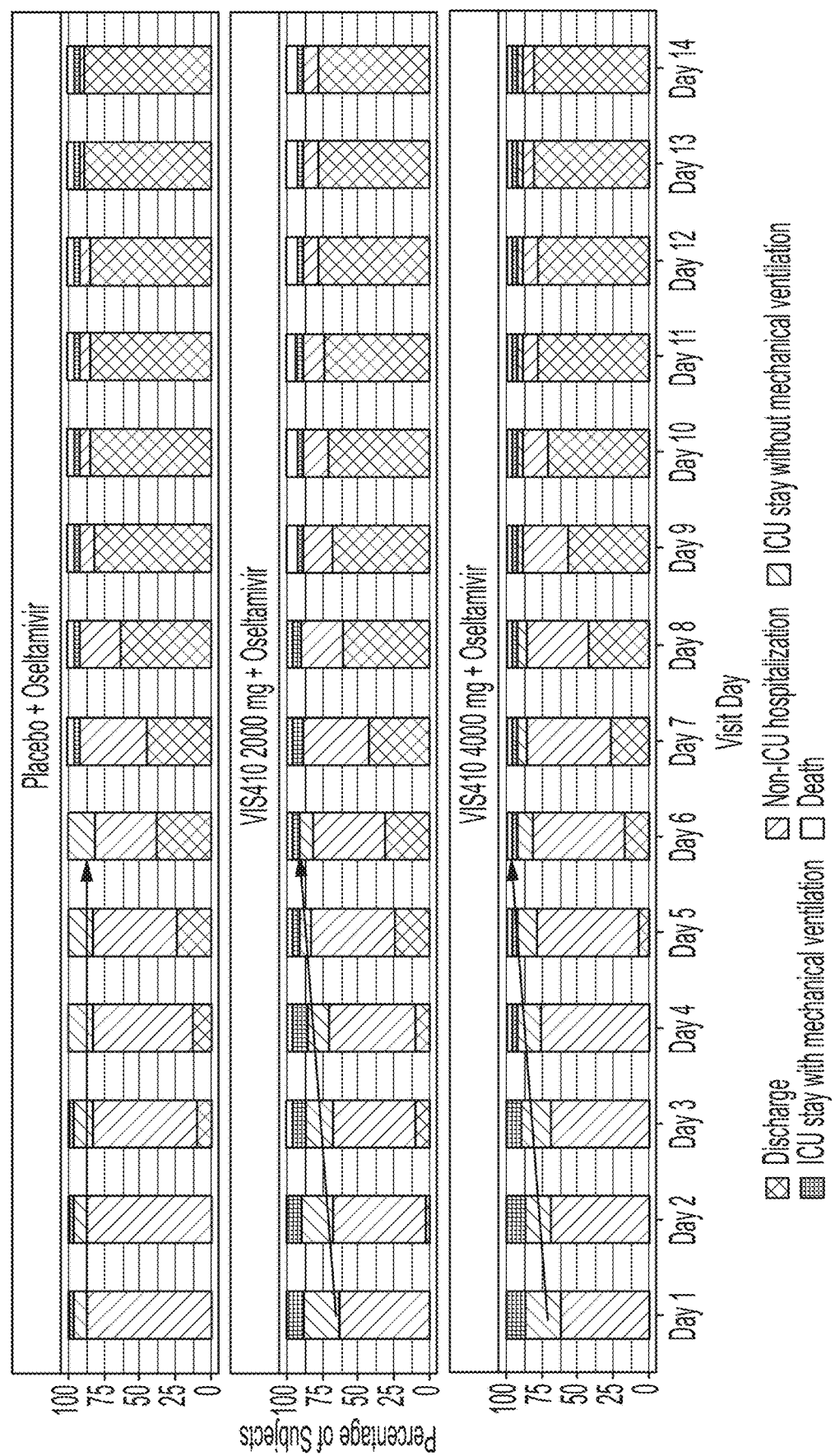

FIG. 18 is a series of graphs showing daily categorization of patients according to disease severity, ranging from death, requiring ICU stay (with or without mechanical ventilation), non-ICU-hospitalization, to discharge, grouped by treatment arm (placebo, VIS410 2000 mg, VIS410 4000 mg).

Figure 19A:
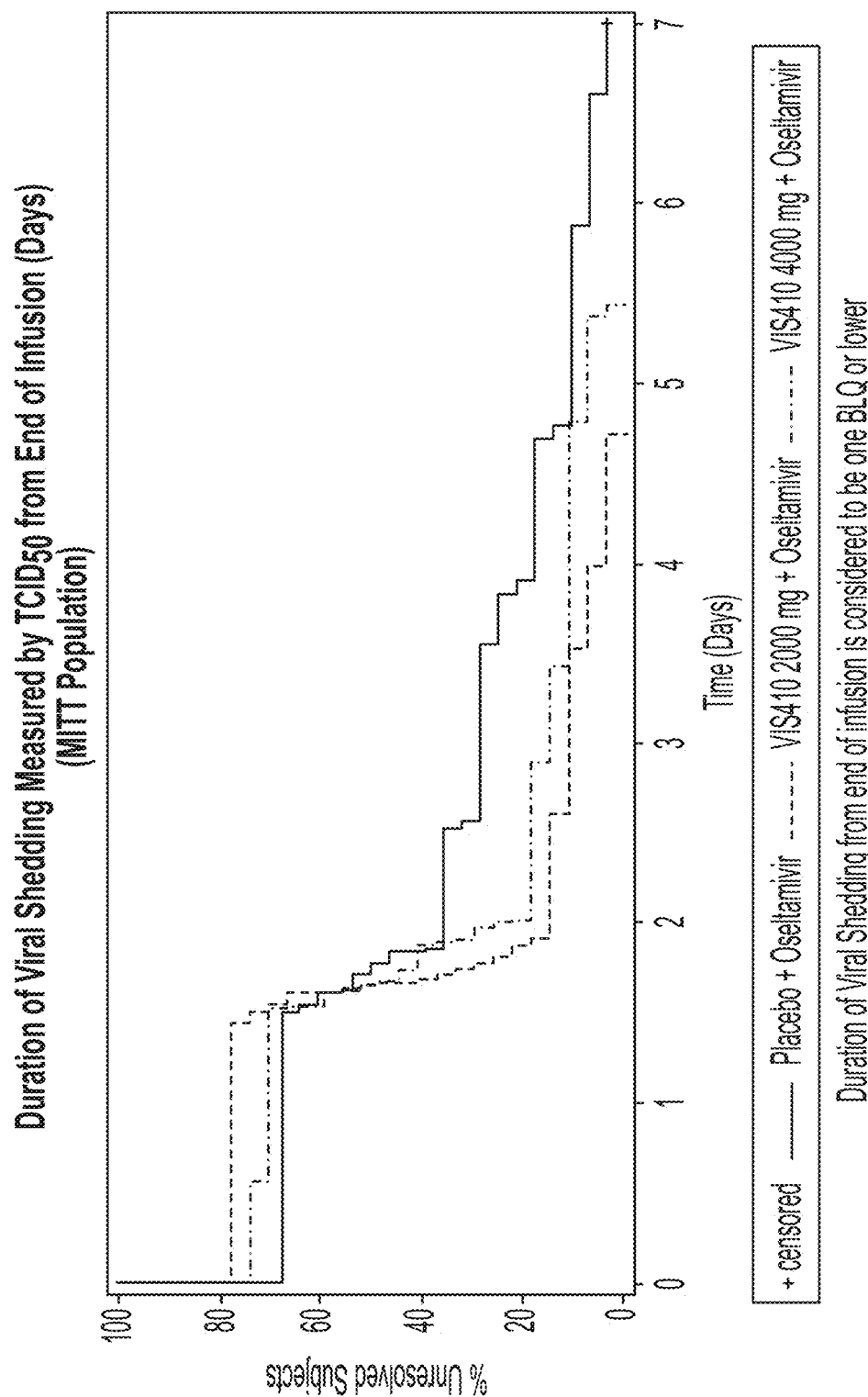

FIG. 19A is a graph showing duration of nasopharyngeal influenza virus shedding in patients over time from the end of infusion, as measured by viral culture TCID50 from the end of infusion. This figure includes patients with positive or negative cultures at baseline.

Figure 19B:
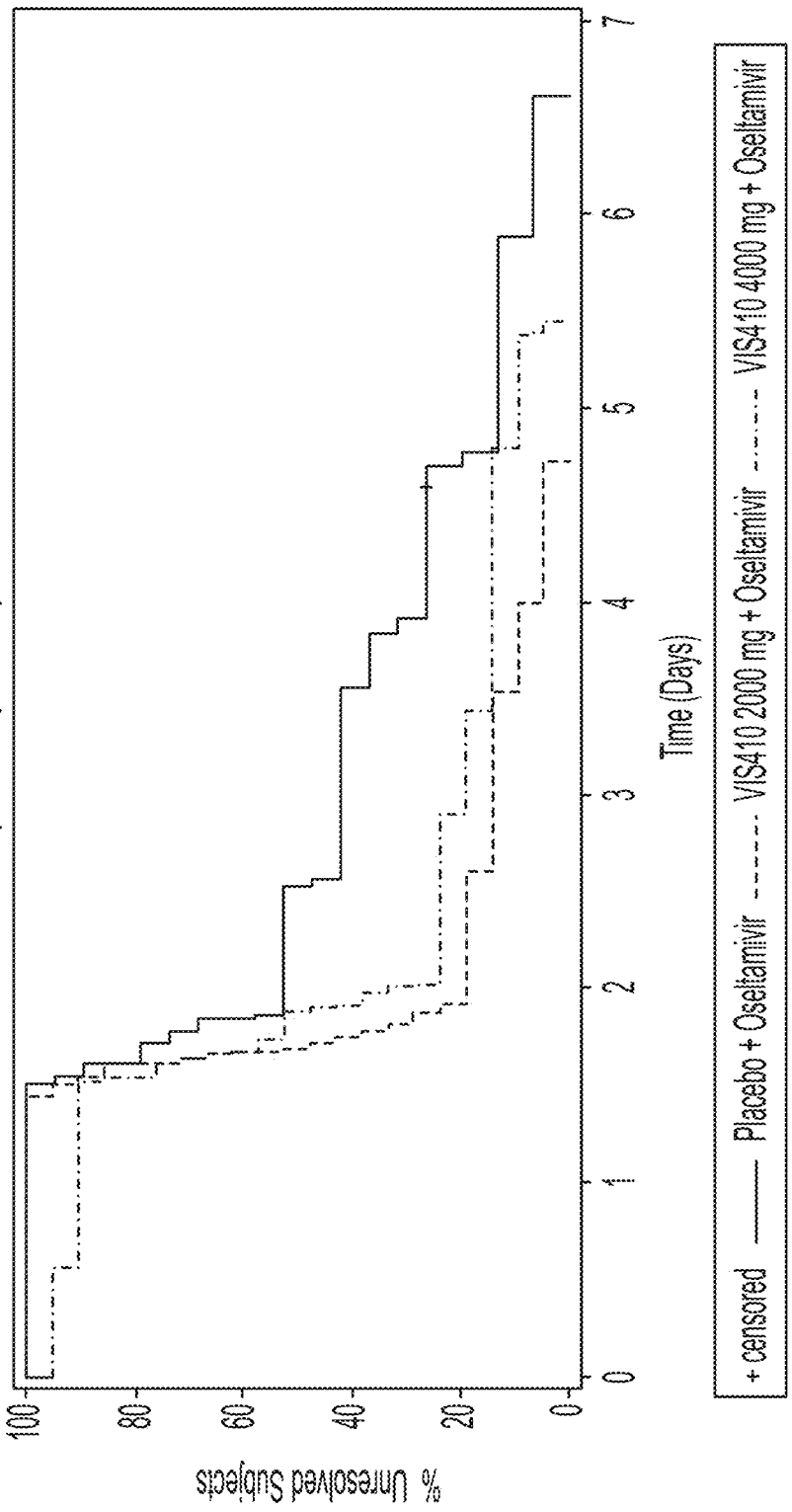

FIG. 19B is a graph showing duration of nasopharyngeal influenza virus shedding in patients over time from the end-of-infusion, as measured by viral culture TCID50. This figure is limited to those patients with a positive baseline viral culture.

Figure 20A:
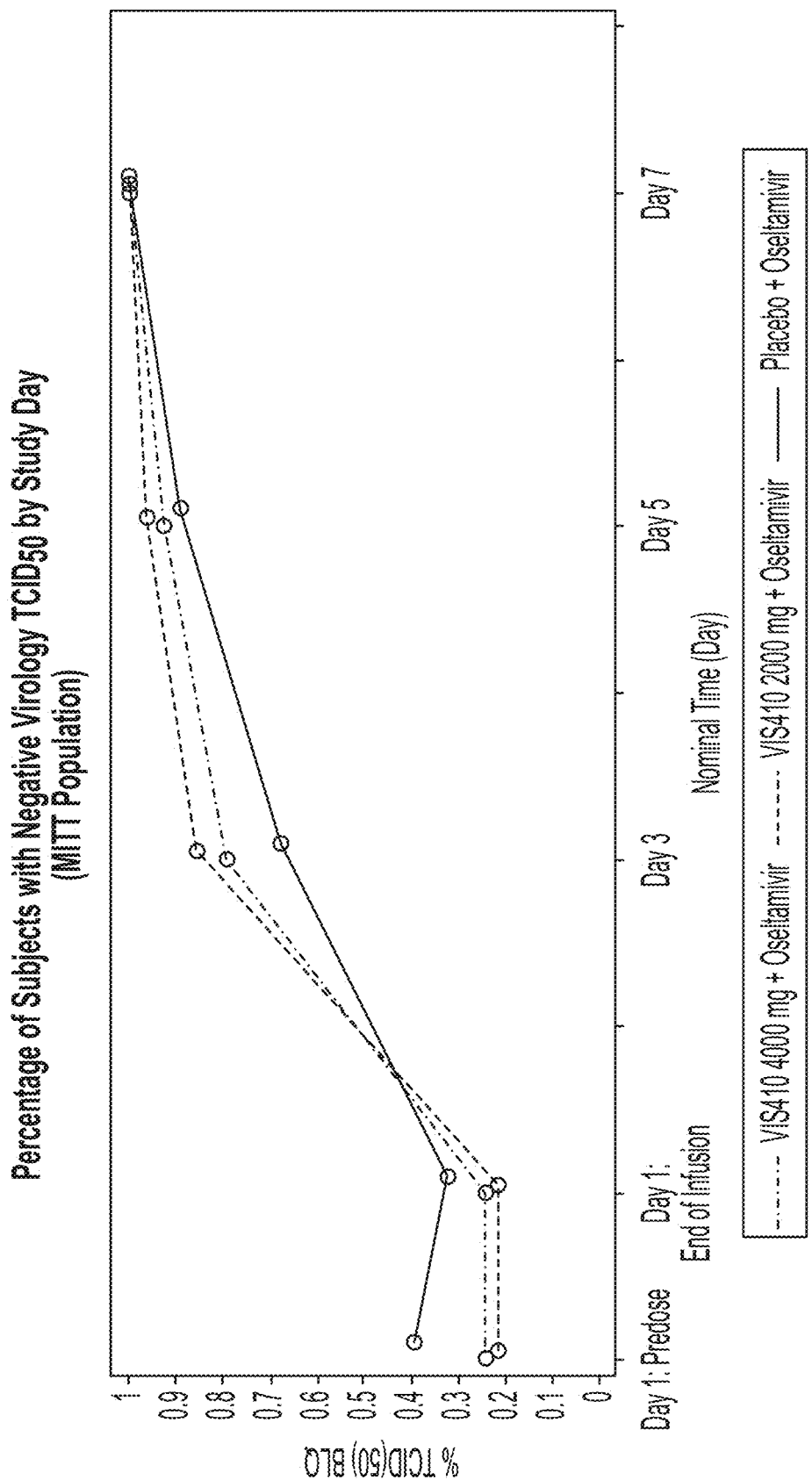
Figure 20B:
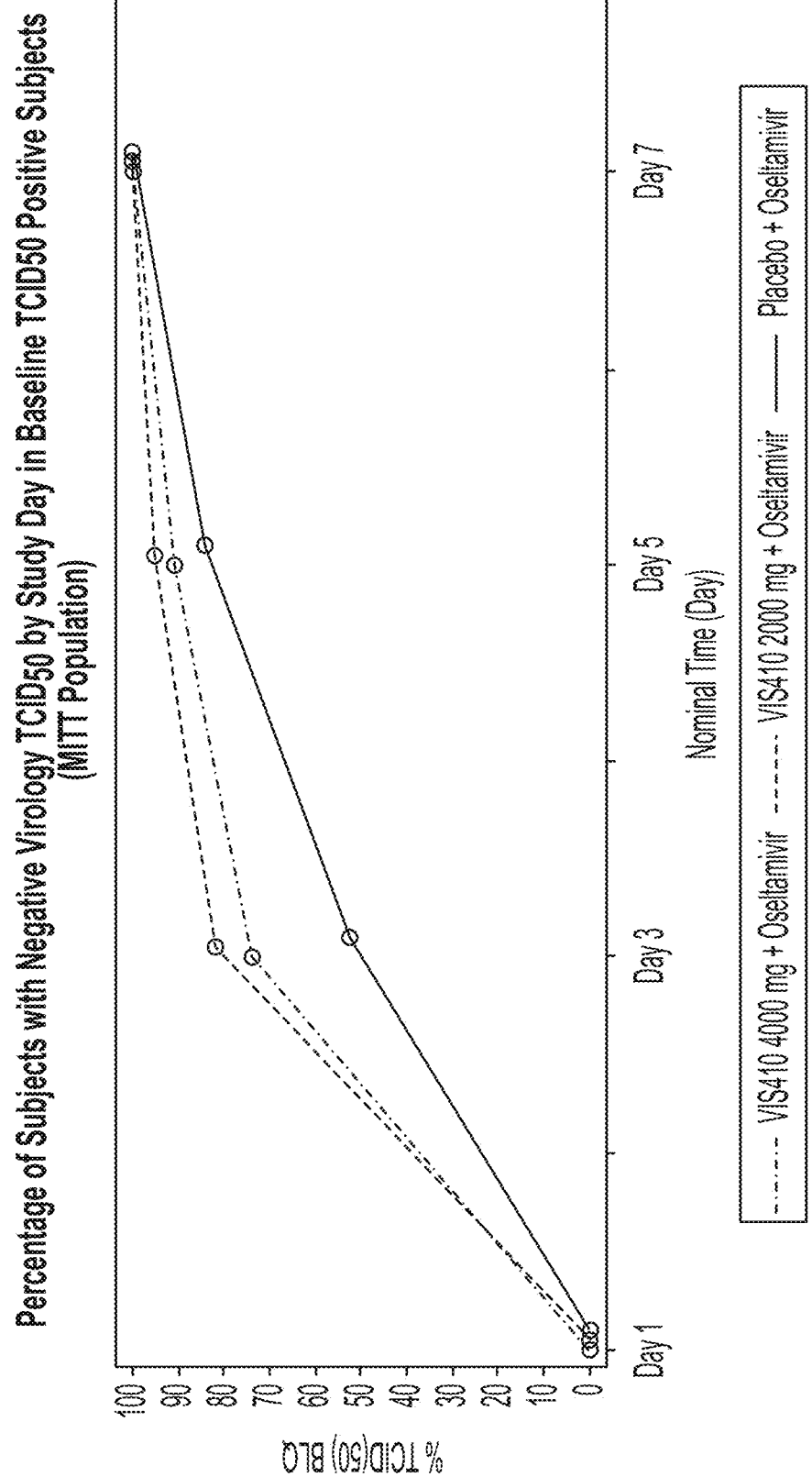

FIGS. 20A-20B are graphs showing percentage of patients exhibiting negative nasopharyngeal influenza virus cultures by study day and by treatment arm. In FIG. 20A, data are plotted for the MITT population (including individuals with positive or negative viral cultures at baseline). In FIG. 20B, data are plotted for the subset of patients in the MITT who had a positive nasopharyngeal influenza virus culture at baseline.

Figure 21A:
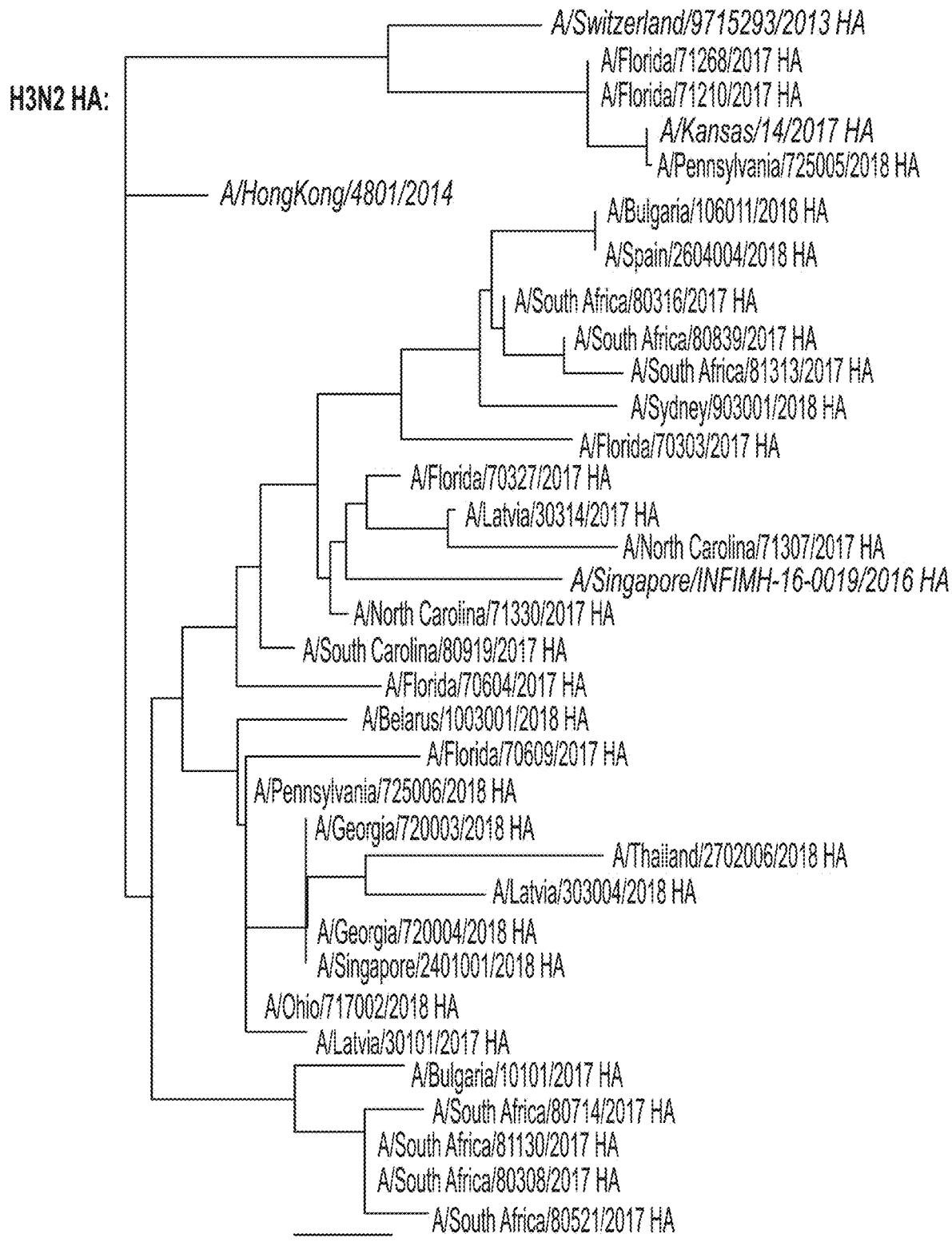
Figure 21B:
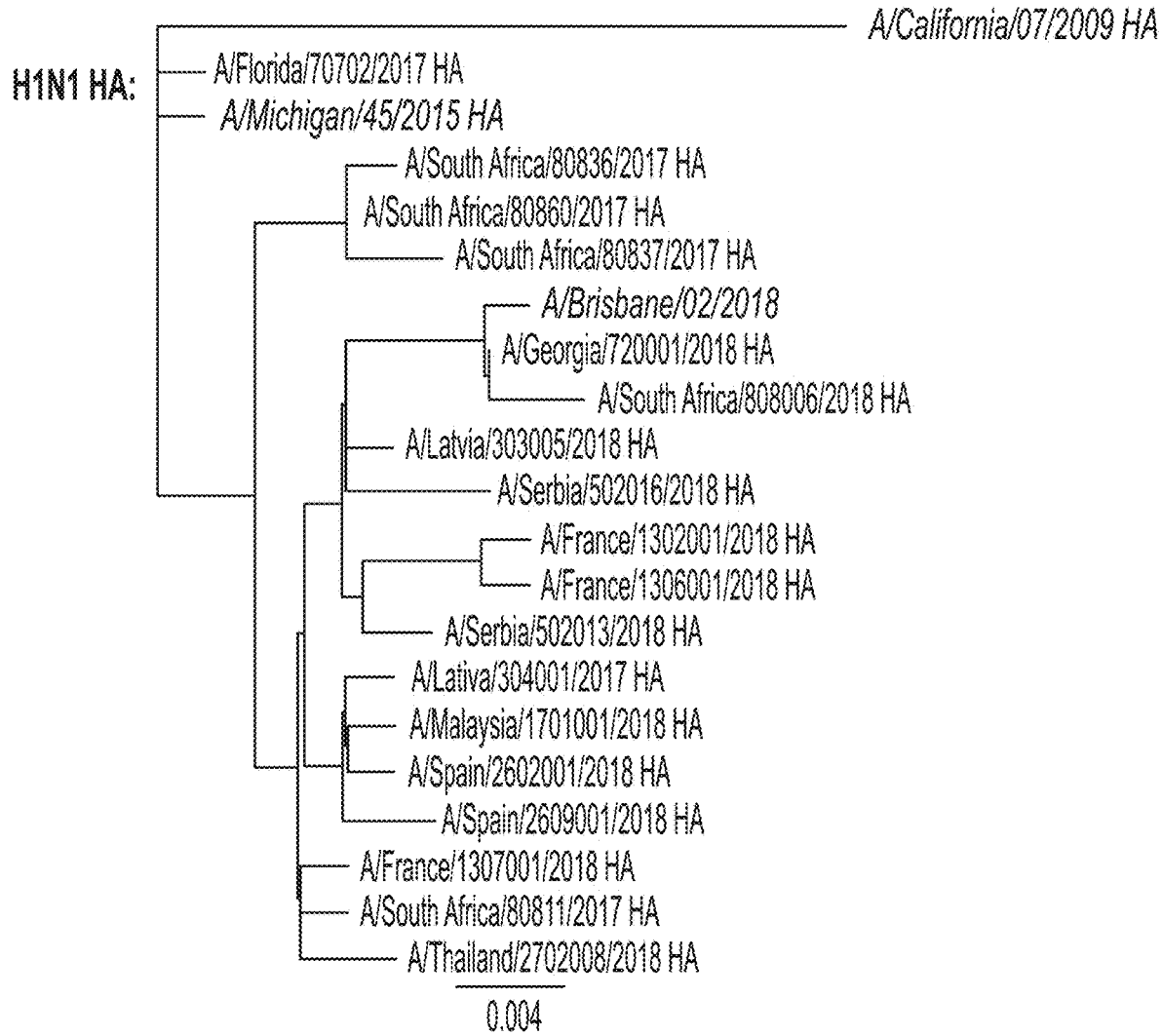

FIGS. 21A-21B are phylogenetic trees showing H3N2 (A) and H1N1 (B) strains with diverse HA genotypes tested for VIS410 $IC_{50}$ by NP-ELISA.

Figure 22:
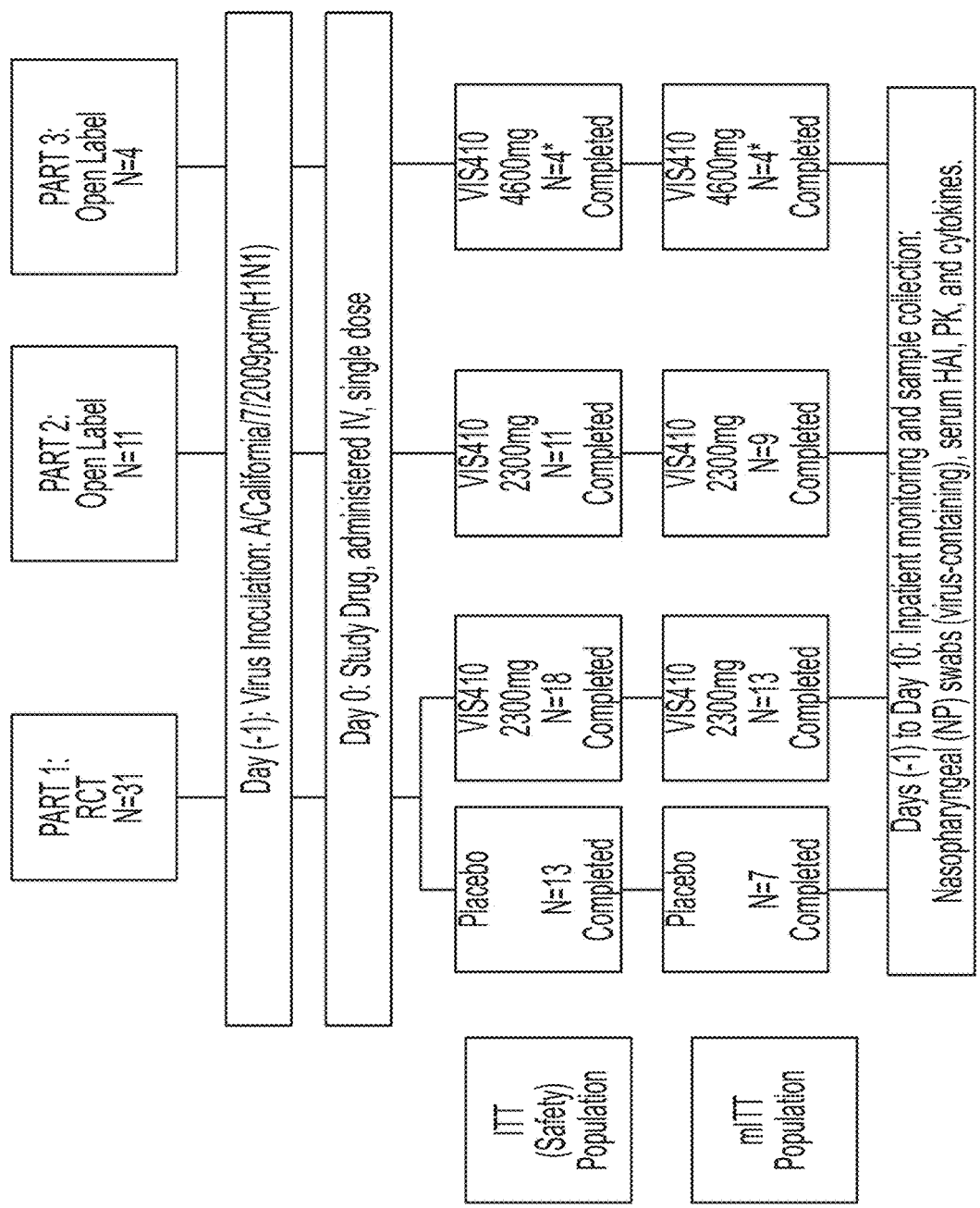

FIG. 22 is a diagram showing the study design for a VIS410 virus challenge study, which enrolled 46 subjects and consisted of three parts. Part 1 was the randomized, placebo-controlled portion of the study, and Parts 2 and 3 were open label to evaluate pretreatment regimens and VIS410 dose escalation. All subjects completed the study except one subject in Part 3(*) who terminated early but was still included in safety and efficacy analyses.

FIGS. 23A-23F are a series of graphs showing the virological results from the VIS410 virus challenge study, Part 1. Mean viral shedding over time in subjects treated with VIS410 (2300 mg, dotted lines and squares) or placebo (solid lines and circles), mITT population, as determined by (A) qRT-PCR or (B) virus culture. Median viral shedding over time in subjects treated with VIS410 (2300 mg, dotted lines and squares) or placebo (solid lines and circles), mITT population, as determined by (C) qRT-PCR or (D) virus culture. Mean viral shedding over time in subjects treated with VIS410 (2300 mg, dotted lines and squares) or placebo (solid lines and circles), ITT population, as determined by (E) qRT-PCR or (F) virus culture. Error bars in all plots represent standard error of the mean.

Figure 24A:
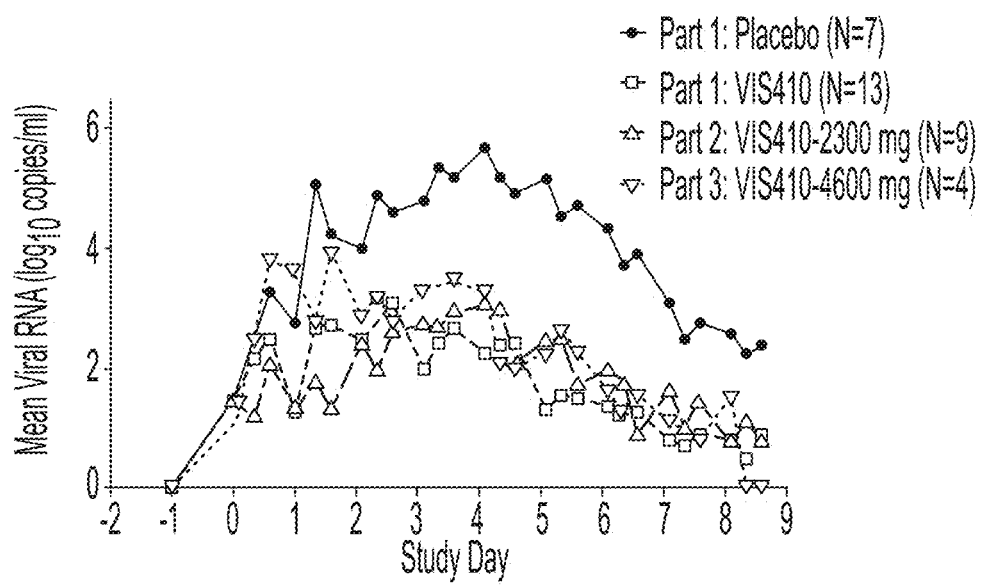
Figure 24B:
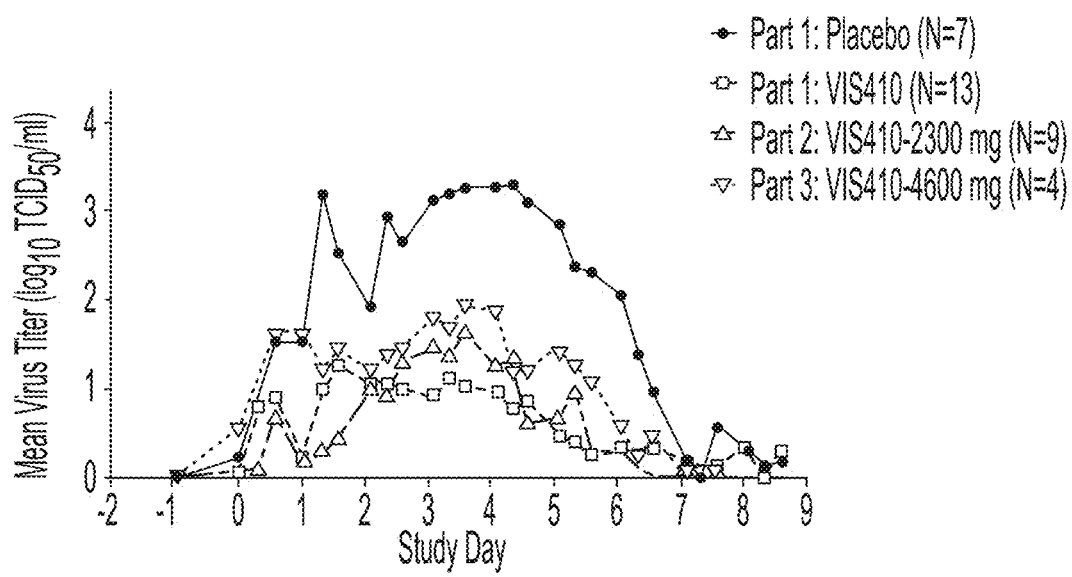

FIGS. 24A-24B are a series of graphs showing virus shedding from the VIS410 challenge study, Parts 1-3. Mean viral shedding over time in subjects treated with placebo (solid dark lines and circles, Part 1), VIS410 (2300 mg, dotted lines and squares, Part 1), VIS410 (2300 mg, long dashed line and triangles, Part 2), or VIS410 (4600 mg, small dotted lines and inverted triangles, Part 3), mITT population, as determined by (A) qRT-PCR or (B) virus culture.

FIGS. 25A-25D are a series of graphs showing clinical symptoms of VIS41-treated (dotted lines) or placebo-treated (solid lines) infected individuals. Mean daily symptom scores, including total symptoms (A) and upper respiratory tract (URT) symptoms, were plotted by treatment group versus study day (mITT, part 1). Error bars in all plots represent standard error of the mean. Kaplan-Meier analysis of time to resolution from peak of total symptoms (C) and URT symptoms (D) are presented by treatment group.

FIGS. 26A-26F are a series of graphs showing analysis of serum cytokines in the VIS410 challenge study, Part 1. Study drug administration occurred at time 0 hours, but for Part 1, the first post-infection (p.i.) measurement of cytokines was 12 hours following infusion. Cytokines by treatment are presented in A, C, and E, for the mITT population and in B, D, and F for the ITT population. IFNγ (A and B), IL-8 (C and D), and TFNα (E and F) serum concentrations (y-axis) are shown by the indicated timepoint (x-axis). Error bars in all plots represent standard error of the mean. Solid lines=Placebo; Dotted lines=VIS410.

FIGS. 27A-27D are a series of graphs showing analysis of serum cytokines in the VIS410 challenge study, Parts 2 and 3. Study drug administration occurred at time 0 hours, but for Parts 2 and 3, the first post-infection (p.i.) measurement of cytokines was 1 hour post-infusion. Cytokines by VIS410 dose are presented in A and C for the ITT population and in B and D by subject reported GI AE severity (ITT). IL-8 (A and B) and TFNα (C and D) serum concentrations (y-axis) are shown by the indicated timepoint (x-axis). Error bars in all plots represent standard error of the mean. Treatment conditions are as indicated in the figure legends.

FIGS. 28A-28D are a series of graphs showing that VIS410 administration did not impact the normal immune response to influenza. (FIG. A) Serum was collected at baseline (prior to infection and study drug dosing), 14 and 28 days following infection was measured for HAI activity against the challenge virus strain. Error bars represent standard error of the mean. (FIGS. B-D) Serum ADCC Activity Versus Avian Influenza Strains (H7N9) Unrelated to the Challenge Strain Virus (H1N1). The mean fold induction of ADCC activity of purified VIS410 against H7N9 HA-expressing target cells was provided as reference (A). (B) The calculated $EC_{50}$ values were 1.1 nM and 6.0 nM against A/Anhui/01/2013 (solid line) and A/Hong Kong/125/2016 (dotted line), respectively, while an irrelevant human IgG1 did not induce ADCC activity. (C-D) Level of induced ADCC activity by sera from subjects pre-dosing (dotted lines) and post-dosing (solid lines) with placebo (circles) or VIS410 (squares) against A/Anhui/01/2013 (C) or A/Hong Kong/125/2016 (D) H7 HA-expressing target cells.

Figure 29:
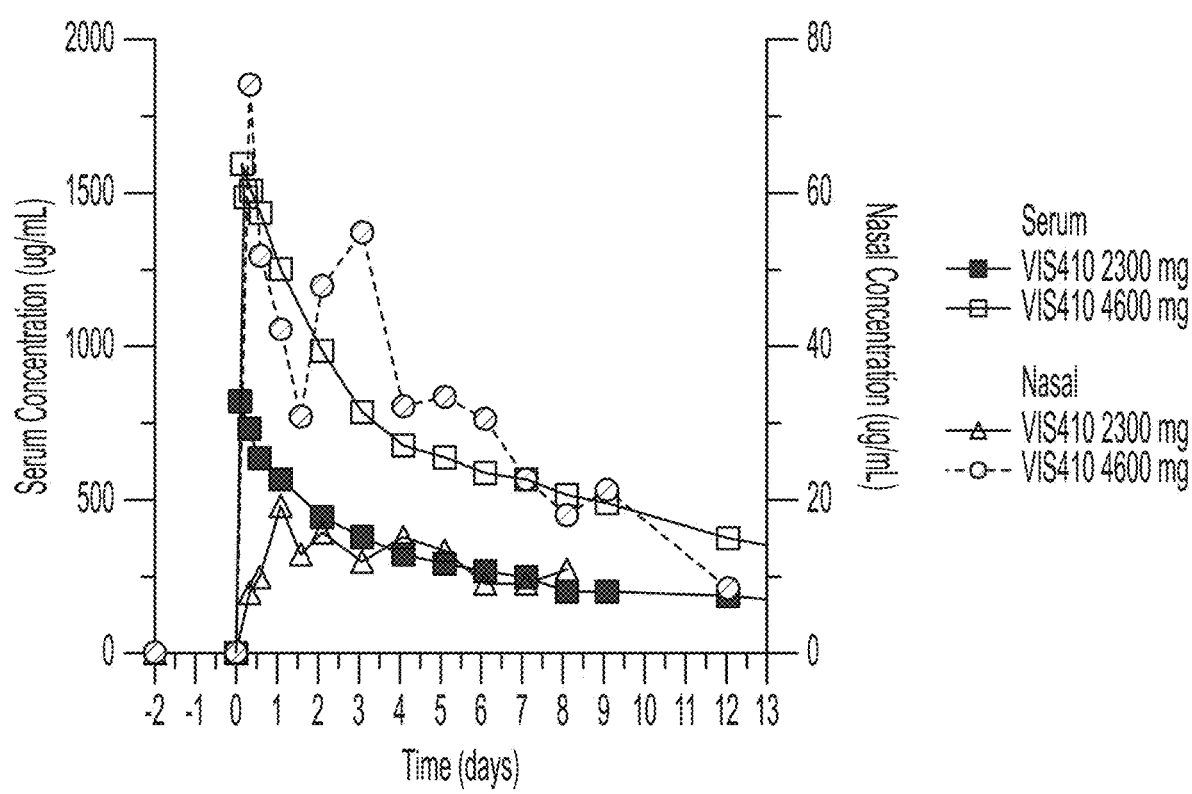

FIG. 29 is a graph showing the mean serum and nasopharyngeal (NP) VIS410 concentration versus time profiles for the VIS410 challenge study. Serum concentrations of VIS410 for 2300 mg dose (filled squares) and 4600 mg dose (open squares) are plotted on the left y-axis versus time (x-axis). NP concentrations of VIS410 for the 2300 mg dose (triangles) and 4600 mg dose (circles) are plotted on the right y-axis versus time (x-axis).

Additional figures include FIGS. 1-27 of International Publication No. WO2013/170139 and U.S. Application Publication No. 2013/0302349, the contents of which are incorporated by reference in their entirety.

DETAILED DESCRIPTION

The disclosure is based, at least in part, on the design and synthesis of antibody molecules that can bind an epitope that is conserved across multiple hemagglutinin subtypes of influenza viruses (e.g., influenza A and influenza B viruses). For example, the antibody molecules described herein are useful as broad-spectrum therapy against disease caused by at least one influenza A strain belonging to Group 1 and one influenza A strain belonging to Group 2 to neutralize infectivity of viruses belonging to both Group 1 and Group 2 (at least one subtype of each).

The antibody molecules were designed by a rational structure-based approach to target a region on the virus that is not fully accessible to the human immune system and, therefore, not amenable to antibody selection through more classical screening approaches. This rational-based approach to the design and development of broad-spectrum antibody molecules allows for the development of more efficacious vaccines for pandemic and seasonal influenza. This approach also allows for the advance preparation of pandemic vaccines so that they are ready to be employed against specific virus subtypes (e.g., avian or swine virus subtypes) that may mutate to become human-adapted and highly transmissible. Vaccines (e.g., seasonal vaccines) that utilize the antibody molecules described herein can generate a more potent immune response without the use of adjuvants and provide broad protection against viral strain variation.

The disclosures herein are based, at least in part, on the preclinical and clinical evaluation of a broadly active monoclonal antibody targeting the highly conserved hemagglutinin (HA) stem region of Influenza A (e.g., VIS410) as a single agent or in combination with other anti-influenza therapies. Without wishing to be bound by theory, it is believed that in an embodiment, including the antibody molecules described herein in treatment or prophylaxis for influenza (e.g., seasonal influenza) can result in beneficial effects, for example, achieving clinical response against drug resistant strains, in patients with severe symptoms or in high risk individuals. In an embodiment, the antibody molecules described herein are suitable for treating older patients or patients exhibiting greater average disease severity prior to treatment (e.g., greater proportion in the ICU, on mechanical ventilation, or presenting with bacterial pneumonia). In an embodiment, administration of an antibody molecule described herein (e.g., VIS410) can lead to faster times to oxygenation and/or vital sign normalization for non-ICU-hospitalized patients, e.g., in a patient subgroup presenting within 72 hours of reported symptom onset or had positive baseline viral cultures. In an embodiment, administration of an antibody molecule described herein (e.g., VIS410) can improve time to clearance of infectious virus in a patient that was viral culture positive prior to treatment. Without wishing to be bound by theory, an antibody molecule described herein (e.g., VIS410) can have dual mechanism of actions, including direct antiviral effects and indirect potentiation of host immunity. In an embodiment, an antibody molecule described herein (e.g., VIS410) is unexpectedly associated with transient elevation of one or more cytokines, e.g., one or more cytokines described herein (e.g., IL-8, TNFα, and/or IL-6). Without wishing to be bound by theory, it is believed that in an embodiment, mild increases in the cytokines can have a therapeutic significance that can help accelerate viral clearance. Without wishing to be bound by theory, it is believed that in an embodiment, an antibody molecule described herein (e.g., VIS410) can engage macrophage or monocyte Fcγ receptors, resulting in transient cytokine elevation.

Definitions

As used herein, the term "antibody molecule" refers to a polypeptide that comprises sufficient sequence from an immunoglobulin heavy chain variable region and/or sufficient sequence from an immunoglobulin light chain variable region, to provide antigen specific binding. It comprises full length antibodies as well as fragments thereof, e.g., Fab fragments, that support antigen binding. Typically, an antibody molecule will comprise heavy chain CDR1, CDR2, and CDR3 and light chain CDR1, CDR2, and CDR3 sequence. Antibody molecules include human, humanized, CDR-grafted antibodies and antigen binding fragments thereof. In some embodiments, an antibody molecule comprises a protein that comprises at least one immunoglobulin variable region segment, e.g., an amino acid sequence that provides an immunoglobulin variable domain or immunoglobulin variable domain sequence.

The VH or VL chain of the antibody molecule can further include all or part of a heavy or light chain constant region, to thereby form a heavy or light immunoglobulin chain, respectively. In one embodiment, the antibody molecule is a tetramer of two heavy immunoglobulin chains and two light immunoglobulin chains.

An antibody molecule can comprise one or both of a heavy (or light) chain immunoglobulin variable region segment. As used herein, the term "heavy (or light) chain immunoglobulin variable region segment," refers to an entire heavy (or light) chain immunoglobulin variable region, or a fragment thereof, that is capable of binding antigen. The ability of a heavy or light chain segment to bind antigen is measured with the segment paired with a light or heavy chain, respectively. In some embodiment, a heavy or light chain segment that is less than a full length variable region will, when paired with the appropriate chain, bind with an affinity that is at least 20, 30, 40, 50, 60, 70, 80, 90, or 95% of what is seen when the full length chain is paired with a light chain or heavy chain, respectively.

An immunoglobulin variable region segment may differ from a reference or consensus sequence. As used herein, to "differ," means that a residue in the reference sequence or consensus sequence is replaced with either a different residue or an absent or inserted residue.

An antibody molecule can comprise a heavy (H) chain variable region (abbreviated herein as VH), and a light (L) chain variable region (abbreviated herein as VL). In another example, an antibody comprises two heavy (H) chain variable regions and two light (L) chain variable regions or antibody binding fragments thereof. The light chains of the immunoglobulin may be of type kappa or lambda. In one embodiment, the antibody molecule is glycosylated. An antibody molecule can be functional for antibody dependent cytotoxicity and/or complement-mediated cytotoxicity, or may be non-functional for one or both of these activities. An antibody molecule can be an intact antibody or an antigen-binding fragment thereof.

Antibody molecules include "antigen-binding fragments" of a full length antibody, e.g., one or more fragments of a full-length antibody that retain the ability to specifically bind to an HA target of interest. Examples of binding fragments encompassed within the term "antigen-binding fragment" of a full length antibody include (i) a Fab fragment, a monovalent fragment consisting of the VL, VH, CL and CH1 domains; (ii) a F(ab') or F(ab')$_2$ fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883. Antibody molecules include diabodies.

As used herein, an antibody refers to a polypeptide, e.g., a tetrameric or single chain polypeptide, comprising the structural and functional characteristics, particularly the antigen binding characteristics, of an immunoglobulin. Typically, a human antibody comprises two identical light chains and two identical heavy chains. Each chain comprises a variable region.

The variable heavy (VH) and variable light (VL) regions can be further subdivided into regions of hypervariability, termed "complementarity determining regions" ("CDR"), interspersed with regions that are more conserved, termed "framework regions" (FR). Human antibodies have three VH CDRs and three VL CDRs, separated by framework regions FR1-FR4. The extent of the FRs and CDRs has been precisely defined (see, Kabat, E. A., et al. (1991) Sequences of Proteins of Immunological Interest, Fifth Edition, U.S. Department of Health and Human Services, NIH Publication No. 91-3242; and Chothia, C. et al. (1987) J. Mol. Biol. 196:901-917). Kabat definitions are used herein. Each VH and VL is typically composed of three CDRs and four FRs, arranged from amino-terminus to carboxyl-terminus in the following order: FR1, CDR1, FR2, CDR2, FR3, CDR3, FR4.

The heavy and light immunoglobulin chains can be connected by disulfide bonds. The heavy chain constant region typically comprises three constant domains, CH1, CH2 and CH3. The light chain constant region typically comprises a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

The term "immunoglobulin" comprises various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgD, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure. Light chains are classified as either kappa or lambda (κ, λ). Each heavy chain class may be bound with either a kappa or lambda light chain.

Suitable antibodies include, but are not limited to, monoclonal, monospecific, polyclonal, polyspecific, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular Immuno-Pharmaceuticals ("SMIPs™"), single chain antibodies, cameloid antibodies, and antibody fragments.

In some embodiments, an antibody is a humanized antibody. A humanized antibody refers to an immunoglobulin comprising a human framework region and one or more CDR's from a non-human, e.g., mouse or rat, immunoglobulin. The immunoglobulin providing the CDR's is often referred to as the "donor" and the human immunoglobulin providing the framework often called the "acceptor," though in some embodiments, no source or no process limitation is implied. Typically a humanized antibody comprises a humanized light chain and a humanized heavy chain immunoglobulin.

An "immunoglobulin domain" refers to a domain from the variable or constant domain of immunoglobulin molecules Immunoglobulin domains typically contain two β-sheets formed of about seven β-strands, and a conserved disulphide bond (see, e.g., A. F. Williams and A. N. Barclay (1988) *Ann. Rev. Immunol.* 6:381-405).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that comprises an immunoglobulin variable domain sequence can associate with another immunoglobulin variable domain sequence to form a target binding structure (or "antigen binding site"), e.g., a structure that interacts with the target antigen.

As used herein, the term antibodies comprises intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. Antibodies for use herein may be of any type (e.g., IgA, IgD, IgE, IgG, or IgM).

The antibody or antibody molecule can be derived from a mammal, e.g., a rodent, e.g., a mouse or rat, horse, pig, or goat. In an embodiment, an antibody or antibody molecule is produced using a recombinant cell. In some embodiments an antibody or antibody molecule is a chimeric antibody, for example, from mouse, rat, horse, pig, or other species, bearing human constant and/or variable regions domains.

A binding agent, as used herein, is an agent that bind, e.g., specifically binds, a target antigen, e.g., HA. Binding agents of the invention share sufficient structural relationship with anti-HA antibody molecules disclosed herein to support specific binding to HA, and in some embodiments, other functional properties of an anti-HA antibody molecule disclosed herein. In some embodiments, a binding agent will exhibit a binding affinity at of at least 10, 20, 30, 40, 50, 60, 70, 80, or 90% of an antibody molecule disclosed herein, e.g., an antibody molecule with which it shares, significant structural homology, e.g., CDR sequences. Binding agents can be naturally occurring, e.g., as are some antibodies, or synthetic. In an embodiment a binding agents is a polypeptide, e.g., an antibody molecule, e.g., an antibody. While some binding agents are antibody molecules, other molecules, e.g., other polypeptides, can also function as binding agents. Polypeptide binding agents can be monomeric or multimeric, e.g., dimeric, trimeric, or tetrameric and can be stabilized by intra- or interchain bonds, e.g., disulfide bonds. They can contain natural or non-naturally occurring amino acid residues. In some embodiments, binding agents are antibody molecules, or other polypeptides, that present one or more CDRs of antibody molecules disclosed herein or that otherwise mimic the structure of an antibody molecule disclosed herein. Binding agents can also comprise aptamers, nucleic acids or other molecular entities. A binding agent can be developed in a variety of ways, e.g., by immunization, by rational design, screening of random structures, or a combination of those or other approaches. Typically a binding agent will act by making contact with substantially the same epitope as an antibody molecule disclosed herein, e.g., an antibody molecule with which it shares, significant structural homology, e.g., CDR sequences. A binding agent can interact with amino acids, saccharides, or combinations thereof. Polypeptides other than antibodies can be used as a scaffold to present sequence, e.g., one or more, or a complete set of heavy chain and/or light chain CDRs, disclosed herein. Exemplary scaffolds include adnectin, zinc finger DNA-binding proteins. protein A, lipoclins, ankryin consensus repeat domain, thioredoxin, anticalins, centyrin, avimer domains, ubiquitin, peptidomimetics, stapled peptides, cystine-knot miniproteins, and IgNARs. In some embodiments, a binding agent is or comprises a nucleic acid, e.g., DNA, RNA or mixtures thereof. In some embodiments, a binding agent, e.g., a nucleic acid, shows secondary, tertiary, or quaternary structure. In some embodiments a binding agent, e.g., a nucleic acid, forms a structure that mimics the structure of an antibody molecule disclosed herein.

A broad-spectrum binding agent, e.g., antibody molecule, as used herein, binds, a plurality of different HA molecules, and optionally neutralizes viruses comprising the different HA molecules. In an embodiment, it binds a first HA and binds a second HA from influenza A Group 1, and optionally neutralizes viruses comprising the first or second HA molecules. In an embodiment, it binds a first HA from an influenza A Group 1 virus and binds a second HA from an influenza A Group 2 virus, and optionally neutralizes viruses comprising the different HA molecules. In an embodiment, it binds a first HA from an influenza A Group 1 or 2 virus and binds a HA from an influenza B virus, and optionally neutralizes viruses comprising the different HA molecules. In an embodiment, it binds, and in an embodiment neutralizes, at least two different clades or clusters of viruses, e.g., from different Groups. In some embodiments, it binds, and in some embodiments neutralizes, all or substantially all strains of Group 1 an/or Group 2 disclosed herein. In an embodiment, a binding agent, e.g., antibody molecule, binds, and in some embodiments, neutralizes: at least one strain from the Group 1 H1, e.g., H1a or H1b, cluster and at least one strain from the Group 2 H3 or H7 cluster. In an embodiment, a binding agent, e.g., antibody molecule, binds, and in some embodiments, neutralizes: at least one strain from the Group 1 H1, e.g., H1a or H1b, cluster and at least one influenza B strain. In an embodiment, a binding agent, e.g., antibody molecule, binds, and in some embodiments, neutralizes: at least one strain from the Group 2 H3 or H7 cluster and at least one influenza B strain. In an embodiment, a binding agent, e.g., antibody molecule, binds, and in some embodiments, neutralizes: at least one strain from the Group 1 H1, e.g., H1a or H1b, cluster, at least one strain from the Group 2 H3 or H7 cluster, and at least one influenza B strain. In an embodiment, the antibody molecule, binds, and optionally, neutralizes: at least one strain from the Group 1 H1 cluster (e.g., an H1N1 virus), and at least one strain from the Group 2 H3 cluster (e.g., H3N2). In an embodiment, the antibody molecule, binds, and optionally, neutralizes: a plurality of strains (e.g., at least 2, 3, 4, 5, 6, 7, 8, 9, 10, 15, 20, 25, 26, 27, 28, 29, or 30 strains) from the Group 1 H1 cluster (e.g., an H1N1 virus), and plurality of strains (e.g., at least 2, 3, 4, 5, 6, 7, 8, 9, 10, 15, 20, 25, 30, 31, 32, 33, 34, or 35 strains) from the Group 2 H3 cluster (e.g., H3N2). In some embodiments, binding agent, e.g., antibody molecule, binds, and optionally neutralizes or mediate infection of particular hosts, e.g., avian, camel, canine, cat, civet, equine, human, mouse, swine, tiger, or other mammal or bird.

The term "combination therapy", as used herein, refers to administration of a plurality of agents, e.g., wherein at least one binding agent, e.g., antibody molecule, disclosed herein is administered to a subject, e.g., a human subject. The introduction of the agents into the subject can be at different times. In some embodiments, the agents are administered in overlapping regimens, or such that the subject is simultaneously exposed to both agents, or such that the response of the subject is better than would be seen with either agent administered alone.

As used herein, an "escape mutant" is a mutated influenza strain that is resistant to neutralization by an anti-HA antibody molecule described herein. In some embodiments, an escape mutant is resistant to neutralization with a binding agent, e.g., antibody molecule, but its parent strain is neutralized by the binding agent, e.g., antibody molecule. Resistance can be tested by various methods, including, but not limited to, genotypic testing (e.g., Sanger sequencing/nested PCR-baseline and last qPCR sample (Ct<32)), and phenotypic testing (e.g., plaque reduction on primary sample, e.g., ViroSpot™ assay (e.g., virus titration—last post-baseline ≥2 $Log_{10}$ $TCID_{50}$/mL) or $IC_{50}$ single passage sample (e.g., antibody titration—last post-baseline ≥1 $Log_{10}$ $TCID_{50}$/mL).

As used herein, "pandemic influenza" refers to a new viral strain that arises due to human adaptation of an influenza strain by mutation or by emergence of a strain by reassortment of different strains of influenza A. The resulting pandemic strain is significantly different from previous strains and most people will have little or no pre-existing immunity. Symptoms and complications may be more severe and more frequent than those typical of seasonal influenza. Examples of past pandemic flu viruses include, e.g., the 2009 H1N1 'swine flu,' the 1957-58 H2N2 'Asian flu' and the 1968 H3N2 influenza strains.

The terms "purified" and "isolated" as used herein in the context of an antibody molecule, e.g., an antibody, or generally a polypeptide, obtained from a natural source, refers to a molecule which is substantially free of contaminating materials from the natural source, e.g., cellular materials from the natural source, e.g., cell debris, membranes, organelles, the bulk of the nucleic acids, or proteins, present in cells. Thus, a polypeptide, e.g., an antibody molecule, that is isolated includes preparations of a polypeptide having less than about 30%, 20%, 10%, 5%, 2%, or 1% (by dry weight) of cellular materials and/or contaminating materials. The terms "purified" and "isolated" when used in the context of a chemically synthesized species, e.g., an antibody molecule, refers to the species which is substantially free of chemical precursors or other chemicals which are involved in the syntheses of the molecule.

A preparation of binding agents, e.g., antibody molecules, as used herein, comprises a plurality of molecules of a binding agent, e.g., antibody molecule, described herein. In some embodiments, the binding agent, e.g., antibody molecule, makes up at least 60, 70, 80, 90, 95, 98, 99, 99.5 or 99.9%, of the preparation, or of the active ingredients of the preparation, by weight or number. In some embodiments, that binding agent is an antibody molecule which makes up at least 60, 70, 80, 90, 95, 98, 99, 99.5 or 99.9%, of the preparation, or of the active ingredients, or polypeptide ingredients, or antibody molecules, of the preparation, by weight or number. In some embodiments, the binding agent is an antibody molecule and the preparation contains no more than 30, 20, 10, 5, 2, 1, or 0.5%, by weight or number, of a contaminant, e.g., a reactant, solvent, precursor or other species, from the source, or used in the preparation, of the antibody molecule, e.g., a species from a cell, reaction mixture, or other system used to produce the antibody molecule.

As used herein, the term "prevent infection" means that a subject (e.g., a human) is less likely to be infected by influenza if the subject receives the antibody prior to (e.g., 1 day, 2 days, 1 week, 2 weeks, 3 weeks, or 1 month of more) before being exposed to influenza.

As used herein, "seasonal influenza" is a strain that is identical or closely related to strains that have been circulating in the human population in recent years and therefore most people are at least partially immune to it. Such a strain is not likely to cause severe disease. Symptoms can include fever, cough, runny nose, and muscle pain, and in rare cases, death can result from complications, such as pneumonia. Outbreaks follow predictable seasonal patterns, annually, and usually in fall and winter and in temperate climates. Infection due to seasonal influenza is commonly referred to as the flu.

As used herein, specific binding, means that a binding agent, e.g., an antibody molecule, binds its antigen with a $K_D$ of equal to or less than $10^{-5}$. In some embodiments, the antibody binds it's antigen with a $K_D$ of equal to or less than $10^{-6}$, $10^{-7}$, $10^{-8}$, $10^{-9}$, $10^{-10}$, $10^{-11}$, or $10^{-12}$.

As used herein, the term "therapeutically effective amount" refers to an amount of a therapeutic agent, e.g., a binding agent, e.g., an antibody molecule, which results in a positive outcome for the subject. In some embodiments, it can be statistically correlated with therapeutic effect or benefit, e.g., the lessening or prevention of a manifestation of an effect or a symptom, when administered to a population of subjects. In some embodiments, it is an amount that also provides a preselected, or reasonable, benefit/risk ratio. In some embodiments, it is an amount effective to reduce the incidence and/or severity of and/or to delay onset of one or more features, symptoms, or characteristics of a disease, disorder, or condition. A therapeutically effective amount is can be administered in a dosing regimen that may comprise one or multiple unit doses.

As used herein, the term "treat infection" means that a subject (e.g., a human) who has been infected with an influenza and experiences symptoms of the influenza (e.g., the flu), will in some embodiments, suffer less severe symptoms and/or will recover faster when the antibody molecule is administered than if the antibody is never administered. In some embodiments, when an infection is treated, an assay to detect virus in the subject will detect less virus after effective treatment for the infection. For example, a diagnostic assay using an antibody molecule, such as an antibody molecule described herein, will detect less or no virus in a biological sample of a patient after administration of an antibody molecule for the effective treatment of the viral infection. Other assays, such as PCR (e.g., qPCR) can also be used to monitor treatment in a patient, to detect the presence, e.g., decreased presence (or absence) after treatment of viral infection in the patient. Treatment can, e.g., partially or completely alleviate, ameliorate, relive, inhibit, reduce the severity of, and/or reduces incidence and optionally, delay onset of, one or more manifestations of the effects or symptoms, features, and/or causes of a particular disease, disorder, and/or condition (e.g., influenza). In some embodiments, treatment is of a subject who does not exhibit signs of the relevant disease, disorder and/or condition and/or of a subject who exhibits only early signs of the disease, disorder, and/or condition. In some embodiments, treatment is of a subject who exhibits one or more established signs of the relevant disease, disorder and/or condition. In some embodiments, treatment is of a subject diagnosed as suffering from influenza.

Calculations of "homology" or "sequence identity" or "identity" between two sequences (the terms are used interchangeably herein) can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

Standards for the use of ordinal scales in clinical trials are described, e.g., MacKenzie and Charlson, Br Med J (Clin Res Ed). 1986; 292(6512):40-3, the content of which is incorporated by reference in its entirety. Without wishing to be bound by theory, ordinal scales can be used in clinical trials to quantify outcomes which are non-dimensional. They can be regarded as either single state or transition measures based on whether they assess the outcome at a single point in time or directly examine change which has occurred between two points in time. In an embodiment, the ordinal scale scores are based on one or more (e.g., two, three, four, or all) parameters chosen from death, ICU stay with mechanical ventilation, ICU stay without mechanical ventilation, non-ICU hospitalization, or discharge.

Hemagglutinin (HA) Polypeptides and Influenza

Influenza viruses are negative sense, single-stranded, segmented RNA envelope viruses. Two glycoproteins, a hemagglutinin (HA) polypeptide and a neuraminidase (NA) polypeptide, are displayed on the outer surface of the viral envelope. There are several Influenza A subtypes, labeled according to an H number (for the type of hemagglutinin) and an N number (for the type of neuraminidase). There are 17 different H antigens (H1 to H17) and nine different N antigens (N1 to N9). Influenza strains are identified by a nomenclature based on the number of the strain's HA polypeptide and NA polypeptide subtypes, for example, H1N1, H1N2, H1N3, H1N4, H1N5, and the like.

HA is the major viral surface glycoprotein that mediates binding and entry of the virus into host cells and is a primary target of neutralizing antibody responses. HA is a trimer of three identical monomers. Each monomer is synthesized as a precursor, $HA_0$, that is proteolytically processed into two disulfide-bonded polypeptide chains, $HA_1$ and $HA_2$. The ectodomain of this protein has (i) a globular head domain possessing receptor binding activity and major antigenic determinants, (ii) a hinge region, and (iii) a stem region where a sequence critical for fusion, the fusion peptide, is located. The viral replication cycle is initiated when the virion attaches via its surface hemagglutinin proteins to sialylated glycan receptors on the host cell and enters the cell by endocytosis. The acidic environment in the endosome induces conformational changes in HA that expose the fusion peptide hidden within the stem region of the trimer. The exposed fusion peptide mediates the fusion of the viral and target cell membranes resulting in the release of the viral ribonucleoprotein into the cell cytoplasm.

Influenza A hemagglutinin subtypes have been divided into two main groups and four smaller clades, and these are further divided into clusters. Group 1 influenza A strains are divided into 3 clades: (i) H8, H9 and H12 ("the H9 cluster"); (ii) H1, H2, H5, H6 and H17 ("the H1a cluster"); and (iii) H11, H13 and H16 ("the H1b cluster"). Group 2 strains are divided into 2 clades: (i) H3, H4 and H14 ("the H3 cluster"); and (ii) H7, H10 and H15 ("the H7 cluster"). The H1b and the H1a clusters are classified together as the H1 cluster. The different HA subtypes do not necessarily share strong amino acid sequence identity, but their overall 3D structures are similar.

Of the 17 HA polypeptide subtypes, only 3 (H1, H2 and H3) have adapted for human infection. These subtypes have in common an ability to bind alpha 2,6 sialylated glycans. In contrast, their avian counterparts preferentially bind to alpha 2,3 sialylated glycans. HA polypeptides that have adapted to infect humans (e.g., of HA polypeptides from the pandemic H1N1 (1918) and H3N2 (1967-68) influenza subtypes) have been characterized by an ability to preferentially bind to α2,6 sialylated glycans in comparison with their avian progenitors that preferentially bind to α2,3 sialylated glycans (see, e.g., Skehel & Wiley, Annu Rev Biochem, 69:531, 2000; Rogers, & Paulson, Virology, 127:361, 1983; Rogers et al., Nature, 304:76, 1983; Sauter et al., Biochemistry, 31:9609, 1992

Further, HA polypeptides that mediate infection of humans preferentially bind to umbrella topology glycans over cone topology glycans (see, e.g., U.S. 2011/0201547). Without wishing to be bound by any particular theory, it has been proposed that the ability to infect human hosts correlates less with binding to glycans of a particular linkage, and more with binding to glycans of a particular topology, even though cone-topology glycans may be α2,6 sialylated glycans. In has been demonstrated that HA polypeptides that mediate infection of humans bind to umbrella topology glycans, often showing preference for umbrella topology glycans over cone topology glycans (See, for example, U.S. Application Publication Nos. 2009/0269342, 2010/0061990, 2009/0081193, and 2008/0241918, and International Publication No. WO2008/073161).

Mature HA polypeptides include three domains, (i) a globular domain (a.k.a., the head domain) consists mainly of the HA1 peptide and contains the receptor (sialylated glycoproteins)-binding region, (ii) a stalk domain (HA1 and HA2) where the membrane fusion peptide resides, and (iii) a transmembrane domain (HA2) that anchors hemagglutinin to the viral envelope. A set of amino acids in the interface of the HA1 and HA2 peptides is highly conserved across all influenza subtypes. The HA1/HA2 membrane proximal region (MPER), including a canonical alpha-helix, is also highly conserved across influenza subtypes.

HA polypeptides interact with the surface of cells by binding to a glycoprotein receptor, known as the HA receptor. Binding of an HA polypeptide to an HA receptor is predominantly mediated by N-linked glycans on the HA receptors. HA polypeptides on the surface of flu virus particles recognize sialylated glycans that are associated with HA receptors on the surface of the cellular host. Following replication of viral proteins and genome by the cellular machinery, new viral particles bud from the host to infect neighboring cells.

Currently, vaccines are administered to subjects, e.g., humans, to prevent the flu, e.g., to prevent infection or to minimize the effects of an infection with influenza virus. Traditional vaccines contain a cocktail of antigens from various strains of influenza and are administered to humans to prevent the human from getting infected with the virus. HA is the main target of influenza A-neutralizing antibodies, and HA undergoes continuous evolution driven by the selective pressure of the antibody response, which is primarily directed against the membrane-distal receptor-binding subdomain of the HA polypeptide. The subject, however, is protected only from strains that are identical to, or closely related to, the strains from which the antigens in the cocktail were derived. The human is still most vulnerable to infection by other strains of the flu that were not included in the cocktail. One of the advantages of the antibodies provided herein is their ability to bind an epitope of HA that is conserved across multiple strains of influenza A, and in some embodiments, influenza B. Thus, administration of an anti-HA antibody described herein will be more effective to protect an individual from infection from a broader spectrum of influenza (e.g., influenza A and, in some embodiments, influenza B) and conditions associate thereof (e.g., secondary infections, e.g., secondary bacterial infections). Further, the antibodies are effective in treating a subject after infection has occurred.

Anti-HA Antibody Molecules

Binding agents, and in particular, the antibody molecules described herein, can bind to influenza A viruses from both Group 1 and Group 2, and in some embodiments also bind influenza B viruses. For example, the antibody molecules described herein can bind to an HA polypeptide on at least 1, 2, 3, 4, 5, 6, 7, 8, 9, 10 or 11 strains from Group 1, and can also bind to an HA polypeptide on at least 1, 2, 3, 4, 5, or 6 strains from Group 2. In another example, the antibody molecules described herein can bind to an HA polypeptide on an influenza strain from at least 1, 2 or 3 clades from Group 1, and can also bind to an HA polypeptide on an influenza strain from one or both clades of Group 2. The antibody molecules described herein inhibit cell entry and thus targeting an early step in the infection process.

The binding agents, and in particular, the antibody molecules featured in the disclosure, can be effective to treat or prevent infection by seasonal or pandemic influenza strains. The binding agents, and in particular the antibody molecules described herein, can be characterized by their ability to prevent or treat a Group 1 or a Group 2 strain of influenza A viruses or, in some embodiments, a strain of influenza B viruses. The binding agents, and in particular the antibody molecules featured in the disclosure, are effective to prevent or treat infection by one or more strains of Group 1, one or more strains of Group 2, and also one or more strains of influenza B viruses. In an embodiment, the binding agent is used to treat or prevent an influenza virus infection caused by an influenza virus chose from an H1N1 virus, an H3N2 virus, an H7N9 virus, or a combination thereof.

The binding agents, and in particular the antibody molecules can be effective to treat the infection when administered the same day as the subject is exposed, or when administered, e.g., 1 day, 2 days, 3 days, 4 days or later after infection, or upon a first symptom experienced by the patient. In an embodiment, the antibody molecule does not cause an antibody dependent enhancement (ADE) in the subject, e.g., as determined by a method described herein. In an embodiment, the antibody molecule does not cause viral resistance, e.g., as determined by a method described herein.

In an embodiment, the antibody molecule reduces the severity of one or more symptoms of influenza virus infection. In an embodiment, the antibody molecule reduces time to symptom resolution in the subject. In an embodiment, the antibody molecule reduces viral load in the subject. In an embodiment, the antibody molecule reduces viral shedding by the subject. In an embodiment, the antibody molecule does not detectably interfere with an endogenous immune response to influenza A in the subject. In an embodiment, the antibody molecule increases antibody-dependent cellular cytotoxicity (ADCC), e.g., against cells infected with an influenza virus (e.g., an influenza A virus, e.g., H1N1 or H7N9).

Strains

The antibody molecules described herein are effective to treat one or more influenza strains of Group 1, one or more influenza strains of Group 2, and also one or more influenza B strains, and specific isolates within these strains. Certain antibody molecules may be more effective for treatment of certain isolates than other isolates. Exemplary influenza strains and isolates are described in the below Table 1. Affinity can also be in reference to a particular isolate of a given Group 1 or Group 2 strain for influenza A viruses, a strain for influenza B viruses, a strain for influenza C viruses, and/or a strain for influenza D viruses. Exemplary isolates are as provided in the above Table 1. Other exemplary influenza virus strains and isolates are also described herein, e.g., in FIG. 18.

TABLE 1

Exemplary Influenza Strains and Isolates

| Type | Group | HA type | Isolate |
|---|---|---|---|
| A | 1 | H1N1 | A/PR/8/34 (aka PR-8) |
| | | | A/Solomon Islands/03/06 |
| | | | A/Solomon Islands/20/1999 |
| | | | A/California/07/2009 |
| | | | A/New Caledonia/20/99 |

TABLE 1-continued

Exemplary Influenza Strains and Isolates

| Type | Group | HA type | Isolate |
|---|---|---|---|
| A | 1 | H2N2 | A/Bangkok/10/83<br>A/Yamagata/120/86<br>A/Osaka/930/88<br>A/Suita/1/89<br>A/California/04/2009<br>A/Okuda/57<br>A/Adachi/2/57<br>A/Kumamoto/1/65<br>A/Kaizuka/2/65<br>A/Izumi/5/65<br>A/Chicken/PA/2004 |
| A | 1 | H5N1 | A/Vietnam/1203/04<br>A/Duck/Singapore/3/97<br>A/Duck/MN/1525/81 |
| A | 1 | H9N2 | A/Hong Kong/1073/2004<br>A/Swine/Hong Kong/9/98<br>A/Guinea fowl/HK/WF10/99 |
| A | 1 | H16N3 | A/black headed gull/Mongolia/1756/2006 |
| A | 2 | H3N2 | X-31<br>A/Victoria/3/75<br>A/Wyoming/03/2003<br>A/Wisconsin/67/2005<br>A/Brisbane/10/2007<br>A/California/7/2004<br>A/New York/55/2004<br>A/Moscow/10/1999<br>A/Aichi/2/68<br>A/Beijing/32/92/X-117<br>A/Fukuoka/C29/85<br>A/Sichuan/2/87<br>A/Ibaraki/1/90<br>A/Suita/1/90<br>A/Perth/16/2009<br>A/Uruguay/716/2007<br>A/Fujian/411/2003<br>A/Panama/2007/99<br>A/Shangdong/09/93<br>A/Hong Kong/4801/2014 |
| A | 2 | H7N7 | A/Netherlands/219/2003 |
| B | | | B/Wisconsin/1/2010 |

Mechanisms of Inhibition

While not being limited by a specific mechanism, HA specific antibodies can inhibit infection by numerous methods, such as by blocking viral attachment to sialic acid residues on surface proteins on host cells, by interfering with the structural transition of HA that triggers fusion activity in the endosome, or by simultaneously inhibiting attachment and virus-cell fusion. In some embodiments, antibody molecules featured herein bind an epitope at the HA trimer interface. Structural changes at the trimer interface are important for fusion of the viral membrane and the endocytic membrane, and the antibody molecules described herein interfere with this critical step of infection. Assays to measure fusogenic activity of HA are known in the art. For example, one fusion assay measures syncytia formation, which occurs in cell-cell fusion events. Cells that express and display an influenza viral strain HA can be used in the assay. Membrane-anchored hemagglutinin in these cells is induced to convert to the fusion conformation by a brief (e.g., 3 minute) exposure to low pH (e.g., pH 5). A 2-3-hour incubation period follows to allow the cells to recover and fuse to form syncytia. A nuclear stain can be used to aid in the visualization of these fusion products, and their count is used as a gauge of fusion activity. A candidate anti-HA antibody can be added either before or after the low pH treatment to determine at which stage of the fusion process the antibody interferes.

Another type of fusion assay monitors content mixing. To measure content mixing, host cells (e.g., erythrocytes) are loaded with a dye (e.g., *Lucifer* yellow) to determine whether the contents of HA-bound host cells could be delivered to HA-expressing cells after exposure to fusion-inducing conditions (e.g., low pH, such as pH less than 6 or pH less than 5). If the dye fails to mix with the contents of the host cells, then the conclusion can be made that fusion is inhibited. See, e.g., Kemble et al., *J. Virol.* 66:4940-4950, 1992. In another example, a fusion assay is performed by monitoring lipid mixing. The lipid mixing assay can be performed by labeling host cells (e.g., erythrocytes) with a fluorescent dye (e.g., R18 (octadecylrhodamine)) or dye pairs (e.g., CPT-PC/DABS-PC) (for fluorescence resonance energy transfer), exposing the host cells and HA-expressing cells to fusion-inducing conditions, and assaying for fluorescence dequenching (FDQ). Lipid mixing leads to dilution of the label into the viral envelope and a consequent dequenching. A lag in dequenching or the absence of dequenching is indicative of membrane fusion inhibition. See, e.g., Kemble et al., *J. Virol.* 66:4940-4950, 1992; and Carr et al., *Proc. Natl. Acad. Sci.* 94:14306-14313, 1997.

Escape Mutants

In some embodiments, influenza strains will rarely if ever produce escape mutants when contacted with the featured antibody molecules. Escape mutants can be identified by methods known in the art. For example, an antibody featured in the disclosure will not produce an escape mutant when the cells are infected with the virus under prolonged or repeated exposure to anti-HA antibodies featured in the disclosure.

One exemplary method includes infection of cells (e.g. MDCK cells) with a fixed amount of influenza A viral particles in the presence of the antibody at a concentration known to attenuate infection rates by 50%. Viral progeny collected after each passaging is used to infect a fresh cell culture in the presence of the same or greater concentration of the antibody. After multiple cycles of infection, e.g., after 15 cycles, 12 cycles, 11 cycles, 10 cycles, 9 cycles, 8 cycles, 7 cycles, 6 cycles, or 5 cycles, of infection under these conditions, the HA nucleotide sequence extracted from 20 viral plaque picks is evaluated for enrichment for mutations that renders the viral isolate resistant to neutralization by the antibody (an escape mutant). If no mutants with reduced sensitivity to the antibody are detected after the multiple rounds of selection, e.g., after 11 rounds, 10 rounds, or 9 rounds of selection, the antibody is determined to be resistant to escape mutations (see, e.g., Throsby et al. (2008) PLoS One, volume 3, e3942).

In another example, an assay that measures minimum inhibitory concentration (MIC) of the neutralizing antibody can be used to identify escape mutants. The MIC of an antibody molecule is the lowest concentration of an antibody molecule that can be mixed with virus to prevent infection of cell culture with influenza. If escape mutants arise within a viral population, then the MIC of a particular antibody will be observed to increase with increased rounds of propagation under the antibody selective pressure, as the proportion of the viral particles that carry the resistance mutation within the population increased. Influenza escape mutants rarely if ever evolve in response to an anti-HA antibody molecule described herein, and therefore the MIC will stay the same over time.

Another assay suitable for monitoring for the development of escape mutants is a Cytopathic Effect (CPE) assay. A CPE assay monitors the ability of an antibody to neutralize (i.e., prevent infection by) an influenza strain. A CPE assay provides the minimal concentration of antibody required in cell culture to neutralize the virus. If escape mutants arise, than the CPE of a particular antibody will increase over time, as the antibody becomes less effective at neutralizing the virus. Viral strains rarely if ever produce escape mutants in response to an anti-HA antibody molecule described herein, and therefore the CPE will stay essentially the same over time.

Quantitative polymerase chain reaction (qPCR) can also be used to monitor for the development of escape mutants. qPCR is useful to monitor the ability of an antibody to neutralize (i.e., prevent infection by) an influenza strain. If an antibody effectively neutralizes a virus, then qPCR performed on cell culture samples will not detect presence of viral genomic nucleic acid. If escape mutants arise, than over time, qPCR will amplify more and more viral genomic nucleic acid. Escape mutants rarely if ever develop in response to an anti-HA antibody molecule described herein, and therefore qPCR will rarely if ever detect viral genomic nucleic acid, even after the passage of time.

Binding and Affinity

In some embodiments, the binding agents, particularly antibody molecules, featured herein bind to two or more of the following: at least one HA polypeptide from a Group 1 influenza strain (e.g., an H1, H2, H5, H6, H8, H9 H12, H11, H13, H16 or H17 polypeptide); at least one HA polypeptide from a Group 2 influenza strain (e.g., an H3, H4, H14, H7, H10, or H15 polypeptide); and at least one HA polypeptide from an influenza B strain. In an embodiment, a binding agent, e.g., an antibody molecule, has a $K_D$ for an HA from a Group 1 influenza strain (e.g., an H1, H2, H5, H6, H8, H9 H12, H11, H13, H16 or H17 polypeptide) of equal to or less than $10^{-6}$, $10^{-7}$, $10^{-8}$, $10^{-9}$, $10^{-10}$, $10^{-11}$, or $10^{-12}$. In an embodiment, a binding agent, e.g., an antibody molecule, has a $K_D$ for an HA from a Group 2 influenza strain (e.g., an H3, H4, H14, H7, H10, or H15 polypeptide) of equal to or less than $10^{-6}$, $10^{-7}$, $10^{-8}$, $10^{-9}$, $10^{-10}$, $10^{-11}$, or $10^{-12}$. In an embodiment, a binding agent, e.g., an antibody molecule, has a $K_D$ for an influenza B HA of equal to or less than $10^{-6}$, $10^{-7}$, $10^{-8}$, $10^{-9}$, $10^{-10}$, $10^{-11}$, or $10^{-12}$. In an embodiment, a binding agent, e.g., an antibody molecule, has: a) a first $K_D$ (representing an affinity for an HA from a Group 1 influenza strain, e.g., an H1, H2, H5, H6, H8, H9 H12, H11, H13, H16 or H17 polypeptide); and b) a second $K_D$ (representing an affinity for an HA from a Group 2 influenza strain, e.g., an H3, H4, H14, H7, H10, or H15 polypeptide), wherein the first and second $K_D$ are one or both of: both equal to or less than $10^{-8}$; and within 10 or 100 fold of each other;

In an embodiment, a binding agent, e.g., an antibody molecule, has a) a first $K_D$ (representing an affinity for an H1, e.g., the H1 from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004); and b) a second $K_D$ (representing an affinity for an H3 polypeptide, e.g., the H3 from an H3N2 strain, e.g., A/Brisbane/59/2007), wherein the first and second $K_D$ are one or both of: both equal to or less than $10^{-8}$; and within 10 or 100 fold of each other. In an embodiment, a binding agent, e.g., an antibody molecule, has: a) a first $K_D$ (representing an affinity for an H1, e.g., the H1 from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004); and b) a second $K_D$ (representing an affinity for an H3 polypeptide, e.g., the H3 from an H3N2 strain, e.g., A/Brisbane/59/2007), wherein the first and second $K_D$ are one or both of: both equal to or less than $10^{-8}$; and within 10 or 100 fold of each other.

In an embodiment, a binding agent, e.g., an antibody molecule, has: a) a first $K_D$ (representing an affinity for an HA from a Group 1 influenza strain, e.g., an H1, H2, H5, H6, H8, H9 H12, H11, H13, H16 or H17 polypeptide and/or an affinity for an HA from a Group 2 influenza strain, e.g., an H3, H4, H14, H7, H10, or H15 polypeptide); and b) a second $K_D$ (representing an affinity for an influenza B HA, e.g., from B/Wisconsin/1/2010); wherein the first and second $K_D$ are one or both of: both equal to or less than $10^{-8}$; and within 10 or 100 fold of each other. In an embodiment, a binding agent, e.g., an antibody molecule, has: a) a first $K_D$ (representing an affinity for an HA from a Group 1 influenza strain, e.g., an H1, e.g., the H1 from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, and/or an affinity for an HA from a Group 2 influenza strain, e.g., an H3 polypeptide, from an H3N2 strain, e.g., from A/Brisbane/59/2007); and b) a second $K_D$ (an affinity for an influenza B HA); wherein the first and second $K_D$ are: one or both of: both equal to or less than $10^{-8}$; and within 10 or 100 fold of each other.

In one embodiment, the antibody molecule binds to at least one HA polypeptide from a Group 1 influenza strain with a higher affinity than a reference anti-HA antibody, and to at least one HA polypeptide from a Group 2 influenza strain with a higher affinity than a reference anti-HA antibody. In another embodiment, the antibody molecule binds to at least one HA polypeptide from an influenza A strain with a higher affinity than a reference anti-HA antibody, and to at least one HA polypeptide from an influenza B strain with a higher affinity than a reference anti-HA antibody. Exemplary reference HA antibodies include Ab 67-11 (U.S. Provisional application No. 61/645,453, filed on the same date as the present application), FI6 (FI6, as used herein, refers to any specifically disclosed FI6 sequence in U.S. Application Publication No. 2010/0080813, US Application Publication No. 2011/0274702, International Publication No. WO2013/011347 or Corti et al., Science 333:850-856, 2011, published online Jul. 28, 2011; FIGS. 12A to 12C of International Publication No. WO2013/170139 or U.S. Application Publication No. 2013/0302349), FI28 (U.S. Application Publication No. 2010/0080813), and C179 (Okuno et al., J. Virol. 67:2552-1558, 1993), F10 (Sui et al., Nat. Struct. Mol. Biol. 16:265, 2009), CR9114 (Dreyfus et al., Science. 2012; 337(6100):1343-1348; published online Aug. 9, 2012), and CR6261 (Ekiert et al., Science 324:246-251, 2009; published online Feb. 26, 2009).

Affinity, or relative affinity or aviditiy, can be measured by methods known in the art, such as by ELISA assay (Enzyme Linked Immunosorbent Assay), Surface Plasmon Resonance (SPR, e.g., by a Biacore™ Assay), or KinExA® assay (Sapidyne, Inc.). Relative binding affinity is expressed herein according to ELISA assay. As used herein, an anti-HA antibody that binds with "high affinity" to a Group 1 HA, to a Group 2 HA, and to an influenza B HA, can bind a Group 1 HA with a Kd less than or equal to 200 pM, e.g., less than or equal to 100 pM, as measured by ELISA, can bind a Group 2 HA with a Kd less than or equal to 200 pM, e.g., less than or equal to 100 pM, as measured by ELISA, and can bind an influenza B HA with a Kd less than or equal to 200 pM, e.g., less than or equal to 100 pM, as measured by ELISA.

Exemplary Anti-HA Antibody Molecules

Provided herein are antibodies that have one or more CDR sequences and one or more framework (FR) sequences as shown in Table 2.

TABLE 2

Heavy and Light Chain CDR and FR Sequences for Anti-HA Antibodies

| CDR/FR Region | Amino Acid Sequence | SEQ ID NO: |
|---|---|---|
| HC CDR1 | [S/T]Y[A/G]MH | 1 |
| HC CDR2 | V[I/V/L]S[Y/F]DG[S/N][Y/N][K/R]YYADSVQG | 2 |
| HC CDR3 | D[S/T][R/K/Q]LR[S/T]LLYFEWLS[Q/S]G[Y/L/V][F/L][N/D][P/Y] | 3 |
| LC CDR1 | Q[S/T][V/L/I][T/S][Y/F/W][N/S/D]YKNYLA | 4 |
| LC CDR1 | Q[S/T][V/L/I][T/S][Y/F/W][N/S/D/Q/R/E]YKNYLA | 170 |
| LC CDR2 | W[A/G]S[T/A/Y/H/K/D][R/L]E[S/T] | 5 |
| LC CDR3 | QQ[Y/H]YRTPP[T/S] | 6 |
| HC FR1 | [E/Q]VQLLE[S/T]GGGLVKPGQSLKLSCAASGFTF[S/T] | 7 |
| HC FR2 | WVRQPPGKGLEWVA | 8 |
| HC FR3 | RFTISRDNSKNTLYLQMNSLRAEDTAVYYCAK | 9 |
| HC FR4 | WG[A/Q]G[T/A][T/M][L/V]TVSS | 10 |
| LC FR1 | [E/D]I[V/Q]MTQSP[D/S][S/T][L/V][A/S][V/A][S/T][L/V/R]G[E/D]R[A/V][T/S]I[N/T/Q/D/R/]C[K/R]SS | 11 |
| LC FR2 | WYQQKPG[Q/K][P/A]PKLLIY | 12 |
| LC FR3 | GVP[D/E/S]RFSGSGSGTDFTLTISSLQ[A/P]ED[V/F/K/D]A[V/T]YYC | 13 |
| LC FR4 | FG[G/Q/T/S/N]GTK[L/V][D/E]IK | 14 |

In one embodiment, the anti-HA antibody comprises a heavy chain and/or a light chain as defined in Table 3 below. The amino acid sequences of the variable heavy and light chains of Table 3 are provided in FIGS. 2 and 3, respectively, or in FIG. 17, of International Publication No. WO2013/170139 or U.S. Application Publication No. 2013/0302349.

TABLE 3

Heavy and Light Chain Amino Acid Sequence Designations for Anti-HA Antibodies

| | Antibody | HC SEQ ID NO: | LC SEQ ID NO: |
|---|---|---|---|
| 1. | Ab A18 | 15 | 28 |
| 2. | Ab 014 | 16 | 29 |
| 3. | Ab 028 | 16 | 30 |
| 4. | Ab 001 | 17 | 31 |
| 5. | Ab 002 | 18 | 31 |
| 6. | Ab 003 | 19 | 31 |
| 7. | Ab 009 | 17 | 32 |
| 8. | Ab 010 | 18 | 32 |
| 9. | Ab 011 | 19 | 32 |
| 10. | Ab 017 | 17 | 33 |
| 11. | Ab B18 | 18 | 33 |
| 12. | Ab 019 | 19 | 33 |
| 13. | Ab 025 | 17 | 34 |
| 14. | Ab 026 | 18 | 34 |
| 15. | Ab 027 | 19 | 34 |
| 16. | Ab 086 | 20 | 34 |
| 17. | Ab 154 | 21 | 29 |
| 18. | Ab 155 | 21 | 30 |
| 19. | Ab 157 | 22 | 29 |
| 20. | Ab 159 | 22 | 35 |
| 21. | Ab 160 | 17 | 36 |
| 22. | Ab 186 | 17 | 37 |
| 23. | Ab 187 | 17 | 38 |
| 24. | Ab 188 | 17 | 39 |
| 25. | Ab 189 | 17 | 40 |
| 26. | Ab 190 | 17 | 41 |
| 27. | Ab 191 | 17 | 42 |
| 28. | Ab 192 | 17 | 43 |
| 29. | Ab 193 | 17 | 44 |
| 30. | Ab 194 | 19 | 37 |
| 31. | Ab 195 | 19 | 38 |
| 32. | Ab 196 | 19 | 39 |
| 33. | Ab 197 | 19 | 40 |
| 34. | Ab 198 | 19 | 41 |
| 35. | Ab 199 | 19 | 42 |
| 36. | Ab 200 | 19 | 43 |
| 37. | Ab 202 | 17 | 45 |
| 38. | Ab 203 | 18 | 45 |
| 39. | Ab 204 | 19 | 45 |
| 40. | Ab 210 | 23 | 45 |
| 41. | Ab 211 | 17 | 46 |
| 42. | Ab 212 | 18 | 46 |
| 43. | Ab 213 | 19 | 46 |
| 44. | Ab 219 | 23 | 46 |
| 45. | Ab A001 | 24 | 47 |
| 46. | Ab A002 | 24 | 48 |
| 47. | Ab A003 | 24 | 49 |
| 48. | Ab 004 | 25 | 47 |
| 49. | Ab 005 | 25 | 48 |
| 50. | Ab 006 | 25 | 49 |
| 51. | Ab 007 | 26 | 47 |
| 52. | Ab 008 | 26 | 48 |
| 53. | Ab A009 | 26 | 49 |
| 54. | Ab A010 | 24 | 50 |
| 55. | Ab A011 | 24 | 51 |
| 56. | Ab 012 | 25 | 50 |
| 57. | Ab 013 | 25 | 51 |
| 58. | Ab A14 | 26 | 50 |
| 59. | Ab 015 | 26 | 51 |
| 60. | Ab 016 | 27 | 47 |

TABLE 3-continued

Heavy and Light Chain Amino Acid Sequence Designations for Anti-HA Antibodies

| | Antibody | HC | SEQ ID NO: | LC | SEQ ID NO: |
|---|---|---|---|---|---|
| 61. | Ab A017 | 27 | 27 | 48 | 48 |
| 62. | Ab C18 | 27 | 27 | 49 | 49 |
| 63. | Ab A019 | 27 | 27 | 50 | 50 |
| 64. | Ab 031 | 24 | 24 | 45 | 45 |
| 65. | Ab 032 | 25 | 25 | 45 | 45 |
| 66. | Ab 033 | 26 | 26 | 45 | 45 |
| 67. | Ab 034 | 27 | 27 | 45 | 45 |
| 68. | Ab 037 | 24 | 24 | 46 | 46 |
| 69. | Ab 038 | 25 | 25 | 46 | 46 |
| 70. | Ab 039 | 26 | 26 | 46 | 46 |
| 71. | Ab 040 | 27 | 27 | 46 | 46 |
| 72. | Ab 043 | 25 | 25 | 60 | 60 |
| 73. | Ab 044 | 25 | 25 | 52 | 52 |
| 74. | Ab 045 | 25 | 25 | 57 | 57 |
| 75. | Ab 046 | 25 | 25 | 59 | 59 |
| 76. | Ab 047 | 25 | 25 | 55 | 55 |
| 77. | Ab 048 | 25 | 25 | 58 | 58 |
| 78. | Ab 049 | 25 | 25 | 54 | 54 |
| 79. | Ab 050 | 25 | 25 | 56 | 56 |
| 80. | Ab 051 | 25 | 25 | 53 | 53 |
| 81. | Ab 052 | 25 | 25 | 61 | 61 |
| 82. | Ab 067 | 25 | 25 | 153 | 153 |
| 83. | Ab 068 | 25 | 25 | 154 | 154 |
| 84. | Ab 069 | 25 | 25 | 155 | 155 |
| 85. | Ab 070 | 25 | 25 | 156 | 156 |
| 86. | Ab 071 | 162 | 162 | 52 | 52 |
| 87. | Ab 072 | 163 | 163 | 52 | 52 |
| 88. | Ab 073 | 25 | 25 | 165 | 165 |
| 89. | Ab 074 | 25 | 25 | 166 | 166 |
| 90. | Ab 075 | 25 | 25 | 167 | 167 |
| 91. | Ab 076 | 25 | 25 | 168 | 168 |
| 92. | Ab 077 | 25 | 25 | 169 | 169 |
| 93. | Ab 078 | 164 | 164 | 52 | 52 |
| 94. | Ab 079 | 164 | 164 | 155 | 155 |
| 95. | Ab 080 | 164 | 164 | 166 | 166 |
| 96. | Ab 081 | 164 | 164 | 169 | 169 |

In one embodiment, the anti-HA antibody comprises a heavy chain as defined in Table 4A below, and/or a light chain as defined in Table 4A below.

TABLE 4A

Heavy and Light Chain Amino Acid Sequence Designations

| HC | SEQ ID NO: | LC | SEQ ID NO: |
|---|---|---|---|
| 15 | 15 | 28 | 28 |
| 16 | 16 | 29 | 29 |
| 17 | 17 | 30 | 30 |
| 18 | 18 | 35 | 35 |
| 19 | 19 | 31 | 31 |
| 21 | 21 | 32 | 32 |
| 22 | 22 | 33 | 33 |
| 20 | 20 | 34 | 34 |
| 23 | 23 | 36 | 36 |
| 24 | 24 | 45 | 45 |
| 25 | 25 | 46 | 46 |
| 26 | 26 | 37 | 37 |
| 27 | 27 | 38 | 38 |
| Hc consensus (HC161) | 161 | 39 | 39 |
| 162 | 162 | 40 | 40 |
| 163 | 163 | 41 | 41 |
| 164 | 164 | 42 | 42 |
| | | 43 | 43 |
| | | 44 | 44 |
| | | 47 | 47 |
| | | 48 | 48 |
| | | 49 | 49 |
| | | 50 | 50 |
| | | 51 | 51 |
| | | 52 | 52 |

TABLE 4A-continued

Heavy and Light Chain Amino Acid Sequence Designations

| HC | SEQ ID NO: | LC | SEQ ID NO: |
|---|---|---|---|
| | | 53 | 53 |
| | | 54 | 54 |
| | | 55 | 55 |
| | | 56 | 56 |
| | | 57 | 57 |
| | | 58 | 58 |
| | | 59 | 59 |
| | | 60 | 60 |
| | | 61 | 61 |
| | | 153 | 153 |
| | | 154 | 154 |
| | | 155 | 155 |
| | | 156 | 156 |
| | | LC consensus (LC62) | 62 |
| | | 165 | 165 |
| | | 166 | 166 |
| | | 167 | 167 |
| | | 168 | 168 |
| | | 169 | 169 |

In one embodiment, an antibody featured in the disclosure comprises a heavy chain sequence as defined in Table 4A and a light chain sequence as defined in Table 4A.

In one embodiment, an antibody featured in the disclosure comprises a heavy chain sequence as defined herein, e.g., in Table 4A, where a dipeptide is fused to the N-terminus. Typically, the dipeptide is isoleucine-aspartic acid (Ile-Asp). In another embodiment, an antibody featured in the disclosure comprises a light chain sequence as defined herein, e.g., in Table 4A, where a dipeptide is fused to the N-terminus. Typically, the dipeptide is Ile-Asp. In yet another embodiment, an antibody featured in the disclosure comprises a heavy chain comprising an Ile-Asp dipeptide and a light chain comprising an Ile-Asp dipeptide. In the propeptide sequence of the heavy chain or light chain polypeptide, the Ile-Asp dipeptide occurs between the signal sequence and FR1. Heavy chain and light chain variable sequences comprising an Ile-Asp dipeptide at the N-terminus are identified in Table 4B.

TABLE 4B

Heavy and Light Chain Amino Acid Sequence Designations, where the Sequence Includes an N-terminal Ile-Asp Dipeptide

| HC | SEQ ID NO: | LC | SEQ ID NO: |
|---|---|---|---|
| 15-ID | 96 | 28-ID | 110 |
| 16-ID | 97 | 29-ID | 111 |
| 17-ID | 98 | 30-ID | 112 |
| 18-ID | 99 | 35-ID | 113 |
| 19-ID | 100 | 31-ID | 114 |
| 21-ID | 101 | 32-ID | 115 |
| 22-ID | 102 | 33-ID | 116 |
| 20-ID | 103 | 34-ID | 117 |
| 23-ID | 104 | 36-ID | 118 |
| 24-ID | 105 | 45-ID | 119 |
| 25-ID | 106 | 46-ID | 120 |
| 26-ID | 107 | 37-ID | 121 |
| 27-ID | 108 | 38-ID | 122 |
| HC consensus ID (161-ID) | 109 | 39-ID | 123 |
| | | 40-ID | 124 |
| | | 41-ID | 125 |
| | | 42-ID | 126 |
| | | 43-ID | 127 |
| | | 44-ID | 128 |
| | | 47-ID | 129 |
| | | 48-ID | 130 |

TABLE 4B-continued

Heavy and Light Chain Amino Acid Sequence Designations, where the Sequence Includes an N-terminal Ile-Asp Dipeptide

| HC | SEQ ID NO: | LC | SEQ ID NO: |
|---|---|---|---|
| | | 49-ID | 131 |
| | | 50-ID | 132 |
| | | 51-ID | 133 |
| | | 52-ID | 134 |
| | | 53-ID | 135 |
| | | 54-ID | 136 |
| | | 55-ID | 137 |
| | | 56-ID | 138 |
| | | 57-ID | 139 |
| | | 58-ID | 140 |
| | | 59-ID | 141 |
| | | 60-ID | 142 |
| | | 61ID | 143 |
| | | 153-ID | 157 |
| | | 154-ID | 158 |
| | | 155-ID | 159 |
| | | 156-ID | 160 |
| | | LC consensus ID (62-ID) | 144 |

In an embodiment, the binding agent, e.g., an anti-hemagglutinin (anti-HA) antibody molecule, or preparation, or isolated preparation thereof, comprising one or more or all of the following properties:

(a) it fails to produce any escape mutants as determined by the failure of a viral titer to recover following at least 10, 9, 8, 7, 6, or 5 rounds of serial infections in cell culture with a mixture of the antibody molecule and an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004;

(b) it produces fewer escape mutants than does a reference anti-HA antibody molecule, e.g., Ab 67-11, FI6, FI28, C179, F10, CR9114, or CR6261, e.g., when tested by the method described in (a);

(c) it prevents infection by at least 1, 2, 3, 4 or 5 influenza subtypes of Group 1, and by at least 1, 2, 3, 4 or 5 influenza subtypes of Group 2;

(d) it inhibits fusogenic activity of the targeted HA;

(e) it treats or prevents infection by a Group 1 virus, such as where the virus is an H1, H5, or H9 virus; and it treats or prevents infection by a Group 2 virus, such as where the virus is an H3 or H7 virus;

(f) it treats or prevents infection by influenza A strains H1N1 and H3N2;

(g) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg, or 1 mg/kg;

(h) it treats or prevents infection by influenza A H5N1 strains;

(i) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg, or 1 mg/kg;

(j) the concentration of antibody molecule required for 50% neutralization of influenza A virus is less than 10 µg/mL;

(k) it treats or prevents infection by an influenza B virus, e.g., B/Wisconsin/1/2010;

(l) it is effective for prevention or treatment of infection, e.g., in humans or mice, with an influenza B virus, e.g., B/Wisconsin/1/2010, when administered at 10 mg/kg, 6 mg/kg, 4 mg/kg, 3 mg/kg, 2 mg/kg, or 1 mg/kg;

(m) the concentration of antibody molecule required for 50% neutralization of influenza B virus, e.g., B/Wisconsin/1/2010, virus is less than 10 µg/mL;

(n) it prevents or minimizes secondary infection (e.g., secondary bacterial infection) or effects thereof on a subject;

(o) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg, or 1 mg/kg;

(p) it binds an epitope which comprises or consists of the hemagglutinin trimer interface; and (q) it binds an epitope other than that bound by a reference anti-HA antibody molecule, e.g., Ab 67-11, FI6, FI28, C179, F10, CR9114, or CR6261, e.g., as determined by structural analysis, e.g., by X-ray crystallography or NMR spectroscopy; or (r) in an embodiment it binds to an epitope, e.g., it has an epitope that overlaps with or is the same as, of an antibody disclosed herein, e.g., as determined by mutational analysis or crystal structure analysis.

In one embodiment, the binding agent, e.g., an anti-HA antibody molecule, has one or more of the following characteristics: the anti-HA antibody molecule prevents infection by at least 1, 2, 3, 4 or 5 influenza subtypes of Group 1, and by at least 1, 2, 3, 4 or 5 influenza subtypes of Group 2; the concentration of the anti-HA antibody molecule required for 50% neutralization of influenza A virus is less than 10 µg/mL; or the anti-HA antibody molecule binds an epitope that comprises or consists of the hemagglutinin trimer interface.

In one embodiment, the binding agent, e.g., an anti-HA antibody molecule, featured in the disclosure treats or prevents infection by a Group 1 virus, such as where the virus is an H1, H2, H5, H6, H8, H9, H12, H11, H13, H16, or H17 virus; and treats or prevents infection by a Group 2 virus, such as where the virus is an H3, H4, H7, H10 or H15 virus. In one embodiment, the binding agent, e.g., an anti-HA antibody molecule, featured in the disclosure prevents infection by at least 1, 2, 3, 4, 5, 6, 7, 8, 9, 10 or 11 influenza subtypes of Group 1, and by at least 1, 2, 3, 4, 5 or 6 influenza subtypes of Group 2. In one embodiment, the binding agent, e.g., an anti-HA antibody molecule, featured in the disclosure treats or prevents infection by one or more of H1N1, H2N2, H5N1, and H9N2, and also treats or prevents infection by one or more of H3N2 and H7N7. In an embodiment, a binding agent, e.g., antibody molecule, binds, and in some embodiments, neutralizes: at least one strain from the Group 1 H1, e.g., H1a or H1b, cluster and at least one strain from the Group 2 H3 or H7 cluster. In an embodiment, a binding agent, e.g., antibody molecule, binds, and in some embodiments, neutralizes: at least one strain from the Group 1 H1, e.g., H1a or H1b, cluster and at least one influenza B strain, e.g., B/Wisconsin/1/2010. In an embodiment, a binding agent, e.g., antibody molecule, binds, and in certain embodiments, neutralizes: at least one strain from the Group 2 H3 or H7 cluster and at least one influenza B strain, e.g., B/Wisconsin/1/2010. In an embodiment, a binding agent, e.g., antibody molecule, binds, and in certain embodiments, neutralizes: at least one strain from the Group 1 H1, e.g., H1a or H1b, cluster, at least one strain from the Group 2 H3 or H7 cluster, and at least one influenza B strain, e.g., B/Wisconsin/1/2010. In one embodiment, the binding agent, e.g., an anti-HA antibody molecule, featured in the disclosure treats or prevents infection by one or more of influenza B viruses, e.g., B/Wisconsin/1/2010.

In one embodiment, the anti-HA antibody molecule is not an anti-HA antibody molecule previously described in the art. For example, the anti-HA antibody molecule is other than one or more or all of Ab 67-11 (U.S. Provisional Application No. 61/645,453), FI6 (FI6, as used herein, refers to any specifically disclosed FI6 sequence in U.S. Application Publication No. 2010/0080813, U.S. Application Publication No. 2011/0274702, International Publication No. WO2013/011347, or Corti et al., *Science* 333:850-856, 2011, published online Jul. 28, 2011; FIGS. 12A to 12C of International Publication No. WO2013/170139 or U.S. Application Publication No. 2013/0302349), FI28 (U.S. Application Publication No. 2010/0080813), C179 (Okuno et al., *J. Virol.* 67:2552-1558, 1993), F10 (Sui et al., *Nat. Struct. Mol. Biol.* 16:265, 2009), CR9114 (Dreyfus et al., *Science.* 2012; 337(6100):1343-1348; published online Aug. 9, 2012), or CR6261 (Ekiert et al., *Science* 324:246-251, 2009; published online Feb. 26, 2009).

In one embodiment, the binding agent, e.g., an anti-HA antibody molecule, neutralizes infection with H1N1 and H3N2 in vitro. In another embodiment, binding agent, e.g., an anti-HA antibody molecule, neutralizes infection with H1N1 and H3N2 in vivo. In one embodiment, the binding agent, e.g., an anti-HA antibody molecule, neutralizes infection with H5N1 in vitro. In another embodiment, binding agent, e.g., an anti-HA antibody molecule, neutralizes infection with H5N1 in vivo. In one embodiment, the binding agent, e.g., an anti-HA antibody molecule, neutralizes infection with an influenza B virus, e.g., B/Wisconsin/1/2010, in vitro. In another embodiment, the binding agent, e.g., an anti-HA antibody molecule neutralizes infection with an influenza B virus, e.g., B/Wisconsin/1/2010, in vivo.

In another embodiment, the concentration of the binding agent, e.g., an anti-HA antibody molecule, required for 50% neutralization of influenza A virus is 10 µg/mL or less, such as 9 µg/mL or less, 8 µg/mL or less, 7 µg/mL or less, 6 µg/mL or less, or 5 µg/mL or less. In another embodiment, the concentration of the binding agent, e.g., an anti-HA antibody molecule, required for 60% neutralization of influenza A virus, 50% neutralization of influenza A virus, or 40% neutralization of influenza A virus is 10 µg/mL or less, such as 9 µg/mL or less, 8 µg/mL or less, 7 µg/mL or less, 6 µg/mL or less, or 5 µg/mL or less.

In yet another embodiment, the binding agent, e.g., an anti-HA antibody molecule, is effective for prevention or treatment of infection, e.g., in humans or mice, with H1N1 and H3N2, such as when administered at 50 mg/kg, 25 mg/kg, 10 mg/kg, 6.0 mg/kg, 5.0 mg/kg, 4.0 mg/kg, 3.0 mg/kg, 2.0 mg/kg, 1.0 mg/kg or less. In still another embodiment, the binding agent, e.g., the anti-HA antibody molecule, is effective for prevention or treatment of infection, e.g., in humans or mice, with H5N1, such as when administered at 50 mg/kg, 25 mg/kg, 10 mg/kg, 6.0 mg/kg, 5.0 mg/kg, 4.0 mg/kg, 3.0 mg/kg, 2.0 mg/kg, 1.0 mg/kg or less.

In another embodiment, a binding agent, e.g., an anti-HA antibody molecule, is effective for the treatment or prevention of a Group 1 virus, where the Group 1 virus is H1, H5, or H9, and in another embodiment, the binding agent, e.g., an anti-HA antibody molecule, is effective for the treatment or prevention of a Group 2 virus, where the Group 2 virus is H3 or H7. In another embodiment, the concentration of the binding agent, e.g., an anti-HA antibody molecule, required for 50% neutralization of influenza B virus, e.g., B/Wisconsin/1/2010, is 10 µg/mL or less, such as 9 µg/mL or less, 8 µg/mL or less, 7 µg/mL or less, 6 µg/mL or less, or 5 µg/mL or less. In another embodiment, the concentration of the binding agent, e.g., an anti-HA antibody molecule, required for 60% neutralization of influenza B virus, e.g., B/Wisconsin/1/2010, 50% neutralization of influenza B virus, e.g., B/Wisconsin/1/2010, or 40% neutralization of influenza B virus, e.g., B/Wisconsin/1/2010, is 10 µg/mL or less, such as 9 µg/mL or less, 8 µg/mL or less, 7 µg/mL or less, 6 µg/mL or less, or 5 µg/mL or less.

In another embodiment, the binding agent, e.g., an anti-HA antibody molecule, is a full length tetrameric antibody, a single chain antibody (scFv), a F(ab')$_2$ fragment, a Fab fragment, or an Fd fragment. In another embodiment, the heavy chain of the antibody molecule is a γ1 heavy chain, and in yet another embodiment, the light chain of the antibody molecule is a κ light chain or a λ light chain. In yet another embodiment, the anti-HA antibody molecule featured in the disclosure is an IgG1 antibody.

In an embodiment, the antibody molecule binds an epitope that has one, two, three, four, five, or all of, the following properties a)-f): a) it includes one, two, or all of, H3 HA1 residues N38, I278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment, the antibody molecule has properties: a) and b). In an embodiment, the antibody molecule has properties: c) and d). In an embodiment, the antibody molecule has properties: a); and c) or d). In an embodiment, the antibody molecule has properties: b); and c) or d). In an embodiment, the antibody molecule has properties: c); and a) or b). In an embodiment, the antibody molecule has properties: d); and a) or b). In an embodiment, the antibody molecule has properties: a), b), c) and d). In an embodiment, the antibody molecule has properties: a), b), c), d), e), and f).

In an embodiment, the antibody molecule has a $K_D$ for H3 of equal to or less than $10^{-6}$, wherein said $K_D$ is increased by at least 2, 5, 10, or 100 fold, by a mutation or mutations in any of: a) H3 HA1 residues N38, I278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$, wherein said $K_D$ is increased by no more than 2, or 5 fold, by a mutation or mutations in any of: c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57. In an embodiment, the antibody molecule has properties: aa) and bb). In an embodiment, the antibody molecule has properties: cc) and dd). In an embodiment, the antibody molecule has properties: aa); and cc) or dd). In an embodiment, the antibody molecule has properties: bb); and cc) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff).

In an embodiment, the antibody molecule has a $K_D$ for H1 of equal to or less than $10^{-6}$, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$, wherein said $K_D$ is increased by no more than 2, or 5-fold, by a mutation or mutations in any of: cc) H1 HA1 residues Q328 and S329; or dd) H1 HA2 residues G1, L2, F3, G4, and D46. In an embodiment, the antibody molecule has one, two, three or all of the following properties: a) and aa); b) and bb); c) and cc); or d) and dd). In an embodiment, the molecule has properties c), cc), d), and dd).

In an embodiment, the binding agent, e.g., a specific binding agent, e.g., an antibody molecule, comprises one or both of: a heavy chain variable region comprising at least, or more than, 60, 65, 70, 75, 80, 85, 87, 90, 95, 98 or 99 percent homology with a heavy chain variable region from Table 3, Table 4A, or Table 4B, or FIG. 2, FIG. 13 or FIG. 17 of International Publication No. WO2013/170139 or U.S. Application Publication No. 2013/0302349; and a light chain variable region comprising at least, or more than, 60, 65, 70, 75, 80, 85, 87, 90, 95, 98 or 99 percent homology with light chain variable region from Table 3, Table 4A, or Table 4B, or FIG. 3, FIG. 14 or FIG. 17 International Publication No. WO2013/170139 or U.S. Application Publication No. 2013/0302349.

In an embodiment, the antibody molecule comprises a heavy chain variable region 25 (SEQ ID NO: 25), or a structurally or functionally related variable heavy chain region as described herein. In an embodiment, the antibody molecule comprises a light chain variable region 52 (SEQ ID NO: 52), 155 (SEQ ID NO: 155), or 45 (SEQ ID NO: 45), or a structurally or functionally related variable light chain region as described herein. In an embodiment, the antibody molecule comprises: a heavy chain variable region 25 (SEQ ID NO: 25), or a structurally or functionally related variable heavy chain region as described herein; and a light chain variable region 52 (SEQ ID NO: 52), 155 (SEQ ID NO: 155), or 45 (SEQ ID NO: 45), or a structurally or functionally related variable light chain region as described herein.

In an embodiment, the antibody molecule comprises a heavy chain variable region comprising one, two, or all of CDR1, CDR2, and CDR3, from heavy chain variable region 25 (SEQ ID NO: 25), or a structurally or functionally related variable heavy chain region as described herein. In an embodiment, the antibody molecule comprises a light chain variable region comprising one, two, or all of CDR1, CDR2, and CDR3, from light chain variable region 52 (SEQ ID NO: 52), 155 (SEQ ID NO: 155), or 45 (SEQ ID NO: 45), or a structurally or functionally related sequence as described herein. In an embodiment, the antibody molecule comprises: a heavy chain variable region comprising one, two, or all of CDR1, CDR2, and CDR3, from heavy chain variable region 25 (SEQ ID NO: 25), or a structurally or functionally related variable heavy chain region as described herein; and a light chain variable region comprising one, two, or all of CDR1, CDR2, and CDR3, from light chain variable region 52 (SEQ ID NO: 52), 155 (SEQ ID NO: 155), or 45 (SEQ ID NO: 45), or a structurally or functionally related variable light chain region as described herein.

In an embodiment, the antibody molecule comprises a heavy chain variable region from FIG. 2 or FIG. 13 of International Publication No. WO2013/170139 or U.S. Application Publication No. 2013/0302349 or a structurally or functionally related variable heavy chain region as described herein. In an embodiment, the antibody molecule comprises a light chain variable region from FIG. 3 or FIG. 14 of International Publication No. WO2013/170139 or U.S. Application Publication No. 2013/0302349, or a structurally or functionally related variable light chain region as described herein. In an embodiment, the antibody molecule comprises one, two, or all of, a CDR1, CDR2, and CDR3 from a heavy chain variable region from FIG. 2 or FIG. 13 International Publication No. WO2013/170139 or U.S. Application Publication No. 2013/0302349, or a structurally or functionally related sequence as described herein. In an embodiment, the antibody molecule comprises one, two, or all of, a CDR1, CDR2, and CDR3 from a light chain variable region from FIG. 3 or FIG. 14 International Publication No. WO2013/170139 or U.S. Application Publication No. 2013/0302349, or a structurally or functionally related sequence as described herein. In an embodiment, the antibody molecule comprises one, two or all of, HC CDR1, HC CDR2, and HC CDR3 and one, two or all of, LC CDR1, LC CDR2, and LC CDR3 from an antibody disclosed in Table 3, or a structurally or functionally related sequence as described herein.

In another embodiment, the antibody molecule comprises the light chain LC45 (SEQ ID NO: 45). In yet another embodiment, the antibody comprises the light chain LC45, and the heavy chain HC25 (SEQ ID NO: 25) or 24 (SEQ ID NO: 24). In one embodiment, the antibody molecule comprises the light chain Ab032 (SEQ ID NO: 45) and the heavy chain 25 (SEQ ID NO: 25). In yet another embodiment, the antibody molecule comprises light chain LC52 (SEQ ID NO: 52) and heavy chain HC25 (SEQ ID NO: 25).

In an embodiment, the antibody molecule comprises one or both of: a) one or more framework regions (FRs) from heavy chain disclosed herein. E.g., the antibody molecule comprises one or more or all of FR1, FR2, FR3, or FR4, or FR sequences that differ individually, or collectively, by no more than 1, 2, 3, 4, of 5 amino acid residues, e.g., conservative residues, from a heavy chain disclosed herein; and b) one or more framework regions (FRs) from light chain disclosed herein. E.g., the antibody molecule comprises one or more or all of FR1, FR2, FR3, or FR4, or FR sequences that differ individually, or collectively, by no more than 1, 2, 3, 4, of 5 amino acid residues, e.g., conservative residues, from light chain disclosed herein.

In one aspect, an anti-HA antibody molecule featured in the disclosure, or preparation, or isolated preparation thereof, comprises: (a) a heavy chain immunoglobulin variable domain comprising a sequence at least 60, 70, 80, 85, 87, 90, 95, 97, 98, or 99, e.g., 90%, homologous, to a heavy chain consensus sequence provided herein, e.g., the heavy chain consensus sequence provided in FIG. 2 or FIG. 13 of International Publication No. WO2013/170139 or U.S. Application Publication No. 2013/0302349, e.g., the heavy chain consensus sequence provided in FIG. 2 of International Publication No. WO2013/170139 or U.S. Application Publication No. 2013/0302349, SEQ ID NO: 161; and (b) a light chain immunoglobulin variable domain comprising a sequence at least 60, 70, 80, 85, 87, 90, 95, 97, 98, or 99, e.g., 95%, homologous, to a light chain consensus sequence provided herein, e.g., the light chain consensus sequence provided in FIG. 3 or FIG. 14 of International Publication No. WO2013/170139 or U.S. Application Publication No. 2013/0302349, e.g., the light chain consensus sequence provided in FIG. 3 of International Publication No. WO2013/170139 or U.S. Application Publication No. 2013/0302349, SEQ ID NO: 62.

For example, in one embodiment, the anti-HA antibody molecule featured in the disclosure comprises one or both of: (a) a heavy chain immunoglobulin variable domain comprising the sequence of SEQ ID NO: 161, or a sequence at least 87% identical to SEQ ID NO: 161; and (b) a light chain immunoglobulin variable domain comprising the sequence SEQ ID NO: 62, or a sequence at least 95% identical to SEQ ID NO: 62.

In another embodiment the antibody molecule comprises: (a) a heavy chain immunoglobulin variable domain comprising the sequence of SEQ ID NO: 161, or a sequence at least 87% identical to SEQ ID NO: 161; and (b) a light chain immunoglobulin variable domain comprising the sequence SEQ ID NO:62, or a sequence at least 95% identical to SEQ ID NO: 62, wherein said antibody molecule: (i) fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) produces fewer escape mutants than does a reference anti-HA antibody molecule, e.g., Ab 67-11, FI6, FI28, C179, F10, CR9114, or CR6261, such as when tested by the method described in (i).

In an embodiment, the disclosure features an antibody molecule comprising one or both of: (a) a heavy chain immunoglobulin variable region comprising the sequence of SEQ ID NO: 161, or a sequence that differs from SEQ ID NO:161 by not more than 1, 2, 3, 4, 5, 6, 8, 10, 11, 12, 13, 14, 15 or 16, e.g., by no more than 2, 3, 4, or 5 amino acids, e.g., conservative amino acids; and (b) a light chain immunoglobulin variable domain comprising the sequence SEQ ID NO:62, or a sequence that differs from SEQ ID NO:62 that differs by no more than 1, 2, 3, 4 or 5 amino acids, e.g., conservative amino acids.

In one embodiment, the 1, 2, 3, 4, 5, 6, 8, 10, 11, 12, 13, 14, 15 or 16 amino acid differences, e.g., conservative amino acid differences, in the heavy chain immunoglobulin variable region are in the FR regions of the heavy chain immunoglobulin variable domain. In another embodiment, the 1, 2, 3, 4 or 5 amino acid differences, e.g., conservative amino acid differences, in the light chain immunoglobulin variable domain are in the FR regions of the light chain immunoglobulin variable domain. In one embodiment, the amino acid differences in the heavy chain immunoglobulin variable region, or in the light chain immunoglobulin variable region, are conservative amino acid changes.

In an embodiment, the binding agent, e.g., an antibody molecule, binds to an epitope, e.g., it has an epitope that overlaps with or is the same as, of an antibody disclosed herein, e.g., as determined by mutational analysis or crystal structure analysis.

In an embodiment, the antibody molecule comprises one or both of: a) one or more framework regions (FRs) from heavy chain consensus sequence disclosed herein. e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from heavy chain consensus sequence disclosed herein; and b) one or more framework regions (FRs) from light chain consensus sequence disclosed herein. e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from light chain consensus disclosed herein. In an embodiment, the binding agent, e.g., an antibody molecule, specifically binds the HA antigen.

In another aspect, the disclosure features, a binding agent, e.g., an antibody molecule, or preparation, or isolated preparation thereof, comprising a structural or functional property of Ab 044.

In an embodiment, the antibody molecule competes with a reference antibody molecule, e.g., an antibody molecule described herein, for binding to a substrate, e.g., an HA. The reference antibody molecule can be: a) an antibody molecule comprising: i) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-D-Y-K-N-Y-L-A (SEQ ID NO:145); a CDR2 comprising the sequence W-G-S-Y-L-E-S(SEQ ID NO:72); and a CDR3 comprising the sequence Q-Q-H-Y-R-T-P-P-S(SEQ ID NO:73); b) an antibody molecule comprises one or both of: (i) a heavy chain immunoglobulin variable region segment comprising SEQ ID NO: 25; and (ii) a light chain variable region segment comprising SEQ ID NO:52; or c) Ab 044.

The HA can be from a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecules or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry.

The antibody molecule can compete with the reference antibody such that binding of the reference antibody is decreased by 50% or more. In an embodiment, the antibody molecule binds to the same epitope, or a portion thereof, which the reference antibody molecule binds. In an embodiment, the antibody molecule does not bind to the same epitope, or a portion thereof, which the reference antibody molecule binds.

In an embodiment, the antibody molecule binds to the same epitope, or a portion thereof, on HA, as does a reference antibody molecule, e.g. an antibody molecule disclosed herein. The reference antibody molecule can be: a) an antibody molecule comprising: i) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-

A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-D-Y-K-N-Y-L-A (SEQ ID NO:145); a CDR2 comprising the sequence W-G-S-Y-L-E-S(SEQ ID NO:72); and a CDR3 comprising the sequence Q-Q-H-Y-R-T-P-P-S (SEQ ID NO:73); b) an antibody molecule comprises one or both of: (i) a heavy chain immunoglobulin variable region segment comprising SEQ ID NO: 25; and (ii) a light chain variable region segment comprising SEQ ID NO:52; or c) Ab 044.

The HA can be HA1 or HA5, e.g., from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004 Binding to the same epitope, or a portion thereof, can be shown by one or more of: a) mutational analysis, e.g., binding to HA, or binding affinity for HA, is decreased or abolished if a residue is mutated; b) analysis, e.g., comparison, of the crystal structure of the antibody molecule and HA and the crystal structure of a reference antibody and HA, e.g., to determine the touch points of each; c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and d) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; or c) flow cytometry.

The antibody molecule can compete with the reference antibody such that binding of the reference antibody is decreased by 50% or more. In an embodiment, the binding agent, e.g., an antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 52.

In an embodiment, the binding agent, e.g., an antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 52, wherein, each HC CDR differs by no more than 1, 2, 3, 4 or 5 amino acids, e.g., 1 or 2, e.g., conservative amino acids, from the corresponding CDR of SEQ ID NO: 25 and each LC CDR differs by no more than 1, 2, 3, 4 or 5 amino acids, e.g., 1 or 2, e.g., conservative amino acids, from the corresponding CDR of SEQ ID NO: 52.

In an embodiment, the binding agent, e.g., an antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 52, wherein the antibody molecule comprises 1, 2, 3, 4, 5, or all of: (i) a HC CDR1 comprising: S at the 1st position and A at the 3rd position in HC CDR1; (ii) a HC CDR2 comprising one or both, e.g., one of: V at the $2^{nd}$ position; or N at the $7^{th}$ position and Q at the $16^{th}$ position in HC CDR2; (iii) a HC CDR3 comprising: R at the 3rd position (and optionally, L at the $3^{rd}$ position); (iv) a LC CDR1 comprising one or both of, e.g., one of: I at the 3rd position; or D at the 6th position in LC CDR1; (v) a LC CDR2 comprising one, two, or three of, e.g., one of: G at the $2^{nd}$ position; Y at the $4^{th}$ position; or L at the $5^{th}$ position in LC CDR2; (vi) a LC CDR3 comprising: S at the $9^{th}$ position in LC CDR3.

In an embodiment, the binding agent, e.g., an antibody molecule, comprises: (a) a heavy chain immunoglobulin variable region segment comprising SEQ ID NO:25 (or a sequence that differs by no more than 1, 2, 3, 4 or 5 amino acids, e.g., conservative amino acids, therefrom); and (b) a light chain variable region segment comprising SEQ ID NO:52 (or a sequence that differs by no more than 1, 2, 3, 4 or 5 amino acids, e.g., conservative amino acids, therefrom).

In an embodiment, the binding agent, e.g., an antibody molecule, comprises one or both of: (a) a heavy chain immunoglobulin variable region segment comprising: a CDR1 comprising the sequence S-Y-A-M-H (SEQ ID NO:68) (or a sequence that differs by no more than, 1, 2, 3, 4, or 5, e.g., 1 or 2 amino acids, e.g., conservative amino acids, therefrom); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom); a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom); and (b) a light chain variable region segment comprising: a CDR1 comprising the sequence: Q-S-I-T-F-D-Y-K-N-Y-L-A (SEQ ID NO:145) (or a sequence that differs by no more than, 1, 2, 3, 4, or 5, e.g., 1 or 2 amino acids, e.g., conservative amino acids, therefrom); a CDR2 comprising the sequence W-G-S-Y-L-E-S(SEQ ID NO:72) (or a sequence that differs by no more than, 1, 2, 3, 4, or 5, e.g., 1 or 2 amino acids, e.g., conservative amino acids, therefrom); a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom).

In an embodiment, the binding agent, e.g., an antibody molecule, comprises one or both of: a) LC CDR1-3, that collectively, differ from the AB 044 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the AB 044 HC CDR1-3 by no more than, 1, 2, 3, 4, 5, 6, 7, 8, 9, or 10, e.g., 1, 2, 3, or 4, amino acids, e.g., conservative amino acids.

In one embodiment, the antibody molecule comprises one or both of: (a) a heavy chain immunoglobulin variable region segment comprising SEQ ID NO: 25; and (b) a light chain variable region segment comprising SEQ ID NO: 52.

In an embodiment, the binding agent is an antibody molecule comprising one or both of: (a) a heavy chain immunoglobulin variable region segment comprising: a CDR1 comprising the sequence S-Y-A-M-H (SEQ ID NO:68) (or a sequence that differs by no more than, 1, 2, or 3, e.g., 1 or 2, amino acids, e.g., conservative amino acids, there from, optionally provided that at least 1 or 2 of the highlighted residue are not changed, e.g., both S and A are not changed); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., V or both N and Q or all three of V, N, and Q are not changed); a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom, optionally provided that R is not changed); and (b) a light chain variable region segment comprising: a CDR1 comprising the sequence: Q-S-I-T-F-D-Y-K-N-Y-L-A (SEQ ID NO:145) (or a sequence that differs by no more than, 1, 2, 3, 4, or 5, e.g., 1 or 2, amino acids, e.g., conservative amino acids, therefrom, optionally provided that at least for 2 of the highlighted residues are not changed, e.g., I or D is not changed); a CDR2 comprising the sequence W-G-S-Y-L-E-S(SEQ ID NO:72) (or a sequence that differs by no more than, 1, 2, 3, 4, or 5, e.g., 1 or 2, amino acids, e.g., conservative amino acids, therefrom, optionally provided that at least 1, 2 or 3 of the highlighted residues are not changed, e.g., 1, 2 or all of G, Y, and L are not changed); a CDR3 comprising the sequence Q-Q-H-Y-R-T-P-P-S(SEQ ID NO:73) (or a sequence that differs by no more than, 1, 2, 3, 4, or 5, e.g., 1 or 2 amino acids, e.g., conservative amino acids, therefrom, optionally provided that at least 1 or both of the highlighted residues are not changed, e.g., S is not changed). In an embodiment a CDR of the light or heavy chain includes one of the highlighted residues, or one of the highlighted combinations of residues, for that CDR, (i.e., while other residues in that CDR might be changed, the highlighted residue or combination of residues, are not changed). E.g., in an embodiment, V or both N and Q, for heavy chain CDR2 are not changed.

In an embodiment, a CDR of the light and a CDR of the heavy chain each includes one of the highlighted residues, or one of the highlighted combinations of residues, for that CDR. In an embodiment each of two CDRs in the antibody molecule includes one of the highlighted residues, or one of the highlighted combinations of residues, for that CDR. In some embodiments, both are in the light chain. In some embodiments, both are in the heavy chain. In an embodiment each of the three CDRs in the heavy chain includes one of the highlighted residues, or one of the highlighted combinations of residues, for that CDR. In an embodiment each of the three CDRs in the light chain includes one of the highlighted residues, or one of the highlighted combinations of residues, for that CDR. In an embodiment each of the six CDRs in the heavy and light chain includes one of the highlighted residues, or one of the highlighted combinations of residues, for that CDR.

In one embodiment, the binding agent is an antibody molecule that comprises one or more or all of the following properties: (a) both S and A in HC CDR1 are unchanged; (b) V or both N and Q or all three of V, N, and Q in HC CDR2 are unchanged; (c) R in HC CDR3 is unchanged; (d) One or both of I and D in LC CDR1 are unchanged. (e) 1, 2 or 3 of G, Y and L in LC CDR2 are unchanged; or (f) S in LC CDR3 is unchanged. In an embodiment, the antibody molecule comprises 1, 2, 3, 4, 5, or all 6 properties selected from (a) to (f). In an embodiment, the antibody molecule comprises a heavy chain having a one or more properties selected from (a), (b), and (c) and a light chain having one or more properties selected from (d), (e), and (f).

In one embodiment, the binding agent, e.g., an antibody molecule, comprises one or both of:

```
(a) a heavy chain immunoglobulin variable region
segment comprising:
                                      (SEQ ID NO: 68)
a CDR1 comprising the sequence
S-Y-A-M-H;

(SEQ ID NO: 69)
a CDR2 comprising the sequence
V-V-S-Y-D-G-N-Y-K-Y-Y-A-D-S-V-Q-G;

(SEQ ID NO: 70)
a CDR3 comprising the sequence
D-S-R-L-R-S-L-L-Y-F-E-W-L-S-Q-G-Y-F-N-P;
and (b) a light chain variable region segment
comprising:
                                      (SEQ ID NO: 145)
a CDR1 comprising the sequence
Q-S-I-T-F-D-Y-K-N-Y-L-A;

(SEQ ID NO: 72)
a CDR2 comprising the sequence
W-G-S-Y-L-E-S;
and (SEQ ID NO: 73)
a CDR3 comprising the sequence
Q-Q-H-Y-R-T-P-P-S.
```

In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) it produces fewer escape mutants than does a reference anti-HA antibody molecule, such as Ab 67-11, FI6, FI28, C179, F10, CR9114, or CR6261, such as when tested by the method described in (i).

In an embodiment, the antibody molecule comprises one or both of: a) one or more framework regions (FRs) from SEQ ID NO: 25 e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 25; and b) one or more framework regions (FRs) from SEQ ID NO: 52. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 52.

In one embodiment, the antibody molecule comprises: (a) a heavy chain immunoglobulin variable region segment that further comprises one or more or all of: an FR1 comprising the sequence Q-V-Q-L-L-E-T-G-G-G-L-V-K-P-G-Q-S-L-K-L-S-C-A-A-S-G-F-T-F-T (SEQ ID NO:74) (or a sequence that differs by no more than, 1, 2, 3, 4, or 5, e.g., 1 or 2, amino acids, e.g., conservative amino acids, therefrom, optionally provided that T is not changed); an FR2 comprising the sequence W-V-R-Q-P-P-G-K-G-L-E-W-V-A (SEQ ID NO:75) (or a sequence that differs by no more than, 1, 2, 3, 4, or 5, e.g., 1 or 2, amino acids, e.g., conservative amino acids, therefrom, optionally provided that W is not changed, or that if changed, is other than R); an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76) (or a sequence that differs by no more than, 1, 2, 3, 4, or 5, e.g., 1 or 2, amino acids, e.g., conservative amino acids, therefrom, optionally provided that one, two or three of I, R, or L is not changed, or that if I is changed it is other than G, if R is changed it is other than P. or if L is changed it is other than A); and an FR4 comprising the sequence W-G-Q-G-T-T-L-T-V-S-S(SEQ ID NO:77) (or a sequence that differs by no more than, 1, 2, 3, 4, or 5, e.g., 1 or 2, amino acids, e.g., conservative amino acids, therefrom) or W-G-Q-G-T-T-V-T-V-S-S(SEQ ID NO:171) (or a sequence that differs by no more than, 1, 2, 3, 4, or 5, e.g., 1 or 2, amino acids, e.g., conservative amino acids, therefrom); and (b) a light chain immunoglobulin variable region segment comprising one or more or all of: an FR1 comprising the sequence D-I-Q-M-T-Q-S-P-S-S-L-S-A-S-V-G-D-R-V-T-I-T-C-R-S-S(SEQ ID NO:78) (or a sequence that differs by no more than, 1, 2, 3, 4, or 5, e.g., 1 or 2, amino acids, e.g., conservative amino acids, therefrom, optionally provided that R is not changed); an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom); an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom). In an embodiment a FR of the light or heavy chain includes one of the highlighted residues, or one of the highlighted combinations of residues, for that FR, (i.e., while other residues in that FR might be changed, the highlighted residue or combination of residues, are not changed). E.g., in an embodiment, one, two or three of I, R, or L for heavy chain FR3 is not changed.

In an embodiment, a FR of the light and a FR of the heavy chain each includes one of the highlighted residues, or one of the highlighted combinations of residues, for that FR. In an embodiment each of two FRs in the antibody molecule includes one of the highlighted residues, or one of the highlighted combinations of residues, for that FR. In some embodiments, both are in the light chain. In some embodiments, both are in the heavy chain. In an embodiment each of FR2 and FR3 in the heavy chain includes one of the highlighted residues, or one of the highlighted combinations of residues, for that FR. In an embodiment each of FR1 and FR2 in the heavy and light chain includes one of the highlighted residues for that FR. In an embodiment all of the highlighted residues in heavy chain FR1-4 are unchanged. In an embodiment all of the highlighted residues in light chain FR1-4 are unchanged. In an embodiment all of the highlighted residues in both heavy and light chain FR1-4 are unchanged. In an embodiment, sequence of FR1 of the heavy chain variable region segment is Q-V-Q-L-L-E-T-G-G-G-L-V-K-P-G-Q-S-L-K-L-S-C-A-A-S-G-F-T-F-T (SEQ ID NO: 74). In an embodiment, sequence of FR1 of the heavy chain variable region segment is E-V-Q-L-L-E-S-G-G-G-L-V-K-P-G-Q-S-L-K-L-S-C-A-A-S-G-F-T-F-T (SEQ ID NO: 183).

In another embodiment, the binding agent, e.g., an antibody molecule, comprises one or more or all of the following properties: (a) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (b) it produces fewer escape mutants than does a reference anti-HA antibody molecule, e.g., Ab 67-11, FI6, FI28, C179, or CR6261, e.g., when tested by the method described in (a); (c) it binds with high affinity to a hemagglutinin (HA) of at least 1, 2, 3, 4 or 5 influenza subtypes of Group 1 and at least 1, 2, 3, 4 or 5 influenza subtypes of Group 2; (d) it treats or prevents infection by at least 1, 2, 3, 4 or 5 influenza subtypes of Group 1, and by at least 1, 2, 3, 4 or 5 influenza subtypes of Group 2; (e) it inhibits fusogenic activity of the targeted HA; (f) it treats or prevents infection by a Group 1 virus, wherein the virus is an H1, H5, or H9 virus; and treats or prevents infection by a Group 2 virus, wherein the virus is an H3 or H7 virus; (g) it treats or prevents infection by influenza A strains H1N1 and H3N2; (h) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg or 1 mg/kg; (i) it treats or prevents infection by influenza A strains H5N1; (j) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg or 1 mg/kg; (k) it binds with high affinity to a hemagglutinin (HA) of an influenza B virus, e.g., B/Wisconsin/1/2010; (l) it treats or prevents infection by an influenza B virus, e.g., B/Wisconsin/1/2010; (m) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg or 1 mg/kg; (n) the concentration of antibody molecule required for 50% neutralization of influenza A virus is less than 10 µg/mL; (o) the concentration of antibody molecule required for 50% neutralization of influenza B virus, e.g., B/Wisconsin/1/2010, is less than 10 µg/mL; (p) it prevents or minimizes secondary infection (e.g., secondary bacterial infection) or effects thereof on a subject; (q) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg or 1 mg/kg; (r) it binds an epitope which comprises or consists of the hemagglutinin trimer interface; and (s) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In an embodiment, the binding agent, e.g., an antibody molecule, specifically binds the HA antigen. In an embodiment, the antibody molecule binds an epitope that has one, two, three, four, five, or all of, the following properties a)-f): a) it includes one, two, or all of, H3 HA1 residues N38, I278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment, the antibody molecule has properties: a) and b). In an embodiment, the antibody molecule has properties: c) and d). In an embodiment, the antibody molecule has properties: a); and c) or d). In an embodiment, the antibody molecule has properties: b); and c) or d). In an embodiment, the antibody molecule has properties: c); and a) or b). In an embodiment, the antibody molecule has properties: d); and a) or b). In an embodiment, the antibody molecule has properties: a), b), c) and d). In an embodiment, the antibody molecule has properties: a), b), c), d), e), and f).

In an embodiment, the antibody molecule has a $K_D$ for H3 of equal to or less than $10^{-6}$, wherein said $K_D$ is increased by at least 2, 5, 10, or 100 fold, by a mutation or mutations in any of: a) H3 HA1 residues N38, I278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$, wherein said $K_D$ is increased by no more than 2, or 5-fold, by a mutation or mutations in any of: c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57.

In an embodiment, the antibody molecule has properties: aa) and bb). In an embodiment, the antibody molecule has properties: cc) and dd). In an embodiment, the antibody molecule has properties: aa); and cc) or dd). In an embodiment, the antibody molecule has properties: bb); and cc) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff).

In an embodiment, the antibody molecule has a $K_D$ for H1 of equal to or less than $10^{-6}$, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$, wherein said $K_D$ is increased by no more than 2, or 5-fold, by a mutation or mutations in any of: cc) H1 HA1 residues Q328 and S329; or dd) H1 HA2 residues G1, L2, F3, G4, and D46.

In an embodiment, the antibody molecule has one, two, three or all of the following properties: a) and aa); b) and bb); c) and cc); d) and dd). In an embodiment, the molecule has properties c), cc), d), and dd).

In another aspect, the disclosure features, a binding agent, e.g., an antibody molecule, or preparation, or isolated preparation thereof, comprising a structural or functional property of Ab 069.

In an embodiment, the antibody molecule competes with a reference antibody molecule, e.g., an antibody molecule described herein, for binding to a substrate, e.g., an HA. The reference antibody molecule can be: a) an antibody molecule comprising: i) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-E-Y-K-N-Y-L-A (SEQ ID NO:172); a CDR2 comprising the sequence W-G-S-Y-L-E-S(SEQ ID NO:72); and a CDR3 comprising the sequence Q-Q-H-Y-R-T-P-P-S(SEQ ID NO:73); b) an antibody molecule comprises one or both of: (i) a heavy chain immunoglobulin variable region segment comprising SEQ ID NO: 25; and (ii) a light chain variable region segment comprising SEQ ID NO:155; or c) Ab 069.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; c) flow cytometry.

The antibody molecule can compete with the reference antibody such that binding of the reference antibody is decreased by 50% or more. In an embodiment, the antibody molecule binds to the same epitope, or a portion thereof, which the reference antibody molecule binds. In an embodiment, the antibody molecule does not bind to the same epitope, or a portion thereof, which the reference antibody molecule binds. In an embodiment, the antibody molecule binds to the same epitope, or a portion thereof, on HA, as does a reference antibody molecule, e.g. an antibody molecule disclosed herein. The reference antibody molecule can be: a) an antibody molecule comprising: i) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-E-Y-K-N-Y-L-A (SEQ ID NO:172); a CDR2 comprising the sequence W-G-S-Y-L-E-S(SEQ ID NO:72); and a CDR3 comprising the sequence Q-Q-H-Y-R-T-P-P-S(SEQ ID NO:73); b) an antibody molecule comprises one or both of: (i) a heavy chain immunoglobulin variable region segment comprising SEQ ID NO: 25; and (ii) a light chain variable region segment comprising SEQ ID NO:155; or c) Ab 069.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Binding to the same epitope, or a portion thereof, can be shown by one or more of: a) mutational analysis, e.g., binding or lack thereof to mutant HA, e.g., if a residue is mutated; b) analysis, e.g., comparison, of the crystal structure of the antibody molecule and HA and the crystal structure of a reference antibody and HA, e.g., to determine the touch points of each; c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; or d) (c) and one or both of (a) and (b);

Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; c) flow cytometry. The antibody molecule can compete with the reference antibody such that binding of the reference antibody is decreased by 50% or more.

In an embodiment, the binding agent, e.g., an antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 155. In an embodiment, the binding agent, e.g., an antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 155, wherein each HC CDR differs by no more than 1, 2, 3, 4 or 5 amino acids, e.g., 1 or 2, e.g., conservative amino acids, from the corresponding CDR of SEQ ID NO: 25 and each LC CDR differs by no more than 1, 2, 3, 4 or 5 amino acids, e.g., 1 or 2, e.g., conservative amino acids, from the corresponding CDR of SEQ ID NO: 155. In an embodiment, the binding agent, e.g., an antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 155, wherein the antibody molecule comprises 1, 2, 3, 4, 5, or all of: (i) a HC CDR1 comprising: S at the 1st position and A at the 3rd position in HC CDR1; (ii) a HC CDR2 comprising one or both, e.g., one of: V at the 2nd position; or N at the 7$^{th}$ position and Q at the 16$^{th}$ position in HC CDR2; (iii) a HC CDR3 comprising: R at the 3rd position (and optionally, L at the 3$^{rd}$ position); (iv) a LC CDR1 comprising one or both of, e.g., one of: I at the 3rd position; or E at the 6th position in LC CDR1; (v) a LC CDR2 comprising one, two or three of, e.g., one of: G at the 2nd position; Y at the 4$^{th}$ position; or L at the 5$^{th}$ position in LC CDR2; (vi) a LC CDR3 comprising: S at the 9$^{th}$ position in LC CDR3. In an embodiment, the binding agent, e.g., an antibody molecule, comprises one or both of: (a) a heavy chain immunoglobulin variable region segment comprising SEQ ID NO:25 (or a sequence that differs by no more than 1, 2, 3, 4 or 5 amino acids, e.g., conservative amino acids, therefrom); and (b) a light chain variable region segment comprising SEQ ID NO:155 (or a sequence that differs by no more than 1, 2, 3, 4 or 5 amino acids, e.g., conservative amino acids, therefrom). In one embodiment, the antibody molecule comprises one or both of: (a) a heavy chain immunoglobulin variable region segment comprising SEQ ID NO: 25; and (b) a light chain variable region segment comprising SEQ ID NO:155.

In an embodiment, the binding agent, e.g., an antibody molecule, comprises one or both of: (a) a heavy chain immunoglobulin variable region segment comprising: a CDR1 comprising the sequence S-Y-A-M-H (SEQ ID NO:68) (or a sequence that differs by no more than, 1, 2, 3, 4, or 5, e.g., 1 or 2 amino acids, e.g., conservative amino acids, therefrom); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom); a CDR3 comprising the sequence D-S-R-L-R-S-L-L-Y-F-E-W-L-S-Q-G-Y-F-N-P (SEQ ID NO:70) (or a sequence that differs by no more than 1, 2, 3, 4, or 5, e.g., 1 or 2 amino acids, e.g., conservative amino acids, therefrom); and (b) a light chain variable region segment comprising: a CDR1 comprising the sequence: Q-S-I-T-F-E-Y-K-N-Y-L-A (SEQ ID NO: 172) or a sequence that differs by no more than, 1, 2, 3, 4, or 5, e.g., 1 or 2 amino acids, e.g., conservative amino acids, therefrom); a CDR2 comprising the sequence W-G-S-Y-L-E-S(SEQ ID NO:72) (or a sequence that differs by no more than, 1, 2, 3, 4, or 5, e.g., 1 or 2 amino acids, e.g., conservative amino acids, therefrom); a CDR3 comprising the sequence Q-Q-H-Y-R-T-P-P-S(SEQ ID NO:73) (or a sequence that differs by no more than, 1, 2, 3, 4, or 5, e.g., 1 or 2 amino acids, e.g., conservative amino acids, therefrom).

In an embodiment, the binding agent, e.g., an antibody molecule, comprises one or both of: a) LC CDR1-3, that collectively, differ from the AB 069 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the AB 069 HC CDR1-3 by no more than, 1, 2, 3, 4, 5, 6, 7, 8, 9, or 10, e.g., 1, 2, 3, or 4, amino acids, e.g., conservative amino acids.

In an embodiment, the binding agent is an antibody molecule comprising one or both of: (a) a heavy chain immunoglobulin variable region segment comprising: a CDR1 comprising the sequence S̲-Y-A̲-M-H (SEQ ID NO:68) (or a sequence that differs by no more than, 1, 2, or 3, e.g., 1 or 2 amino acids, e.g., conservative amino acids, therefrom, optionally provided that at least 1 or 2 of the highlighted residues are not changed, e.g., both S̲ and A̲ are not changed); a CDR2 comprising the sequence V-V̲-S-Y-D-G-N̲-Y-K-Y-Y-A-D-S-V-Q̲-G (SEQ ID NO:69) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., V̲ or both N̲ and Q̲ or all three of V̲, N̲, and Q̲ are not changed); a CDR3 comprising the sequence D-S-R̲-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom optionally provided that, R̲ is not changed); and (b) a light chain variable region segment comprising: a CDR1 comprising the sequence: Q-S-I̲-T-F̲-E̲-Y-K-N-Y-L-A (SEQ ID NO: 172) or a sequence that differs by no more than, 1, 2, 3, 4, or 5, e.g., 1 or 2 amino acids, e.g., conservative amino acids, therefrom, optionally provided that at least 1 or 2 of the highlighted residues are not changed, e.g., I or E is not changed); a CDR2 comprising the sequence W-G-S-Y-L-E-S(SEQ ID NO:72) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., 1, 2 or all of G, Y, and L are not changed); a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom, optionally provided that, at least one or both of the highlighted residues are not changed, e.g., S is not changed).

In an embodiment, a CDR of the light or heavy chain includes one of the highlighted residues, or one of the highlighted combinations of residues, for that CDR, (i.e., while other residues in that CDR might be changed, the highlighted residue or combination of residues, are not changed). In an embodiment a CDR of the light and a CDR of the heavy chain each includes one of the highlighted residues, or one of the highlighted combinations of residues, for that CDR. In an embodiment, each of two CDRs in the antibody molecule includes one of the highlighted residues, or one of the highlighted combinations of residues, for that CDR. In some embodiments, both are in the light chain. In some embodiments, both are in the heavy chain. In an embodiment, each of the three CDRs in the heavy chain includes one of the highlighted residues, or one of the highlighted combinations of residues, for that CDR. In an embodiment, each of the three CDRs in the light chain includes one of the highlighted residues, or one of the highlighted combinations of residues, for that CDR. In an embodiment, each of the six CDRs in the heavy and light chain includes one of the highlighted residues, or one of the highlighted combinations of residues, for that CDR.

In one embodiment, the binding agent is an antibody molecule that comprises one or more or all of the following properties: (a) both S and A in HC CDR1 are unchanged; (b) V or both N and or all three of V, N, and Q in HC CDR2 are unchanged; (c) R in HC CDR3 is unchanged; (d) one or both of I and E in LC CDR1 are unchanged; (e) 1, 2 or 3 of G, Y and L in LC CDR2 are unchanged; (f) S in LC CDR3 is unchanged. In an embodiment, the antibody molecule comprises 1, 2, 3, 4, 5, or all 6 properties selected from (a) to (f). In an embodiment, the antibody molecule comprises a heavy chain having a one or more properties selected from (a), (b), and (c) and a light chain having one or more properties selected from (d), (e), and (f). In one embodiment, the antibody molecule comprises one or both of: (a) a heavy chain immunoglobulin variable region segment comprising: a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); a CDR3 comprising the sequence D-S-R-L-R-S-L-L-Y-F-E-W-L-S-Q-G-Y-F-N-P (SEQ ID NO:70); and (b) a light chain variable region segment comprising: a CDR1 comprising the sequence Q-S-I-T-F-E-Y-K-N-Y-L-A (SEQ ID NO: 172); a CDR2 comprising the sequence W-G-S-Y-L-E-S(SEQ ID NO: 72); and a CDR3 comprising the sequence Q-Q-H-Y-R-T-P-P-S (SEQ ID NO: 73).

In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) it produces fewer escape mutants than does a reference anti-HA antibody molecule, such as Ab 67-11, FI6, FI28, C179, F10, CR9114, or CR6261, such as when tested by the method described in (i).

In an embodiment, the antibody molecule comprises one or both of: a) one or more framework regions (FRs) from SEQ ID NO: 25, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 25; and b) one or more framework regions (FRs) from SEQ ID NO: 155, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 155.

In one embodiment, the antibody molecule comprises: (a) a heavy chain immunoglobulin variable region segment that further comprises one or more or all of: an FR1 comprising the sequence Q-V-Q-L-L-E-T-G-G-G-L-V-K-P-G-Q-S-L-K-L-S-C-A-A-S-G-F-T-F-T (SEQ ID NO:74) (or a sequence that differs by no more than, 1, 2, 3, 4, or 5, e.g., 1 or 2, amino acids, e.g., conservative amino acids, therefrom, optionally provided that T is not changed); an FR2 comprising the sequence W-V-R-Q-P-P-G-K-G-L-E-W-V-A (SEQ ID NO:75) (or a sequence that differs by no more than, 1, 2, 3, 4, or 5, e.g., 1 or 2, amino acids, e.g., conservative amino acids, therefrom, optionally provided that W is not changed, or that if changed, is other than R); an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76) (or a sequence that differs by no more than, 1, 2, 3, 4, or 5, e.g., 1 or 2, amino acids, e.g., conservative amino acids, therefrom, optionally provided that one, two or three of I, R, or L is not changed, or that if I is changed it is other than G, if R is changed it is other than P. or if L is changed it is other than A); and (b) the light chain immunoglobulin variable region segment comprises one or more or all of: an FR1 comprising the sequence D-I-Q-M-T-Q-S-P-S-S-L-S-A-S-V-G-D-R-V-T-I-T-C-R-S-S(SEQ ID NO:78) (or a sequence that differs by no more than, 1, 2, 3, 4, or 5, e.g., 1 or 2 amino acids, e.g., conservative amino acids, therefrom, optionally provided that R is not changed); an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom); an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom). In an embodiment a FR of the light or heavy chain includes one of the highlighted residues, or one of the highlighted combinations of residues, for that FR, (i.e., while other residues in that FR might be changed, the highlighted residue or combination of residues, are not changed). E.g., in an embodiment, one, two or three of I, R, or L for heavy chain FR3 is not changed.

In an embodiment, a FR of the light and a FR of the heavy chain each includes one of the highlighted residues, or one of the highlighted combinations of residues, for that FR. In an embodiment each of two FRs in the antibody molecule includes one of the highlighted residues, or one of the highlighted combinations of residues, for that FR. In some embodiments, both are in the light chain. In some embodiments, both are in the heavy chain. In an embodiment each of FR2 and FR3 in the heavy chain includes one of the highlighted residues, or one of the highlighted combinations of residues, for that FR. In an embodiment each of FR1 and FR2 in the heavy and light chain includes one of the highlighted residues for that FR. In an embodiment all of the highlighted residues in heavy chain FR1-4 are unchanged. In an embodiment all of the highlighted residues in light chain FR1-4 are unchanged. In an embodiment all of the highlighted residues in both heavy and light chain FR1-4 are unchanged.

In another embodiment, the binding agent, e.g., an antibody molecule, comprises one or more or all of the following properties: (a) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (b) it produces fewer escape mutants than does a reference anti-HA antibody molecule, e.g., Ab 67-11, FI6, FI28, C179, or CR6261, e.g., when tested by the method described in (a); (c) it binds with high affinity to a hemagglutinin (HA) of at least 1, 2, 3, 4 or 5 influenza subtypes of Group 1 and at least 1, 2, 3, 4 or 5 influenza subtypes of Group 2; (d) it treats or prevents infection by at least 1, 2, 3, 4 or 5 influenza subtypes of Group 1, and by at least 1, 2, 3, 4 or 5 influenza subtypes of Group 2; (e) it inhibits fusogenic activity of the targeted HA; (f) it treats or prevents infection by a Group 1 virus, wherein the virus is an H1, H5, or H9 virus; and treats or prevents infection by a Group 2 virus, wherein the virus is an H3 or H7 virus; (g) it treats or prevents infection by influenza A strains H1N1 and H3N2; (h) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg or 1 mg/kg; (i) it treats or prevents infection by influenza A strains H5N1; (j) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg or 1 mg/kg; (k) it binds with high affinity to a hemagglutinin (HA) of an influenza B virus, e.g., B/Wisconsin/1/2010; (l) it treats or prevents infection by an influenza B virus, e.g., B/Wisconsin/1/2010; (m) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg or 1 mg/kg; (n) the concentration of antibody molecule required for 50% neutralization of influenza A virus is less than 10 μg/mL; (o) the concentration of antibody molecule required for 50% neutralization of influenza B virus, e.g., B/Wisconsin/1/2010, is less than 10 μg/mL; (p) it prevents or minimizes secondary infection (e.g., secondary bacterial infection) or effects thereof on a subject; (q) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg or 1 mg/kg; (r) it binds an epitope which comprises or consists of the hemagglutinin trimer interface; and (s) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In an embodiment, the binding agent, e.g., an antibody molecule, specifically binds the HA antigen. In an embodiment, the antibody molecule binds an epitope that has one, two, three, four, five, or all of, the following properties a)-f): a) it includes one, two, or all of, H3 HA1 residues N38, I278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment, the antibody molecule has properties: a) and b). In an embodiment, the antibody molecule has properties: c) and d). In an embodiment, the antibody molecule has properties: a); and c) or d). In an embodiment, the antibody molecule has properties: b); and c) or d). In an embodiment, the antibody molecule has properties: c); and a) or b). In an embodiment, the antibody molecule has properties: d); and a) or b). In an embodiment, the antibody molecule has properties: a), b), c) and d). In an embodiment, the antibody molecule has properties: a), b), c), d), e), and f).

In an embodiment, the antibody molecule has a $K_D$ for H3 of equal to or less than $10^{-6}$, wherein said $K_D$ is increased by at least 2, 5, 10, or 100 fold, by a mutation or mutations in any of: a) H3 HA1 residues N38, I278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$, wherein said $K_D$ is increased by no more than 2, or 5-fold, by a mutation or mutations in any of: c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57. In an embodiment, the antibody molecule has properties: aa) and bb). In an embodiment, the antibody molecule has properties: cc) and dd). In an embodiment, the antibody molecule has properties: aa); and cc) or dd). In an embodiment, the antibody molecule has properties: bb); and cc) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff).

In an embodiment, the antibody molecule has a $K_D$ for H1 of equal to or less than $10^{-6}$, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$, wherein said $K_D$ is increased by no more than 2, or 5-fold, by a mutation or mutations in any of: cc) H1 HA1 residues Q328 and S329; or dd) H1 HA2 residues G1, L2, F3, G4, and D46;

In an embodiment, the antibody molecule has one, two, three or all of the following properties: a) and aa); b) and bb); c) and cc); d) and dd). In an embodiment, the molecule has properties c), cc), d), and dd). In an embodiment, the molecule has properties c), cc), d), and dd). In another aspect, the disclosure features, a binding agent, e.g., an antibody molecule, or preparation, or isolated preparation thereof, comprising a structural or functional property of Ab 032.

In an embodiment, the antibody molecule competes with a reference antibody molecule, e.g., an antibody molecule described herein, for binding to a substrate, e.g., an HA. The reference antibody molecule can be: a) an antibody molecule comprising: i) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-N-Y-K-N-Y-L-A (SEQ ID NO: 71); a CDR2 comprising the sequence W-G-S-Y-L-E-S(SEQ ID NO: 72); and a CDR3 comprising the sequence Q-Q-H-Y-R-T-P-P-S(SEQ ID NO:73); b) an antibody molecule comprises one or both of: (i) a heavy chain immunoglobulin variable region segment comprising SEQ ID NO: 25; and (ii) a light chain variable region segment comprising SEQ ID NO: 45; or c) Ab 032.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecule or the reference antibody molecule to decrease binding of the other to a substrate, e.g., HA, e.g., HA1_ or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry.

The antibody molecule can compete with the reference antibody such that binding of the reference antibody is decreased by 50% or more. In an embodiment, the antibody molecule binds to the same epitope, or a portion thereof, which the reference antibody molecule binds. In an embodiment, the antibody molecule does not bind to the same epitope, or a portion thereof, which the reference antibody molecule binds. In an embodiment, the antibody molecule binds to the same epitope, or a portion thereof, on HA, as does a reference antibody molecule, e.g. an antibody molecule disclosed herein. The reference antibody molecule can be: a) an antibody molecule comprising: i) a heavy chain immunoglobulin variable region segment comprising a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-N-Y-K-N-Y-L-A (SEQ ID NO: 71); a CDR2 comprising the sequence W-G-S-Y-L-E-S(SEQ ID NO:72); and a CDR3 comprising the sequence Q-Q-H-Y-R-T-P-P-S(SEQ ID NO:73); b) an antibody molecule comprises one or both of: (i) a heavy chain immunoglobulin variable region segment comprising SEQ ID NO: 25; and (ii) a light chain variable region segment comprising SEQ ID NO:45; or c) Ab 32.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Binding to the same epitope, or a portion thereof, can be shown by one or more of: a) mutational analysis, e.g., binding to HA, or binding affinity for HA, is decreased or abolished if a residue is mutated; b) analysis, e.g., comparison, of the crystal structure of the antibody molecule and HA and the crystal structure of a reference antibody and HA, e.g., to determine the touch points of each; c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and d) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry. The antibody molecule can compete with the reference antibody such that binding of the reference antibody is decreased by 50% or more.

In an embodiment, the binding agent, e.g., an antibody molecule, comprises one or both of: a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45. In an embodiment, the binding agent, e.g., an antibody molecule, comprises one or both of: a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45, wherein each HC CDR differs by no more than 1, 2, 3, 4 or 5 amino acids, e.g., 1 or 2, e.g., conservative amino acids, from the corresponding CDR of SEQ ID NO: 25 and each LC CDR differs by no more than 1, 2, 3, 4 or 5 amino acids, e.g., 1 or 2, e.g., conservative amino acids, from the corresponding CDR of SEQ ID NO: 45.

In an embodiment, the binding agent, e.g., an antibody molecule, comprises one or both of: a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45, wherein the antibody molecule comprises 1, 2, 3, 4, 5, or all of: (i) a HC CDR1 comprising: S at the 1st position and A at the 3rd position in HC CDR1; (ii) a HC CDR2 comprising one or both, e.g., one of: V at the 2$^{nd}$ position; or N at the 7$^{th}$ position and Q at the 16$^{th}$ position in HC CDR2; (iii) a HC CDR3 comprising: R at the 3rd position (and optionally, L at the 3$^{rd}$ position); (iv) a LC CDR1 comprising: I at the 3rd position; (v) a LC CDR2 comprising one, two, or three of, e.g., one of: G at the 2$^{nd}$ position; Y at the 4$^{th}$ position; or L at the 5$^{th}$ position in LC CDR2; (vi) a LC CDR3 comprising: S at the 9$^{th}$ position in LC CDR3; In an embodiment, the binding agent, e.g., an antibody molecule, comprises one or both of: (a) a heavy chain immunoglobulin variable region segment comprising SEQ ID NO:25 (or a sequence that differs by no more than 1, 2, 3, 4 or 5 amino acids, e.g., conservative amino acids, therefrom); and (b) a light chain variable region segment comprising SEQ ID NO:155 (or a sequence that differs by no more than 1, 2, 3, 4 or 5 amino acids, e.g., conservative amino acids, therefrom).

In one embodiment, the antibody molecule comprises one or both of: (a) a heavy chain immunoglobulin variable region segment comprising SEQ ID NO: 25; and (b) a light chain variable region segment comprising SEQ ID NO:155. In an embodiment, the binding agent, e.g., an antibody molecule, comprises one or both of: (a) a heavy chain immunoglobulin variable region segment comprising a CDR1 comprising the sequence S-Y-A-M-H (SEQ ID NO:68) (or a sequence that differs by no more than, 1, 2, 3, 4, or 5, e.g., 1 or 2 amino acids, e.g., conservative amino acids, therefrom); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom); a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom); and (b) a light chain variable region segment comprising a CDR1 comprising the sequence: Q-S-I-T-F N-Y-K-N-Y-L-A (SEQ ID NO:71) (or a sequence that differs by no more than, 1, 2, 3, 4, or 5, e.g., 1 or 2 amino acids, e.g., conservative amino acids, therefrom); a CDR2 comprising the sequence W-G-S-Y-L-E-S(SEQ ID NO:72) (or a sequence that differs by no more than, 1, 2, 3, 4, or 5, e.g., 1 or 2 amino acids, e.g., conservative amino acids, therefrom); a CDR3 comprising the sequence Q-Q-H-Y-R-T-P-P-S(SEQ ID NO:73) (or a sequence that differs by no more than, 1, 2, 3, 4, or 5, e.g., 1 or 2 amino acids, e.g., conservative amino acids, therefrom). In an embodiment, the binding agent, e.g., an antibody molecule, comprises one or both of: a) LC CDR1-3, that collectively, differ from the AB 032 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the AB 032 HC CDR1-3 by no more than, 1, 2, 3, 4, 5, 6, 7, 8, 9, or 10, e.g., 1, 2, 3, or 4, amino acids, e.g., conservative amino acids. In an embodiment, the binding agent is an antibody molecule comprising one or both of: (a) a heavy chain immunoglobulin variable region segment comprising a CDR1 comprising the sequence S-Y-A-M-H (SEQ ID NO:68) (or a sequence that differs by no more than, 1, 2, or 3, e.g., 1 or 2 amino acids, e.g., conservative amino acids, therefrom, optionally provided that at least 1 or 2 of the highlighted residues are not changed, e.g., both S and A are not changed); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom, provided that, e.g., at least 1, 2, or 3 of the highlighted residues are not changed, e.g., V or both N and Q or all three of V, N, and Q are not changed); a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom, optionally provided that R is not changed); and (b) a light chain variable region segment comprising a CDR1 comprising the sequence: Q-S-I-T-F-N-Y-K-N-Y-L-A (SEQ ID NO: 71) or a sequence that differs by no more than, 1, 2, 3, 4, or 5, e.g., 1 or 2 amino acids, e.g., conservative amino acids, therefrom, optionally provided that at least 1 or 2 of the highlighted residues are not changed, e.g., I is not changed); a CDR2 comprising the sequence W-G-S-Y-L-E-S(SEQ ID NO:72) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., 1, 2 or all of G, Y, and L are not changed); a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom, optionally provided that at least one or both of the highlighted residues are not changed, e.g., S is not changed). In an embodiment a CDR of the light or heavy chain includes one of the highlighted residues, or one of the highlighted combinations of residues, for that CDR, (i.e., while other residues in that CDR might be changed, the highlighted residue or combination of residues, are not changed).

In an embodiment, a CDR of the light and a CDR of the heavy chain each includes one of the highlighted residues, or one of the highlighted combinations of residues, for that CDR. In an embodiment each of two CDRs in the antibody molecule includes one of the highlighted residues, or one of the highlighted combinations of residues, for that CDR. In some embodiments, both are in the light chain. In some embodiments, both are in the heavy chain. In an embodiment, each of the three CDRs in the heavy chain includes one of the highlighted residues, or one of the highlighted combinations of residues, for that CDR. In an embodiment, each of the three CDRs in the light chain includes one of the highlighted residues, or one of the highlighted combinations of residues, for that CDR. In an embodiment each of the six CDRs in the heavy and light chain includes one of the highlighted residues, or one of the highlighted combinations of residues, for that CDR.

In one embodiment, the binding agent is an antibody molecule that comprises one or more or all of the following properties: (a) both S and A in HC CDR1 are unchanged. (b) V or both N and Q or all three of V, N, and Q in HC CDR2 are unchanged. (c) R in HC CDR3 is unchanged. (d) I in LC CDR1 is unchanged. (e) 1, 2 or 3 of G, Y, and L in LC CDR2 are unchanged; (f) S in LC CDR3 is unchanged. In an embodiment, the antibody molecule comprises 1, 2, 3, 4, 5, or all 6 properties selected from (a) to (f). In an embodiment, the antibody molecule comprises a heavy chain having a one or more properties selected from (a), (b), and (c) and a light chain having one or more properties selected from (d), (e), and (f).

In one embodiment, the antibody molecule comprises one or both of: (a) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); a CDR3 comprising the sequence D-S-

R-L-R-S-L-L-Y-F-E-W-L-S-Q-G-Y-F-N-P (SEQ ID NO:70); and (b) a light chain variable region segment comprising a CDR1 comprising the sequence Q-S-I-T-F-N-Y-K-N-Y-L-A (SEQ ID NO: 71); a CDR2 comprising the sequence W-G-S-Y-L-E-S(SEQ ID NO:72); and a CDR3 comprising the sequence Q-Q-H-Y-R-T-P-P-S(SEQ ID NO:73).

In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) it produces fewer escape mutants than does a reference anti-HA antibody molecule, such as Ab 67-11, FI6, FI28, C179, F10, CR9114, or CR6261, such as when tested by the method described in (i).

In an embodiment, the antibody molecule comprises one or both of: a) one or more framework regions (FRs) from SEQ ID NO: 25, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 25; and b) one or more framework regions (FRs) from SEQ ID NO: 45, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 45.

In one embodiment, the antibody molecule comprises: (a) a heavy chain immunoglobulin variable region segment that further comprises one or more or all of: an FR1 comprising the sequence Q-V-Q-L-L-E-T-G-G-G-L-V-K-P-G-Q-S-L-K-L-S-C-A-A-S-G-F-T-F-T (SEQ ID NO:74) (or a sequence that differs by no more than, 1, 2, 3, 4, or 5, e.g., 1 or 2, amino acids, e.g., conservative amino acids, therefrom, optionally provided that T is not changed); an FR2 comprising the sequence W-V-R-Q-P-P-G-K-G-L-E-W-V-A (SEQ ID NO:75) (or a sequence that differs by no more than, 1, 2, 3, 4, or 5, e.g., 1 or 2, amino acids, e.g., conservative amino acids, therefrom, optionally provided that W is not changed, or that if changed, is other than R); an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76) (or a sequence that differs by no more than, 1, 2, 3, 4, or 5, e.g., 1 or 2, amino acids, e.g., conservative amino acids, therefrom, optionally provided that one, two or three of I, R, or L is not changed, or that if I is changed it is other than G, if R is changed it is other than P. or if L is changed it is other than A); and an FR4 comprising the sequence W-G-Q-G-T-T-L-T-V-S-S(SEQ ID NO:77) (or a sequence that differs by no more than, 1, 2, 3, 4, or 5, e.g., 1 or 2 amino acids, e.g., conservative amino acids, therefrom) or W-G-Q-G-T-T-V-T-V-S-S(SEQ ID NO:171) (or a sequence that differs by no more than, 1, 2, 3, 4, or 5, e.g., 1 or 2 amino acids, e.g., conservative amino acids, therefrom); and (b) the light chain immunoglobulin variable region segment comprises one or more or all of: an FR1 comprising the sequence D-I-Q-M-T-Q-S-P-S-S-L-S-A-S-V-G-D-R-V-T-I-T-C-R-S-S(SEQ ID NO:78) (or a sequence that differs by no more than, 1, 2, 3, 4, or 5, e.g., 1 or 2 amino acids, e.g., conservative amino acids, therefrom, optionally provided that R is not changed); an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom); an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom). In an embodiment a FR of the light or heavy chain includes one of the highlighted residues, or one of the highlighted combinations of residues, for that FR, (i.e., while other residues in that FR might be changed, the highlighted residue or combination of residues, are not changed). E.g., in an embodiment, one, two or three of I, R, or L for heavy chain FR3 is not changed.

In an embodiment, a FR of the light and a FR of the heavy chain each includes one of the highlighted residues, or one of the highlighted combinations of residues, for that FR. In an embodiment, each of two FRs in the antibody molecule includes one of the highlighted residues, or one of the highlighted combinations of residues, for that FR. In some embodiments, both are in the light chain. In some embodiments, both are in the heavy chain. In an embodiment each of FR2 and FR3 in the heavy chain includes one of the highlighted residues, or one of the highlighted combinations of residues, for that FR. In an embodiment, each of FR1 and FR2 in the heavy and light chain includes one of the highlighted residues for that FR. In an embodiment, all of the highlighted residues in heavy chain FR1-4 are unchanged. In an embodiment, all of the highlighted residues in light chain FR1-4 are unchanged. In an embodiment all of the highlighted residues in both heavy and light chain FR1-4 are unchanged.

In another embodiment, the binding agent, e.g., an antibody molecule, comprises one or more or all of the following properties: (a) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (b) it produces fewer escape mutants than does a reference anti-HA antibody molecule, e.g., Ab 67-11, FI6, FI28, C179, or CR6261, e.g., when tested by the method described in (a); (c) it binds with high affinity to a hemagglutinin (HA) of at least 1, 2, 3, 4 or 5 influenza subtypes of Group 1 and at least 1, 2, 3, 4 or 5 influenza subtypes of Group 2; (d) it treats or prevents infection by at least 1, 2, 3, 4 or 5 influenza subtypes of Group 1, and by at least 1, 2, 3, 4 or 5 influenza subtypes of Group 2; (e) it inhibits fusogenic activity of the targeted HA; (f) it treats or prevents infection by a Group 1 virus, wherein the virus is an H1, H5, or H9 virus; and treats or prevents infection by a Group 2 virus, wherein the virus is an H3 or H7 virus; (g) it treats or prevents infection by influenza A strains H1N1 and H3N2; (h) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg or 1 mg/kg; (i) it treats or prevents infection by influenza A strains H5N1; (j) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg or 1 mg/kg; (k) it binds with high affinity to a hemagglutinin (HA) of an influenza B virus, e.g., B/Wisconsin/1/2010; (l) it treats or prevents infection by an influenza B virus, e.g., B/Wisconsin/1/2010; (m) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg or 1 mg/kg; (n) the concentration of antibody molecule required for 50% neutralization of influenza A virus is less than 10 µg/mL; (o) the concentration of antibody molecule required for 50% neutralization of influenza B virus, e.g., B/Wisconsin/1/2010, is less than 10 µg/mL; (p) it prevents or minimizes secondary infection (e.g., secondary bacterial infection) or effects thereof on a subject; (q) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg or 1 mg/kg; (r) it binds an epitope which comprises or consists of the hemagglutinin trimer interface; and (s) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In an embodiment, the binding agent, e.g., an antibody molecule, specifically binds the HA antigen. In an embodiment, the antibody molecule binds an epitope that has one, two, three, four, five, or all of, the following properties a)-f): a) it includes one, two, or all of, H3 HA1 residues N38, 1278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57. In an embodiment, the antibody molecule has properties: a) and b). In an embodiment, the antibody molecule has properties: c) and d). In an embodiment, the antibody molecule has properties: a; and c or d. In an embodiment, the antibody molecule has properties: b); and c) or d). In an embodiment, the antibody molecule has properties: c); and a) or b). In an embodiment, the antibody molecule has properties: d); and a) or b). In an embodiment, the antibody molecule has properties: a), b), c) and d). In an embodiment, the antibody molecule has properties: a), b), c), d), e), and f). In an embodiment, the antibody molecule has a $K_D$ for H3 of equal to or less than $10^{-6}$, wherein said $K_D$ is increased by at least 2, 5, 10, or 100 fold, by a mutation or mutations in any of: a) H3 HA1 residues N38, 1278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$, wherein said $K_D$ is increased by no more than 2, or 5-fold, by a mutation or mutations in any of: c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57.

In an embodiment, the antibody molecule has properties: aa) and bb). In an embodiment, the antibody molecule has properties: cc) and dd). In an embodiment, the antibody molecule has properties: aa); and cc) or dd). In an embodiment, the antibody molecule has properties: bb); and c) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff).

In an embodiment, the antibody molecule has a $K_D$ for H1 of equal to or less than $10^{-6}$, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$, wherein said $K_D$ is increased by no more than 2, or 5 fold, by a mutation or mutations in any of: cc) H1 HA1 residues Q328 and S329; or dd) H1 HA2 residues G1, L2, F3, G4, and D46; In an embodiment, the antibody molecule has one, two, three or all of the following properties: a) and aa); b) and bb); c) and cc); d) and dd). In an embodiment, the molecule has properties c), cc), d), and dd).

In another aspect, the disclosure features, a binding agent, e.g., an antibody molecule, or preparation, or isolated preparation thereof, comprising a structural or functional property of Ab 031. In an embodiment, the antibody molecule competes with a reference antibody molecule, e.g., an antibody molecule described herein, for binding to a substrate, e.g., an HA. The reference antibody molecule can be:

a) an antibody molecule comprising: i) a heavy chain immunoglobulin variable region segment comprising a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-N-Y-K—N-Y-L-A (SEQ ID NO:71); a CDR2 comprising the sequence W-G-S-Y-L-E-S(SEQ ID NO:72); and a CDR3 comprising the sequence Q-Q-H-Y-R-T-P-P-S(SEQ ID NO:73); b) an antibody molecule comprises one or both of: (i) a heavy chain immunoglobulin variable region segment comprising SEQ ID NO: 24; and (ii) a light chain variable region segment comprising SEQ ID NO:45; or c) Ab 031. The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/

08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry. The antibody molecule can compete with the reference antibody such that binding of the reference antibody is decreased by 50% or more.

In an embodiment, the antibody molecule binds to the same epitope, or a portion thereof, which the reference antibody molecule binds. In an embodiment, the antibody molecule does not bind to the same epitope, or a portion thereof, which the reference antibody molecule binds. In an embodiment, the antibody molecule binds to the same epitope, or a portion thereof, on HA, as does a reference antibody molecule, e.g. an antibody molecule disclosed herein. The reference antibody molecule can be: a) an antibody molecule comprising: i) a heavy chain immunoglobulin variable region segment comprising a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-N-Y-K-N-Y-L-A (SEQ ID NO:71); a CDR2 comprising the sequence W-G-S-Y-L-E-S(SEQ ID NO:72); and a CDR3 comprising the sequence Q-Q-H-Y-R-T-P-P-S(SEQ ID NO:73); b) an antibody molecule comprises one or both of: (i) a heavy chain immunoglobulin variable region segment comprising SEQ ID NO: 24; and (ii) a light chain variable region segment comprising SEQ ID NO:45; or c) Ab 031. The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Binding to the same epitope, or a portion thereof, can be shown by one or more of: a) mutational analysis, e.g., binding to HA, or binding affinity for HA, is decreased or abolished if a residue is mutated; b) analysis, e.g., comparison, of the crystal structure of the antibody molecule and HA and the crystal structure of a reference antibody and HA, e.g., to determine the touch points of each; c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; d) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry. The antibody molecule can compete with the reference antibody such that binding of the reference antibody is decreased by 50% or more. In an embodiment, the binding agent, e.g., an antibody molecule, comprises one or both of: a heavy chain variable region comprising least 60, 70, 80, 85, 90, 95, 98 or 99 percent homology with SEQ ID NO: 24; and a light chain variable region comprising least 60, 70, 80, 85, 90, 95, 98 or 99 percent homology with SEQ ID NO: 45. In an embodiment, the binding agent, e.g., an antibody molecule, comprises one or both of: a heavy chain variable region comprising least 60, 70, 80, 85, 90, 95, 98 or 99 percent homology with SEQ ID NO: 24; and a light chain variable region comprising least 60, 70, 80, 85, 90, 95, 98 or 99 percent homology with SEQ ID NO: 45, wherein, optionally, each HC CDR differs by no more than 1, 2, 3, 4 or 5 amino acids, e.g., 1 or 2, e.g., conservative amino acids, from the corresponding CDR of SEQ ID NO: 24 and each LC CDR differs by no more than 1, 2, 3, 4 or 5 amino acids, e.g., 1 or 2, e.g., conservative amino acids, from the corresponding CDR of SEQ ID NO: 45.

In an embodiment, the binding agent, e.g., an antibody molecule, comprises one or both of: a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45, wherein the antibody molecule comprises 1, 2, 3, 4, 5, or all of: (i) a HC CDR1 comprising: S at the 1st position and A at the 3rd position in HC CDR1; (ii) a HC CDR2 comprising one or both, e.g., one of: V at the 2nd position; or N at the $7^{th}$ position and Q at the $16^{th}$ position in HC CDR2; (iii) a HC CDR3 comprising: R at the 3rd position (and optionally, L at the $3^{rd}$ position); (iv) a LC CDR1 comprising: I at the 3rd position; (v) a LC CDR2 comprising one, two, or three of, e.g., one of: G at the 2nd position; Y at the $4^{th}$ position; or L at the $5^{th}$ position in LC CDR2; (vi) a LC CDR3 comprising: S at the $9^{th}$ position in LC CDR3.

In an embodiment, the binding agent comprises an antibody molecule comprising: (a) a heavy chain immunoglobulin variable region segment comprising SEQ ID NO:24 (or a sequence that differs by no more than 1, 2, 3, 4 or 5 amino acids, e.g., conservative amino acids, therefrom); and (b) a light chain variable region segment comprising SEQ ID NO:45 (or a sequence that differs by no more than 1, 2, 3, 4 or 5 amino acids, e.g., conservative amino acids, therefrom). In one embodiment, the antibody molecule comprises one or both of: (a) a heavy chain immunoglobulin variable region segment comprising SEQ ID NO: 24; and (b) a light chain variable region segment comprising SEQ ID NO:45. In an embodiment, the binding agent, e.g., an antibody molecule, comprises one or both of: (a) a heavy chain immunoglobulin variable region segment comprising a CDR1 comprising the sequence S-Y-A-M-H (SEQ ID NO:68) (or a sequence that differs by no more than, 1, 2, 3, 4, or 5, e.g., 1 or 2 amino acids, e.g., conservative amino acids, therefrom); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom); and a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom); and (b) a light chain variable region segment comprising a CDR1 comprising the sequence Q-S-I-T-F-N-Y-K-N-Y-L-A (SEQ ID NO:71) (or a sequence that differs by no more than, 1, 2, 3, 4, or 5, e.g., 1 or 2 amino acids, e.g., conservative amino acids, therefrom); a CDR2 comprising the sequence W-G-S-Y-L-E-S(SEQ ID NO: 72) (or a sequence that differs by no more than, 1, 2, 3, 4, or 5, e.g., 1 or 2 amino acids, e.g., conservative amino acids, therefrom); and a CDR3 comprising the sequence Q-Q-H-Y-R-T-P-P-S(SEQ ID NO:73) (or a sequence that differs by no more than, 1, 2, 3, 4, or 5, e.g., 1 or 2 amino acids, e.g., conservative amino acids, therefrom).

In an embodiment, the binding agent, e.g., an antibody molecule, comprises one or both of: a) LC CDR1-3, that collectively, differ from the AB 031 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the AB 031 HC CDR1-3 by no more than, 1, 2, 3, 4, 5, 6, 7, 8, 9, or 10, e.g., 1, 2, 3, or 4, amino acids, e.g., conservative amino acids. In an embodiment, the binding agent, e.g., an antibody molecule, comprises one or both of: (a) a heavy chain immunoglobulin variable region segment comprising a CDR1 comprising the sequence S-Y-A-M-H (SEQ ID NO:68) (or a sequence that differs by no more than, 1, 2, or 3, e.g., 1 or 2 amino acids, e.g., conservative amino acids, therefrom, optionally provided that at least 1 or 2 of the highlighted residues are not changed, e.g., both S and A are not changed); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom, provided that, e.g., at least 1, 2, or 3 of the highlighted residues are not changed, e.g., V or both N and Q or all three of V, N, and Q are not changed); a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom optionally provided that, e.g., R is not changed); and (b) a light chain variable region segment comprising a CDR1 comprising the sequence Q-S-I-T-F-N-Y-K-N-Y-L-A (SEQ ID NO: 71) or a sequence that differs by no more than, 1, 2, 3, 4, or 5, e.g., 1 or 2 amino acids, e.g., conservative amino acids, therefrom, optionally provided that at least 1 or 2 of the highlighted residues are not changed, e.g., I is not changed); a CDR2 comprising the sequence W-G-S-Y-L-E-S(SEQ ID NO:72) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., 1, 2 or all of G, Y, and L are not changed); a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom, optionally provided that at least one or both of the highlighted residues are not changed, e.g., S is not changed). In an embodiment a CDR of the light or heavy chain includes one of the highlighted residues, or one of the highlighted combinations of residues, for that CDR, (i.e., while other residues in that CDR might be changed, the highlighted residue or combination of residues, are not changed).

In an embodiment a CDR of the light and a CDR of the heavy chain each includes one of the highlighted residues, or one of the highlighted combinations of residues, for that CDR. In an embodiment each of two CDRs in the antibody molecule includes one of the highlighted residues, or one of the highlighted combinations of residues, for that CDR. In some embodiments, both are in the light chain. In some embodiments, both are in the heavy chain. In an embodiment each of the three CDRs in the heavy chain includes one of the highlighted residues, or one of the highlighted combinations of residues, for that CDR. In an embodiment each of the three CDRs in the light chain includes one of the highlighted residues, or one of the highlighted combinations of residues, for that CDR. In an embodiment each of the six CDRs in the heavy and light chain includes one of the highlighted residues, or one of the highlighted combinations of residues, for that CDR.

In one embodiment, the binding agent is an antibody molecule that comprises one or more or all of the following properties: (a) both S and A in HC CDR1 are unchanged; (b) V or both N and Q or all three of V, N, and Q in HC CDR2 are unchanged; (c) R in HC CDR3 is unchanged; (d) I in LC CDR1 is unchanged; (e) 1, 2 or 3 of G, Y, and L in LC CDR2 are unchanged; (f) S in LC CDR3 is unchanged. In an embodiment, the antibody molecule comprises 1, 2, 3, 4, 5, or all 6 properties selected from (a) to (f). In an embodiment, the antibody molecule comprises a heavy chain having a one or more properties selected from (a), (b), and (c) and a light chain having one or more properties selected from (d), (e), and (f).

In the embodiment, the antibody molecule comprises one or both of: (a) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and (b) a light chain variable region segment comprising a CDR1 comprising the sequence Q-S-I-T-F-N-Y-K-N-Y-L-A (SEQ ID NO:71); a CDR2 comprising the sequence W-G-S-Y-L-E-S(SEQ ID NO:72); and a CDR3 comprising the sequence Q-Q-H-Y-R-T-P-P-S(SEQ ID NO:73). In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) it produces fewer escape mutants than does a reference anti-HA antibody molecule, e.g., Ab 67-11, FI6, FI28, C179, F10, CR9114, or CR6261, e.g., when tested by the method described in (i).

In an embodiment, the antibody molecule comprises one or both of: a) one or more framework regions (FRs) from SEQ ID NO: 24, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 24; and b) one or more framework regions (FRs) from SEQ ID NO: 45, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 45.

In one embodiment, the antibody molecule comprises: (a) a heavy chain immunoglobulin variable region segment that further comprises one or more or all of: an FR1 comprising the sequence E-V-Q-L-L-E-S-G-G-G-L-V-K-P-G-Q-S-L-K-L-S-C-A-A-S-G-F-T-F-T (SEQ ID NO:82) (or a sequence that differs by no more than, 1, 2, 3, 4, or 5, e.g., 1 or 2 amino acids, e.g., conservative amino acids, therefrom, optionally provided that T is not changed); an FR2 comprising the sequence W-V-R-Q-P-P-G-K-G-L-E-W-V-A (SEQ ID NO:75) (or a sequence that differs by no more than, 1, 2, 3, 4, or 5, e.g., 1 or 2 amino acids, e.g., conservative amino acids, therefrom, optionally provided that W is not changed, or that if changed, is other than R); an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76) (or a sequence that differs by no more than, 1, 2, 3, 4, or 5, e.g., 1 or 2 amino acids, e.g., conservative amino acids, therefrom, optionally provided that one, two or three of I, R, or L is not changed, or that if I is changed it is other than G, if R is changed it is other than P. or if L is changed it is other than A); and an FR4 comprising the sequence W-G-Q-G-T-T-L-T-V-S-S(SEQ ID NO:77) (or a sequence that differs by no more than, 1, 2, 3, 4, or 5, e.g., 1 or 2 amino acids, e.g., conservative amino acids, therefrom) or W-G-Q-G-T-T-V-T-V-S-S(SEQ ID NO:171) (or a sequence that differs by no more than, 1, 2, 3, 4, or 5, e.g., 1 or 2 amino acids, e.g., conservative amino acids, therefrom); and (a) a light chain immunoglobulin variable region segment further comprises one or more or all of: an FR1 comprising the sequence D-I-Q-M-T-Q-S-P-S-S-L-S-A-S-V-G-D-R-V-T-I-T-C-R-S-S(SEQ ID NO:78) (or a sequence that differs by no more than, 1, 2, 3, 4, or 5, e.g., 1 or 2 amino acids, e.g., conservative amino acids, therefrom, optionally provided that R is not changed); an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom); an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom). In an embodiment a FR of the light or heavy chain includes one of the highlighted residues, or one of the highlighted combinations of residues, for that FR, (i.e., while other residues in that FR might be changed, the highlighted residue or combination of residues, are not changed). E.g., in an embodiment, one, two or three of I, R, or L for heavy chain FR3 is not changed. In an embodiment a FR of the light and a FR of the heavy chain each includes one of the highlighted residues, or one of the highlighted combinations of residues, for that FR.

In an embodiment each of two FRs in the antibody molecule includes one of the highlighted residues, or one of the highlighted combinations of residues, for that FR. In some embodiments, both are in the light chain. In some embodiments, both are in the heavy chain. In an embodiment, each of FR2 and FR3 in the heavy chain includes one of the highlighted residues, or one of the highlighted combinations of residues, for that FR. In an embodiment, each of FR1 and FR2 in the heavy and light chain includes one of the highlighted residues for that FR. In an embodiment, all of the highlighted residues in heavy chain FR1-4 are unchanged. In an embodiment, all of the highlighted residues in light chain FR1-4 are unchanged. In an embodiment, all of the highlighted residues in both heavy and light chain FR1-4 are unchanged.

In one embodiment, the antibody molecule comprises: (a) the heavy chain immunoglobulin variable region segment comprises one or more or all of an FR1 comprising the sequence E-V-Q-L-L-E-S-G-G-G-L-V-K-P-G-Q-S-L-K-L-S-C-A-A-S-G-F-T-F-T (SEQ ID NO:82); an FR2 comprising the sequence W-V-R-Q-P-P-G-K-G-L-E-W-V-A (SEQ ID NO:75); an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76); and an FR4 comprising the sequence W-G-Q-G-T-T-L-T-V-S-S(SEQ ID NO:77) or W-G-Q-G-T-T-V-T-V—S-S(SEQ ID NO:171); and (b) the light chain immunoglobulin variable region segment comprising one or more or all of an FR1 comprising the sequence D-I-Q-M-T-Q-S-P-S-S-L-S-A-S-V-G-D-R-V-T-I-T-C-R-S-S(SEQ ID NO:78); an FR2 comprising the sequence W-Y-Q-Q-K-P-G-K-A-P-K-L-L-I-Y (SEQ ID NO:79); an FR3 comprising the sequence G-V-P-S-R-F-S-G-S-G-S-G-T-D-F-T-L-T-I-S-S-L-Q-P-E-D-F-A-T-Y-Y-C(SEQ ID NO:80); and an FR4 comprising the sequence F-G-Q-G-T-K-V-E-I-K (SEQ ID NO:81).

In another embodiment, the antibody molecule comprises one or more or all of the following properties: (a) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (b) it produces fewer escape mutants than does a reference anti-HA antibody molecule, e.g., Ab 67-11, FI6, FI28, C179, F10, CR9114, or CR6261, e.g., when tested by the method described in (a); (c) it binds with high affinity to a hemagglutinin (HA) of at least 1, 2, 3, 4 or 5 influenza subtypes of Group 1 and at least 1, 2, 3, 4 or 5 influenza subtypes of Group 2; (d) it treats or prevents infection by at least 1, 2, 3, 4 or 5 influenza subtypes of Group 1, and by at least 1, 2, 3, 4 or 5 influenza subtypes of Group 2; (e) it inhibits fusogenic activity of the targeted HA; (f) it treats or prevents infection by a Group 1 virus, wherein the virus is an H1, H5, or H9 virus; and treats or prevents infection by a Group 2 virus, wherein the virus is an H3 or H7 virus; (g) it treats or prevents infection by influenza A strains H1N1 and H3N2; (h) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg, or 1 mg/kg; (i) it treats or prevents infection by influenza A strains H5N1; (j) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg, or 1 mg/kg; (k) it binds with high affinity to a hemagglutinin (HA) of an influenza B virus, e.g., B/Wisconsin/1/2010; (l) it treats or prevents infection by an influenza B virus, e.g., B/Wisconsin/1/2010; (m) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg, or 1 mg/kg; (n) the concentration of antibody molecule required for 50% neutralization of influenza A virus is less than 10 µg/mL; (o) the concentration of antibody molecule required for 50% neutralization of influenza B virus, e.g., B/Wisconsin/1/2010, is less than 10 µg/mL; (p) it prevents or minimizes secondary infection (e.g., secondary bacterial infection) or effects thereof on a subject; (q) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg, or 1 mg/kg; (r) it binds an epitope which comprises or consists of the hemagglutinin trimer interface; and (s) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In another aspect, the disclosure features an antibody molecule comprising: (a) a heavy chain immunoglobulin variable region segment comprising SEQ ID NO:24 (or a sequence that differs by no more than 1, 2, 3, 4 or 5 amino acids, e.g., conservative amino acids, therefrom); and (b) a light chain variable region segment comprising SEQ ID NO:45 (or a sequence that differs by no more than 1, 2, 3, 4 or 5 amino acids, e.g., conservative amino acids, therefrom). In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza a virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and (ii) it produces fewer escape mutants than does a reference anti-HA antibody molecule, such as Ab 67-11, FI6, FI28, C179, F10, CR9114, or CR6261, such as when tested by the method described in (i).

In an embodiment, the binding agent, e.g., an antibody molecule, specifically binds the HA antigen. In an embodiment, the antibody molecule binds an epitope that has one, two, three, four, five, or all of, the following properties a)-f): a) it includes one, two, or all of, H3 HA1 residues N38, I278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57. In an embodiment, the antibody molecule has properties: a) and b). antibody molecule has properties: c) and d). In an embodiment, the antibody molecule has properties: a); and c) or d). In an embodiment, the antibody molecule has properties: b); and c) or d). In an embodiment, the antibody molecule has properties: c); and a) or b). In an embodiment, the antibody molecule has properties: d); and a) or b). In an embodiment, the antibody molecule has properties: a), b), c) and d). In an embodiment, the antibody molecule has properties: a), b), c), d), e), and f). In an embodiment, the antibody molecule has a $K_D$ for H3 of equal to or less than $10^{-6}$, wherein said $K_D$ is increased by at least 2, 5, 10, or 100 fold, by a mutation or mutations in any of: a) H3 HA1 residues N38, I278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$, wherein said $K_D$ is increased by no more than 2, or 5 fold, by a mutation or mutations in any of: c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57. In an embodiment, the antibody molecule has properties: aa) and bb). In an embodiment, the antibody molecule has properties: cc; and dd. In an embodiment, the antibody molecule has properties: aa); and cc) or dd). In an embodiment, the antibody molecule has properties: bb); and cc) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff). In an embodiment, the antibody molecule has a $K_D$ for H1 of equal to or less than $10^{-6}$, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$, wherein said $K_D$ is increased by no more than 2, or 5 fold, by a mutation or mutations in any of: cc) H1 HA1 residues Q328 and S329; or dd) H1 HA2 residues G1, L2, F3, G4, and D46; In an embodiment, the antibody molecule has one, two, three or all of the following properties: a) and aa); b) and bb); c) and cc); d) and dd). In an embodiment, the molecule has properties c), cc), d), and dd).

In another aspect, the disclosure features, a binding agent, e.g., an antibody molecule, or preparation, or isolated preparation thereof, comprising a structural or functional property of one or both a heavy chain variable region and a light chain variable region disclosed herein.

In an embodiment, the antibody molecule competes with a reference antibody molecule, e.g., an antibody molecule described herein, for binding to a substrate, e.g., an HA. The reference antibody molecule can be: a) an antibody molecule comprising the heavy and light CDRs from: a heavy chain variable region from Table 3, Table 4A, or Table 4B, or FIG. 2, FIG. 13, or FIG. 17, of International Publication No. WO2013/170139 or U.S. Application Publication No. 2013/0302349; and a light chain variable region from Table 3, Table 4A, or Table 4B, or FIG. 3, FIG. 14, or FIG. 17, of International Publication No. WO2013/170139 or U.S. Application Publication No. 2013/0302349; b) an antibody molecule that comprises: (i) a heavy chain immunoglobulin variable region segment from Table 3, Table 4A, or Table 4B, or FIG. 2, FIG. 13, or FIG. 17, of International Publication No. WO2013/170139 or U.S. Application Publication No. 2013/0302349; and (ii) a light chain variable region segment from Table 3, Table 4A, or Table 4B, or FIG. 3, FIG. 14, or FIG. 17, of International Publication No. WO2013/170139 or U.S. Application Publication No. 2013/0302349; or c) an antibody disclosed herein.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry. The antibody molecule can compete with the reference antibody such that binding of the reference antibody is decreased by 50% or more. In an embodiment, the antibody molecule binds to the same epitope, or a portion thereof, which the reference antibody molecule binds. In an embodiment, the antibody molecule does not bind to the same epitope, or a portion thereof, which the reference antibody molecule binds.

In an embodiment, the antibody molecule binds to the same epitope, or a portion thereof, on HA, as does a reference antibody molecule, e.g. an antibody molecule disclosed herein. The reference antibody molecule can be: a) an antibody molecule comprising the heavy and light CDRs from: a heavy chain variable region from Table 3, Table 4A, or Table 4B, or FIG. 2, FIG. 13, or FIG. 17, of International Publication No. WO2013/170139 or U.S. Application Publication No. 2013/0302349; and a light chain variable region from Table 3, Table 4A, or Table 4B, or FIG. 3, FIG. 14, or FIG. 17, of International Publication No. WO2013/170139 or U.S. Application Publication No. 2013/0302349; b) an antibody molecule that comprises: (i) a heavy chain immunoglobulin variable region segment from Table 3, Table 4A, or Table 4B, FIG. 2, FIG. 13, or FIG. 17, of International Publication No. WO2013/170139 or U.S. Application Publication No. 2013/0302349; and (ii) a light chain variable region segment from Table 3, Table 4A, or Table 4B, FIG. 3, FIG. 14, or FIG. 17, of International Publication No. WO2013/170139 or U.S. Application Publication No. 2013/0302349; or c) an antibody disclosed herein.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Binding to the same epitope, or a portion thereof, can be shown by one or more of: a) mutational analysis, e.g., binding to HA, or binding affinity for HA, is decreased or abolished if a residue is mutated; b) analysis, e.g., comparison, of the crystal structure of the antibody molecule and HA and the crystal structure of a reference antibody and HA, e.g., to determine the touch points of each; c) competition of the two antibodies for binding to HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and d) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry. The antibody molecule can compete with the reference antibody such that binding of the reference antibody is decreased by 50% or more; d) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and e) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art.

In an embodiment, the binding agent, e.g., an antibody molecule, comprises one or both of: a heavy chain variable region comprising least 60, 70, 80, 85, 90, 95, 98 or 99 percent homology with a reference heavy chain from Table 3, Table 4A, or Table 4B, or FIG. 2, FIG. 13 or FIG. 17, of International Publication No. WO2013/170139 or U.S. Application Publication No. 2013/0302349; and a light chain variable region comprising least 60, 70, 80, 85, 90, 95, 98 or 99 percent homology with reference light chain from Table 3, Table 4A, or Table 4B, or FIG. 3, FIG. 14 or FIG. 17, of International Publication No. WO2013/170139 or U.S. Application Publication No. 2013/0302349, wherein, optionally, each HC CDR differs by no more than 1, 2, 3, 4 or 5 amino acids, e.g., 1 or 2, e.g., conservative amino acids, from the corresponding HC CDR from its reference heavy chain and each LC CDR differs by no more than 1, 2, 3, 4 or 5 amino acids, e.g., 1 or 2, e.g., conservative amino acids, from the corresponding CDR in its reference light chain. In an embodiment, the binding agent, e.g., an antibody molecule, comprises: a heavy chain variable region comprising least 60, 70, 80, 85, 90, 95, 98 or 99 percent homology with a heavy chain from Table 3 and a light chain variable region comprising least 60, 70, 80, 85, 90, 95, 98 or 99 percent homology with the corresponding light chain from Table 3. In an embodiment, the binding agent, e.g., an antibody molecule, comprises: a heavy chain variable region comprising least 60, 70, 80, 85, 90, 95, 98 or 99 percent homology with a heavy chain from Table 4A and a light chain variable region comprising least 60, 70, 80, 85, 90, 95, 98 or 99 percent homology with the corresponding light chain from Table 4A. In an embodiment, the binding agent, e.g., an antibody molecule, comprises: a heavy chain variable region comprising least 60, 70, 80, 85, 90, 95, 98 or 99 percent homology with a heavy chain from Table 4B and a light chain variable region comprising least 60, 70, 80, 85, 90, 95, 98 or 99 percent homology with the corresponding light chain from Table 4B.

In an embodiment, the binding agent, e.g., an antibody molecule, comprises one or both of: a heavy chain variable region from Table 3, Table 4A, or Table 4B, or FIG. 2, FIG. 13, or FIG. 17, of International Publication No. WO2013/170139 or U.S. Application Publication No. 2013/0302349; and a light chain variable region from Table 3, Table 4A, or Table 4B, or FIG. 3, FIG. 14, or FIG. 17, of International Publication No. WO2013/170139 or U.S. Application Publication No. 2013/0302349. In an embodiment, the binding agent, e.g., an antibody molecule, comprises: a heavy chain variable region from Table 3 and the corresponding light chain from Table 3; a heavy chain from Table 4A and the corresponding light chain from Table 4A; or a heavy chain from Table 4B and the corresponding light chain from Table 4B.

In an embodiment, the binding agent, e.g., an antibody molecule, comprises one or both of: (a) a heavy chain immunoglobulin variable region segment comprising a CDR1, a CDR2 and a CDR3 from a heavy chain sequence of Table 3, Table 4A, or Table 4B, or FIG. 2, FIG. 13, or FIG. 17, of International Publication No. WO2013/170139 or U.S. Application Publication No. 2013/0302349 (or CDRs that, individually or collectively, differ therefrom by no more than, 1, 2, 3, 4, or 5, e.g., 1 or 2 amino acids, e.g., conservative amino acids)); and (b) a light chain immunoglobulin variable region segment comprising a CDR1, a CDR2 and a CDR3 from a light chain sequence of Table 3, Table 4A, or Table 4B, or FIG. 3, FIG. 14, or FIG. 17, of International Publication No. WO2013/170139 or U.S. Application Publication No. 2013/0302349 (or CDRs that, individually or collectively, differ therefrom by no more than, 1, 2, 3, 4, or 5, e.g., 1 or 2 amino acids, e.g., conservative amino acids). In an embodiment, the binding agent, e.g., an antibody molecule, comprises one or both of: CDRs from a heavy chain of Table 3 and the light chain CDRs from the corresponding light chain from Table 3. In an embodiment, the binding agent, e.g., an antibody molecule, comprises one or both of: CDRs from a heavy chain of Table 4A and the light chain CDRs from the corresponding light chain from Table 4A. In an embodiment, the binding agent, e.g., an antibody molecule, comprises one or both of: CDRs from a heavy chain of Table 4B and the light chain CDRs from the corresponding light chain from Table 4B.

In some embodiments, the binding agent, e.g., an antibody molecule, comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (ii) it produces fewer escape mutants than does a reference anti-HA antibody molecule, e.g., Ab 67-11, FI6, FI28, C179, F10, CR9114, or CR6261, e.g., when tested by the method described in (i); and (iii) it is other than Ab 67-11 and FI6.

In one embodiment, the antibody molecule comprises one or both of: (a) a heavy chain immunoglobulin variable region segment comprising a CDR1, a CDR2; and a CDR3 from a heavy chain sequence of FIG. 2, FIG. 13, or FIG. 17, of International Publication No. WO2013/170139 or U.S. Application Publication No. 2013/0302349; and (b) a light chain immunoglobulin variable region segment comprising a CDR1, a CDR2 and a CDR3 from a light chain sequence of FIG. 3, FIG. 14, or FIG. 17, of International Publication No. WO2013/170139 or U.S. Application Publication No. 2013/0302349. In one embodiment, the antibody molecule comprises: (a) a heavy chain immunoglobulin variable region segment from FIG. 2 or FIG. 17; and (b) a light chain immunoglobulin variable region segment from FIG. 3 or FIG. 17.

In one embodiment, the heavy chain immunoglobulin variable region further comprises an Isoleucine-Aspartate (Ile-Asp) dipeptide at the N-terminus. In another embodiment, the light chain immunoglobulin variable region further comprises an Ile-Asp dipeptide at the N-terminus. In yet another embodiment, both the heavy chain immunoglobulin variable region and the light chain immunoglobulin variable region or an antibody featured in the disclosure further comprises an Ile-Asp dipeptide at the N-terminus. In other embodiment the Ile-Asp dipeptide is absent from one or both the heavy and light chain.

In one embodiment, the binding agent, e.g., an antibody molecule, further comprises one or more or all of the following: (a) it treats or prevents infection by at least 1, 2, 3, 4 or 5 influenza subtypes of Group 1, and by at least 1, 2, 3, 4 or 5 influenza subtypes of Group 2; (b) it inhibits fusogenic activity of the targeted HA; (c) it treats or prevents infection by a Group 1 virus, wherein the virus is an H1, H5, or H9 virus; and treats or prevents infection by a Group 2 virus, wherein the virus is an H3 or H7 virus; (d) it treats or prevents infection by influenza A strains H1N1 and H3N2; (e) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg, or 1 mg/kg; (f) it treats or prevents infection by influenza A strains H5N1; (g) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg, or 1 mg/kg; (h) it binds with high affinity to a hemagglutinin (HA) of an influenza B virus, e.g., B/Wisconsin/1/2010; (i) it treats or prevents infection by an influenza B virus, e.g., B/Wisconsin/1/2010; (j) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg, or 1 mg/kg; (k) the concentration of antibody molecule required for 50% neutralization of influenza A virus is less than 10 µg/mL; (l) the concentration of antibody molecule required for 50% neutralization of influenza B virus, e.g., B/Wisconsin/1/2010, is less than 10 µg/mL; (m) it prevents or minimizes secondary infection (e.g., secondary bacterial infection) or effects thereof on a subject; (n) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg, or 1 mg/kg; (o) it binds an epitope which comprises or consists of the hemagglutinin trimer interface; and (p) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In an embodiment, the antibody molecule comprises one or both of: a) one or more framework regions (FRs) from heavy chain disclosed herein, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from heavy chain disclosed herein; and b) one or more framework regions (FRs) from light chain disclosed herein, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from light chain disclosed herein.

In an embodiment, the binding agent, e.g., an antibody molecule, specifically binds the HA antigen. In an embodiment, the antibody molecule binds an epitope that has one, two, three, four, five, or all of, the following properties a)-f): a) it includes one, two, or all of, H3 HA1 residues N38, I278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57. In an embodiment, the antibody molecule has properties: a) and b). In an embodiment, the antibody molecule has properties: c) and d). In an embodiment, the antibody molecule has properties: a); and c) or d). In an embodiment, the antibody molecule has properties: b); and c) or d). In an embodiment, the antibody molecule has properties: c); and a) or b). In an embodiment, the antibody molecule has properties: d); and a) or b). In an embodiment, the antibody molecule has properties: a), b), c) and d). In an embodiment, the antibody molecule has properties: a), b), c), d), e), and f). In an embodiment, the antibody molecule has a $K_D$ for H3 of equal to or less than $10^{-6}$, wherein said $K_D$ is increased by at least 2, 5, 10, or 100 fold, by a mutation or mutations in any of: a) H3 HA1 residues N38, I278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$, wherein said $K_D$ is increased by no more than 2, or 5 fold, by a mutation or mutations in any of: c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57. In an embodiment, the antibody molecule has properties: aa) and bb). In an embodiment, the antibody molecule has properties: cc) and dd). In an embodiment, the antibody molecule has properties: aa); and cc) or dd). In an embodiment, the antibody molecule has properties: bb); and cc) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff). In an embodiment, the antibody molecule has a $K_D$ for H1 of equal to or less than $10^{-6}$, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$, wherein said $K_D$ is increased by no more than 2, or 5 fold, by a mutation or mutations in any of: cc) H1 HA1 residues Q328 and S329; or dd) H1 HA2 residues G1, L2, F3, G4, and D46; In an embodiment, the antibody molecule has one, two, three or all of the following properties: a) and aa); b) and bb); c) and cc); d) and dd). In an embodiment, the molecule has properties c), cc), d), and dd).

In one aspect, the disclosure features an anti-hemagglutinin (anti-HA) binding agent, e.g., antibody molecule, or preparation, or isolated preparation thereof, comprising: (a) a heavy chain immunoglobulin variable region segment comprising one or more or all of a CDR1 comprising the sequence G-F-T-F-[S/T]-[S/T]-Y-[A/G]-M-H (SEQ ID NO: 184), or a sequence that differs from SEQ ID NO: 184 by no more than 1 or 2 residues; a CDR2 comprising the sequence V-[I/V/L-]-S-[Y/F]-D-G-[S/N]-[Y/N]-[K/R]-Y-Y-A-D-S-V-Q-G (SEQ ID NO:2) or a sequence that differs from SEQ ID NO:2 by no more than 1 or 2 residues; and a CDR3 comprising the sequence D-[S/T]-[R/K/Q]-L-R-[S/T]-L-L-Y-F-E-W-L-S-[Q/S]-G-[Y/L/V]-[F/L]-[N/D]-[P/Y] (SEQ ID NO:3), or a sequence that differs from SEQ ID NO:3 by no more than 1 or 2 residues; and (b) a light chain variable region segment comprising one or more or all of a CDR1 comprising the sequence [K/R]-S-S-Q-[S/T]-[V/L/I]-[T/S]-[Y/F/W]-[N/S/D]-Y-K-N-Y-L-A (SEQ ID NO: 185) or a sequence that differs from SEQ ID NO: 185 by no more than 1 or 2 residues, or comprising the sequence [K/R]-S-S-Q-[S/T]-[V/L/I]-[T/S]-[Y/F/W]-[N/S/D/Q/R/E]-Y-K-N-Y-L-A (SEQ ID NO: 186) or a sequence that differs from SEQ ID NO: 186 by no more than 1 or 2 residues or [K/R]-S-S-Q-[S/T]-[V/L/I]-[T/S]-[Y/F/W]-[N/S/D/E]-Y-K-N-Y-L-A (SEQ ID NO: 189) or a sequence that differs from SEQ ID NO:189 by no more than 1 or 2 residues; a CDR2 comprising the sequence W-[A/G]-S-[T/A/Y/H/K/D]-[R/L]-E-[S/T] (SEQ ID NO:5) or a sequence that differs from SEQ ID NO:5 by no more than 1 or 2 residues; a CDR3 comprising the sequence Q-Q-[Y/H]-Y-R-T-P-P-[T/S] (SEQ ID NO:6) or a sequence that differs from SEQ ID NO:6 by no more than 1 or 2 residues;

optionally, provided that, if the light chain variable region segment comprises: a CDR1 comprising the sequence K-S-S-Q-S-V-T-Y-N-Y-K-N-Y-L-A (SEQ ID NO:83); a CDR2 comprising the sequence W-A-S-T-R-E-S(SEQ ID NO:84); and a CDR3 comprising the sequence Q-Q-Y-Y-R-T-P-P-T (SEQ ID NO:85); then the heavy chain variable region segment comprises one or more of the following: (a) CDRs other than the following: a CDR1 comprising the sequence S-Y-G-M-H (SEQ ID NO:86); a CDR2 comprising the sequence V—I-S-Y-D-G-S—Y-K-Y-Y-A-D-S-V-Q-G (SEQ ID NO:87); or a CDR3 comprising the sequence D-S-E-L-R-S-L-L-Y-F-E-W-L-S-Q-G-Y-F-N-P (SEQ ID NO:88); or (b) FRs other than the following: an FR1 other than E-V-Q-L-L-E-S-G-G-G-L-V-K-P-G-Q-S-L-K-L-S-C-A-A-S-G-F-T-F-T (SEQ ID NO:82); an FR2 other than W-V-R-Q-P-P-G-K-G-L-E-W-V-A (SEQ ID NO:75); an FR3 other than R-F-T-I-S-R-D-N-S-K-N-T-L-Y-L-Q-M-N-S-L-R-A-E-D-T-A-V-Y-Y-C-A-K (SEQ ID NO:76); or an FR4 other than W-G-A-G-T-T-L-T-V-S-S(SEQ ID NO:89); (c) a CDR1 where the amino residue at position 5 of SEQ ID NO: 184 is an S, the amino acid residue at position 6 of SEQ ID NO: 184 is a T, or the amino acid residue at position 8 of SEQ ID NO: 184 is an A; (d) a CDR2 wherein the amino residue at position 2 of SEQ ID NO:2 is a V or an L, the amino acid at position 4 is an F, the amino acid at position 7 is an N, the amino acid at position 8 is a Y, or the amino acid at position 9 is a R; (e) a CDR3 wherein the amino residue at position 2 of SEQ ID NO:3 is a T, the amino acid residue at position 3 of SEQ ID NO:3 is an R, a K, or a Q, the amino acid residue at position 6 of SEQ ID NO:3 is a T, the amino acid residue at position 15 of SEQ ID NO:3 is an S, the amino acid residue at position 17 of SEQ ID NO:3 is an L, or a V, the amino acid residue at position 18 of SEQ ID NO:3 is an L, the amino acid residue at position 19 of SEQ ID NO:3 is a D, or the amino acid residue at position 20 of SEQ ID NO:3 is a Y; (f) an FR1 wherein the amino residue at position 11 of SEQ ID NO:7 is a Q, or the amino acid residue at position 7 of SEQ ID NO:7 is a T; (g) an FR4 wherein the amino residue at position 3 of SEQ ID NO:10 is a Q, the amino acid residue at position 5 of SEQ ID NO:10 is an A; the amino acid residue at position 6 of SEQ ID NO:10 is an M, or the amino acid residue at position 7 of SEQ ID NO:10 is a V; or (h) it produces fewer escape mutants than does a reference anti-HA antibody molecule, e.g., Ab 67-11, FI6, FI28, C179, F10, CR9114, or CR6261, e.g., when tested by a method disclosed herein, and also provided that, if the heavy chain immunoglobulin variable region segment comprises: a CDR1 comprising the sequence S-Y-G-M-H (SEQ ID NO:86); a CDR2 comprising the sequence V—I-S-Y-D-G-S—Y-K-Y-Y-A-D-S-V-Q-G (SEQ ID NO:87); and a CDR3 comprising the sequence D-S-E-L-R-S-L-L-Y-F-E-W-L-S-Q-G-Y-F-N-P (SEQ ID NO:88), then the light chain variable region segment comprises one of more of the following: (a) CDRs other than the following: CDR1 KSSQSVTYNYKNYLA (SEQ ID NO:83); CDR2 WASTRES (SEQ ID NO:84); or CDR3 QQYYRTPPT (SEQ ID NO:85); (b) FRs other than the following: FR1 comprising the sequence EIVMTQSPDSLAVSLGERATINC (SEQ ID NO:90); FR2 comprising the sequence WYQQKPGQPPKLLIY (SEQ ID NO:91); FR3 comprising the sequence GVPDRFSGSGSGTDFTLTISSLQAEDVAVYYC (SEQ ID NO:92); or FR4 comprising the sequence FGGGTKLDIK (SEQ ID NO:93); (c) a CDR1 wherein the amino residue at position 1 of SEQ ID NO: 185 is an R, the amino residue at position 5 of SEQ ID NO: 185 is a T, the amino residue at position 6 of SEQ ID NO: 185 is an L or an I, the amino residue at position 7 of SEQ ID NO:185 is an S, the amino residue at position 8 of SEQ ID NO: 185 is an F or a W, or the amino residue at position 9 of SEQ ID NO: 185 is an S or a D; (d) a CDR2 wherein the amino residue at position 2 of SEQ ID NO:5 is a G, the amino residue at position 4 of SEQ ID NO:5 is an A, a Y, an H, a K, or a D, the amino residue at position 5 of SEQ ID NO:5 is an L, the amino residue at position 7 of SEQ ID NO:5 is a T; (e) a CDR3 wherein the amino residue at position 3 of SEQ ID NO:6 is an H; the amino acid residue at position 9 of SEQ ID NO:6 is an S; (f) an FR1 wherein the amino residue at position 1 of SEQ ID NO:11 is a D; the amino residue at position 3 of SEQ ID NO:11 is a Q, the amino residue at position 9 of SEQ ID NO:11 is an S, the amino residue at position 10 of SEQ ID NO:11 is a T, the amino residue at position 11 of SEQ ID NO:11 is a V, the amino residue at position 12 of SEQ ID NO:11 is an S, the amino residue at position 13 of SEQ ID NO:11 is an A, the amino residue at position 14 of SEQ ID NO:11 is a T, the amino residue at position 15 of SEQ ID NO:11 is a V or an R, the amino residue at position 17 of SEQ ID NO:11 is a D, the amino residue at position 20 of SEQ ID NO:11 is an S, the amino residue at position 22 of SEQ ID NO:11 is a T, a Q, a D, or an R; (g) an FR2 wherein the amino residue at position 8 of SEQ ID NO:12 is a K; or the amino residue at position 9 of SEQ ID NO: 12 is an A; (h) an FR3 wherein the amino residue at position 4 of SEQ ID NO: 13 is an E or an S; the amino residue at position 24 of SEQ ID NO: 13 is a P, the amino residue at position 27 of SEQ ID NO: 13 is an F, a K, or a D, the amino residue at position 29 of SEQ ID NO: 13 is a T; (i) an FR4 wherein the amino residue at position 3 of SEQ ID NO:14 is a Q, a T, an S, or an N, the amino residue at position 7 of SEQ ID NO:14 is a V, or the amino residue at position 8 of SEQ ID NO:14 is an E; or (j) it produces fewer escape mutants than does a reference anti-HA antibody molecule, e.g., Ab 67-11, FI6, FI28, C179, F10, CR9114, or CR6261, e.g., when tested by a method disclosed herein; and further provided that if the light chain variable region segment comprises: a CDR 1 comprising the sequence K-S-S-Q-S-V-T-F-N-Y-K-N-Y-L-A (SEQ ID NO:146); a CDR2 comprising the sequence W-A-S-A-R-E-S(SEQ ID NO:147); and a CDR3 comprising the sequence Q-Q-H-Y-R-T-P-P-T (SEQ ID NO:148); then the heavy chain variable region segment comprises one or more of the following: CDRs other than the CDR's described at FIG. 12 of International Publication No. WO2013/170139 or U.S. Application Publication No. 2013/0302349; or FRs other than the FRs described at FIG. 12 of International Publication No. WO2013/170139 or U.S. Application Publication No. 2013/0302349.

In one embodiment, the heavy chain CDR sequences, collectively, differ from the recited sequences by no more than 5, 4, 3, 2 or 1 amino acid residues; and the light chain CDR sequences, collectively, differ from the recited sequences by no more than 5, 4, 3, 2 or 1 amino acid residues.

In another embodiment, an antibody featured in the disclosure is other than an antibody known in the art. For example, the antibody is not Ab 67-11 (U.S. Provisional application No. 61/645,453) FI6 (FI6, as used herein, refers to any specifically disclosed FI6 sequence in U.S. Application Publication No. 2010/0080813, US Application Publication No. 2011/0274702, International Publication No. WO2013/011347 or Corti et al., Science 333:850-856, 2011, published online Jul. 28, 2011; FIGS. 12A to 12C of International Publication No. WO2013/170139 or U.S. Application Publication No. 2013/0302349), FI28 (U.S. Application Publication No. 2010/0080813), and C179 (Okuno et al., J. Virol. 67:2552-1558, 1993), F10 (Sui et al., Nat. Struct. Mol. Biol. 16:265, 2009), CR9114 (Dreyfus et al., Science. 2012; 337(6100):1343-1348; published online Aug. 9, 2012), and CR6261 (Ekiert et al., Science 324:246-251, 2009; published online Feb. 26, 2009). In one embodiment, an antibody featured in the disclosure is other than Ab 67-11 (U.S. Provisional application No. 61/645,453, filed on the same date as the present application).

Variants

In an embodiment, an antibody molecule, e.g., an antibody featured in the disclosure has a variable heavy chain immunoglobulin domain that is at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to a heavy chain disclosed herein, e.g., from Table 3, Table 4A, or Table 4B, or FIG. 2, FIG. 13 or FIG. 17, of International Publication No. WO2013/170139 or U.S. Application Publication No. 2013/0302349, e.g. consensus sequence of SEQ ID NO: 161, and has a variable light chain immunoglobulin domain that is at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to a light chain disclosed herein, e.g., from Table 3, Table 4A, or Table 4B, or FIG. 3, FIG. 14 or FIG. 17, of International Publication No. WO2013/170139 or U.S. Application Publication No. 2013/0302349, e.g., the consensus sequence of SEQ ID NO: 62. The consensus sequences were determined through the analysis of biochemical and biophysical properties of several hundred computationally designed VH/VL combinations. The consensus sequences represent the amino acid sequences in which each amino acid is the one that occurs most frequently at that site when multiple sequences comprising desirable biochemical and biophysical data are aligned.

An exemplary anti-HA binding antibody has one or more CDRs, e.g., all three HC CDRs and/or all three LC CDRs of a particular antibody disclosed herein, or CDRs that are, in sum, at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to such an antibody. In one embodiment, the H1 and H2 hypervariable loops have the same canonical structure as those of an antibody described herein. In one embodiment, the L1 and L2 hypervariable loops have the same canonical structure as those of an antibody described herein.

In one embodiment, the amino acid sequence of the HC and/or LC variable domain sequence is at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to the amino acid sequence of the HC and/or LC variable domain of an antibody described herein. The amino acid sequence of the HC and/or LC variable domain sequence can differ by at least one amino acid, but no more than ten, eight, six, five, four, three, or two amino acids from the corresponding sequence of an antibody described herein. For example, the differences may be primarily or entirely in the framework regions.

In certain embodiments, the amino acid differences are conservative amino acid differences (e.g., conservative amino acid substitutions). A "conservative" amino acid substitution is one in which the amino acid residue is replaced with an amino acid residue comprising a similar side chain. Families of amino acid residues comprising similar side chains have been defined in the art. These families include, e.g., amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The amino acid sequences of the HC and LC variable domain sequences can be encoded by a nucleic acid sequence that hybridizes under high stringency conditions to a nucleic acid sequence described herein or one that encodes a variable domain or an amino acid sequence described herein. In one embodiment, the amino acid sequences of one or more framework regions (e.g., FR1, FR2, FR3, and/or FR4) of the HC and/or LC variable domain are at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to corresponding framework regions of the HC and LC variable domains of an antibody described herein. In one embodiment, one or more heavy or light chain framework regions (e.g., HC FR1, FR2, and FR3) are at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to the sequence of corresponding framework regions from a human germline antibody.

Validation of Epitopes

In one embodiment, the antibodies featured in the disclosure are useful for validating a vaccine based on a particular epitope. For example, an epitope that is the target of an antibody featured in the disclosure can be assessed by computation methods to identify a peptide framework suitable for supporting the epitope conformation, such as to stabilize an epitope that is transient or minimally accessible in nature. Computational abstraction of the epitope and framework properties allows automated screening of databases to identify candidate acceptor peptide scaffolds. The acceptor scaffold can have a particular tertiary structure that includes, for example, one or more of a beta sheet, a beta sandwich, a loop, or an alpha or beta helix. The candidate epitope-scaffold antigens can be assayed in vitro, such as to identify binding properties with an antibody featured in the disclosure, e.g., binding affinity or structure analysis of the epitope-scaffold/antibody complex, or in vitro neutralization. The ability of the epitope-scaffold to generate an immune response (e.g., to generate antibodies) can be tested by administering the epitope-scaffold to an animal (e.g., in a mammal, such as a rat, a mouse, a guinea pig, or a rabbit), and then testing sera for the presence of anti-epitope-scaffold antibodies, e.g., by ELISA assay. The ability of the epitope-scaffold to elicit protection against infection by an influenza A Group 1 or Group 2 strain, or by both types of influenza strains, or an influenza B strain, can be assessed in vivo, such as in an animal (e.g., in a mammal) Thus, an antibody featured in the disclosure can provide validation that the epitope is functionally important and that targeting the epitope will provide protection from infection with a Group 1 or Group 2 influenza strain, or both types of strains, or an influenza B strain.

Production of Antibody Molecules

The nucleic acids (e.g., the genes) encoding an antibody molecule generated by a method described herein can be sequenced, and all or part of the nucleic acids can be cloned into a vector that expresses all or part of the nucleic acids. For example, the nucleic acids can include a fragment of the gene encoding the antibody, such as a single chain antibody (scFv), a F(ab')$_2$ fragment, a Fab fragment, or an Fd fragment. The disclosure also provides host cells comprising the nucleic acids encoding an antibody or fragment thereof as described herein. The host cells can be, for example, prokaryotic or eukaryotic cells, e.g., mammalian cells, or yeast cells, e.g., *Pichia* (see, e.g., Powers et al. (2001) *J. Immunol. Methods* 251:123-35), Hanseula, or *Saccharomyces*.

Antibody molecules, particularly full-length antibody molecules, e.g., IgGs, can be produced in mammalian cells. Exemplary mammalian host cells for recombinant expression include Chinese Hamster Ovary (CHO) cells (including dhfr⁻ CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell. In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216; 4,634,665; and 5,179,017). Exemplary selectable marker genes include the dihydrofolate reductase (DHFR) gene (for use in dhfr host cells with methotrexate selection/amplification) and the neo gene (for G418 selection).

In an exemplary system for recombinant expression of an antibody molecule (e.g., a full-length antibody or an antigen-binding portion thereof), a recombinant expression vector encoding both the antibody heavy chain and the antibody light chain is introduced into dhfr− CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody molecule is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G. For example, purified antibodies can be concentrated to about 100 mg/mL to about 200 mg/mL using protein concentration techniques that are known in the art.

Antibody molecules can also be produced by a transgenic animal. For example, U.S. Pat. No. 5,849,992 describes a method for expressing an antibody molecule in the mammary gland of a transgenic mammal A transgene is constructed that includes a milk-specific promoter and nucleic acid sequences encoding the antibody molecule of interest, e.g., an antibody described herein, and a signal sequence for secretion. The milk produced by females of such transgenic mammals includes, secreted therein, the antibody of interest, e.g., an antibody described herein. The antibody molecule can be purified from the milk, or for some applications, used directly. Antibody molecules can also be expressed in vivo, following administration of a vector containing nucleic acids encoding the antibody heavy chain and the antibody light chain. Vector mediated gene-transfer is then used to engineer secretion of the anti-HA antibody into circulation. For example, an anti-HA antibody heavy chain and an anti-HA antibody light chain as described herein are cloned into an adeno-associated virus (AAV)-based vector, and each of the anti-HA antibody heavy chain and the anti-HA antibody light chain are under control of a promoter, such as a cytomegalovirus (CMV) promoter. Administration of the vector to a subject, such as to a patient, e.g., a human patient, such as by intramuscular injection, results in expression of an anti-HA antibody, and secretion into the circulation.

Modifications of Binding Agents

Binding, agents, e.g., antibody molecules can be modified to have numerous properties, e.g., to have altered, e.g., extended half-life, to be associated with, e.g., covalently bound to detectable moieties, e.g., labels, to be associated with, e.g., covalently bound to toxins, or to have other properties, e.g., altered immune functions. Antibody molecules may include modifications, e.g., modifications that alter Fc function, e.g., to decrease or remove interaction with an Fc receptor or with C1q, or both. In one example, the human IgG1 constant region can be mutated at one or more residues.

For some antibody molecules that include an Fc domain, the antibody production system may be designed to synthesize antibody molecules in which the Fc region is glycosylated. The Fc domain can be produced in a mammalian expression system that appropriately glycosylates the residue corresponding to asparagine 297. The Fc domain can also include other eukaryotic post-translational modifications. Other suitable Fc domain modifications include those described in WO2004/029207. For example, the Fc domain can be an XmAb® Fc (Xencor, Monrovia, Calif.). The Fc domain, or a fragment thereof, can have a substitution in an Fcγ Receptor (FcγR) binding region, such as the domains and fragments described in WO05/063815. In some embodiments, the Fc domain, or a fragment thereof, has a substitution in a neonatal Fc Receptor (FcRn) binding region, such as the domains and fragments described in WO05047327. In other embodiments, the Fc domain is a single chain, or fragment thereof, or modified version thereof, such as those described in WO2008143954. Other suitable Fc modifications are known and described in the art.

Antibody molecules can be modified, e.g., with a moiety that improves its stabilization and/or retention in circulation, e.g., in blood, serum, lymph, bronchoalveolar lavage, or other tissues, e.g., by at least 1.5, 2, 5, 10, or 50-fold. For example, an antibody molecule generated by a method described herein can be associated with a polymer, e.g., a substantially non-antigenic polymer, such as a polyalkylene oxide or a polyethylene oxide. Suitable polymers will vary substantially by weight. Polymers comprising molecular number average weights ranging from about 200 to about 35,000 daltons (or about 1,000 to about 15,000, and 2,000 to about 12,500) can be used.

For example, an antibody molecule generated by a method described herein can be conjugated to a water soluble polymer, e.g., a hydrophilic polyvinyl polymer, e.g. polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides that comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparan.

Binding agents, e.g., antibody molecules, as disclosed herein, can by conjugated to another entity or moiety (e.g., to a cytotoxic or cytostatic moiety, a label or detectable moiety, or a therapeutic moiety). Exemplary moieties include: a cytotoxic or cytostatic agent, e.g., a therapeutic agent, a drug, a compound emitting radiation, molecules of plant, fungal, or bacterial origin, or a biological protein (e.g., a protein toxin) or particle (e.g., a recombinant viral particle, e.g., via a viral coat protein), a detectable agent; a pharmaceutical agent, and/or a protein or peptide that can mediate association of the antibody or antibody portion with another molecule (such as a streptavidin core region or a polyhistidine tag). A binding agent, e.g., an antibody molecule, as disclosed herein, can be functionally linked by any suitable method (e.g., chemical coupling, genetic fusion, covalent binding, noncovalent association or otherwise) to one or more other molecular entities.

Binding agents, e.g., antibody molecules, disclosed herein can be conjugated with a detectable moiety, e.g., a label or imaging agent. Such moieties can include enzymes (e.g., horseradish peroxidase, beta-galactosidase, luciferase, alkaline phosphatase, acetylcholinesterase, glucose oxidase and the like), radiolabels (e.g., $^3$H, $^{14}$C, $^{15}$N, $^{35}$S, $^{90}$Y, $^{99}$Tc, $^{111}$In, $^{125}$I, $^{131}$I and the like), haptens, fluorescent labels (e.g., FITC, rhodamine, lanthanide phosphors, fluorescein, fluorescein isothiocyanate, rhodamine, 5-dimethylamine-1-napthalenesulfonyl chloride, phycoerythrin and the like), phosphorescent molecules, chemiluminescent molecules, chromophores, luminescent molecules, photoaffinity molecules, colored particles or affinity ligands, such as biotin, predetermined polypeptide epitopes recognized by a secondary reporter (e.g., leucine zipper pair sequences, or binding sites for secondary antibodies, metal binding domains, epitope tags). In some embodiments, a moiety, e.g., a detectable moiety, e.g., a label, is attached by spacer arms of various lengths to reduce potential steric hindrance.

In some embodiments, a binding agent, e.g., antibody molecule, disclosed herein, is derivatized with a detectable enzyme and is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A binding agent, e.g., antibody molecule, disclosed herein, may also be derivatized with a prosthetic group (e.g., streptavidin/biotin and avidin/biotin). For example, an antibody may be derivatized with biotin, and detected through indirect measurement of avidin or streptavidin binding.

In some embodiments, the moiety comprises paramagnetic ions and NMR-detectable substances, among others. For example, in some embodiments, a paramagnetic ion is one or more of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II), and/or bismuth (III). Binding agents, e.g., antibody molecules, as disclosed herein, can be modified to be associated with, e.g., conjugated to, a therapeutic agent, e.g., an agent comprising anti-viral activity, anti-inflammatory activity, or cytotoxic activity, etc. In some embodiments, therapeutic agents can treat symptoms or causes of influenza infection (e.g., for example, anti-viral, pain-relief, anti-inflammatory, immunomodulatory, sleep-inducing activities, etc.).

Treatment Methods and Administration

The binding agents, e.g., antibody molecules, featured in the disclosure, can be used to treat a subject, e.g., a subject, e.g., a human subject, infected with, or at risk for becoming infected with, an influenza virus.

Any human is candidate to receive an antibody molecule featured in the disclosure for treatment or prevention of an infection by an influenza virus. Humans at high risk of infection, such as immunocompromised individuals, and humans who are at high risk of exposure to influenza virus are particularly suited to receive treatment with the antibody molecule Immunocompromised individuals include the elderly (65 years and older) and children (e.g., 6 months to 18 years old), and people with chronic medical conditions. People at high risk of exposure include heath care workers, teachers and emergency responders (e.g., firefighters, policemen). In an embodiment, the subject is hospitalized. In an embodiment, the subject is not hospitalized.

The antibody molecules described herein can also be used to prevent or reduce (e.g., minimize) secondary infection (e.g., secondary bacterial infection) or a risk of comprising secondary infection associated with influenza, or any effects (e.g., symptoms or complications) thereof on a subject. Opportunistic secondary bacterial infections (e.g., secondary bacterial pneumonia, e.g., primarily with *Streptococcus pneumonia*) contribute significantly to the overall morbidity and mortality associated with seasonal and pandemic influenza infections. The antibody molecules described herein can be used to prevent or reduce (e.g., minimize) the complications from secondary, opportunistic infections (e.g., bacterial infections) in a subject.

In an aspect, the disclosure features a method of treating or preventing an influenza virus infection, or a symptom thereof, comprising administering to the subject an effective amount of an anti-HA antibody molecule described herein, e.g., in accordance with a method described herein. In some embodiments, the anti-HA antibody molecule is administered in a single dose (e.g., a single infusion). In another aspect, the disclosure features a method of treating or preventing a plurality of influenza virus infections, or symptoms thereof, in a population of subjects in need thereof, comprising administering to a plurality of the subjects an effective amount of an anti-HA antibody molecule described herein, e.g., in accordance with a method described herein. In an embodiment, the population of subjects is being exposed to influenza virus under pandemic conditions. An antibody molecule can be administered to a subject, e.g., a human subject, by a variety of methods. For many applications, the route of administration is one of: intravenous injection or infusion, subcutaneous injection, or intramuscular injection. An antibody molecule can be administered as a fixed dose, or in a mg/kg dose. The antibody molecule can be administered intravenously (IV) or subcutaneously (SC). For example, the antibody molecule can be administered at a fixed unit dose of between about 50-600 mg IV, e.g., every 4 weeks, or between about 50-100 mg SC (e.g., 75 mg), e.g., at least once a week (e.g., twice a week). In one embodiment, the antibody molecule is administered IV at a fixed unit dose of 50 mg, 60 mg, 80 mg, 100 mg, 120 mg, 130 mg, 140 mg, 150 mg, 160 mg, 180 mg, 200 mg, 300 mg, 400 mg, 500 mg, or 600 mg or more. Administration of the IV dose can be once or twice or three times or more per week, or once every two, three, four, or five weeks, or less frequently.

An anti-HA antibody molecule featured in the disclosure can also be administered intravenously, such as a fixed unit dose between 500 mg and 5000 mg, e.g., between 500 mg and 4000 mg, between 500 mg and 3000 mg, between 1000 mg and 3000 mg, between 1500 mg and 3000 mg, between 2000 mg and 3000 mg, between 1800 mg and 2500 mg, between 2500 mg and 3000 mg, between 500 mg and 2500 mg, between 500 mg and 2000 mg, between 500 mg and 1500 mg, between 500 mg and 1000 mg, between 1000 mg and 2500 mg, between 1500 mg and 2000 mg, or between 2000 mg and 2500 mg, e.g., 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, 4000 mg, 4100 mg, 4200 mg, 4300 mg, 4400 mg, 4500 mg, 4600 mg, 4700 mg, 4800 mg, 4900 mg, or 5000 mg. In an embodiment, the antibody molecule is administered at a dose of 2300 mg. In an embodiment, the antibody molecule is administered at a dose of 4600 mg. In an embodiment, the antibody molecule is administered intravenously over a period of 1-3 hours, e.g., 1-2 hours or 2 to 3 hours, e.g., 2 hours. In an embodiment, the antibody molecule is administered as a single dose. In one embodiment, the antibody molecule is administered SC at a fixed unit dose of 50 mg, 60 mg, 70 mg, 75 mg, 80 mg, 100 mg, or 120 mg or more. Administration of the SC dose can be once or twice or three times or more per week, or once every two, three, four, or five weeks, or less frequently. An anti-HA antibody molecule featured in the disclosure can also be administered by inhalation, such as by intranasal or by oral inhalation, such as at a fixed unit dose of 50 mg, 60 mg, 80 mg, 100 mg, 120 mg, 130 mg, 140 mg, 150 mg, 160 mg, 180 mg, 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, or more.

In an embodiment, the antibody molecule is administered in an amount that does not cause an ADE in the subject, e.g., as determined by a method described herein. In an embodiment, the antibody molecule is administered in an amount that does not cause viral resistance, e.g., as determined by a method described herein. In one embodiment, an anti-HA antibody is administered to a subject via vector-mediated gene transfer, such as through the delivery of a vector encoding the heavy chain and the light chain of an anti-HA antibody, and the antibody is expressed from the heavy chain and light chain genes in the body. For example, nucleic acids encoding a heavy chain and a light chain can be cloned in a AAV vector, such as a self-complementary AAV vector, the scAAV vector administered to a human by injection, such as by IM injection, and the antibody is expressed and secreted into the circulation of the human.

An antibody molecule can also be administered in a bolus at a dose of between about 1 and 50 mg/kg, e.g., between about 1 and 10 mg/kg, between about 1 and 25 mg/kg or about 25 and 50 mg/kg, e.g., about 50 mg/kg, 25 mg/kg, 10 mg/kg, 6.0 mg/kg, 5.0 mg/kg, 4.0 mg/kg, 3.0 mg/kg, 2.0 mg/kg, 1.0 mg/kg, or less. Modified dose ranges include a dose that is less than about 3000 mg/subject, about 1500 mg/subject, about 1000 mg/subject, about 600 mg/subject, about 500 mg/subject, about 400 mg/subject, about 300 mg/subject, about 250 mg/subject, about 200 mg/subject, or about 150 mg/subject, typically for administration every fourth week or once a month. The antibody molecule can be administered, for example, every three to five weeks, e.g., every fourth week, or monthly.

Dosing can be adjusted according to a patient's rate of clearance of a prior administration of the antibody. For example, a patient may not be administered a second or follow-on dose before the level of antibodies in the patient's system has dropped below a pre-determined level. In one embodiment, a sample from a patient (e.g., plasma, serum, blood, urine, or cerebrospinal fluid (CSF)) is assayed for the presence of antibodies, and if the level of antibodies is above a pre-determined level, the patient will not be administered a second or follow-on dose. If the level of antibodies in the patient's system is below a pre-determined level, then the patient is administered a second or follow-on dose. A patient whose antibody levels are determined to be too high (above the pre-determined level) can be tested again after one or two or three days, or a week, and if the level of antibody in the patient samples has dropped below the pre-determined level, the patient may be administered a second or follow-on dose of antibody.

In certain embodiments, the antibody may be prepared with a carrier that will protect the drug against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Controlled Drug Delivery (Drugs and the Pharmaceutical Sciences), Second Edition, J. Robinson and V. H. L. Lee, eds., Marcel Dekker, Inc., New York, 1987.

Pharmaceutical compositions can be administered with a medical device. For example, pharmaceutical compositions can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules are discussed in, e.g., U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system comprising multi-chamber compartments; and U.S. Pat. No. 4,475,196, which discloses an osmotic drug delivery system. Of course, many other such implants, delivery systems, and modules are also known. In some embodiments, the binding agent, e.g., an antibody molecule, is administered buccally, orally, or by nasal delivery, e.g., as a liquid, spray, or aerosol, e.g., by topical application, e.g., by a liquid or drops, or by inhalation.

An antibody molecule described herein can be administered with one or more additional therapeutic agents, e.g., a second drug, for treatment of a viral infection, or a symptom of the infection. The antibody molecule and the one or more second or additional agents can be formulated together, in the same formulation, or they can be in separate formulations, and administered to a patient simultaneously or sequentially, in either order.

Dosage regimens are adjusted to provide the desired response, such as a therapeutic response or a combinatorial therapeutic effect. Generally, any combination of doses (either separate or co-formulated) of an antibody molecule and a second or additional agent can be used in order to provide a subject with both agents in bioavailable quantities. Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with another agent.

A pharmaceutical composition may include a "therapeutically effective amount" of an agent described herein. In some embodiments, where the antibody molecule is administered in combination with a second or additional agent, such effective amounts can be determined based on the combinatorial effect of the administered first and second or additional agent. A therapeutically effective amount of an agent may also vary according to factors such as the disease state, age, sex, and weight of the individual, and the ability of the compound to elicit a desired response in the individual, such as amelioration of at least one infection parameter, or amelioration of at least one symptom of the infection, such as chills, fever, sore throat, muscle pain, headache, coughing, weakness, fatigue and general discomfort. A therapeutically effective amount is also one in which any toxic or detrimental effects of the composition are outweighed by the therapeutically beneficial effects.

In an embodiment, administration of a binding agent, e.g., antibody molecule, provided, e.g., as a pharmaceutical preparation, is by one of the following routes: oral, intravenous, intramuscular, intra-arterial, subcutaneous, intraventricular, transdermal, intradermal, rectal, intravaginal, intraperitoneal, topical (as by liquids, powders, ointments, creams, sprays, or drops), mucosal, nasal, buccal, enteral, sublingual; intratracheal instillation, bronchial instillation, and/or inhalation; and/or as an oral spray, nasal spray, and/or aerosol. In an embodiment, the method described herein further comprises determining the presence or absence of an anti-drug antibody (ADA) in the subject. In an embodiment, the subject is selected for administration of an antibody molecule described herein on the basis of the absence of an ADA in the subject. ADA can be detected, e.g., by ELISA, in a sample from the subject.

Combination Treatments and Exemplary Second or Additional Agents

Binding agents, e.g., antibody molecules, provided e.g., as pharmaceutical compositions, can be administered either alone or in combination with one or more other therapy, e.g., the administration of a second or additional therapeutic agent.

In some embodiments, the combination can result in a lower dose of the antibody molecule or of the other therapy being needed, which, in some embodiments, can reduce side effects. In some embodiments, the combination can result in enhanced delivery or efficacy of one or both agents. The agents or therapies can be administered at the same time (e.g., as a single formulation that is administered to a patient or as two separate formulations administered concurrently) or sequentially in any order. Such second or additional agents include vaccines, anti-viral agents, and/or additional antibodies. In typical embodiments the second or additional agent is not co-formulated with the binding agent, e.g., antibody molecule, though in others it is. In some embodiments, the binding agent, e.g., antibody molecule, and the second or additional agent are administered such that one or more of the following is achieved: therapeutic levels, or therapeutic effects, of one overlap the other; detectable levels of both are present at the same time; or the therapeutic effect is greater than what would be seen in the absence of either the binding agent, e.g., antibody molecule, or the second or additional agent. In some embodiments, each agent will be administered at a dose and on a time schedule determined for that agent.

The second or additional agent can be, for example, for treatment or prevention of influenza. For example, the binding agents, e.g., antibody molecules, e.g., therapeutic antibodies, provided herein can be administered in combination with a vaccine, e.g., a vaccine described herein or a mixture (a.k.a. a cocktail) of influenza peptides to stimulate the patient's immune system to prevent infection with particular strains of influenza A. In other examples, the second or additional agent is an anti-viral agent (e.g., an anti-NA or anti-M2 agent), a pain reliever, an anti-inflammatory, an antibiotic, a steroidal agent, a second therapeutic antibody molecule (e.g., an anti-HA antibody), an adjuvant, a protease or glycosidase (e.g., sialidase), etc.

Four drugs have been approved for the treatment of acute influenza: three drugs that target the viral neuraminidase (NA) activity (oseltamivir, peramivir, and zanamivir) and a drug targeting the PA subunit of the viral RNA polymerase (baloxavir-marboxil) that was recently approved in Japan and the U.S. in 2018. The neuraminidase inhibitors (NAIs) are used off label as standard-of-care for critically ill hospitalized patients with influenza. Baloxavir marboxil may also be used for treating hospitalized patients with influenza.

Exemplary anti-viral agents include, e.g., vaccines, neuraminidase inhibitors or nucleoside analogs. Exemplary anti-viral agents can include, e.g., zidovudine, gangcyclovir, vidarabine, idoxuridine, trifluridine, foscarnet, acyclovir, ribavirin, amantadine, remantidine, saquinavir, indinavir, ritonavir, alpha-interferons and other interferons, a neuraminidase inhibitor (e.g., zanamivir (Relenza®), oseltamivir (Tamiflu®), laninamivir, peramivir), rimantadine, a PB2 inhibitor (e.g., pimodivir), and an endonuclease inhibitor (e.g., the cap-dependent endonuclease inhibitor, e.g., baloxavir marboxil).

In an embodiment, the antiviral agent is an endonuclease (e.g., cap-dependent endonuclease (CEN) inhibitor or an PA (viral RNA polymerase PA subunit) inhibitor. In an embodiment, the endonuclease inhibitor or PA inhibitor is baloxavir. Baloxavir is described, e.g., in Antiviral Res. 2018; 160: 109-117, the content of which is incorporated by reference in its entirety. Cap-dependent endonuclease (CEN) resides in the PA subunit of the influenza virus and mediates the critical "cap-snatching" step of viral RNA transcription. Baloxavir acid (BXA) is generally considered to be an active form of baloxavir marboxil (BXM). Without wishing to be bound by theory, it is believed that in an embodiment, BXA can inhibit both viral RNA transcription via selective inhibition of CEN activity and viral replication.

In an embodiment, the antiviral agent is an inhibitor of influenza virus basic protein 2 (PB2), a component of the viral RNA replication complex. In an embodiment, the PB2 inhibitor is pimodivir. Pimodivir is described, e.g., in Nucleic Acids Res. 2018; 46(2): 956-971, the content of which is incorporated by reference in its entirety. Influenza RNA-dependent RNA polymerase is typically a heterotrimer with subunits PA, PB1 and PB2. Without wishing to be bound by theory, it is believed that it binds the conserved 3' and 5' ends of each of the eight negative-sense RNA genome segments and is responsible for transcription and replication of the genomic RNA in the nucleus of infected cells. Transcription is typically initiated by short capped primers originated from nascent host Pol II transcripts, and therefore a host sequence of 10-14 nucleotides in length precede the virally encoded sequences in the resultant chimeric viral mRNA.

Exemplary second antibody molecules include, for example, Ab 67-11 (U.S. Provisional application No. 61/645,453, FI6 (U.S. Application Publication No. 2010/0080813), FI28 (U.S. Application Publication No. 2010/0080813), C179 (Okuno et al., J. Virol. 67:2552-8, 1993), F10 (Sui et al., Nat. Struct. Mol. Biol. 16:265, 2009), CR9114 (Dreyfus et al., Science 337:1343, 2012), or CR6261 (Ekiert et al., Science 324:246, 2009). Thus, Ab 044 can be used in combination of any of those antibodies. In other embodiments, two or more binding agents, e.g., antibody molecules disclosed herein, can be administered in combination, e.g., Ab 044 can be administered in combination with Ab 032. In the case of combinations, two agents can be administered as part of the same dosage unit or administered separately. Other exemplary agents useful for treating the symptoms associated with influenza infection are acetaminophen, ibuprofen, aspirin, and naproxen.

In one embodiment, the antibody molecule and the second or additional agent are provided as a co-formulation, and the co-formulation is administered to the subject. It is further possible, e.g., at least 24 hours before or after administering the co-formulation, to administer separately one dose of the antibody formulation and then one dose of a formulation containing a second or additional agent. In another implementation, the antibody molecule and the second or additional agent are provided as separate formulations, and the step of administering includes sequentially administering the antibody molecule and the second or additional agent. The sequential administrations can be provided on the same day (e.g., within one hour of one another or at least 3, 6, or 12 hours apart) or on different days.

In some embodiments, the antibody molecule and the second or additional agent are each administered as a plurality of doses separated in time. The antibody molecule and the second or additional agent are generally each administered according to a regimen. The regimen for one or both may have a regular periodicity. The regimen for the antibody molecule can have a different periodicity from the regimen for the second or additional agent, e.g., one can be administered more frequently than the other. In one implementation, one of the antibody molecule and the second or additional agent is administered once weekly and the other once monthly. In another implementation, one of the antibody molecule and the second or additional agent is administered continuously, e.g., over a period of more than 30 minutes but less than 1, 2, 4, or 12 hours, and the other is administered as a bolus. In some embodiments, sequential administrations are administered. The time between administration of the one agent and another agent can be minutes, hours, days, or weeks. The use of an antibody molecule described herein can also be used to reduce the dosage of another therapy, e.g., to reduce the side-effects associated with another agent that is being administered. Accordingly, a combination can include administering a second or additional agent at a dosage at least 10, 20, 30, or 50% lower than would be used in the absence of the antibody molecule. The antibody molecule and the second or additional agent can be administered by any appropriate method, e.g., subcutaneously, intramuscularly, or intravenously.

In some embodiments, each of the antibody molecule and the second or additional agent is administered at the same dose as each is prescribed for monotherapy. In other embodiments, the antibody molecule is administered at a dosage that is equal to or less than an amount required for efficacy if administered alone. Likewise, the second or additional agent can be administered at a dosage that is equal to or less than an amount required for efficacy if administered alone. In some cases, the formulations described herein, e.g., formulations containing an antibody molecule featured in the disclosure, include one or more second or additional agents, or are administered in combination with a formulation containing one or more second or additional agents. In an embodiment a binding agent, e.g., antibody molecule, provided, e.g., as a pharmaceutical preparation, is administered by inhalation or aerosol delivery of a plurality of particles, e.g., particles comprising a mean particle size of 4, 5, 6, 7, 8, 9, 10, 11, 12, or 13 microns.

Pharmaceutical Compositions

The binding agents, e.g., antibody molecules, featured in the disclosure can be formulated as pharmaceutical compositions, such as for the treatment or prevention of influenza.

Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The compositions comprising antibody molecules can be formulated according to methods known in the art. Pharmaceutical formulation is a well-established art, and is further described in Gennaro (ed.), Remington: The Science and Practice of Pharmacy, 20$^{th}$ ed., Lippincott, Williams & Wilkins (2000) (ISBN: 0683306472); Ansel et al., Pharmaceutical Dosage Forms and Drug Delivery Systems, 7$^{th}$ Ed., Lippincott Williams & Wilkins Publishers (1999) (ISBN: 0683305727); and Kibbe (ed.), Handbook of Pharmaceutical Excipients American Pharmaceutical Association, 3$^{rd}$ ed. (2000) (ISBN: 091733096X).

Pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Typically, compositions for the agents described herein are in the form of injectable or infusible solutions. Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular (IM), intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and by intrasternal injection or by infusion.

Pharmaceutical compositions may be provided in a sterile injectable form (e.g., a form that is suitable for subcutaneous injection or intravenous infusion). In some embodiments, pharmaceutical compositions are provided in a liquid dosage form that is suitable for injection or topical application. In some embodiments, pharmaceutical compositions are provided as in dry form, e.g., as powders (e.g. lyophilized and/or sterilized preparations). The Pharmaceutical composition can be provided under conditions that enhance stability, e.g., under nitrogen or under vacuum. Dry material can be reconstituted with an aqueous diluent (e.g., water, buffer, salt solution, etc.) prior to injection.

In one embodiment, the pharmaceutical composition containing an anti-HA antibody is administered intranasally. In another embodiment, the pharmaceutical composition containing an anti-HA antibody is administered by inhalation, such as by oral or by nasal inhalation. In some embodiments, the pharmaceutical composition is suitable for buccal, oral or nasal delivery, e.g., as a liquid, spray, or aerosol, e.g., by topical application, e.g., by a liquid or drops, or by inhalation). In some embodiments, a pharmaceutical preparation comprises a plurality of particles, suitable, e.g., for inhaled or aerosol delivery. In some embodiments, the mean particle size of 4, 5, 6, 7, 8, 9, 10, 11, 12, or 13 microns. In some embodiments, a pharmaceutical preparation is formulated as a dry powder, suitable, e.g., for inhaled or aerosol delivery. In some embodiments, a pharmaceutical preparation is formulated as a wet powder, through inclusion of a wetting agent, e.g., water, saline, or other liquid of physiological pH. In some embodiments, a pharmaceutical preparation is provided as drops, suitable, e.g., for delivery to the nasal or buccal cavity. In some embodiments, the pharmaceutical composition is disposed in a delivery device, e.g., a syringe, a dropper or dropper bottle, an inhaler, or a metered dose device, e.g., an inhaler.

In one embodiment, a pharmaceutical composition contains a vector, such as an adenovirus-associated virus (AAV)-based vector, that encodes a heavy chain of an anti-HA antibody molecule, and a light chain of an anti-HA antibody molecule featured in the disclosure. The composition containing the vector can be administered to a subject, such as a patient, such as by injection, e.g., IM injection. Genes encoding the anti-HA antibody under control of, for example, cytomegalovirus (CMV) promoters, are expressed in the body, and the recombinant anti-HA antibody molecule is introduced into the circulation. See, e.g., Balazs et al., Nature 30:481:81-84, 2011.

Pharmaceutical compositions typically should be sterile and stable under the conditions of manufacture and storage. A pharmaceutical composition can also be tested to insure it meets regulatory and industry standards for administration. The composition can be formulated as a solution, microemulsion, dispersion, liposome, or other ordered structure suitable to high drug concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A pharmaceutical composition may be provided, prepared, packaged, and/or sold in bulk, as a single unit dose, and/or as a plurality of single unit doses. Typically, a bulk preparation will contain at least 2, 5, 10, 20, 50, or 100 unit doses. A unit dose is typically the amount introduced into the patient in a single administration. In some embodiments, only a portion of a unit dose is introduced. In some embodiments, a small multiple, e.g., as much as 1.5, 2, 3, 5, or 10 times a unit dose is administered. The amount of the active ingredient is generally equal to a dose which would be administered to a subject and/or a convenient fraction of such a dose such as, for example, one-half or one-third of such a dose.

Immunogens and Vaccines

Antibodies of the invention have elucidated epitopes that are useful for inducing immunity to, and in some embodiments, provide protection from, one or more, e.g., at least two, influenza strains. These epitopes are referred to herein as "broad range immunogens." As used herein, the term "broad range vaccine" refers to a preparation comprising a broad range immunogen, or a nucleic acid encoding a broad range immunogen, that can induce formation of antibodies or immunity against the broad range immunogen or an organism, e.g., an influenza virus. Additional immunogens and vaccines, and uses thereof, are described in International Publication No. WO2013/170139 or U.S.

Application Publication No. 2013/0302349, the contents of which are hereby incorporated by reference in their entirety.

Epitope

HAs exist in nature as homotrimers of proteolytically processed mature subunits. Each subunit of the trimer is synthesized as a precursor. A precursor molecule is proteolytically processed into two disulfide bonded polypeptide chains to form a mature HA polypeptide. The mature HA polypeptide includes two domains: (1) a core HA-1 domain that extends from the base of the molecule through the fibrous stem to the membrane distal head region that contains the glycan receptor binding domain, returning to fibrous region ending in the cleavage site, and (2) HA-2 domain that includes the stem region and the transmembrane domain of HA. HA-1 includes a glycan binding site. The glycan binding site may be responsible for mediating binding of HA to the HA-receptor. The HA-2 domain acts to present the HA-1 domain. The HA trimer can be stabilized by polar and non-polar interactions between the three long HA alpha-helices of the stem of HA monomers.

HA sequences from all influenza subtypes share a set of amino acids in the interface of the HA-1 and HA-2 domains that are well conserved. The HA-1/HA-2 interface membrane proximal epitope region (MPER) that includes the canonical α-helix and residues in its vicinity are also conserved across a broad spectrum of subtypes. (Ekiert et al., Science. 324(5924):246, 2009; Sui et al., Nat Struct Mol Biol. 16(3):265, 2009).

Ab 044 has high affinity for HA's from Group 1 and Group 2. It binds a conformational epitope that is broadly conserved across a plurality of influenza strains. Numerous amino acid residues distributed along the linear sequences of HA from different strains/subtypes contribute the Ab 044 conformational epitope. The interaction of Ab 044 with H3 was analyzed by docking studies and residues bound by (or not bound by) Ab 044 were identified. The Fv of Ab 044 was docked against HA of group I and II strains using ZDOCK. The structure of the HA antigen was modeled using the SWISS MODEL homology modeling server keeping the solved crystal structure of H1N1 as the template. ZDOCK uses shape complementarity along with desolvation and electrostatic energy terms ('ZRANK') to rank docked poses. To ensure the docked poses do not deviate significantly from the native complex, mapped epitope and paratope residues by alanine scanning are forced to be included in the binding interface.

For comparison studies, amino acids that bind (or do not bind) FI6 were taken from published US patent application US 2011/0274702 A1, Neutralizing Anti-Influenza A Virus Antibodies and Uses Thereof, filed Jul. 18, 2011.

ZDOCK is a Fast Fourier Transform based protein docking program. It was developed by Zhiping Weng at the University of Massachusetts Medical School. In ZDOCK, two PDB files are input and the output is the predicted structure of their complex. The program searches all possible binding modes in the translational and rotational space between the two proteins and evaluates each by an energy scoring function. The protein's structure is converted to a digital signal and a Fast Fourier Transform technique used to reduce computational time. ZDOCK is discussed in Pierce B G, Hourai Y, Weng Z. (2011) Accelerating Protein Docking in ZDOCK Using an Advanced 3D Convolution Library. PLoS One 6(9): e24657, Pierce B, Tong W, Weng Z. (2005) M-ZDOCK: A Grid-based Approach for $C_n$ Symmetric Multimer Docking. Bioinformatics 21(8): 1472-1476; Mintseris J, Pierce B, Wiehe K, Anderson R, Chen R, Weng Z. (2007) Integrating Statistical Pair Potentials into Protein Complex Prediction. Proteins 69(3): 511-520; and Chen R, Li L, Weng Z. (2003) ZDOCK: An Initial-stage Protein Docking Algorithm. Proteins 52(1): 80-7.

SWISS-MODEL is a fully automated protein structure homology-modeling server. It is accessible via the ExPASy web server, or from the program DeepView (Swiss Pdb-Viewer). Swiss-Model is discussed in Arnold K., Bordoli L., Kopp J., and Schwede T. (2006). The SWISS-MODEL Workspace: A web-based environment for protein structure homology modelling. Bioinformatics, 22, 195-201; Kiefer F, Arnold K, Künz M, Bordoli L, Schwede T (2009). The SWISS-MODEL Repository and associated resources. *Nucleic Acids Research.* 37, D387-D392; and Peitsch, M. C. (1995) Protein modeling by E-mail Bio/Technology 13: 658-660.

H3 residues that bind Ab 044 and H3 residues that bind FI6 are discussed below.

H3 HA1

The amino acid sequence of H3 HA1 is provided below, as SEQ ID NO: 173. Residues N38, 1278, and D291 shown in dashed boxes, are bound by Ab 044 but not by FI6; Residues Q327, T328, and R329 shown in dotted boxes, are bound by FI6 but not by Ab 044; residues T318, R321, and V323 shown in solid boxes, are bound by both Ab 044 and FI6.

(SEQ ID NO: 173)

| | | | | | |
|---|---|---|---|---|---|
| QDLPGNDNST | ATLCLGHHAV | PNGTLVKTIT | DDQIEVTNAT | ELVQSSSTGK | ICNNPHRILD |
| GIDCTLIDAL | LGDPHCDVFQ | NETWDLFVER | SKAFSNCYPY | DVPDYASLRS | LVASSGTLEF |
| ITEGFTWTGV | TQNGGSNACK | RGPGSGFFSR | LNWLTKSGST | YPVLNVTMPN | NDNFDKLYIW |
| GIHHPSTNQE | QTSLYVQASG | RVTVSTRRSQ | QTIIPNIGSR | PWVRGLSSRI | SIYWTIVKPG |
| DVLVINSNGN | LIAPRGYFKM | RTGKSSIMRS | DAPIDTCISE | CITPNGSIPN | DKPFQNVNKI |
| TYGACPKYVK | QNTLKLATGM | RNVPEKQTR | | | |

H3 HA2

The amino acid sequence of H3 HA21 is provided below, as SEQ ID NO: 174 Residue N12 shown in a dash box, is bound by Ab 044 but not by FI6; Residues G1, L2, F3, G4, and D46 shown in dotted boxes, are bound by FI6 but not by Ab 044; residues A7, E11, I18, D19, G20, W21, L38, K39, T41, Q42, A43, I45, I48, N49, L52, N53, I56, and E57, shown in solid boxes, are bound by both Ab 044 and FI6.

(SEQ ID NO: 174)

| | | | | | |
|---|---|---|---|---|---|
| GLFGAIAGFI | ENGWEGMIDG | WYGFRHQNSE | GTGQAADLKS | TQAAIDQING | KLNRVIEKTN |
| EKFHQIEKEF | SEVEGRIQDL | EKYVEDTKID | LWSYNAELLV | ALENQHTIDL | TDSEMNKLFE |
| KTRRQLRENA | EEMGNGCFKI | YHKCDNACIE | SIRNGTYDHD | VYRDEALNNR | FQIKG |

H1 residues that bind Ab 044 and H1 residues that bind FI6 are discussed below.

H1 HA1

The amino acid sequence of H1 HA1 is provided below, as SEQ ID NO: 181. Residues H31, N279, and 5292 shown in dashed boxes, are bound by Ab 044 but not by FI6. Residues Q328 and S329 shown in dotted boxes, are bound by FI6 but not by Ab 044. Residues T319, R322, and I324 shown in solid boxes, are bound by both Ab 044 and FI6.

(SEQ ID NO: 181)

| | | | | |
|---|---|---|---|---|
| TNADTI CIGYHANNST | DTVDTVLEKN | VTVTHSVNLL | | |
| EDSHNGKLCK | LKGIAPLQLG | KCNIAGWLLG | NPECDLLLTA | SSWSYIVETS |
| NSENGTCYPG | DFIDYEELRE | QLSSVSSFEK | FEIFPKTSSW | PNHETTKGVT |
| AACSYAGASS | FYRNLLWLTK | KGSSYPKLSK | SYVNNKGKEV | LVLWGVHHPP |
| TGTDQQSLYQ | NADAYVSVGS | SKYNRRFTPE | IAARPKVRDQ | AGRMNYYWTL |
| LEPGDTITFE | ATGNLIAPWY | AFALNRGSGS | GIITSDAPVH | DCNTKCQTPH |
| GAINSSLPFQ | NIHPVTIGEC | PKYVRSTKLR | MATGLRNIPS | IQS |

H1 HA2

The amino acid sequence of H1 HA2 is provided below, as SEQ ID NO: 182. Residues G12 shown in a dashed box, is bound by Ab 044 but not by FI6. Residues G1, L2, F3, G4, and D46 shown in dotted boxes, are bound by FI6 but not by Ab 044. Residues A7, E11, I18, D19, G20, W21, Q38, K39, T41, Q42, N43, I45, I48, T49, V52, N53, I56, and E57 shown in solid boxes, are bound by both Ab 044 and FI6.

```
                                                            (SEQ ID NO: 182)
GLFGAIAGF    IEGWTGMID   GWYGYHHQNE   QGSGYAADQK   STQNAIDGIT
NKVNSVIEKM   NTQFTAVGKE  FNNLERRIEN   LNKKVDDGFL   DIWTYNAELL
VLLENERTLD   FHDSNVRNLY  EKVKSQLKNN   AKEIGNGCFE   FYHKCDDACM
ESVRNGTYDY   PKYSEESKLN  REEIDGVKLE   SMGVYQILAI   YSTVASSLVL
LVSLGAISFW   MCSNGSLQCR  ICI
```

A three-dimensional representation of H3 HA with the amino acids residues that are predicted to be part of Ab 044 epitope but not part of FI6's epitope highlighted (i.e., the highlighted amino acids are unique to Ab 044's epitope) is depicted in FIG. 26 of International Publication No. WO2013/170139 or U.S. Application Publication No. 2013/0302349. A three-dimensional representation of H3 HA with the amino acid residues that are part of FI6's epitope but not predicted to be part of Ab 044's epitope highlighted is depicted in FIG. 27 of International Publication No. WO2013/170139 or U.S. Application Publication No. 2013/0302349.

Diagnostic Methods

The methods described herein can further include a diagnostic step as described herein. The binding agents, e.g., antibody molecules, provided herein are useful for identifying the presence of influenza in a biological sample, e.g., a patient sample, such as a fluid sample, e.g., a blood, serum, saliva, mucous, or urine sample, or a tissue sample, such as a biopsy. In one embodiment, a patient sample is contacted with a binding agent, e.g., an antibody molecule, featured in the disclosure, and binding is detected. Binding can be detected with a number of formats and means of detection, e.g., with an antigen capture assay, such as an ELISA assay or Western blot, or an immunohistochemistry assay. In some embodiments, the binding agent, e.g., an antibody molecule, is provided, e.g., coupled to an insoluble matrix, e.g., a bead or other substrate, and a detection molecule used to detect binding of HA.

Binding of binding agent, e.g., antibody molecule, to HA, can be detected with a reagent comprising a detectable moiety, e.g., a reagent, e.g., an antibody, which binds the binding agent, e.g., antibody molecule. In some embodiments, the binding agent, e.g., antibody molecule, has a detectable moiety. Suitable detectable moieties include enzymes (e.g., horseradish peroxidase, beta-galactosidase, luciferase, alkaline phosphatase, acetylcholinesterase, glucose oxidase and the like), radiolabels (e.g., $^3$H, $^{14}$C, $^{15}$N, $^{35}$S, $^{90}$Y, $^{99}$Tc, $^{111}$In, $^{125}$I, $^{131}$I), haptens, fluorescent labels (e.g., FITC, rhodamine, lanthanide phosphors, fluorescein, fluorescein isothiocyanate, rhodamine, 5-dimethylamine-1-napthalenesulfonyl chloride, phycoerythrin and the like), phosphorescent molecules, chemiluminescent molecules, chromophores, luminescent molecules, photoaffinity molecules, colored particles or affinity ligands, such as biotin, predetermined polypeptide epitopes recognized by a secondary reporter (e.g., leucine zipper pair sequences, or binding sites for secondary antibodies, metal binding domains, epitope tags). In some embodiments, labels are attached by spacer arms of various lengths to reduce potential steric hindrance.

In some embodiments, a human is tested for presence of influenza virus be a method described herein, and if the test is positive, binding agents, e.g., antibody molecules, e.g., an antibody provided herein, is administered. The binding agents, e.g., antibody molecules, e.g., an antibody, provided herein can be used for cytology assays, such as to identify an HA in a cell. The assay can be a colorimetric assay. A biological sample from a normal (non-infected) individual is used as a control. The diagnostic assay can be performed in vitro. The diagnostic assay can also be performed to determine infection of cells in culture, e.g., of mammalian cells in culture. The antibody molecules can be used in in vitro assays.

Because the antibody molecules featured herein bind a broad spectrum of HA subtypes, the diagnostic assays featured in the disclosure can detect the presence of influenza virus in patients infected with a variety of distinct strains of influenza. A patient sample can be further tested with subtype specific antibodies, or other assays (e.g., RFLP (Restriction Fragment Length Polymorphism), PCR (Polymerase Chain Reaction), RT-PCR (Reverse Transcription coupled to Polymerase Chain Reaction), Northern blot, Southern blot or DNA sequencing) to further determine the particular strain of virus. In one embodiment, a patient determined to be infected with influenza A can be further administered an antibody molecule featured in the disclosure, to treat the infection. Also provided are solid substrates, e.g., beads, dipsticks, arrays, and the like, on which is disposed a binding agent, e.g., antibody molecule.

Kits

A binding agent, e.g., an antibody molecule, disclosed herein, e.g., generated by the methods described herein, can be provided in a kit, e.g., for use in a method described herein. The kit can include one or more other components, e.g., containers, buffers or other diluents, delivery devices, and the like.

In one embodiment, the kit includes materials for administering an antibody molecule to a subject, such as for treatment or prevention of infection by influenza viruses. For example, the kit can include one or more or all of: (a) a container that contains a composition that includes an antibody molecule, optionally (b) a container that contains a composition that includes a second therapeutic agent, and optionally (c) informational material. In another embodiment, the kit includes materials for using an antibody molecule in a diagnostic assay, such as for detection of HA in a biological sample. For example, the kit can include one or more or all of: (a) a container that contains a composition that includes an antibody molecule, optionally (b) a container that contains a reagents, e.g., labeled with a detectable moiety, to detect the antibody, e.g., for use in an ELISA or immunohistochemistry assay, and optionally (c) informational material. In other embodiments, the kit comprises a binding agent, e.g., antibody molecule, comprising a detectable moiety.

In an embodiment, the kit comprises a solid substrate, e.g., bead, dipstick, array, and the like, on which is disposed a binding agent, e.g., antibody molecule. The informational material can be descriptive, instructional, marketing or other material that relates to the methods described herein and/or the use of the agents for therapeutic benefit, or for a diagnostic assay. The informational material of the kits is not limited in its form. In one embodiment, the informational material can include information about production of the antibody, concentration, date of expiration, batch or production site information, and so forth. In one embodiment, the informational material relates to methods of administering the antibody, e.g., in a suitable dose, dosage form, or mode of administration (e.g., a dose, dosage form, or mode of administration described herein), to treat a subject who has an infection, e.g., viral infection or secondary infection (e.g., secondary bacterial infection). In another embodiment, the informational material relates to methods for using the antibody molecule for a diagnostic assay, e.g., to detect the presence of influenza viruses in a biological sample. The information can be provided in a variety of formats, including printed text, computer readable material, video recording, or audio recording, or information that provides a link or address to substantive material. In addition to the agent, the composition in the kit can include other ingredients, such as a solvent or buffer, a stabilizer, or a preservative. The agent can be provided in any form, e.g., a liquid, dried or lyophilized form, and substantially pure and/or sterile. When the agents are provided in a liquid solution, the liquid solution typically is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more units of dosage forms (e.g., a dosage form described herein) of the agents. The containers can include a combination unit dosage, e.g., a unit that includes both the antibody molecule and the second or additional agent, such as in a desired ratio. For example, the kit can include a plurality of syringes, ampoules, foil packets, blister packs, or medical devices each containing, for example, a single combination unit dose. The containers of the kits can be air tight, waterproof (e.g., impermeable to changes in moisture or evaporation), and/or light-tight.

The kit optionally includes a device suitable for administering the composition, e.g., a syringe or device for delivering particles or aerosols, e.g., an inhaler, a spray device, or a dropper or other suitable delivery device. The device can be provided pre-loaded with one or both of the agents or can be empty but suitable for loading. The invention is further illustrated by the following examples, which should not be construed as further limiting.

Other Embodiments

The antibody molecule described herein can be encoded by a nucleic acid molecule, e.g., an isolated nucleic acid molecule. In an embodiment, the nucleic acid molecule comprises a nucleotide sequence that encodes a heavy chain immunoglobulin variable region segment featured in the disclosure. In another embodiment, the nucleic acid molecule comprises a nucleotide sequence encoding a light chain immunoglobulin variable region segment featured in the disclosure. In yet another aspect, the nucleic acid molecule comprises a nucleotide sequence that encodes a heavy chain immunoglobulin variable region segment featured in the disclosure and a light chain immunoglobulin variable region segment featured in the disclosure. In an embodiment, the nucleic acid molecule is present in a vector, e.g., a recombinant vector (e.g., an expression vector). In an embodiment, the vector comprises a nucleic acid molecule that comprises a nucleotide sequence that encodes a heavy chain immunoglobulin variable region segment featured in the disclosure, a nucleotide sequence that encodes a light chain immunoglobulin variable region segment featured in the disclosure, or both. In one embodiment, the nucleic acid molecule in the recombinant vector includes a nucleotide sequence encoding (a) a heavy chain immunoglobulin variable region segment comprising the amino acid sequence of: S-Y-A-M-H (SEQ ID NO:68) in CDR1; V-V-S-Y-D-G-N-Y-K-Y-Y-A-D-S-V-Q-G (SEQ ID NO:69) in CDR2; and D-S-R-L-R-S-L-L-Y-F-E-W-L-S-Q-G-Y-F-N-P (SEQ ID NO:70) in CDR3; and (b) a light chain immunoglobulin variable region segment comprising the amino acid sequence of: Q-S-I-T-F-D-Y-K-N-Y-L-A (SEQ ID NO:145) in CDR1; W-G-S-Y-L-E-S(SEQ ID NO:72) in CDR2; and Q-Q-H-Y-R-T-P-P-S(SEQ ID NO:73) in CDR3.

In an embodiment, the antibody molecule described herein is produced from a cell containing a recombinant vector featured in the disclosure, such as a recombinant vector comprising a nucleic acid sequence that encodes a heavy chain immunoglobulin variable region, or a recombinant vector comprising a nucleic acid sequence that encodes a light chain immunoglobulin variable region. In one embodiment, the cell contains a recombinant vector comprising a nucleic acid sequence that encodes a heavy chain immunoglobulin variable region, and a recombinant vector comprising a nucleic acid sequence that encodes a light chain immunoglobulin variable region. In yet another embodiment, the cell contains a recombinant vector comprising a nucleic acid sequence that encodes a heavy chain immunoglobulin variable region, and a nucleic acid sequence that encodes a light chain immunoglobulin variable region. In an embodiment, the antibody molecule is produced, e.g., by providing a host cell comprising a nucleic acid sequence expressing a heavy chain segment and a nucleic acid sequence expressing a light chain segment and expressing the nucleic acids in the host cell. In one embodiment, the nucleic acid sequence expressing the heavy chain segment and the nucleic acid sequence expressing the light chain segment are on the same recombinant expression vector. In another embodiment, the nucleic acid sequence expressing the heavy chain segment and the nucleic acid sequence expressing the light chain segment are on separate recombinant expression vectors.

In an embodiment, a pharmaceutical composition containing an antibody molecule featured in the disclosure, and a pharmaceutically acceptable carrier, is used in a method described herein.

In an embodiment, the method described herein treats or prevents an infection with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010), in a subject, e.g., a human subject, that comprises: administering a binding agent, e.g., an antibody molecule, featured in the disclosure to a subject, e.g., human subject, in need thereof. In one embodiment, the influenza A virus is an H1, H5, H9, H3 or H7 strain, such as an H1N1 strain, an H3N2 strain, or an H5N1 strain of influenza A virus. In an embodiment, the administration results in, or correlates with, one or more of a reduction in the incidence or severity of a symptom or manifestation of an influenza infection, or the delay or onset of a symptom or manifestation of an influenza infection. In an embodiment, the administration results in, or correlates with, one or more of a reduction in the incidence or severity of a symptom or manifestation of a secondary infection, or the delay or onset of a symptom or manifestation of a secondary infection. In some embodiments, the subject, e.g., a human subject, has been administered, or the method comprises, administering, or recommending the administration of, a second or additional therapy.

In some embodiments, the antibody molecule is administered in combination with a second or additional agent or therapy. In some embodiments, the second or additional therapy comprises administration of a vaccine or an antiviral therapy, e.g., an anti-NA or an anti-M2 therapy. In an embodiment, the second or additional therapy comprises an administration of a vaccine, e.g., a vaccine described herein or a mixture (a.k.a. a cocktail) of influenza peptides to stimulate the patient's immune system to prevent infection with particular strains of influenza A. In an embodiment, the second or additional agent comprises administering an antiviral agent, a pain reliever, an anti-inflammatory, an antibiotic, a steroidal agent, a second therapeutic antibody molecule (e.g., an anti-HA antibody), an adjuvant, a protease or glycosidase (e.g., sialidase). In an embodiment, the second or additional agent comprises, acyclovir, ribavirin, amantadine, rimantadine, a neuraminidase inhibitor (e.g., zanamivir (Relenza®), oseltamivir (Tamiflu®), laninamivir, peramivir), or rimantadine.

In an embodiment, the second or additional agent comprises a second antibody molecule, e.g., Ab 67-11 (U.S. Provisional application No. 61/645,453, FI6 (U.S. Application Publication No. 2010/0080813), FI28 (U.S. Application Publication No. 2010/0080813), C179 (Okuno et al., J. Virol. 67:2552-8, 1993), F10 (Sui et al., Nat. Struct. Mol. Biol. 16:265, 2009), CR9114 (Dreyfus et al., Science 337: 1343, 2012), or CR6261 (see, e.g., Ekiert et al., Science 324:246, 2009). Thus, Ab 044 can be used in combination of any of those antibodies. In an embodiment, the second or additional agent comprises a second or additional binding agent, e.g., antibody molecule, e.g., an anti-HA antibody, e.g., an anti-HA antibody disclosed herein. E.g., two or more of Ab 044, Ab 069, Ab 032, and Ab 031 can be administered. E.g., Ab 044 can be administered in combination with Ab 069 or Ab 032. In the case of combinations, two agents can be administered as part of the same dosage unit or administered separately. Other exemplary agents useful for treating the symptoms associated with influenza infection are acetaminophen, ibuprofen, aspirin, and naproxen.

In an embodiment, the binding agent, e.g., an antibody molecule, is administered to a human subject suffering from or susceptible to an influenza infection. In an embodiment, the binding agent, e.g., an antibody molecule, is administered prior to known exposure to influenza, or to particular influenza subtypes or strains. In an embodiment, the binding agent, e.g., an antibody molecule, is administered prior to manifestation of effects or symptoms of influenza infection, or to one or more particular effects manifestation of effects or symptoms of influenza infection. In an embodiment, the binding agent, e.g., an antibody molecule, is administered after known exposure to influenza, or to particular influenza subtypes or strains. In an embodiment, the binding agent, e.g., an antibody molecule, is administered after manifestation of effects or symptoms of influenza infection, or after observation of one or more particular effects manifestation of effects or symptoms of influenza infection. In an embodiment, the binding agent, e.g., an antibody molecule, is administered in response to, or to treat or prevent, a manifestation of an effect or a symptom of influenza infection, e.g., inflammation, fever, nausea, weight loss, loss of appetite, rapid breathing, increase heart rate, high blood pressure, body aches, muscle pain, eye pain, fatigue, malaise, dry cough, runny nose, and/or sore throat.

In an embodiment, the method further comprises, testing the human subject for the influenza virus, e.g., with a method disclosed herein. In some embodiments, the administration is responsive to a positive test for influenza.

In an embodiment, the method described herein treats a subject, e.g., a human subject, an infected with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010) by administering a binding agent, e.g., an antibody molecule, featured in the disclosure. For example, the influenza A virus is an H1, H5, H9, H3 or H7 strain, such as an H1N1 strain, an H3N2 strain, or an H5N1 strain of influenza A virus. In one embodiment, a binding agent, e.g., an anti-HA antibody, described herein is administered instead of a vaccine for prevention of influenza. In another embodiment, the binding agent, e.g., anti-HA antibody molecule, is administered in combination with (simultaneously or sequentially with) a vaccine for prevention of the flu.

In an embodiment, the method further comprises detecting influenza (e.g., influenza A or influenza B) virions in a biological sample, such as by contacting the sample with a binding agent, e.g., an antibody molecule, featured in the disclosure, and then detecting the binding of the antibody molecule to the sample. In one embodiment, the method of detecting the influenza virus (e.g., influenza A or influenza B virus) is performed in vitro.

In an embodiment, the method further includes: (a) providing a sample from a patient; (b) contacting the sample with a binding agent, e.g., an antibody molecule, featured in the disclosure, and (c) determining whether the binding agent, e.g., an antibody molecule, featured in the disclosure binds a polypeptide in the sample, where if the binding agent, e.g., an antibody molecule, binds a polypeptide in the sample, then the patient is determined to be infected with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/ 2004, or an influenza B virus, e.g., e.g., B/Wisconsin/1/ 2010). In one embodiment, the patient is determined to be infected with an influenza virus (e.g., an influenza A virus, e.g., a Group 1 strain, e.g., an H1N1 strain, e.g., A/South Carolina/1/1918, A/Puerto Rico/08/1934, or A/California/ 04/2009, or an H5N1 strain, e.g., A/Indonesia/5/2005 or A/Vietnam/1203/2004, or an influenza B virus, e.g., B/Wisconsin/1/2010), and the patient is further administered a binding agent, e.g., an antibody molecule, disclosed herein, e.g., the binding agent, e.g., an antibody molecule, with which the test was performed.

In an embodiment, the method further includes inducing immunity to one or more influenza strains, or preventing, delaying or reducing infection with an influenza strain, or symptom thereof, in a vertebrate, e.g., a human. The method comprises administering to the vertebrate, e.g., a human, a broad range vaccine, or broad range immunogen, described herein.

In an embodiment, the broad range vaccine, or broad range immunogen, induces an immune response against, or confers protection against, one or more influenza strains. In an embodiment, the broad range vaccine, or broad range immunogen, induces an immune response against, or confers protection against, two influenza strains. In an embodiment, the broad range vaccine, or broad range immunogen, induces an immune response against, or confers protection against, two Group 1 influenza strains. In an embodiment, the broad range vaccine induces, or broad range immunogen, an immune response against, or confers protection against, at least one Group 1 strain, and a second strain from Group 1, Group 2 or an influenza B strain. In one embodiment, the influenza A virus is an H1, H5, H9, H3 or H7 strain, such as an H1N1 strain, an H3N2 strain, or an H5N1 strain of influenza A virus.

In an embodiment, the administration results in, or correlates with, one or more of: a reduction in the chance of an infection, a reduction in the incidence or severity of a symptom or manifestation of an influenza infection, or the delay or onset of a symptom or manifestation of an influenza infection. In an embodiment, the administration results in, or correlates with, one or more of: a reduction in the incidence or severity of a symptom or manifestation of a secondary infection, or the delay or onset of a symptom or manifestation of a secondary infection.

In some embodiments, the subject, e.g., a human subject, has been administered, or the method comprises, administering, or recommending the administration of, a second or additional therapy. In some embodiments, the broad range vaccine is administered in combination with a second or additional agent or therapy. In some embodiments, the second or additional agent comprises administration of another vaccine or another anti-viral therapy, e.g., an anti-NA or an anti-M2 therapy. In an embodiment, the second or additional agent comprises administration of a vaccine comprising a mixture (a.k.a. a cocktail) of influenza peptides to stimulate the patient's immune system to prevent infection with particular strains of influenza A. In an embodiment, the second or additional agent comprises administering an anti-viral agent, a pain reliever, an anti-inflammatory, an antibiotic, a steroidal agent, a second therapeutic antibody molecule (e.g., an anti-HA antibody), an adjuvant, a protease or glycosidase (e.g., sialidase). In an embodiment, the second or additional agent comprises, acyclovir, ribavirin, amantadine, rimantadine, a neuraminidase inhibitor (e.g., zanamivir (Relenza®), oseltamivir (Tamiflu®), laninamivir, peramivir), or rimantadine. In an embodiment, the second or additional agent comprises an antibody molecule, e.g., Ab 67-11 (U.S. Provisional application No. 61/645,453, FI6 (U.S. Application Publication No. 2010/0080813), FI28 (U.S. Application Publication No. 2010/0080813), C179 (Okuno et al., *J. Virol.* 67:2552-8, 1993), F10 (Sui et al., *Nat. Struct. Mol. Biol.* 16:265, 2009), CR9114 (Dreyfus et al., *Science* 337:1343, 2012), or CR6261 (Ekiert et al., *Science* 324:246, 2009). In an embodiment, the second or additional agent comprises an antibody molecule disclosed herein, e.g., an antibody molecule selected from Ab-044, Ab 069, Ab 032, and Ab 031 antibody molecules. In the case of combinations, two agents can be administered as part of the same dosage unit or administered separately. Other exemplary second or additional agents useful for treating the symptoms associated with influenza infection are acetaminophen, ibuprofen, aspirin, and naproxen.

In an embodiment, the method further comprises, testing the human subject for the influenza virus, e.g., with a method disclosed herein. In some embodiments, the administration is responsive to a positive test for influenza. In an embodiment, the method further comprises reducing the severity of influenza in a population. The method includes administering a broad range vaccine, or broad range immunogen, to sufficient individuals in the population to prevent or decrease the chance of influenza virus transmission to another individual in the population.

Anti-HA antibody molecules described herein are also disclosed in International Publication No. WO2013/170139, U.S. Pat. Nos. 8,877,200, 9,096,657, and U.S. Patent Application Publication No. US 2013/0302349. The contents of the aforesaid publications are incorporated by reference in their entirety.

TABLE 4C

Nucleic acid and amino acid sequences

Figure 1:
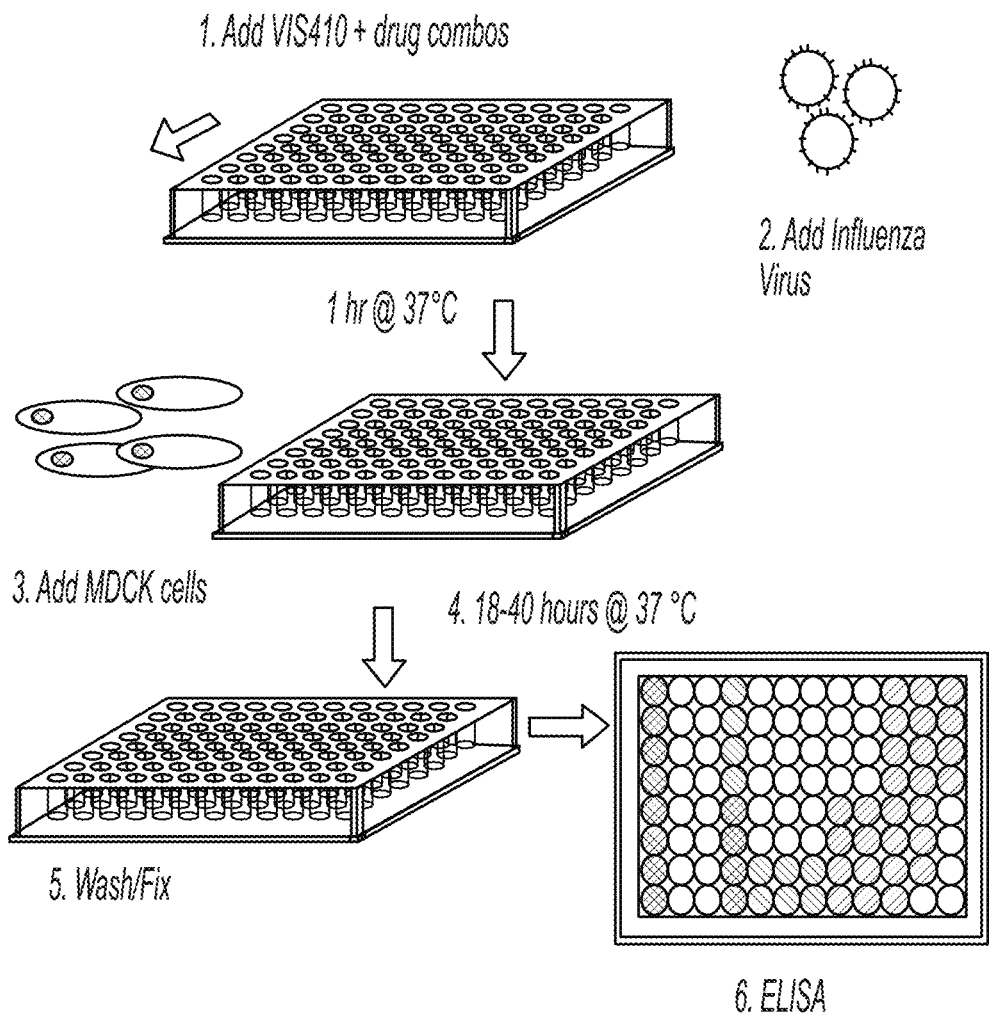
FIG. 1 is a diagram showing an overview of an exemplary microneutralization protocol.

| SEQ ID NO. | Lab no. | Source | Comment | Sequence |
|---|---|---|---|---|
| 1 | n.a. | Table 2 | Consensus AA sequence of HC CDR1 | [S/T]Y[A/G]MH |
| 2 | n.a. | Table 2 | Consensus AA sequence of HC CDR2 | V[I/V/L]S[Y/F]DG[S/N][Y/N][K/R]YYADSVQG |
| 3 | n.a. | Table 2 | Consensus AA sequence of HC CDR3 | D[S/T][R/K/Q]LR[S/T]LLYFEWLS[Q/S]G[Y/L/V][F/L][N/D][P/Y] |
| 4 | n.a. | Table 2 | Consensus AA sequence of LC CDR1 | Q[S/T][V/L/I][T/S][Y/F/W][N/S/D]YKNYLA |
| 170 | n.a. | Table 2 | Consensus AA sequence of LC CDR1 | Q[S/T][V/L/I][T/S][Y/F/W][N/S/D/Q/R/E]YKNYLA |
| 5 | n.a. | Table 2 | Consensus AA sequence of LC CDR2 | W[A/G]S[T/A/Y/H/K/D][R/L]E[S/T] |
| 6 | n.a. | Table 2 | Consensus AA sequence of LC CDR3 | QQ[Y/H]YRTPP[T/S] |
| 7 | n.a. | Table 2 | Consensus AA sequence of HC FR1 | [E/Q]VQLLE[S/T]GGGLVKpGQSLKLSCAASGFTF[S/T] |
| 8 | n.a. | Table 2 | Consensus AA sequence of HC FR2 | WVRQPPGKGLEWVA |
| 9 | n.a. | Table 2 | Consensus AA sequence of HC FR3 | RFTISRDNSKNTLYLQMNSLRAEDTAVYYCAK |
| 10 | n.a. | Table 2 | Consensus AA sequence of HC FR4 | WG[A/Q]G[T/A][T/M][L/V]TVSS |
| 11 | n.a. | Table 2 | Consensus AA sequence of LC FR1 | [E/D]I[V/Q]MTQSP[D/S][S/T][L/V][A/S][V/A][S/T][L/V/R]G[E/D][R/A/V][T/S][I][N/T/Q/D/R/C][K/R]SS |
| 12 | n.a. | Table 2 | Consensus AA sequence of LC FR2 | WYQKPG[Q/K][P/A]PKLLIY |
| 13 | n.a. | Table 2 | Consensus AA sequence of LC FR3 | GVP[D/E/S]RFSGSGSGTDFTLTISSLQ[A/P]ED[V/F/K/D]A[V/T]YYC |
| 14 | n.a. | Table 2 | Consensus AA sequence of LC FR4 | FG[G/Q/T/S/N]GTK[L/V][D/E]IK |
| 15 | 15 VH15 | Table 3, Table 4A, FIG. 2 | AA sequence of HC VR of Ab A18; entire HC domain is in FIG. 1; ID version is in FIG. 13; NT sequence is in Example 1 | EVQLLESGGGLVKPGQSLKLSCAASGFTFTSYGMHWVRQPPGKGLEWVAVISYDGSYKYYADSVQG RFTISRDNSKNTLYLQMNSLRAEDTAVYYCAKDSRLRSLLYFEWLSQGYFNPWGAGTTLTVSS |
| 28 | 28 VL28 | Table 3, Table 4A, FIG. 3 | AA sequence of LC VR of Ab A18; entire LC domain is in FIG. 1; ID version is in FIG. 14; NT sequence is in Example 1 | EIVMTQSPDSLAVSLGERATINCKSSQSVTYNYKNYLAWYQQKPGQPPKLLIYWASTRESGVPDRF SGSGSGTDFTLTISSLQAEDVAVYYCQQYYRTPPTFGGGTKLDIK |
| 16 | 16 VH16 | Table 3, Table 4A, FIG. 2 | AA sequence of HC VR of Abs 014,028; ID version is in FIG. 13; NT sequence is in Example 1 | EVQLLESGGGLVKPGQSLKLSCAASGFTFSSYGMHWVRQPPGKGLEWVAVVSYDGSNKYYADSVQG RFTISRDNSKNTLYLQMNSLRAEDTAVYYCAKDTKLRSLLYFEWLSSGLLDYWGQGAMVTVSS |
| 29 | 29 VL29 | Table 3, Table 4A, FIG. 3 | AA sequence of LC of Abs 014, 154,157; ID version is in FIG. 14; NT sequence is in Example 1 | EIVMTQSPDSLAVSLGERATINCKSSQSVTFSYKNYLAWYQQKPGQPPKLLIYWASTRESGVPDRF SGSGSGTDFTLTISSLQAEDVAVYYCQQYYRTPPTFGGGTKLDIK |

TABLE 4C-continued

Nucleic acid and amino acid sequences

| SEQ ID NO. | Lab no. | Source | Comment | Sequence |
|---|---|---|---|---|
| 30 | VL30 | Table 3 Table 4A FIG. 3 | AA sequence of LC VR of Abs 028, 155; ID version is in FIG. 14; NT sequence is in Example 1 | EIVMTQSPDSLAVSLGERATINCKSSQSVTFDYKNYAWYQQKPGQPPKLLIYWASTRESGVPDRFS GSGSGTDFTLTISSLQAEDVAVYYCQQYRTPPTFGGGTKLDIK |
| 17 | VH17 | Table 3 Table 4A FIG. 2 | AA sequence of HC VR of Abs 001, 009, 017, 025, 160, 186, 187, 188, 189, 190, 191, 192, 193, 202, 211; ID version is in FIG. 13; | EVQLLESGGGLVKPGQSLKLSCAASGFTFTSYGMHWVRQPPGKGLEWVAVVSDGNYKYYADSVQG RFTISRDNSKNTLYLQMNSLRAEDTAVYYCAKDSRLRSLLYFEWLSQGYFNPWGAGTLLTVSS |
| 31 | VL31 | Table 3 Table 4A FIG. 3 | AA sequence of LC VR of Abs 001, 002, 003; ID version is in FIG. 14; | EIVMTQSPDSLAVSLGERATINCKSSQTVTFNYKNYLAWYQQKPGQPPKLLIYWASTRESGVPDRF SGSGSGTDFTLTISSLQAEDVAVYYCQQHRTPSFGGGTKLDIK |
| 18 | VH18 | Table 3 Table 4A FIG. 2 | AA sequence of HC VR of Abs 002, 010, B18, 026, 203, 212; ID version is in FIG. 13; | EVQLLESGGGLVKPGQSLKLSCAASGFTFTSYGMHWVRQPPGKGLEWVAVLSDGNYKYYADSVQG RFTISRDNSKNTLYLQMNSLRAEDTAVYYCAKDSRLRSLLYFEWLSQGYFNPWGAGTLLTVSS |
| 19 | VH19 | Table 3 Table 4A FIG. 2 | AA sequence of HC VR of Abs 003, 011, 019, 027, 194, 195, 196, 197, 198, 199, 200, 204, 213; ID version is in FIG. 13; | EVQLLESGGGLVKPGQSLKLSCAASGFTFTTYAMHWVRQPPGKGLEWVAVLSDGNYKYYADSVQG RFTISRDNSKNTLYLQMNSLRAEDTAVYYCAKDSRLRSLLYFEWLSQGYFNPWGAGTLLTVSS |
| 32 | VL32 | Table 3 Table 4A FIG. 3 | AA sequence of LC VR of Abs 009, 010, 011; ID version is in FIG. 14; | EIVMTQSPDSLAVSLGERATINCKSSQTLSFNYKNYLAWYQQKPGQPPKLLIYWASTRESGVPDRF SGSGSGTDFTLTISSLQAEDVAVYYCQQHRTPSFGGGTKLDIK |
| 33 | VL33 | Table 3 Table 4A FIG. 3 | AA sequence of LC VR of Abs 017, B18, 019; ID version is in FIG. 14; | EIVMTQSPDSLAVSLGERATINCKSSQTVTFNYKNYLAWYQQKPGQPPKLLIYWASTRESGVPDRF SGSGSGTDFTLTISSLQAEDVAVYYCQQHRTPSFGGGTKLDIK |
| 34 | VL34 | Table 3 Table 4A FIG. 3 | AA sequence of LC VR of Abs 025, 026, 027; ID version is in FIG. 14; | EIVMTQSPDSLAVSLGERATINCKSSQTLSFNYKNYLAWYQQKPGQPPKLLIYFASTRESGVPDRF SGSGSGTDFTLTISSLQAEDVAVYYCQQHRTPSFGGGTKLDIK |
| 20 | VH20 | Table 3 Table 4A FIG. 2 | AA sequence of HC VR of Ab 086; ID version is in FIG. 13; | EVQLLESGGGLVKPGQSLKLSCAASGFTFTTYAMHWVRQPPGKGLEWVAVVSFDGNNRYYADSVQG RFTISRDNSKNTLYLQMNSLRAEDTAVYYCAKDSQLRSLLYFEWLSSGVLDYWGQGAMVTVSS |
| 21 | VH21 | Table 3 Table 4A FIG. 2 | AA sequence of HC VR of Abs 154,155; ID version is in FIG. 13; | EVQLLESGGGLVKPGQSLKLSCAASGFTFSSYGMHWVRQPPGKGLEWVAVVSTDGNNKYYADSVQG RFTISRDNSKNTLYLQMNSLRAEDTAVYYCAKDSKLRSLLYFEWLSGLLDYWGQGAMVTVSS |
| 22 | VH22 | Table 3 Table 4A FIG. 2 | AA sequence of HC VR of Abs 157, 159; ID version is in FIG. 13; | EVQLLESGGGLVKPGQSLKLSCAASGFTFTTYAMHWVRQPPGKGLEWVAVVSTDGNNKYYADSVQG RFTISRDNSKNTLYLQMNSLRAEDTAVYYCAKDSKLRSLLYFEWLSGLLDYWGQGAMVTVSS |
| 35 | VL35 | Table 3 Table 4A FIG. 3 | AA sequence of LC VR of Ab 159; ID version is in FIG. 14; | EIVMTQSPDSLAVSLGERATINCKSSQVTWSYKNYLAWYQQKPGQPPKLLIYWASTRESGVPDRF SGSGSGTDFTLTISSLQAEDVAVYYCQQYRTPPTFGGGTKLDIK |

TABLE 4C-continued

Nucleic acid and amino acid sequences

| SEQ ID NO. | Lab no. | Source | Comment | Sequence |
|---|---|---|---|---|
| 36 | 36 VL36 | Table 3 Table 4A FIG. 3 | AA sequence of LC VR of Ab 160; ID version is in FIG. 14; | EIVMSQSPDTLAVTLGERASINCKSSQTVTFNYKNYLAWYQQKPGQPPKVLIYWASARETGVPERF SGSGSGTDFTLTISSLQAEDVAVYCQQHRTPPSFGQGTKLEIK |
| 37 | 37 VL37 | Table 3 Table 4A FIG. 3 | AA sequence of LC VR of Abs 186, 194; ID version is in FIG. 14; | EIVMTQSPDSLAVSLGERATINCKSSQTVTFNYKNYLAWYQQKPGQPPKLLIYWASTRESGVPDRF SGSGSGTDFTLTISSLQAEDVAVYCQQHRTPPSFGTGTKLDIK |
| 38 | 38 VL38 | Table 3 Table 4A FIG. 3 | AA sequence of LC VR of Abs 187, 195; ID version is in FIG. 14; | EIVMTQSPDSLAVSLGERATINCKSSQTVTFNYKNYLAWYQQKPGQPPKLLIYWASTRESGVPDRF SGSGSGTDFTLTISSLQAEDVAVYCQQHRTPPSFGSGTKLDIK |
| 39 | 39 VL39 | Table 3 Table 4A FIG. 3 | AA sequence of LC VR of Abs 188, 196; ID version is in FIG. 14; | EIVMTQSPDSLAVSLGERATINCKSSQTVTFNYKNYLAWYQQKPGQPPKLLIYWASTRESGVPDRF SGSGSGTDFTLTISSLQAEDVAVYCQQHRTPPSFGNGTKLDIK |
| 40 | 40 VL40 | Table 3 Table 4A FIG. 3 | AA sequence of LC VR of Abs 189, 197; ID version is in FIG. 14; | EIVMTQSPDSLAVSLGERATINCKSSQTVTFNYKNYLAWYQQKPGQPPKLLIYWASTRESGVPDRF SGSGSGTDFTLTISSLQAEDVAVYCQQHRTPPSFGNGTKLDIK |
| 41 | 41 VL41 | Table 3 Table 4A FIG. 3 | AA sequence of LC VR of Abs 190, 198; ID version is in FIG. 14; | EIVMTQSPDSLAVSLGERATINCKSSQTLSFNYKNYLAWYQQKPGQPPKLLIYWASTRESGVPDRF SGSGSGTDFTLTISSLQAEDVAVYCQQHRTPPSFGTGTKLDIK |
| 42 | 42 VL42 | Table 3 Table 4A FIG. 3 | AA sequence of LC VR of Abs 191, 199; ID version is in FIG. 14; | EIVMTQSPDSLAVSLGERATINCKSSQTLSFNYKNYLAWYQQKPGQPPKLLIYWASTRESGVPDRF SGSGSGTDFTLTISSLQAEDVAVYCQQHRTPPSFGSGTKLDIK |
| 43 | 43 VL43 | Table 3 Table 4A FIG. 3 | AA sequence of LC VR of Abs 192, 200; ID version is in FIG. 14; | EIVMTQSPDSLAVSLGERATINCKSSQTLSFNYKNYLAWYQQKPGQPPKLLIYWASTRESGVPDR FSGSGSGTDFTLTISSLQAEDVAVYCQQHRTPPSFGQGTKLDIK |
| 44 | 44 VL44 | Table 3 Table 4A FIG. 3 | AA sequence of LC VR of Abs 193; ID version is in FIG. 14; | EIVMTQSPDSLAVSLGERATINCKSSQTLSFNYKNYLAWYQQKPGQPPKLLIYWASTRESGVPDRF SGSGSGTDFTLTISSLQAEDVAVYCQQHRTPPSFGNGTKLDIK |
| 45 | 45 VL45 | Table 3 Table 4A FIG. 3 | AA sequence of LC VR of Abs 202, 203, 204, 210, 031, 032, 033, 034; ID version is in FIG. 14; NT sequence is in Example 1 | DIQMTQSPSSLSASVGDRVTITCRSSQSITFNYKNYLAWYQQKPGKAPKLLIYWGSYLESGVPSRF SGSGSGTDFTLTISSLQPEDFATYYCQQHRTPPSFGQGTKVEIK |
| 46 | 46 VL46 | Table 3 Table 4A FIG. 3 | AA sequence of LC VR of Abs 211, 212, 213, 219, 037, 038, 039, 040; ID version is in FIG. 14; | DIQMTQSPSSLSASVGDRVTITCRSSQSITFNYKNYLGWYQQKPGKAPKLLIYWGSYLESGVPSRF SGSGSGTDFTLTISSLQPEDFATYYCQQHRTPPSFGQGTKVEIK |
| 23 | 23 VH23 | Table 3 Table 4A FIG. 2 | AA sequence of HC VR of Abs 210, 219 ; ID version is in FIG. 13; | EVQLLESGGGLVKPGQSLKLSCAASGFTFTSYGMHWVRQPPGKGLEWVAVVSDGNYKYYADSVQG RFTISRDNSKNTLYLQMNSLRAEDTAVYYCAKDSKLRSLLYFEWLSQGYFNPWGAGTLTVSS |

TABLE 4C-continued

Nucleic acid and amino acid sequences

| SEQ ID NO. | Lab no. | Source | Comment | Sequence |
|---|---|---|---|---|
| 24 | 24 VH24 | Table 3 Table 4A FIG. 2 | AA sequence of HC VR of Abs A001, A002, A003, A010, A011, 031, 037; ID version is in FIG. 13; NT sequence is in Example 1 | EVQLLESGGGLVKPGQSLKLSCAASGFTFTSYAMHWVRQPPGKGLEWVAVVSYDGNYKYADSVQG RFTISRDNSKNTLYLQMNSLRAEDTAVYYCAKDSRLRSLLYFEWLSQGYFNPWGQGTTLTVSS |
| 47 | 47 VL47 | Table 3 Table 4A FIG. 3 | AA sequence of LC VR of Abs A001, 004, 007, 016; ID version is in FIG. 14; | DIVMTQSPDTLAVTLGERATIQCKSSQTVTFNYKNYLAWYQQKPGQPPKLLIYWASTRESGVPDRF SGSGSGTDFTLTITSLQAEDVAVYYCQQHRTPSFGQGTKLDIK |
| 48 | 48 VL48 | Table 3 Table 4A FIG. 3 | AA sequence of LC VR of Abs 002, 005, 008, A017; ID version is in FIG. 14; | DIVMTQSPDTVAVTVGERATIRCKSSQTVTFNYKNYLAWYQQKPGQPPKLLIYWASTRESGVPDRF SGSGSGTDFTLTISSLQAEDVAVYYCQQHRTPSFGQGTKLDIK |
| 25 | 25 VH25 | Table 3 Table 4A FIG. 2 | AA sequence of HC VR of Abs 004, 005, 006, 012, 013, 032, 038, 043, 044, 045, 046, 047, 048, 049, 050, 051, 052, 067, 068, 069, 070, 073, 074, 075, 076, 077; ID version is in FIG. 13; NT sequence is in Example 1 | QVQLLETGGGLVKPGQSLKLSCAASGFTFTSYAMHWVRQPPGKGLEWVAVVSYDGNYKYADSVQG RFTISRDNSKNTLYLQMNSLRAEDTAVYYCAKDSRLRSLLYFEWLSQGYFNPWGQGTTLTVSS |
| 49 | 49 VL49 | Table 3 Table 4A FIG. 3 | AA sequence of LC VR of Abs A003, 006, A009, C18; ID version is in FIG. 14; | DIVMTQSPDTVAVTLGERATIDCKSSQTVTFNYKNYLAWYQQKPGQPPKLLIYWASTRESGVPDRF SGSGSGTDFTLTISSLQAEDVAVYYCQQHRTPSFGQGTKLDIK |
| 26 | 26 VH26 | Table 3 Table 4A FIG. 2 | AA sequence of HC VR of Abs 007, 008, A009, A14, 015, 033, 039; ID version is in FIG. 13; | EVQLLESGGGLVKPGQSLKLSCAASGFTFTSYAMHWVRQPPGKGLEWVAVVSYDGNYKYADSVQG RFTISRDNSKNTLYLQMNSLRAEDTAVYYCAKDSQLRTLLYFEWLSQGYFNPWGQGTTLTVSS |
| 50 | 50 VL50 | Table 3 Table 4A FIG. 3 | AA sequence of LC VR of Abs A010 012, A14, A019; ID version is in FIG. 14; | DIVMTQSPDTVAVTVGERATIRCKSSQTVTFNYKNYLAWYQQKPGQPPKLLIYWASTRESGVPDRF SGSGSGTDFTLTISSLQAEDVAVYYCQQHRTPSFGQGTKLDIK |
| 51 | 51 VL51 | Table 3 Table 4A FIG. 3 | AA sequence of LC VR of Abs A011, 013, 015; ID version is in FIG. 14; | DIVMTQSPDTLAVSRGERATIDCKSSQTVTFNYKNYLAWYQQKPGQPPKLLIYWASTRESGVPDRF SGSGSGTDFTLTISSLQAEDEAVYYCQQHRTPSFGQGTKLDIK |
| 27 | 27 VH27 | Table 3 Table 4A FIG. 2 | AA sequence of HC VR of Abs 016, A017, C18, A019, 034, 040; ID version is in FIG. 13; | EVQLLESGGGLVKPGQSLKLSCAASGFTFTSYAMHWVRQPPGKGLEWVAVVSYDGNYKYADSVQG RFTISRDNSKNTLYLQMNSLRAEDTAVYYCAKDSRLRTLLYFEWLSQGYFDPWGQGTTLTVSS |
| 60 | 60 VL60 | Table 3 Table 4A FIG. 3 | AA sequence of LC VR of Ab 043; ID version is in FIG. 14; | DIQMTQSPSSLSASVGDRVTITCRSSQSITFNYKNYLAWYQQKPGKAPKLLIYWGSYLESGVPSRF SGSGSGTDFTLTISSLQPEDFATYYCQQYRTPSFGQGTKVEIK |
| 52 | 52 VL52 | Table 3 Table 4A FIG. 3 | AA sequence of LC VR of Abs 044, 071, 072, 078; ID version is in FIG. 14; NT sequence is in Example 1 | DIQMTQSPSSLSASVGDRVTITCRSSQSITFDYKNYLAWYQQKPGKAPKLLIYWGSYLESGVPSRF SGSGSGTDFTLTISSLQPEDFATYYCQQHRTPSFGQGTKVEIK |

TABLE 4C-continued

Nucleic acid and amino acid sequences

| SEQ ID NO. | Lab no. | Source | Comment | Sequence |
|---|---|---|---|---|
| 57 | 57 VL57 | Table 3 Table 4A FIG. 3 | AA sequence of LC VR of Ab 045; ID version is in FIG. 14; | DIQMTQSPSSLSASVGDRVTITCRSSQSITFNYKNYLAWYQQKPGKAPKLLIYWGSYLESGVPSRF SGSGSGTDFTLTISSLQPEDVATYYCQQHYRTPPSFGQGTKVEIK |
| 59 | 59 VL59 | Table 3 Table 4A FIG. 3 | AA sequence of LC VR of Ab 046; ID version is in FIG. 14; | DIQMTQSPSSLSASVGDRVTITCRSSQSITFNYKNYLAWYQQKPGKAPKLLIYWGSYLESGVPSRF SGSGSGTDFTLTISSLQPEDDATYYCQQHYRTPPSFGQGTKVEIK |
| 55 | 55 VL55 | Table 3 Table 4A FIG. 3 | AA sequence of LC VR of Ab 047; ID version is in FIG. 14; | DIQMTQSPSSLSASVGDRVTITCRSSQSITFNYKNYLAWYQQKPGKAPKLLIYWGSKLESGVPSRF SGSGSGTDFTLTISSLQPEDFATYYCQQHYRTPPSFGQGTKVEIK |
| 58 | 58 VL58 | Table 3 Table 4A FIG. 3 | AA sequence of LC VR of Ab 048; ID version is in FIG. 14; | DIQMTQSPSSLSASVGDRVTITCRSSQSITFNYKNYLAWYQQKPGKAPKLLIYWGSYLESGVPSRF SGSGSGTDFTLTISSLQPEDKATYYCQQHYRTPPSFGQGTKVEIK |
| 54 | 54 VL54 | Table 3 Table 4A FIG. 3 | AA sequence of LC VR of Ab 049; ID version is in FIG. 14; | DIQMTQSPSSLSASVGDRVTITCRSSQSITFNYKNYLAWYQQKPGKAPKLLIYWGSHLESGVPSRF SGSGSGTDFTLTISSLQPEDFATYYCQQHYRTPPSFGQGTKVEIK |
| 56 | 56 VL56 | Table 3 Table 4A | AA sequence of LC VR of Ab 050; ID version is in FIG. 14; | DIQMTQSPSSLSASVGDRVTITCRSSQSITFNYKNYLAWYQQKPGKAPKLLIYWGSDLESGVPSRF SGSGSGTDFTLTISSLQPEDFATYYCQQHYRTPPSFGQGTKVEIK |
| 53 | 53 VL53 | Table 3 Table 4A FIG. 3 | AA sequence of LC VR of Ab 051; ID version is in FIG. 14; | DIQMTQSPSSLSASVGDRVTITCRSSQSITFNYKNYLAWYQQKPGKAPKLLIYWGSTLESGVPSRF SGSGSGTDFTLTISSLQPEDFATYYCQQHYRTPPSFGQGTKVEIK |
| 61 | 61 VL61 | Table 3 Table 4A FIG. 3 | AA sequence of LC VR of Ab 052; ID version is in FIG. 14; | DIQMTQSPSSLSASVGDRVTITCRSSQSITFNYKNYLAWYQQKPGKAPKLLIYWGSTRESGVPSRF SGSGSGTDFTLTISSLQPEDFATYYCQQHYRTPPSFGQGTKVEIK |
| 153 | 153 VL153 | Table 3 Table 4A FIG. 3 | AA sequence of LC VR of Ab 067; ID version is in FIG. 14; | DIQMTQSPSSLSASVGDRVTITCRSSQSITFQYKNYLAWYQQKPGKAPKLLIYWGSYLESGVPSRF SGSGSGTDFTLTISSLQPEDFATYYCQQHYRTPPSFGQGTKVEIK |
| 154 | 154 VL154 | Table 3 Table 4A | AA sequence of LC VR of Ab 068; ID version is in FIG. 14; | DIQMTQSPSSLSASVGDRVTITCRSSQSITFRYKNYLAWYQQKPGKAPKLLIYWGSYLESGVPSRF SGSGSGTDFTLTISSLQPEDFATYYCQQHYRTPPSFGQGTKVEIK |
| 155 | 155 VL155 | Table 3 Table 4A | AA sequence of LC VR of Abs 069, 079; ID version is in FIG. 14 | DIQMTQSPSSLSASVGDRVTITCRSSQSITFEYKNYLAWYQQKPGKAPKLLIYWGSYLESGVPSRF SGSGSGTDFTLTISSLQPEDFATYYCQQHYRTPPSFGQGTKVEIK |
| 156 | 156 VL156 | Table 3 Table 4A FIG. 3 | AA sequence of LC VR of Ab 070; ID version is in FIG. 14; | DIQMTQSPSSLSASVGDRVTITCRSSQSITFDYKNYLAWYQQKPGKAPKLLIYWGSTRESGVPSRF SGSGSGTDFTLTISSLQPEDFATYYCQQHYRTPPSFGQGTKVEIK |

TABLE 4C-continued

Nucleic acid and amino acid sequences

| SEQ ID NO. | Lab no. | Source | Comment | Sequence |
|---|---|---|---|---|
| 162 | 162 VL162 | Table 3 Table 4A FIG. 17 | AA sequence of HC VR of Ab 071 | EVQLLESGGGLVKPGQSLKLSCAASGFSFSTYAMHWVRQPPGKGLEWVAVVSYDGNYKYYADTVQG RFTISRDNSKNTLYLQMNSLRAEDTAVYYCAKDSRLRSLLYFEWLSQGYFNPWGQGTTLTVSS |
| 163 | 163 VL163 | Table 3 Table 4A FIG. 17 | AA sequence of HC VR of Ab 072 | EVQLLESGGGLVKPGQSLRLSCAASGFSFSTYAMHWVRQPPGKGLEWVAVVSYDGNYKYYADSVQG RFTISRDNSKNTLYLQMNSLRAEDTAVYYCAKDSRLRSLLYFEWLSQGYFNPWGQGTTLTVSS |
| 165 | 165 VL165 | Table 3 Table 4A FIG. 17 | AA sequence of LC VR of Ab 073 | DIQMTQSPSSLSASVGDRVTITCRSSQSITWNYKNYLAWYQQKPGKAPKLLIYWGSYLESGVPSRF SGSGSGTDFTLTISSLQPEDFATYYCQQHRTPSFGQGTKVEIK |
| 166 | 166 VL166 | Table 3 Table 4A FIG. 17 | AA sequence of LC VR of Abs 074, 080 | DIQMTQSPSSLSASVGDRVTITCRSSQSITWDYKNYLAWYQQKPGKAPKLLIYWGSYLESGVPSRF SGSGSGTDFTLTISSLQPEDFATYYCQQHRTPSFGQGTKVEIK |
| 167 | 167 VL167 | Table 3 Table 4A FIG. 17 | AA sequence of LC VR of Ab 075 | DIQMTQSPSSLSASVGDRVTITCRSSQSITWQYKNYLAWYQQKPGKAPKLLIYWGSYLESGVPSRF SGSGSGTDFTLTISSLQPEDFATYYCQQHRTPSFGQGTKVEIK |
| 168 | 168 VL168 | Table 3 Table 4A FIG. 17 | AA sequence of LC VR of Ab 076 | DIQMTQSPSSLSASVGDRVTITCRSSQSITWRYKNYLAWYQQKPGKAPKLLIYWGSYLESGVPSRF SGSGSGTDFTLTISSLQPEDFATYYCQQHRTPSFGQGTKVEIK |
| 169 | 169 VL169 | Table 3 Table 4A FIG. 17 | AA sequence of LC VR of Abs 077, 081 | DIQMTQSPSSLSASVGDRVTITCRSSQSITWEYKNYLAWYQQKPGKAPKLLIYWGSYLESGVPSRF SGSGSGTDFTLTISSLQPEDFATYYCQQHRTPSFGQGTKVEIK |
| 164 | 164 VL164 | Table 3 Table 4A FIG. 17 | AA sequence of Abs 078, 079, 080, 081 | QVQLLETGGGLVKPGQSLKLSCAASGFTFTSYAMHWVRQPPGKGLEWVAVVSYDGNYKYYADSVQG RFTISRDNSKNTLYLQMNSLRAEDTAVYYCAKDNSKLRSLLYFEWLSQGYFNPWGQGTTVTVSS |
| 161 | HC161 | Table 4B FIG. 2 | AA sequence of HC VR consensus; ID version is in FIG. 13; | EVQLLESGGGLVKPGQSLKLSCAASGFTFSSYGMHWVRQPPGKGLEWVAVVSYDGSNKYYADSVQG RFTISRDNSKNTLYLQMNSLRAEDTAVYYCAKDSKLRSLLYFEWLSSGLLDYWGQGAMVTVSS |
| 62 | LC62 | Table 4A FIG. 3 | AA sequence of LC VR consensus; ID version is in FIG. 14; | DIQMTQSPSSLSASVGDRVTITCRSSQSITFNYKNYLAWYQQKPGKAPKLLIWGSYLESGVPSRF SGSGSGTDFTLTISSLQPEDFATYYCQQHRTPSFGQGTKVEIK |
| 96 | 15-ID | Table 4B FIG. 13 | AA sequence of HC VR of Ab A18; non-ID version is in FIG. 2; | IDEVQLLESGGGLVKPGQSLKLSCAASGFTFTSYGMHWVRQPPGKGLEWVAVISYDGSYKYYADSV QGRFTISRDNSKNTLYLQMNSLRAEDTAVYYCAKDSRLRSLLYFEWLSQGYFNPWGAGTTLTVSS |
| 110 | 28-ID | Table 4B FIG. 14 | AA sequence of LC VR of Ab A18; non-ID version is in FIG. 3 | IDEIVMTQSPDSLAVSLGERATINCKSSQSVTNYKNYLAWYQQKPGQPPKLLIYWASTRESGVPD RFSGSGSGTDFTLTISSLQAEDVAVYYCQQYYRTPPTFGGGTKLDIK |
| 97 | 16-ID | Table 4B FIG. 13 | AA sequence of HC VR of Abs 014, 028; non-ID version is in FIG. 2; | IDEVQLLESGGGLVKPGQSLKLSCAASGFTFSSYGMHWVRQPPGKGLEWVAVVSYDGSNKYYADSV QGRFTISRDNSKNTLYLQMNSLRAEDTAVYYCAKDTKLRSLLYFEWLSSGLLDYWGQGAMVTVSS |

TABLE 4C-continued

Nucleic acid and amino acid sequences

| SEQ ID NO. | Lab no. | Source | Comment | Sequence |
|---|---|---|---|---|
| 111 | 29-ID | Table 4B FIG. 14 | AA sequence of LC VR of Abs 014, 154,157; non-ID version is in FIG. 3; | IDEIVMTQSPDSLAVSLGERATINCKSSQSVTFSYKNYLAWYQQKPGQPPKLLIYWASTRESGVPD RFSGSGSGTDFTLTISSLQAEDVAVYYCQQYYRTPPTFGGGTKLDIK |
| 98 | 17-ID | Table 4B FIG. 13 | AA sequence of HC VR of Ab 001, 009, 017, 025, 160, 186, 187, 188, 189, 190, 191, 192, 193, 202, 211; non-ID version is in FIG. 2; | IDEVQLLESGGGLVKPGQSLKLSCAASGFTFTSYGMHWVRQPPGKGLEWAVVSYDGNYKYYADSV QGRFTISRDNSKNTLYLQMNSLRAEDTAVYYCAKDSRLRSLLYFEWLSQGYFNPWGAGTTLTVSS |
| 112 | 30-ID | Table 4B FIG. 14 | AA sequence of LC VR of Abs 028, 155; non-ID version is in FIG. 3; | IDEIVMTQSPDSLAVSLGERATINCKSSQSVTFDYKNYLAWYQQKPGQPPKLLIYWASTRESGVPD RFSGSGSGTDFTLTISSLQAEDVAVYYCQQYYRTPPTFGGGTKLDIK |
| 99 | 18-ID | Table 4B FIG. 13 | AA sequence of HC VR of Abs 002, 010, B18, 026, 203, 212; non-ID version is in FIG. 2; | IDEVQLLESGGGLVKPGQSLKLSCAASGFTFTSYGMHWVRQPPGKGLEWAVLSYDGNYKYYADSV QGRFTISRDNSKNTLYLQMNSLRAEDTAVYYCAKDSRLRSLLYFEWLSQGYFNPWGAGTTLTVSS |
| 113 | 35-ID | Table 4B FIG. 14 | AA sequence of LC VR of Ab 159; non-ID version is in FIG. 3; | IDEIVMTQSPDSLAVSLGERATINCKSSQSVTWSYKNYLAWYQQKPGQPPKLLIYWASTRESGVPD RFSGSGSGTDFTLTISSLQAEDVAVYYCQQYYRTPPTFGGGTKLDIK |
| 100 | 19-ID | Table 4B FIG. 13 | AA sequence of HC VR of Abs 003, 011, 019, 027, 194, 195, 196, 197, 198, 199, 200, 204, 213; non-ID version is in FIG. 2; | IDEVQLLESGGGLVKPGQSLKLSCAASGFTFTTYAMHWVRQPPGKGLEWAVLSYDGNYKYYADSV QGRFTISRDNSKNTLYLQMNSLRAEDTAVYYCAKDSKLRSLLYFEWLSQGYFNPWGAGTTLTVSS |
| 114 | 31-ID | Table 4B FIG. 14 | AA sequence of LC VR of Abs 001, 002,003; non-ID version is in FIG. 3; | IDEIVMTQSPDSLAVSLGERATINCKSSQTVTFNYKNYLAWYQQKPGQPPKLLIYWASTRESGVPD RFSGSGSGTDFTLTISSLQAEDVAVYYCQQHYRTPPSFGGGTKLDIK |
| 101 | 21-ID | Table 4B FIG. 13 | AA sequence of HC VR of Abs 154,155; non-ID version is in FIG. 2; | IDEVQLLESGGGLVKPGQSLKLSCAASGFTFSSYGMHWVRQPPGKGLEWAVVSYDGNNKYYADSV QGRFTISRDNSKNTLYLQMNSLRAEDTAVYYCAKDSKLRSLLYFEWLSSGLLDYWGQGAMVTVSS |
| 115 | 32-ID | Table 4B FIG. 14 | AA sequence of LC VR of Abs 009, 010, 011; non-ID version is in FIG. 3; | IDEIVMTQSPDSLAVSLGERATINCKSSQTLSFNYKNYLAWYQQKPGQPPKLLIYWASTRESGVPD RFSGSGSGTDFTLTISSLQAEDVAVYYCQQHYRTPPSFGGGTKLDIK |
| 102 | 22-ID | Table 4B FIG. 13 | AA sequence of HC VR of Abs 157, 159; non-ID version is in FIG. 2; | IDEVQLLESGGGLVKPGQSLKLSCAASGFTFTTYAMHWVRQPPGKGLEWAVVSYDGNNKYYADSV QGRFTISRDNSKNTLYLQMNSLRAEDTAVYYCAKDSKLRSLLYFEWLSSGLLDYWGQGAMVTVSS |
| 116 | 33-ID | Table 4B FIG. 14 | AA sequence of LC VR of Abs 017, B18, 019; non-ID version is in FIG. 3; | IDEIVMTQSPDSLAVSLGERATINCKSSQTVTFNYKNYLAWYQQKPGQPPKLLIYFASTRESGVPD RFSGSGSGTDFTLTISSLQAEDVAVYYCQQHYRTPPSFGGGTKLDIK |
| 103 | 20-ID | Table 4B FIG. 13 | AA sequence of HC VR of Ab 086; non-ID version is in FIG. 2; | IDEVQLLESGGGLVKPGQSLKLSCAASGFTFTTYAMHWVRQPPGKGLEWAVVSFDGNNRYYADSV QGRFTISRDNSKNTLYLQMNSLRAEDTAVYYCAKDSQLRSLLYFEWLSSGVLDYWGQGAMVTVSS |
| 117 | 34-ID | Table 4B FIG. 14 | AA sequence of LC VR of Abs 025, 026, 027, 086; non-ID version is in FIG. 3; | IDEIVMTQSPDSLAVSLGERATINCKSSQTLSFNYKNYLAWYQQKPGQPPKLLIYFASTRESGVPD RFSGSGSGTDFTLTISSLQAEDVAVYYCQQHYRTPPSFGGGTKLDIK |
| 104 | 23-ID | Table 4B FIG. 13 | AA sequence of HC VR of Abs 210,219; non-ID version is in FIG. 2; | IDEVQLLESGGGLVKPGQSLKLSCAASGFTFTSYGMHWVRQPPGKGLEWAVVSYDGNYKYYADSV QGRFTISRDNSKNTLYLQMNSLRAEDTAVYYCAKDSKLRSLLYFEWLSQGYFNPWGAGTTLTVSS |
| 118 | 36-ID | Table 4B FIG. 14 | AA sequence of LC VR of Ab 160; non-ID version is in FIG. 3; | IDEIVMSQSPDTLAVTLGERASINCKSSQTVTFNYKNYLAWYQQKPGQPPKVLIYWASARETGVPE RFSGSGSGTDFTLTISSLQAEDVAVYYCQQHYRTPPSFGQGTKLEIK |

TABLE 4C-continued

Nucleic acid and amino acid sequences

| SEQ ID NO. | Lab no. | Source | Comment | Sequence |
|---|---|---|---|---|
| 105 | 24-ID | Table 4B FIG. 13 | AA sequence of HC VR of Abs A001, A002, A003, A010, A011, 031, 037; non-ID version is in FIG. 2; | IDEVQLLESGGGLVKPGQSLKLSCAASGFTFTSYAMHWRQPPGKGLEWVAVVSYDGNKYYADSV QGRFTISRDNSKNTLYLQMNSLRAEDTAVYYCAKDSRLRSLLYFEWLSQGYFNPWGQGTTLTVSS |
| 119 | 45-ID | Table 4B FIG. 14 | AA sequence of LC VR of Abs 202, 203, 204, 210, 031, 032, 033, 034; non-ID version is in FIG. 3; | IDDIQMTQSPSSLSASVGDRVTITCRSSQSITFNYKNYLAWYQQKPGKAPKLLIYWGSYLESGVPS RFSGSGSGTDFTLTISSLQPEDFATYYCQQHYRTPPSFGQGTKVEIK |
| 106 | 25-ID | Table 4B FIG. 13 | AA sequence of HC VR of Abs 004, 005, 006, 012, 013, 032, 038, 043, 044, 045, 046, 047, 048, 049, 050, 051, 052, 067, 068, 069, 070, 073, 074, 075, 076, 077; non-ID version is in FIG. 2; | IDQVQLLETGGGLVKPGQSLKLSCAASGFTFTSYAMHWRQPPGKGLEWVAVVSYDGNYKYYADSV QGRFTISRDNSKNTLYLQMNSLRAEDTAVYYCAKDSRLRSLLYFEWLSQGYFNPWGQGTTLTVSS |
| 120 | 46-ID | Table 4B FIG. 14 | AA sequence of LC VR of Abs 211, 212, 213, 219, 037, 038, 039, 040; non-ID version is in FIG. 3; | IDDIQMTQSPSSLSASVGDRVTITCRSSQSITFNYKNYLGWYQQKPGKAPKLLIYWGSYLESGVPS RFSGSGSGTDFTLTISSLQPEDFATYYCQQHYRTPPSFGQGTKVEIK |
| 107 | 26-ID | Table 4B FIG. 13 | AA sequence of HC VR of Abs 007, 008, A009, A14, 015, 033, 039; non-ID version is in FIG. 2; | IDEVQLLESGGGLVKPGQSLKLSCAASGFTFTSYAMHWRQPPGKGLEWVAVVSYDGNKYYADSV QGRFTISRDNSKNTLYLQMNSLRAEDTAVYYCAKDSQLRTLLYFEWLSQGYFDPWGQGTTLTVSS |
| 121 | 37-ID | Table 4B FIG. 14 | AA sequence of LC VR of Abs 186, 194; non-ID version is in FIG. 3; | IDEIVMTQSPDSLAVSLGERATINCKSSQTVTFNYKNYLAWYQQKPGQPPKLLIYWASTRESGVPD RFSGSGSGTDFTLTISSLQAEDVAVYYCQQHYRTPPSFGTKLDIK |
| 108 | 27-ID | Table 4B FIG. 13 | AA sequence of HC VR of Abs 016, A017, C18, A019, 034, 040; non-ID version is in FIG. 2; | IDEVQLLESGGGLVKPGQSLKLSCAASGFTFTSYAMHWRQPPGKGLEWVAVVSYDGNKYYADSV QGRFTISRDNSKNTLYLQMNSLRAEDTAVYYCAKDSRLRTLLYFEWLSQGYFDPWGQGTTLTVSS |
| 122 | 38-ID | Table 4B FIG. 14 | AA sequence of LC VR of Abs 187, 195; non-ID version is in FIG. 3; | IDEIVMTQSPDSLAVSLGERATINCKSSQTVTFNYKNYLAWYQQKPGQPPKLLIYWASTRESGVPD RFSGSGSGTDFTLTISSLQAEDVAVYYCQQHYRTPPSFGSGTKLDIK |
| 109 | 161-ID | Table 4B FIG. 13 | AA sequence of HC VR consensus ID; non-ID version is in FIG. 2; | IDEVQLLESGGGLVKPGQSLKLSCAASGFTFSSYGMHWRQPPGKGLEWVAVVSYDGSNKYYADSV QGRFTISRDNSKNTLYLQMNSLRAEDTAVYYCAKDSKLRSLLYFEWLSSGLLDYWGQGAMVTVSS |
| 123 | 39-ID | Table 4B FIG. 14 | AA sequence of LC VR of Abs 188, 196; non-ID version is in FIG. 3; | IDEIVMTQSPDSLAVSLGERATINCKSSQTVTFNYKNYLAWYQQKPGQPPKLLIYWASTRESGVPD RFSGSGSGTDFTLTISSLQAEDVAVYYCQQHYRTPPSFGQGTKVEIK |
| 124 | 40-ID | Table 4B FIG. 14 | AA sequence of LC VR of Abs 189, 197; non-ID version is in FIG. 3; | IDEIVMTQSPDSLAVSLGERATINCKSSQTVTFNYKNYLAWYQQKPGQPPKLLIYWASTRESGVPD RFSGSGSGTDFTLTISSLQAEDVAVYYCQQHYRTPPSFGNGTKLDIK |
| 125 | 41-ID | Table 4B FIG. 14 | AA sequence of LC VR of Abs 190, 198; non-ID version is in FIG. 3; | IDEIVMTQSPDSLAVSLGERATINCKSSQTLSFNYKNYLAWYQQKPGQPPKLLIYWASTRESGVPD RFSGSGSGTDFTLTISSLQAEDVAVYYCQQHYRTPPSFGTKLDIK |
| 126 | 42-ID | Table 4B FIG. 14 | AA sequence of LC VR of Abs 191, 199; non-ID version is in FIG. 3; | IDEIVMTQSPDSLAVSLGERATINCKSSQTLSFNYKNYLAWYQQKPGQPPKLLIYWASTRESGVPD RFSGSGSGTDFTLTISSLQAEDVAVYYCQQHYRTPPSFGSFGTKLDIK |

TABLE 4C-continued

Nucleic acid and amino acid sequences

| SEQ ID NO. | Lab no. | Source | Comment | Sequence |
|---|---|---|---|---|
| 127 | 43-ID | Table 4B FIG. 14 | AA sequence of LC VR of Abs 192, 200; non-ID version is in FIG. 3; | IDEIVMTQSPDSLAVSLGERATINCKSSQTLSFNYKNYLAWYQQKPGQPPKLLIYWASTRESGVPD RFSGSGSGTDFTLTISSLQAEDVAVYYCQQHYRTPPSFGQGTKLDIK |
| 128 | 44-ID | Table 4B FIG. 14 | AA sequence of LC VR of Abs 193; non-ID version is in FIG. 3; | IDEIVMTQSPDSLAVSLGERATINCKSSQTLSFNYKNYLAWYQQKPGQPPKLLIYWASTRESGVPD RFSGSGSGTDFTLTISSLQAEDVAVYYCQQHYRTPPSFGNGTKLDIK |
| 129 | 47-ID | Table 4B FIG. 14 | AA sequence of LC VR of Abs A001, 004, 007, 016 | IDDIVMTQSPDTLAVTLGERATIQCKSSQTVTFNYKNYLAWYQQKPGQPPKLLIYWASTRESGVPD RFSGSGSGTDFTLTITSLQAEDVAVYYCQQHYRTPPSFGQGTKLDIK |
| 130 | 48-ID | Table 4B FIG. 14 | AA sequence of LC VR of Abs A002, 005, 008, A017; non-ID version is in FIG. 3; | IDDIVMTQSPDTVAVTVGERATINCKSSQTVTFNYKNYLAWYQQKPGQPPKLLIYWASTRESGVPD RFSGSGSGTDFTLTISSLQAEDVAVYYCQQHYRTPPSFGQGTKLDIK |
| 131 | 49-ID | Table 4B FIG. 14 | AA sequence of LC VR of Abs A003, 006, A009, C18; non-ID version is in FIG. 3; | IDDIVMTQSPDTVAVTLGERATIDCKSSQTVTFNYKNYLAWYQQKPGQPPKLLIYWASTRESGVPD RFSGSGSGTDFTLTISSLQAEDVAVYYCQQHYRTPPSFGQGTKLDIK |
| 132 | 50-ID | Table 4B FIG. 14 | AA sequence of LC VR of Abs A010 012, A14, A019; non-ID version is in FIG. 3; | IDDIVMTQSPDTLAVTVGERATIRCKSSQTVTFNYKNYLAWYQQKPGQPPKLLIYWASTRESGVPD RFSGSGSGTDFTLTISSLQAEDVAVYYCQQHYRTPPSFGQGTKLDIK |
| 133 | 51-ID | Table 4B FIG. 14 | AA sequence of LC VR of Ab A011, 013, 015; non-ID version is in FIG. 3; | IDDIVMTQSPDTLAVSRGERATINCKSSQTVTFNYKNYLAWYQQKPGQPPKLLIYWASTRESGVPD RFSGSGSGTDFTLTISSLQAEDVAVYYCQQHYRTPPSFGQGTKLDIK |
| 134 | 52-ID | Table 4B FIG. 14 | AA sequence of LC VR of Abs 044, 071, 072, 078; non-ID version is in FIG. 3; | IDDIQMTQSPSSLSASVGDRVTITCRSSQSITFDYKNYLAWYQQKPGKAPKLLIYWGSYLESGVPS RFSGSGSGTDFTLTISSLQPEDFATYYCQQHYRTPPSFGQGTKVEIK |
| 135 | 53-ID | Table 4B FIG. 14 | AA sequence of LC VR of Ab 051; non-ID version is in FIG. 3; | IDDIQMTQSPSSLSASVGDRVTITCRSSQSITFNYKNYLAWYQQKPGKAPKLLIYWGSYLESGVPS RFSGSGSGTDFTLTISSLQPEDFATYYCQQHYRTPPSFGQGTKVEIK |
| 136 | 54-ID | Table 4B FIG. 14 | AA sequence of LC VR of Ab 049; non-ID version is in FIG. 3; | IDDIQMTQSPSSLSASVGDRVTITCRSSQSITFNYKNYLAWYQQKPGKAPKLLIYWGSHLESGVPS RFSGSGSGTDFTLTISSLQPEDFATYYCQQHYRTPPSFGQGTKVEIK |
| 137 | 55-ID | Table 4B FIG. 14 | AA sequence of LC VR of Ab 047; non-ID version is in FIG. 3; | IDDIQMTQSPSSLSASVGDRVTITCRSSQSITFNYKNYLAWYQQKPGKAPKLLIYWGSKLESGVPS FRSGSGSGTDFTLTISSLQPEDFATYYCQQHYRTPPSFGQGTKVEIK |
| 138 | 56-ID | Table 4B FIG. 14 | AA sequence of LC VR of Ab 050; non-ID version is in FIG. 3; | IDDIQMTQSPSSLSASVGDRVTITCRSSQSITFNYKNYLAWYQQKPGKAPKLLIYWGSDLESGVPS RFSGSGSGTDFTLTISSLQPEDFATYYCQQHYRTPPSFGQGTKVEIK |
| 139 | 57-ID | Table 4B FIG. 14 | AA sequence of LC VR of Ab 045; non-ID version is in FIG. 3; | IDDIQMTQSPSSLSASVGDRVTITCRSSQSITFNYKNYLAWYQQKPGKAPKLLIYWGSYLESGVPS RFSGSGSGTDFTLTISSLQPEDVATYYCQQHYRTPPSFGQGTKVEIK |
| 140 | 58-ID | Table 4B FIG. 14 | AA sequence of LC VR of Ab 048; non-ID version is in FIG. 3; | IDDIQMTQSPSSLSASVGDRVTITCRSSQSITFNYKNYLAWYQQKPGKAPKLLIYWGSYLESGVPS RFSGSGSGTDFTLTISSLQPEDKATYYCQQHYRTPPSFGQGTKVEIK |
| 141 | 59-ID | Table 4B FIG. 14 | AA sequence of LC VR of Ab 046; non-ID version is in FIG. 3; | IDDIQMTQSPSSLSASVGDRVTITCRSSQSITFNYKNYLAWYQQKPGKAPKLLIYWGSYLESGVPS RFSGSGSGTDFTLTISSLQPEDDATYYCQQHYRTPPSFGQGTKVEIK |
| 142 | 60-ID | Table 4B FIG. 14 | AA sequence of LC VR of Ab 043; non-ID version is in FIG. 3; | IDDIQMTQSPSSLSASVGDRVTITCRSSQSITFNYKNYLAWYQQKPGKAPKLLIYWGSYLESGVPS RFSGSGSGTDFTLTISSLQPEDFATYYCQQYYRTPPSFGQGTKVEIK |

TABLE 4C-continued

Nucleic acid and amino acid sequences

| SEQ ID NO. | Lab no. | Source | Comment | Sequence |
|---|---|---|---|---|
| 143 | 61-ID | Table 4B FIG. 14 | AA sequence of LC VR of Ab 052; non-ID version is in FIG. 3; | IDDIQMTQSPSSLSASVGDRVTITCRSSQSITFNYKNYLAWYQQKPGKAPKLLIYWGSTRESGVPS RFSGSGSGTDFTLTISSLQPEDFATYYCQQHYRTPPSFGQGTKVEIK |
| 157 | 153-ID | Table 4B FIG. 14 | AA sequence of LC VR of Ab 067; non-ID version is in FIG. 3; | IDDIQMTQSPSSLSASVGDRVTITCRSSQSITFQYKNYLAWYQQKPGKAPKLLIYWGSYLESGVPS RFSGSGSGTDFTLTISSLQPEDFATYYCQQHYRTPPSFGQGTKVEIK |
| 158 | 154-ID | Table 4B FIG. 14 | AA sequence of LC VR of Ab 068; non-ID version is in FIG. 3; | IDDIQMTQSPSSLSASVGDRVTITCRSSQSITFRYKNYLAWYQQKPGKAPKLLIYWGSYLESGVPS RFSGSGSGTDFTLTISSLQPEDFATYYCQQHYRTPPSFGQGTKVEIK |
| 159 | 155-ID | Table 4B FIG. 14 | AA sequence of LC VR of Abs 069, 079; non-ID version is in FIG. 3; | IDDIQMTQSPSSLSASVGDRVTITCRSSQSITFEYKNYLAWYQQKPGKAPKLLIYWGSYLESGVPS RFSGSGSGTDFTLTISSLQPEDFATYYCQQHYRTPPSFGQGTKVEIK |
| 160 | 156-ID | Table 4B FIG. 14 | AA sequence of LC VR of Ab 070; non-ID version is in FIG. 3; | IDDIQMTQSPSSLSASVGDRVTITCRSSQSITFDYKNYLAWYQQKPGKAPKLLIYWGSTRESGVPS RFSGSGSGTDFTLTISSLQPEDFATYYCQQHYRTPPSFGQGTKVEIK |
| 144 | 62-ID | Table 4B FIG. 14 | AA sequence of LC VR consensus ID; non-ID version is in FIG. 3; | IDDIQMTQSPSSLSASVGDRVTITCRSSQSITFNYKNYLAWYQQKPGKAPKLLIYWGSYLESGVPS RFSGSGSGTDFTLTISSLQPEDFATYYCQQHYRTPPSFGQGTKVEIK |
| 63 | VH16 | Example 1 | NT sequence of HC VR of Abs 014, 028 | GAGGTACAGCTCCTCGAATCTGGGAGGGACTGGTCAAACCCGGTCAATCGCTCAATCTCTGTGT GCAGCGTCAGGTTTACGTTCAGCTGATGACGGAGCAATAAGTACTACGCCGATTCAGTGCAAGGT CGGTTTACCATTCGAGGGATAACAAGAACACGCTCACTTGTGCAGATGAACTCACTTAGACCG GAAGATACCGCTGTGTACTATTGCCAAAGACACAAAGCTGCCATGTCACAGTATCCAGCGCTGACT TTGTCCTCGGGGTTGCTGCTGACTATTGGGGGCAGGCGCCCATGTCACAGTATCCAGCGCTGACT AAGGGGCCC |
| 64 | VL29 | Example 1 | NT sequence of LC VR of Abs 014, 154, 157 | GAGATCGTGATGACGCAGAGCCCCGATAGCCTCGCTGTCTCATTGGGGAACGGGCCACGATTAAC TGCAAATCCTCACAGTCGGTGACTTTGACTATAAGAATTACCTGGCATGGTATCAGCAGAAGCCG GGTCAACCCCAAAGTGTGATCACTGGCCTTCACACGCGAGTCGGAGTCCGAGTCCAAGCGATTT TCGGGTTCAGGGTCCGGCACTGACTTTACCCTGACACAATTTCATCGCTTCAAGCGGAGGATAGCA GTGTACTATTGTCAGCAGTATTACAGAACACCTCCACCTTCGAGGGGAACAGAAACTTGACATC AAGGGATCC |
| 65 | VL30 | Example 1 | NT sequence of LC VR of Abs 028, 155 | NT: GAGATCGTGATGACGCAGAGCCCCGATAGCCTCGCTGTCTCATTGGGAACGGGCCACGATTAAC TGCAAATCCTCACAGTCGGTGACTTTGACTATAAGAATTACCTGGCATGGTATCAGCAGAAGCCG GGTCAACCCCAAAGTGTCCGGCACTGACTTGATCTACTGGCCTTCACACGCGAGTCGGAGTCCGAGTCCGATTT TCGGGTTCAGGGTCCGGCACTGACTTTACCCTGACACAATTTCATCGCTTCAAGCGGAGGATAGCA GTGTACTATTGTCAGCAGTATTACAGAACACCTCCACCTTCGAGGGGAACAGAAACTTGACATC AAGGGATCC |
| 66 | VH15 | Example 1 | NT sequence of HC VR of Ab A18 | GAAGTGCAACTCCTCGAGTCTGGAGGAGGAGTTTGGTGAAACTGGGACAGCCTCCTTGCAAACTGAGCTGT GCACAAGCGGGTTCACGTTCAGCGATGCAGTCGTACGGACCGCAGCCTCCCGGGAAGGA CTTGAATGGGTCGCCGTCATCTCATACAGACGGGTGTACAAATACTGGTCTATCTTCAGATGAACTCGTCAGGCT CGCTTCACAATTCCCGGACAATTCACCCGTCTATTACTGCGGAAGATTCGGACTACCCTTTGTACTTTGAGTGG CTGTCGCAGGGATTTCAACCATGGAGCCATGGGGAGCCACTTGACCGTATCAAGCGCGTCAACA AAGGGCCCC |

TABLE 4C-continued

Nucleic acid and amino acid sequences

| SEQ ID NO. | Lab no. | Source | Comment | Sequence |
|---|---|---|---|---|
| 187 | VL28 | Example 1 | NT sequence of EC VR of Ab A18 | GAAATTGTAATGACCAGAGCCCTGATAGCTTGCCGTGTCCCTGGGTGAGAGGGCGCAATCAAT TGTAAGTCATCACAGTCGTCAGTAGTACAACTACAAGAACTACCTGGCTGTGTATCAACAGAACCC GGGCAGCCGGCCAAATTGCTCATTATTGGCTTCGACACGGGAGTCGGGTGTGCCAGACCGCTTC TCCGGGTCAGGATCGGGAACTTCACGTTGACTTCGTCCTCCAGGCAGAGATGTAGCC GTCTACTATTGCCAACAGTATTACGAACGCCCTACATTTGGAGGCGGACCAAACTTGACATC AAGGGATCCGTGGCCGCCCCCAGCGTCTTCATCTTCCCGCCAGCGACGAGCAGCTGAAGTCGGGC ACGGCCAGCGTGTGCTGCCTGAACAACTTCTACCCCCGAGGCGAGGACTCCAGTGGAAGTG GACAACGCCCTGCAGAGCGGAACGAGCCAGGAGAGCGTGACAGAGCAGGACTCCAAGGACAGCACC TACGCCTCCAGCAGCACCCTGACGCTGAGCAAGGCCGACTACGAGAAGCACAAGGTCTACGCCTGC GAGGTGACCCACCAGGGCCTCTCGAGCCCCGTGACCAAGAGCTTCAACCGGGGCGAGTG |
| 149 | VL52 | Example 1 | NT sequence of LC VR of Abs 044, 071, 072, 078 | GACATTCAGATGACTCAGTCGCCTTCGTCATTGTCCGCCTCCGTGGGTGATAGGGTCACGATCACG TGCCGGAGCAGCCAGTCCATCACTCATCAATAACAAAACTATTTGGCATGGTATCAACAGAAACCC GGAAAGGCCCCGAAGCTCCTGATCTACTACTGGGTTCATATCTTGAGTCGGGGGTCCCGTCGAGATTT TCGGGCAGCGGCGATCAGGACGGATTTCACGCTGACACTATTCAGCCCGAGGACTTTGCG ACATATTACTGTCAACAGCACTAGGACACCCCCATCTTCGGACAGGGGACTAAAGTAGAAATC AAGGGATCCGTGGCCGCCCCAGCGTCTTCATCTTCCCGCCAGCGACGAGCAGCTGAAGTCGGGC ACGGCCAGCGTGTGCCTGCTGAACAACTTCTACCCCGAGGCGAGGACTCCAGTGGAAGTG GACAACGCCCTGCAGAGCGGAACGAGCCAGGAGAGCGTGACAGAGCAGGACTCCAAGGACAGCACC TACAGCCTCAGCAGCACCCTGACGCTGAGCAAGGCCGACTACGAGAAGCACAAGGTCTACGCCTGC GAGGTGACCCACCAGGGCCTCTCGAGCCCCGTGACCAAGAGCTTCAACCGGGGAGTGCTGA |
| 150 | VL45 | Example 1 | NT sequence of LC VR of Abs 202, 203, 204, 210, 031, 032, 033, 034 | GACATTCAGATGACTCAGTCGCCTTCGTCATTGTCCGCCTCCGTGGGTGATAGGGTCACGATCACG TGCCGGAGCAGCCAGTCCATCACTCACTTCAATAACAAAACTATTTGGCATGGTATCAACAGAAACCC GGAAAGGCCCCGAAGCTCCTGATCTACTACTGGGTTCATATCTTGAGTCGGGGGTCCCGTCGAGATTT TCGGGCAGCGGATCAGGGACGGATTTCACGCTGACCATTGTCACTCAGCCCGAGGACTTTGCG ACATATTACTGTCAACAGCACTACGAGGACACCCCCATCTTCGGACAGGGGACTAAAGTAGAAATC AAGGGATCCGTGGCCGCCCCAGCGTCTTCATCTTCCCGCCAGCGACGAGCAGCTGAAGTCGGGC ACGGCCAGCGTGTGCCTGCTGAACAACTTCTACCCCGAGGCGAGGACTCCAGTGGAAGTG GACAACGCCCTGCAGAGCGGAACGAGCCAGGAGAGCGTGACAGAGCAGGACTCCAAGGACAGCACC TACAGCCTCAGCAGCACCCTGACGCTGAGCAAGGCCGACTACGAGAAGCACAAGGTCTACGCCTGC GAGGTGACCCACCAGGGCCTCTCGAGCCCCGTGACCAAGAGCTTCAACCGGGGCGAGTGCTGAGAA TTC |
| 151 | VH25 | Example 1 | NT sequence of HC VR of Abs 004, 005, 006, 012, 013, 032, 038, 043, 044, 045, 046, 047, 048, 049, 050, 051, 052, 067, 068, 069, 070, 073, 074, 075, 076, 077 | CAGGTACAATTGCTTGAGACAGGTGGAGACTCGTGAAGCCAGGTCAGTCATTGAAACTGAGCTGT GCCGCATCCGGGTTCACATTCACTTCCTACGGATGCACTGGGTTCCGCCAGCCTCCCGGAAAGGGA CTTGAGTGTGGGTCGCTGTGAGTATCGTATGATGGAATTACAAATACTATCCAGACTCCGTGAAGGC CGGTTTCACGATTAGCAGAGATAACCCCAAGAACATACCCTTTACTCCAAATGAACTGTCTCCGAGCG GAGGACACCGCGGGTGGTACTTCAACCCGTGGCCGTGGCTTCGGAGAAGAATTCAGGAACACTGACCGTTGGATCGTGCTGCTTACTCAGCCTCGACT TTGTCACAGGGGTCCAGCGTGTTCCCGCTGGCGCCCCAGCAGCAGCGCTGTCTGAAGAACAGCGCCCTGACG GCCTGCCTGCGTCAAGGACTACTTCCCCGAGCCGGTGACCGTGTCGTGGAACAGCGGCGCGCTGACG AGCGGGGTCCACACCTTCCCGGCTGTCCTACAGTCTCCTCAGGACTGTATCTGCAACGTGAATCACAAGCCCAGCAACAC ACCAAGGTCTACGACAAGAAGTGGAGCCCTGCAGCCCCATCTGCGAACAAAACTCACATGCCCACCGTGC CCAGGTACTGAACTCCTGGGGGACCGTCAGTCTTCCTCTTCCCCAAAACCCAAGGACACCCTC ATGATCTCCCGGACCCCTGAGGTCACATGCGTGGTGGTGGACGTGAGCCACGAAGACCCTGAGGTC |

TABLE 4C-continued

Nucleic acid and amino acid sequences

| SEQ ID NO. | Lab no. | Source | Comment | Sequence |
|---|---|---|---|---|
| | VH24 | Example 1 | NT sequence of HC VR of Abs A001, A002, A003, AD10, AD11, 031, 037 | AAGTTCAACTGGTACGTGGACGGCGTGGAGGTGCATAATGCCAAGACAAAGCCGGGAGGAGCAG<br>TACAACAGCACGTACCGTGGTGCAGCGTCTCACCGTCGTCTGCACCAGGACTGGCTGAATGGCAAG<br>GAGTACAAGTGCAAGGTCTCCAACAAAGCCCTCCAGCCCGTGAGAAAACATCTCCAAAGCC<br>AAAGGTGAGCCCCGAGAACCACAGGTGTACACCCTGCCCCCATCCCGGGATGAGCTGACCAAGAAC<br>CAGGTCAGCCTGACCTGCCTGGTCAAAGGCTTCTATCCCAGCGACATCGCCGTGGAGTGGGAGAGC<br>AATGGGCAGCCGGAGAACAACTACAAGACCACGCCTCCCGTGCTGGACTCCGACGGCTCCTTCTTC<br>CTCTACAGCAAGCTCACCGTGGACAAGAGCAGGTGGCAGCAGGGGAACGTCTTCTCATGCTCCGTG<br>ATGCATGAGGCTCTGCACAACCACTACACGCAGAAGAGCCTCTCCCTGTCTCCGGGTAAATGA |
| 152 | | | | GAAGTACAATTGCTTGAGTGCGGGTGGAGGACTCGTGAAGCCAGGTCAGTCATTGAAACTGAGCTGT<br>GCCGCATCCGGATTCACATTCACTTCCTACGCGATGCACTGGGTCCGCCAGCCTCCCGGAAAGGGA<br>CTTGAGTGGGTCGCTGTGATATCGGAATGGGAATTACAAATACTATGCAGACTCCGTGCAAGGC<br>CGGTTTACGATTAGCAGGGACAACTCGAAGAATACCCTTTACCTCCAAATGAACTCGTCCGACCG<br>GAGGACACGGCGGTGTATTATTGCGCGAAGGGAATTCAGCGTTGAGATGCCTTGGAATGCCGGTCAGC<br>TTGTCACAGGGGTACTTCAACCCTGGGGTCAGGGAACAACACTGACCGTCAGCTCAGCCTCGACT<br>AAAGGCCCAGCTGTTCCCCTCGAAGGACTATTCCCGAGCAGCGAGCAGTGTCGTGGAACAGCGGCGCTGACG<br>GCTGCCTCGTCCACACCTTCCCGGCTGTCAGAGACGCTCTACTTCCGTGCTGAGCAGCGTGTC<br>ACCGTGCCCAGCAGCAGCCTGGGACCCAGACGTACATCTGCAACGTAACCGTGAACCAAGCCTGAAC<br>ACCAAGGTCGACAAGAAGTGGAGCCTCCGAAAGCTCTTCCTCTTCCCCCCAAAACCAAGGACACCCTC<br>CCAGTACTGAACTCTCGGGGGACCCGTCAGTCTCCTCCGTGGTGGACGTGAGCCACGAAGACCCCTGAGGTC<br>ATGATCTCCGACCCCGTCAGTCCATGCGTGGTGGACGTAGCGAGCCACGAAGACCCCTGAGGTC<br>AAGTTCAACTGGTACGTGGACGGCGTGGAGGTGCATAATGCCAAGACAAAGCCGGGAGGAGCAG<br>TACAACAGCACGTACCGTGGTGCAGCGTCTCACCGTCGTCTGCACCAGGACTGGCTGAATGGCAAG<br>GAGTACAAGTGCAAGGTCTCCAACAAAGCCCTCCAGCCCCCATCGAGAAAACATCTCCAAAGCC<br>AAAGGTGAGCCCCGAGAACCACAGGTGTACACCCTGCCCCCATCCCGGGATGAGCTGACCAAGAAC<br>CAGGTCAGCCTGACCTGCCTGGTCAAAGGCTTCTATCCCAGCGACATCGCCGTGGAGTGGGAGAGC<br>AATGGGCAGCCGGAGAACAACTACAAGACCACGCCTCCCGTGCTGGACTCCGACGGCTCCTTCTTC<br>CTCTACAGCAAGCTCACCGTGGACAAGAGCAGGTGGCAGCAGGGGAACGTCTTCTCATGCTCCGTG<br>ATGCATGAGGCTCTGCACAACCACTACACGCAGAAGAGCCTCTCCCTGTCTCCGGGTAAATGA |
| 94 | 15 | FIG. 1 | AA sequence of HC of Ab A18 | EVQLLESGGGLVKPGQSLKLSCAASGFTFTSYGMHWVRQPPGKGLEWVAVISYDGSYKYYADSVQG<br>RFTISRDNSKNTLYLQMNSLRAEDTAVYYCAKDSRLRSLLYFEWLSQGYFNPWGAGTTLTVSSAST<br>KGPSVFPLAPSSKSTSGGTAALGCLVKDYFPEPVTVSWNSGALTSGVHTFPAVLQSSGLYSLSSVV<br>TVPSSSLGTQTYICNVNHKPSNTKVDKKVEPKSCDKTHTCPPCGTELLGGPSVFLFPPKPKDTL<br>MISRTPEVTCVVVDVSHEDPEVKFNWYVDGVEVHNAKTKPREEQYNSTYRVVSVLTVLHQDWLNGK<br>EYKCKVSNKALPAPIEKTISKAKGEPREPQVYTLPPSRDELTKNQVSLTCLVKGFYPSDIAVEWES<br>NGQPENNYKTTPPVLDSDGSFFLYSKLITVDKSRWQQGNVFSCSVMHEALHNHYTQKSLSLSPGK |
| 188 | 28 | FIG. 1 | AA sequence of LC of Ab A18 | EIVMTQSPDSLAVSLGERATINCKSSQSVTYNYKNYLAWYQQKPGQPPKLLIYWASTRESGVPDRF<br>SGSGSGTDFTLTISSLQAEDVAVYYCQQYYRTPPTFGGGTKLDIKGSVAAPSVFIFPPSDEQLKSG<br>TASVVCLLNNFYPREAKVQMKVDNALQSGNSQESVTEQDSKDSTYSLSSTLTLSKADYEKHKVYAC<br>EVTHQGLSSPVTKSFNRGE |
| 145 | n.a. | see text | AA sequence of LC CDR1 of Ab 044 | QSITFDYKNYLA |
| 146 | n.a. | see text | AA sequence of LC CDR1 of F16 VK | KSSQSVTFNYKNYLA |

TABLE 4C-continued

Nucleic acid and amino acid sequences

| SEQ ID NO. | Lab no. | Source | Comment | Sequence |
|---|---|---|---|---|
| 147 | n.a. | see text | AA sequence of LC CDR2 of FI6 VK | WASARES |
| 148 | n.a. | see text | AA sequence of LC CDR3 of FI6 VK | QQHYRTPPT |
| 68 | n.a. | see text | AA sequence of HC CDR1 of Abs 044, 069, 032, 031 | SYAMH |
| 69 | n.a. | see text | AA sequence of HC CDR2 of Abs 044, 069, 032, 031 | VVSYDGNYKYYADSVQG |
| 70 | n.a. | see text | AA sequence of HC CDR3 of Abs 044, 069, 032, 031 | DSRLRSLLYFEWLSQGYFNP |
| 71 | n.a. | see text | AA sequence of LC CDR1 of Abs 032, 031 | QSITFNYKNYLA |
| 72 | n.a. | see text | AA sequence of LC CDR2 of Abs 044, 069, 032, 031 | WGSYLES |
| 73 | n.a. | see text | AA sequence of LC CDR3 of Abs 044, 069, 032, 031 | QQHYRTPPS |
| 74 | n.a. | see text | AA sequence of HC FR1 of Ab 069 | QVQLLETGGGLVKPGQSLKLSCAASGFTFT |
| 75 | n.a. | see text | AA sequence of HC FR2 of Ab 069 | WVRQPPGKGLEWVA |
| 76 | n.a. | see text | AA sequence of HC FR3 of Ab 069 | RFTISRDNSKNTLYLQMNSLRAEDTAVYYCAK |
| 77 | n.a. | see text | AA sequence of HC FR4 of Ab 069 | WGQGTLTVSS |
| 78 | n.a. | see text | AA sequence of LC FR1 of Ab 069 | DIQMTQSPSSLSASVGDRVTITCRSS |
| 79 | n.a. | see text | AA sequence of LC FR2 of Ab 069 | WYQQKPGKAPKLLIY |
| 80 | n.a. | see text | AA sequence of LC FR3 of Ab 069 | GVPSRFSGSGSGTDFTLTISSLQPEDFATYYC |
| 81 | n.a. | see text | AA sequence of LC FR4 of Ab 069 | FGQGTKVEIK |
| 82 | n.a. | see text | AA sequence of HC FR1 of Ab 031 | EVQLLESGGGLVKPGQSLKLSCAASGFTFT |
| 83 | n.a. | see text | AA sequence of LC CDR1 of Ab A18 et al. | KSSQSVTYNYKNYLA |
| 84 | n.a. | see text | AA sequence of LC CDR2 of Ab A18 et al. | WASTRES |
| 85 | n.a. | see text | AA sequence of LC CDR3 of Ab A18 et al. | QQYRTPPT |
| 86 | n.a. | see text | AA sequence of HC CDR1 of Ab A18 et al. | SYGMH |
| 87 | n.a. | see text | AA sequence of HC CDR2 of Ab A18 et al. | VISYDGSYKYYADSVQG |
| 88 | n.a. | see text | AA sequence of an HC CDR3 | DSELRSLLYFEWLSQGYFNP |
| 89 | n.a. | see text | AA sequence of HC FR4 of Ab A18 et al. | WGAGTTLTVSS |

TABLE 4C-continued

Nucleic acid and amino acid sequences

Figure 12:
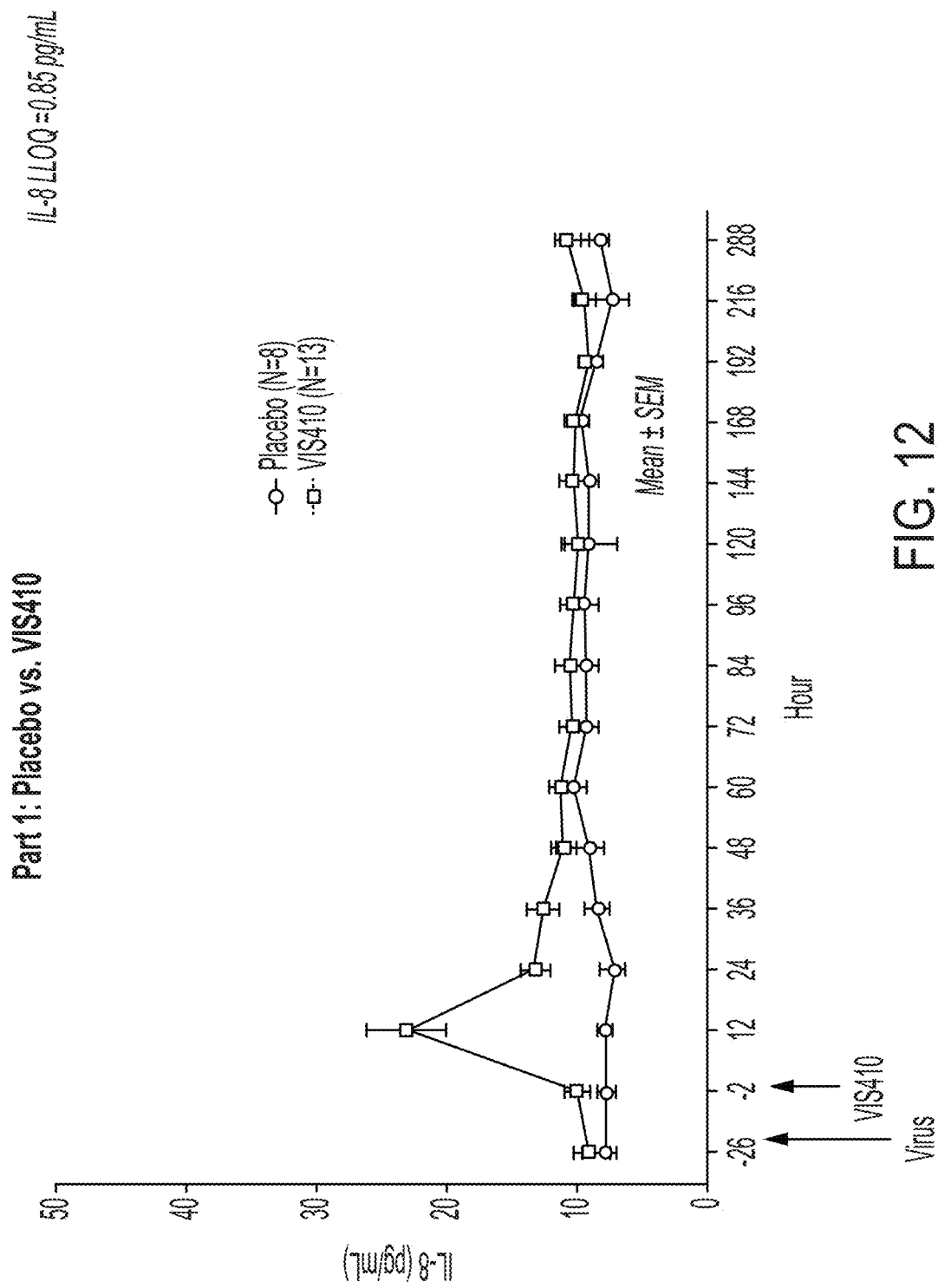
FIG. 12 is a graph showing levels of serum IL-8 in patients administered either 2300 mg of VIS410 or placebo at varying time points before and after the administration. An increase in serum IL-8 level to approximately 25 pg/mL was detected in VIS410 treated patients at about 12 hours after administration, the first timepoint post infusion. Mean IL-8 levels had decreased toward baseline values at the following assessment, 24 hours post infusion. No IL-8 increase was detected in patients administered the placebo.

| SEQ ID NO. | Lab no. | Source | Comment | Sequence |
|---|---|---|---|---|
| 90 | n.a. | see text | AA sequence of LC FR1 of Ab A18 et al. | EIVMTQSPDSLAVSLGERATINC |
| 91 | n.a. | see text | AA sequence of LC FR2 of Ab A18 et al. | WYQQKPGQPPKLLIY |
| 92 | n.a. | see text | AA sequence of LC FR3 of Ab A18 et al. | GVPDRFSGSGSGTDFTLTISSLQAEDVAVYYC |
| 93 | n.a. | see text | AA sequence of LC FR4 of Ab A18 et al. | FGGGTKLDIK |
| 171 | n.a. | see text | AA sequence of HC FR4 of Ab 078 et al | WGQGTTVTVSS |
| 172 | n.a. | see text | AA sequence of LC CDR1 of Ab 069 | QSITFEYKNYLA |
| 173 | n.a. | see text | AA sequence of H3 HA1 | QDLPGNDNSTATLCLGHHAVPNGTLVKTITDDQIEVTNATELVQSSTGKICNNPHRILDGIDCTL IDALLGDPHCDVFQNETWDLFVERSKAFSNCYPYDVDPDYASLRSLVASSGTLEFITEGFTWTGVTQ NGGSNACKRGPGSGFFSRLNWLTKSGSTYPVLNVTMPNNDNFDKLYIWGIHHPSTNQEQTSLYVQA SGRVTVSTRRSQQTTIPNIGSRPWVRGLSSRISIYWTIVKPGDVLVINSNGNLIAPRGYFKMRTGK SSIMRSDAPIDTCISECITPNGSIPNDKPFQNVNKITYGACPKYVKQNTLKLATGMRNVPEKQTR |
| 174 | n.a. | see text | AA sequence of H3 HA2 | GLFGAIAGFIENGWEGMIDGWYGFRHQNSEGTGQAADLKSTQAAIDQINGKLNRVIEKTNEKFHQI EKEFSEVEGRIQDLEKYVEDTKIDLWSYNAELLVALENQHTIDLTDSEMNKLFEKTRRQLRENAEE MGNGCFKIYHKCDNACIESIRNGTYDHDVYRDEALNNRFQIKG |
| 175 | n.a. | FIG. 12 | AA sequence of HC VR of FI6 | QVQLVQSGGGVVQPGRSLRLSCVASGFTFSTYAMHWVRQAPGRGLEWVAVISYDGNYKYADSVKG RFSISRDNSNNTLHLEMNTLRTEDTALYYCAKDSQLRSLLYFEWLSQGYFDPWGQGTLTVTS |
| 176 | n.a. | FIG. 12 | AA sequence of HC VR of FI370 | QVQLVQSGGGVVPPGRSLRLSCAASGFTFSTYGMHWVRQAPGKGLEWVAVISYDGNYKYADSVRG RFTISRDNSKNTLNLDMNSLRTEDTALYYCAKDSQLRSLLYFDWLSQGYFDHWGQGTLVTVSS |

TABLE 4C-continued

Nucleic acid and amino acid sequences

| SEQ ID NO. | Lab no. | Source | Comment | Sequence |
|---|---|---|---|---|
| 177 | n.a. | FIG. 12 | AA sequence of HC VR of FI6 variant 1 | QVQLVESGGGVVQPGRSLRLSCAASGFTFSSYGMHWVRQAPGKGLEWVAVISYDGSNKYYADSVKG RFTISRDNSKNTLYLQMNSLRAEDTAVYYCAKDSQLRSLLYFDWLSQGYFDYWGQGTLVTVSS |
| 178 | n.a. | FIG. 12 | AA sequence of HC VR of FI6 variant 3 | QVQLVESGGGVVQPGRSLRLSCAASGFTFSTYAMHWVRQAPGKGLEWVAVISYDANYKYYADSVKG RFTISRDNSKNTLYLQMNSLRAEDTAVYYCAKDSQLRSLLYFEWLSQGYFDYWGQGTLVTVSS |
| 179 | n.a. | FIG. 12 | AA sequence of HC VR of FI6/370 | QVQLVQSGGGVVQPGRSLRLSCAASGFTFSTYGMHWVRQAPGKGLEWVAVISYDGNYKYYADSVKG RFTISRDNSKNTLYLEMNSLRTEDTALYYCAKDSQLRSLLYFDWLSQGYFDHWGQGTLVTVSS |
| 180 | n.a. | FIG. 12 | AA sequence of kappa LC VR of FI6 | DIQMTSQPDSLAVSLGARATINCKSSQSVTFNYKNYLAWYQQKPGQPPKVLIYWASARESGVPDRF SGSGSGTDFTLTISSLQAEDVAVYYCQQHYRTPPTFGQGTKVEIK |
| 181 | | See text | AA sequence of H1 HA1 | TNADTICIGYHANNSTDTVDTVLEKNVTVTHSVNLLEDSHNGKLCKLKGIAPLQLGKCNIAGWLLG NPECDLLLTASSWSYIVETSNSENGTCYPGDFIDYEELREQLSSVSSFEKFEIFPKTSSWPNHETT KGVTAACSYAGASSFYRNLLWLTKKGSSYPKLSKSYVNNKGKEVLVLWGVHHPPTGTDQQSLYQNA DAYVSVGSSKYNRRFTPEIAARPKVRDQAGRMNYYWTLLEPGDTITFEATGNLIAPWYAFALNRGS GSGIITSDAPVHDCNTKCQTPHGAINSSLPFQNIHPVTIGECPKYVRSTKLRMATGLRNIPSIQS |
| 182 | | See text | AA sequence of H1 HA2 | GLFGAIAGFIEGGWTGMIDGWYGYHHQNEQGSGYAADQKSTQNAIDGITNKVNSVIEKMNTQFTAV GKEFNNLERRIENLNKKVDDGFLDIWTYNAELLVLLENERTLDFHDSNVRNLYEKVKSQLKNNAKE IGNGCFEFYHKCDDACMESVRNGTYDYPKYSEESKLNREEIDGVKLESMGVYQILAIYSTVASSLV LLVSLGAISFWMCSNGSLQCRICI |

Figure and Example numbers in the above table are based on International Publication No. WO2013/170139 or U.S. Application Publication No. 2013/0302349.

The present disclosure also includes any of the following numbered paragraphs:

1. A combination comprising an anti-HA antibody molecule described herein, e.g., VIS410, and one or more (e.g., two or three) anti-viral agents, for use in treating or preventing an influenza virus infection, or a symptom hereof, in a subject (e.g., a human subject).

2. A method of treating or preventing an influenza virus infection, or a symptom thereof, in a subject (e.g., a human subject), comprising administering to the subject a combination of an anti-HA antibody molecule described herein, e.g., VIS410, and one or more (e.g., two, three, or four) anti-viral agents.

3. The combination for use of paragraph 1, or the method of paragraph 2, wherein the one or more anti-viral agents comprise a neuraminidase inhibitor.

4. The combination for use of paragraph 1, or the method of paragraph 2, wherein the one or more anti-viral agents do not comprise a neuraminidase inhibitor.

5. The combination for use of paragraph 3 or 4, or the method of paragraph 3 or 4, wherein the neuraminidase inhibitor comprises one, two, or all of oseltamivir, peramivir, or zanamivir.

6. The combination for use of any of paragraphs 1 or 3-5, or the method of any of paragraphs 2-5, wherein the one or more anti-viral agents comprise an endonuclease inhibitor (e.g., a cap-dependent endonuclease inhibitor).

7. The combination for use of any of paragraphs 1 or 3-5, or the method of any of paragraphs 2-5, wherein the one or more anti-viral agents do not comprise an endonuclease inhibitor (e.g., a cap-dependent endonuclease inhibitor).

8. The combination for use of paragraph 6 or 7, or the method of paragraph 6 or 7, wherein the endonuclease inhibitor (e.g., the cap-dependent endonuclease inhibitor) comprises baloxavir marboxil.

9. The combination for use of any of paragraphs 1 or 3-8, or the method of any of paragraphs 2-7, wherein the one or more anti-viral agents comprise a polymerase basic protein 2 (PB2) inhibitor.

10. The combination for use of any of paragraphs 1 or 3-8, or the method of any of paragraphs 2-7, wherein the one or more anti-viral agents does not comprise a PB2 inhibitor.

11. The combination for use of paragraph 9 or 10, or the method of paragraph 9 or 10, wherein the PB2 inhibitor comprises pimodivir.

12. The combination for use of any of paragraphs 1 or 3-11, or the method of any of paragraphs 2-11, wherein the one or more anti-viral agents comprise one, two, three, four, or all of oseltamivir, peramivir, zanamivir, baloxavir marboxil, or pimodivir.

13. The combination for use of paragraph 12, or the method of paragraph 12, wherein the one or more anti-viral agents comprise oseltamivir.

14. The combination for use of paragraph 12 or 13, or the method of paragraph 12 or 13, wherein the one or more anti-viral agents comprise peramivir.

15. The combination for use of any of paragraphs 12-14, or the method of any of paragraphs 12-14, wherein the one or more anti-viral agents comprise zanamivir.

16. The combination for use of any of paragraphs 12-15, or the method of any of paragraphs 12-15, wherein the one or more anti-viral agents comprise baloxavir marboxil.

17. The combination for use of any of paragraphs 12-16, or the method of any of paragraphs 12-16, wherein the one or more anti-viral agents comprise pimodivir.

18. The combination for use of paragraph 1, or the method of paragraph 2, wherein the one or more anti-viral agents comprise a neuraminidase inhibitor and an endonuclease inhibitor (e.g., a cap-dependent endonuclease inhibitor).

19. The combination for use paragraph 18, or the method of paragraph 18, wherein the one or more anti-viral agents comprise (a) one, two, or all of oseltamivir, peramivir, or zanamivir, and (b) baloxavir marboxil.

20. The combination for use of paragraph 1, or the method of paragraph 2, wherein the one or more anti-viral agents comprise a neuraminidase inhibitor and a PB2 inhibitor.

21. The combination for use paragraph 20, or the method of paragraph 20, wherein the one or more anti-viral agents comprise (a) one, two, or all of oseltamivir, peramivir, or zanamivir, and (b) pimodivir.

22. The combination for use of paragraph 1, or the method of paragraph 2, wherein the one or more anti-viral agents comprise an endonuclease inhibitor (e.g., a cap-dependent endonuclease inhibitor) inhibitor and a PB2 inhibitor.

23. The combination for use paragraph 22, or the method of paragraph 22, wherein the one or more anti-viral agents comprise baloxavir and pimodivir.

24. The combination for use of paragraph 1, or the method of paragraph 2, wherein the one or more anti-viral agents comprise a neuraminidase inhibitor, an endonuclease inhibitor (e.g., a cap-dependent endonuclease inhibitor) inhibitor, and a PB2 inhibitor.

25. The combination for use paragraph 24, or the method of paragraph 24, wherein the one or more anti-viral agents comprise (a) one, two, or all of oseltamivir, peramivir, or zanamivir, (b) pimodivir baloxavir, and (c) pimodivir.

26. The combination for use of any of paragraphs 1 or 3-25, or the method of any of paragraphs 2-25, wherein the anti-HA antibody molecule (e.g., VIS410) is administered prior to, concurrently with, or subsequent to, the one or more anti-viral agents.

27. The combination for use of any of paragraphs 1 or 3-26, or the method of any of paragraphs 2-26, wherein the anti-HA antibody molecule (e.g., VIS410) is administered before any of the one or more antiviral agents.

28. The combination for use of any of paragraphs 1 or 3-26, or the method of any of paragraphs 2-26, wherein the anti-HA antibody molecule (e.g., VIS410) is administered after any of the one or more antiviral agents.

29. The combination for use of any of paragraphs 1 or 3-26, or the method of any of paragraphs 2-26, wherein the anti-HA antibody molecule (e.g., VIS410) is administered before at least one of the one or more antiviral agents and after at least one of the one or more antiviral agents.

30. The combination for use of any of paragraphs 1 or 3-29, or the method of any of paragraphs 2-29, wherein the anti-HA antibody molecule (e.g., VIS410) is administered, e.g., intravenously, at a dose of between 500 mg and 5000 mg, e.g., between 500 mg and 4500 mg, between 500 mg and 4000 mg, between 500 mg and 3500 mg, between 500 mg and 3000 mg, between 500 mg and 2500 mg, between 500 mg and 2000 mg, between 500 mg and 1500 mg, between 500 mg and 1000 mg, between 1000 mg and 5000 mg, between 1500 mg and 5000 mg, between 2000 mg and 5000 mg, between 2500 mg and 5000 mg, between 3000 mg and 5000 mg, between 3500 mg and 5000 mg, between 4000 mg and 5000 mg, between 4500 mg and 5000 mg, between 1000 mg and 4500 mg, between 1500 mg and 4000 mg, between 2000 mg and 3500 mg, between 2500 mg and 3000 mg, between 500 mg and 1500 mg, between 1000 mg and 2000 mg, between 1500 mg and 2500 mg, between 2000 mg and 3000 mg, between 2500 mg and 3500 mg, between 3000 mg and 4000 mg, between 4000 mg and 5000 mg, e.g., about 500 mg, 1000 mg, 1500 mg, 2000 mg, 2500 mg, 3000 mg, 3500 mg, 4000 mg, 4500 mg, or 5000 mg, e.g., as a single dose.

31. The combination for use of any of paragraphs 1 or 3-30, or the method of any of paragraphs 2-30, wherein the anti-HA antibody molecule (e.g., VIS410) is administered, e.g., intravenously, at a dose of between 1500 mg and 2500 mg (e.g., about 2000 mg) or between 3500 mg and 4500 mg (e.g., about 4000 mg), e.g., as a single dose.

32. The combination for use of any of paragraphs 1 or 3-31, or the method of any of paragraphs 2-31, wherein the one or more anti-viral agents (e.g., oseltamivir) is administered, e.g., orally, at a dose of between 25 mg and 150 mg, e.g., between 25 mg and 125 mg, between 25 and 100 mg, between 25 mg and 75 mg, between 25 mg and 50 mg, between 50 mg and 150 mg, between 75 mg and 150 mg, between 100 mg and 150 mg, between 125 mg and 150 mg, between 125 mg and 150 mg, between 50 mg and 125 mg, between 75 mg and 100 mg, between 50 mg and 100 mg, between 75 mg and 125 mg, e.g., about 25 mg, 50 mg, 75 mg, 100 mg, 125 mg, or 150 mg, e.g., once every twelve hours, once every day, once every two days, or once every three days, e.g., for at least 1, 2, 3, 4, 5, 6, 7, 8, 9, 10, 11, 12, 13, or 14 days.

33. The combination for use of any of paragraphs 1 or 3-32, or the method of any of paragraphs 2-32, wherein the one or more anti-viral agents comprises oseltamivir, and wherein oseltamivir is administered, e.g., orally, at a dose between 50 mg and 100 mg (e.g., about 75 mg), once every twelve hours or once every day, e.g., for 5 to 10 days.

34. The combination for use of any of paragraphs 1 or 3-33, or the method of any of paragraphs 2-33, wherein the one or more anti-viral agents (e.g., peramivir) is administered, e.g., intravenously (e.g., over 10-60 minutes, e.g., 15-30 minutes), at a dose of between 100 mg and 1000 mg, e.g., between 100 mg and 900 mg, between 100 and 800 mg, between 100 and 700 mg, between 100 and 600 mg, between 100 and 500 mg, between 100 and 400 mg, between 100 and 300 mg, between 100 and 200 mg, between 200 mg and 1000 mg, between 300 mg and 1000 mg, between 400 mg and 1000 mg, between 500 mg and 1000 mg, between 600 mg and 1000 mg, between 700 mg and 1000 mg, between 800 mg and 1000 mg, between 900 mg and 1000 mg, between 200 mg and 900 mg, between 300 mg and 800 mg, between 400 mg and 700 mg, between 500 mg and 600 mg, between 100 mg and 300 mg, between 200 mg and 400 mg, between 300 mg and 500 mg, between 400 mg and 600 mg, between 500 mg and 700 mg, between 600 mg and 800 mg, between 700 mg and 900 mg, or between 800 mg and 1000 mg, e.g., about 100 mg, 200 mg, 300 mg, 400 mg, 500 mg, 600 mg, 700 mg, 800 mg, 900 mg, or 1000 mg, e.g., as a single dose.

35. The combination for use of any of paragraphs 1 or 3-34, or the method of any of paragraphs 2-34, wherein the one or more anti-viral agents comprises peramivir, and wherein peramivir is administered, e.g., intravenously, at a dose between 400 mg and 800 mg (e.g., about 600 mg), e.g., as a single dose.

36. The combination for use of any of paragraphs 1 or 3-35, or the method of any of paragraphs 2-35, wherein the one or more anti-viral agents (e.g., zanamivir) is administered, e.g., by inhalation, at a dose of between 1 mg and 50 mg, e.g., between 1 mg and 40 mg, between 1 mg and 30 mg, between 1 mg and 20 mg, between 1 mg and 10 mg, between 1 mg and 5 mg, between 1 mg and 2 mg, between 2 mg and 50 mg, between 5 mg and 50 mg, between 10 mg and 50 mg, between 20 mg and 50 mg, between 30 mg and 50 mg, between 40 mg and 50 mg, between 2 mg and 40 mg, between 5 mg and 30 mg, between 10 mg and 20 mg, between 1 mg and 5 mg, between 2 mg and 10 mg, between 5 mg and 20 mg, between 10 mg and 30 mg, between 20 mg and 40 mg, between 30 mg and 50 mg, e.g., about 1 mg, 2 mg, 5 mg, 10 mg, 20 mg, 30 mg, 40 mg, or 50 mg, e.g., once every twelve hours, once every day, once every two days, or once every three days, e.g., for at least 1, 2, 3, 4, 5, 6, 7, 8, 9, 10, 11, 12, 13, 14, 15, 16, 17, 18, 19, 20, 21, 22, 23, 24, 25, 26, 27, or 28 days.

37. The combination for use of any of paragraphs 1 or 3-36, or the method of any of paragraphs 2-36, wherein the one or more anti-viral agents comprises zanamivir, and wherein zanamivir is administered, e.g., by inhalation, at a dose of between 5 mg and 15 mg (e.g., about 10 mg), once every twelve hours or once a day, e.g., for 5-10 days.

38. The combination for use of any of paragraphs 1 or 3-37, or the method of any of paragraphs 2-37, wherein the one or more anti-viral agents (e.g., baloxavir marboxil) is administered, e.g., orally, at a dose of between 10 mg and 200 mg, e.g., between 10 mg and 180 mg, between 10 mg and 160 mg, between 10 mg and 140 mg, between 10 mg and 120 mg, between 10 mg and 100 mg, between 10 mg and 80 mg, between 10 mg and 60 mg, between 10 mg and 40 mg, between 10 mg and 20 mg, between 20 mg and 200 mg, between 40 mg and 200 mg, between 60 mg and 200 mg, between 80 mg and 200 mg, between 100 mg and 200 mg, between 120 mg and 200 mg, between 140 mg and 200 mg, between 160 mg and 200 mg, between 180 mg and 200 mg, between 20 mg and 180 mg, between 40 mg and 160 mg, between 60 mg and 140 mg, between 80 mg and 120 mg, between 10 mg and 30 mg, between 20 mg and 40 mg, between 30 mg and 50 mg, between 40 mg and 60 mg, between 50 mg and 70 mg, between 60 mg and 80 mg, between 70 mg and 90 mg, between 80 mg and 100 mg, between 90 mg and 110 mg, between 100 mg and 120 mg, between 110 mg and 130 mg, between 120 mg and 140 mg, between 130 mg and 150 mg, between 140 mg and 160 mg, between 150 mg and 170 mg, between 160 mg and 180 mg, between 170 mg and 190 mg, e.g., about 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, or 200 mg, e.g., as a single dose.

39. The combination for use of any of paragraphs 1 or 3-38, or the method of any of paragraphs 2-38, wherein the one or more anti-viral agents comprises baloxavir marboxil, and wherein baloxavir marboxil is administered, e.g., orally, at a dose of between 20 mg to 60 mg (e.g., about 40 mg), e.g., for a subject having a weight of less than 80 kg, or between 60 mg and 100 mg (e.g., about 80 mg), e.g., for a subject having a weight of 80 kg or more, e.g., as a single dose.

40. The combination for use of any of paragraphs 1 or 3-39, or the method of any of paragraphs 2-39, the one or more anti-viral agents (e.g., pimodivir) is administered, e.g., orally, at a dose of between 100 mg and 1000 mg, e.g., between 100 mg and 900 mg, between 100 mg and 800 mg, between 100 mg and 700 mg, between 100 mg and 600 mg, between 100 mg and 500 mg, between 100 mg and 400 mg, between 100 mg and 300 mg, between 100 mg and 200 mg, between 200 mg and 1000 mg, between 300 mg and 1000 mg, between 400 mg and 1000 mg, between 500 mg and 1000 mg, between 600 mg and 1000 mg, between 700 mg and 1000 mg, between 800 mg and 1000 mg, between 900 mg and 1000 mg, between 200 mg and 900 mg, between 300 mg and 800 mg, between 400 mg and 700 mg, between 500 mg and 600 mg, between 100 mg and 300 mg, between 200 mg and 400 mg, between 300 mg and 500 mg, between 400 mg and 600 mg, between 500 mg and 700 mg, between 600 mg and 800 mg, between 700 mg and 900 mg, between 800 mg and 1000 mg, e.g., about 100 mg, 200 mg, 300 mg, 400 mg, 500 mg, 600 mg, 700 mg, 800 mg, 900 mg, or 1000 mg, e.g., twice a day, once a day, once every two days, or once every three days.

41. The combination for use of any of paragraphs 1 or 3-40, or the method of any of paragraphs 2-40, wherein the one or more anti-viral agents comprises pimodivir, and wherein pimodivir is administered, e.g., orally, at a dose of between 200 mg to 400 mg (e.g., about 300 mg), e.g., twice a day.

42. The combination for use of any of paragraphs 1 or 3-40, or the method of any of paragraphs 2-40, wherein the one or more anti-viral agents comprises pimodivir, and wherein pimodivir is administered, e.g., orally, at a dose of between 500 mg to 700 mg (e.g., about 600 mg), e.g., twice a day.

43. The combination for use of any of paragraphs 1 or 3-42, or the method of any of paragraphs 2-42, wherein the one or more anti-viral agents is administered within 12, 24, 36, 48, 60, or 72 hours of onset of an influenza symptom.

44. The combination for use of any of paragraphs 1 or 3-43, or the method of any of paragraphs 2-43, wherein the one or more anti-viral agents is administered within 1, 2, 3, 4, 5, 6, 7, 8, 9, 10, 11, 12, 13, or 14 days of exposure to an influenza virus or an influenza infection (e.g., latent or acute).

45. The combination for use of any of paragraphs 1 or 3-44, or the method of any of paragraphs 2-44, wherein the one or more anti-viral agents is administered within 1, 2, 3, 4, 5, 6, 7, 8, 9, 10, 11, 12, 13, or 14 days of an influenza outbreak.

46. The combination for use of any of paragraphs 1 or 3-45, or the method of any of paragraphs 2-45, wherein the subject is infected with, or is at risk of being infected with, an influenza virus A.

47. The combination for use of any of paragraphs 1 or 3-46, or the method of any of paragraphs 2-46, wherein the subject is infected with, or is at risk of being infected with, a Group 1 influenza virus (e.g., an H1, H2, H5, H6, H8, H9, H11, H12, H13, or H16 influenza virus, or a combination thereof).

48. The combination for use of any of paragraphs 1 or 3-47, or the method of any of paragraphs 2-47, wherein the subject is infected with, or is at risk of being infected with, a Group 2 influenza virus (e.g., an H3, H4, H7, H10, H14, or H15 influenza virus, or a combination thereof).

49. The combination for use of any of paragraphs 1 or 3-48, or the method of any of paragraphs 2-48, wherein the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof.

50. The combination for use of any of paragraphs 1 or 3-49, or the method of any of paragraphs 2-49, wherein the subject is infected with, or is at risk of being infected with, an H1N1 or H3N2 influenza virus, or a combination thereof.

51. The combination for use of any of paragraphs 1 or 3-50, or the method of any of paragraphs 2-50, wherein the subject is infected with, or is at risk of being infected with, an influenza virus that is resistant to one, two, three, or all of oseltamivir, peramivir, zanamivir, or baloxavir marboxil.

52. The combination for use of any of paragraphs 1 or 3-51, or the method of any of paragraphs 2-51, wherein the subject is infected with, or is at risk of being infected with, a secondary bacterial infection.

53. The combination for use of any of paragraphs 1 or 3-52, or the method of any of paragraphs 2-52, wherein the combination results in an enhanced antiviral activity, in vitro or in vivo, e.g., as determined by an assay described (e.g., an in vitro antiviral assay, e.g., NP ELISA or CPE assay).

54. The combination for use of any of paragraphs 1 or 3-53, or the method of any of paragraphs 2-53, wherein the combination results in a synergistic antiviral activity, in vitro or in vivo, e.g., as determined by an assay described herein (e.g., MacSnyergy II analysis).

55. The combination for use of any of paragraphs 1 or 3-53, or the method of any of paragraphs 2-53, wherein the combination results in an additive antiviral activity, in vitro or in vivo, e.g., as determined by an assay described herein (e.g., MacSnyergy II analysis).

56. An anti-HA antibody molecule described herein, e.g., VIS410, for use in treating or preventing an influenza virus infection, or a symptom hereof, in a subject (e.g., a human subject), wherein the subject is infected with, or is at risk of being infected with, an influenza virus that is resistant to an antiviral agent described herein.

57. A method of treating or preventing an influenza virus infection, or a symptom thereof, in a subject (e.g., a human subject), comprising administering to the subject an anti-HA antibody molecule described herein, e.g., VIS410, wherein the subject is infected with, or is at risk of being infected with, an influenza virus that is resistant to an antiviral agent described herein.

58. The antibody molecule for use of paragraph 56, or the method of paragraph 57, further comprising acquiring knowledge that an influenza virus that is resistant to the antiviral agent is present in the subject.

59. The antibody molecule for use of paragraph 56 or 58, or the method of paragraph 57 or 58, further comprising determining the presence of an influenza virus that is resistant to the antiviral agent in a sample from the subject, e.g., by an assay described herein.

60. The antibody molecule for use of any of paragraphs 56 or 58-59, or the method of any of paragraphs 57-59, wherein the antibody molecule is administered or used responsive to a determination of the presence of an influenza virus that is resistant to the antiviral agent.

61. The antibody molecule for use of any of paragraphs 56 or 58-60, or the method of any of paragraphs 57-60, further comprising evaluating a subject who is infected with, or is at risk of being infected with, an influenza virus that is resistant to the antiviral agent.

62. The antibody molecule for use of any of paragraphs 56 or 58-61, or the method of any of paragraphs 57-61, further comprising selecting a subject who is infected with, or is at risk of being infected with, an influenza virus that is resistant to the antiviral agent.

63. The antibody molecule for use of any of paragraphs 56 or 58-62, or the method of any of paragraphs 57-62, wherein the subject is undergoing or has undergone a treatment comprising the antiviral agent.

64. The antibody molecule of use of paragraph 63, or the method of paragraph 63, wherein responsive to a determination of the presence of an influenza virus that is resistant to the antiviral agent, the antiviral agent is discontinued.

65. The antibody molecule for use of paragraph 63 or 64, or the method of paragraph 63 or 64, wherein the antibody molecule is administered or used after cessation of the antiviral agent.

66. The antibody molecule for use of any of paragraphs 56 or 58-65, or the method of any of paragraphs 57-65, wherein the antibody molecule is administered or used as a single agent.

67. The antibody molecule for use of any of paragraphs 56 or 58-65, or the method of any of paragraphs 57-65, wherein the antibody molecule is administered or used in combination with a second antiviral agent, e.g., an antiviral agent described herein.

68. The antibody molecule for use of any of paragraphs 56 or 58-67, or the method of any of paragraphs 57-67, wherein the anti-HA antibody molecule (e.g., VIS410) is administered, e.g., intravenously, at a dose of between 500 mg and 5000 mg, e.g., between 500 mg and 4500 mg, between 500 mg and 4000 mg, between 500 mg and 3500 mg, between 500 mg and 3000 mg, between 500 mg and 2500 mg, between 500 mg and 2000 mg, between 500 mg and 1500 mg, between 500 mg and 1000 mg, between 1000 mg and 5000 mg, between 1500 mg and 5000 mg, between 2000 mg and 5000 mg, between 2500 mg and 5000 mg, between 3000 mg and 5000 mg, between 3500 mg and 5000 mg, between 4000 mg and 5000 mg, between 4500 mg and 5000 mg, between 1000 mg and 4500 mg, between 1500 mg and 4000 mg, between 2000 mg and 3500 mg, between 2500 mg and 3000 mg, between 500 mg and 1500 mg, between 1000 mg and 2000 mg, between 1500 mg and 2500 mg, between 2000 mg and 3000 mg, between 2500 mg and 3500 mg, between 3000 mg and 4000 mg, between 4000 mg and 5000 mg, e.g., about 500 mg, 1000 mg, 1500 mg, 2000 mg, 2500 mg, 3000 mg, 3500 mg, 4000 mg, 4500 mg, or 5000 mg, e.g., as a single dose.

69. The antibody molecule for use of any of paragraphs 56 or 58-68, or the method of any of paragraphs 57-68, wherein the anti-HA antibody molecule (e.g., VIS410) is administered, e.g., intravenously, at a dose of between 1500 mg and 2500 mg (e.g., about 2000 mg) or between 3500 mg and 4500 mg (e.g., about 4000 mg), e.g., as a single dose.

70. The antibody molecule for use of any of paragraphs 56 or 58-69, or the method of any of paragraphs 57-69, wherein the antiviral agent comprises an endonuclease inhibitor (e.g., a cap-dependent endonuclease inhibitor).

71. The antibody molecule for use of paragraph 70, or the method of paragraph 70, wherein the endonuclease inhibitor comprises baloxavir marboxil.

72. The antibody molecule for use of any of paragraphs 56 or 58-71, or the method of any of paragraphs 57-71, wherein the antiviral agent comprises a neuraminidase inhibitor.

73. The antibody molecule for use of paragraph 72, or the method of paragraph 72, wherein the neuraminidase inhibitor comprises oseltamivir, peramivir, or zanamivir, or a combination thereof.

74. The antibody molecule for use of any of paragraphs 56 or 58-73, or the method of any of paragraphs 57-73, wherein the antiviral agent comprises a PB2 inhibitor.

75. The antibody molecule for use of paragraph 74, or the method of paragraph 74, wherein the PB2 inhibitor comprises pimodivir.

76. The antibody molecule for use of any of paragraphs 56 or 58-75, or the method of any of paragraphs 57-75, wherein the influenza virus is an H1N1, H1N2, H2N2, H3N2, H5N1, H6N1, H7N2, H7N3, H7N7, H7N9, H9N2, or H10N7 influenza virus, or a combination thereof.

77. The antibody molecule for use of any of paragraphs 56 or 58-76, or the method of any of paragraphs 57-76, wherein the influenza virus is an H1N1 or H3N2 influenza virus, or a combination thereof.

78. The antibody molecule for use any of paragraphs 56 or 58-77, or the method of any of paragraphs 57-77, wherein the influenza virus has a mutation (e.g., a substitution) at position 38 of the polymerase acidic protein (PA), e.g., an I38T or I38F substitution.

79. A method of evaluating a subject (e.g., a human subject), the method comprising:
acquiring acknowledge that the subject is infected with, or is at risk of being infected with, an influenza virus that is resistant to an antiviral agent described herein; and
selecting the subject for a treatment comprising an anti-HA antibody molecule described herein, e.g., VIS410.

80. A method of evaluating a therapy, the method comprising:
acquiring acknowledge that a subject (e.g., a human subject) is infected with, or is at risk of being infected with, an influenza virus that is resistant to an antiviral agent described herein; and
selecting a treatment comprising an anti-HA antibody molecule described herein, e.g., VIS410, for treating or preventing influenza in the subject.

81. An anti-HA antibody molecule described herein, e.g., VIS410, for use in treating or preventing an influenza virus infection, or a symptom hereof, in a subject (e.g., a human subject), wherein the anti-HA antibody molecule is administered (e.g., the administration is continued, or the dosage is maintained), responsive to a change (e.g., a transient change) in the level of one or more (e.g., 2, 3, 4, 5, 6, or more) cytokines in the subject.

82. A method of treating or preventing an influenza virus infection, or a symptom thereof, in a subject (e.g., a human subject), comprising administering (e.g., the administration is continued, or the dosage is maintained) to the subject an anti-HA antibody molecule described herein, e.g., VIS410, responsive to a change (e.g., a transient change) in the level of one or more (e.g., 2, 3, 4, 5, 6, or more) cytokines in the subject.

83. The antibody molecule for use of paragraph 81, or the method of paragraph 82, wherein a change (e.g., a transient change) in the level of the one or more cytokines is indicative that the subject is responsive, or partial responsive, to the anti-HA antibody molecule.

84. The antibody molecule for use of paragraph 81 or 83, or the method of paragraph 82 or 83, wherein responsive to a change (e.g., a transient change) in the level of one or more cytokines, the administration of the antibody molecule (e.g., VIS410) is continued.

85. An anti-HA antibody molecule described herein, e.g., VIS410, for use in treating or preventing an influenza virus infection, or a symptom hereof, in a subject (e.g., a human subject),
wherein administration of the anti-HA antibody molecule is modified, responsive to a change (e.g., a transient change) in the level of one or more (e.g., 2, 3, 4, 5, 6, or more) cytokines in the subject.

86. A method of treating or preventing an influenza virus infection, or a symptom thereof, in a subject (e.g., a human subject), comprising modifying the administration of an anti-HA antibody molecule described herein, e.g., VIS410, to the subject, responsive to a change (e.g., a transient change) in the level of one or more (e.g., 2, 3, 4, 5, 6, or more) cytokines in the subject.

87. The antibody molecule for use of paragraph 85, or the method of paragraph 86, wherein a change (e.g., a transient change) in the level of one or more cytokines is indicative that the subject experiences, has experienced, or is likely to experience an adverse event, e.g., an adverse event described herein, e.g., a gastrointestinal adverse event (e.g., diarrhea, nausea, vomiting, and/or abdominal pain).

88. The antibody molecule for use of paragraph 85 or 87, or the method of paragraph 86 or 87, wherein responsive to a change (e.g., a transient change) in the level of one or more cytokines, the administration of the antibody molecule (e.g., VIS410) is reduced (e.g., reduced dose) or discontinued.

89. The antibody molecule for use of any of paragraphs 81, 83-85, or 87-88, or the method of any of paragraphs 82-84 or 86-88, further comprising acquiring acknowledge that the level of one or more cytokines is changed. 90. The antibody molecule for use of any of paragraphs 81, 83-85, or 87-89, or the method of any of paragraphs 82-84 or 86-89, further comprising determining that the level of one or more cytokines is changed.

91. The antibody molecule for use of paragraph 90, or the method of paragraph 90, wherein the level of one or more cytokines is determined periodically, e.g., every week, every two weeks, every three weeks, every four weeks, every six weeks, or every eight weeks.

92. The antibody molecule for use of any of paragraphs 81, 83-85, or 87-91, or the method of any of paragraphs 82-84 or 86-91, wherein the level of one or more cytokines is increased, decreased, or increased then decreased.

93. The antibody molecule for use of any of paragraphs 81, 83-85, or 87-92, or the method of any of paragraphs 82-84 or 86-92, wherein the level of one or more cytokines is changed (e.g., increased or decreased) by at least 10%, 20%, 30%, 40%, 50%, 60%, 70%, 80%, 90%, or 100%, or at least 2, 3, 4, 5, 6, 7, 8, 9, or 10 fold, compared to the level prior to administration of the anti-HA antibody molecule.

94. The antibody molecule for use of any of paragraphs 81, 83-85, or 87-93, or the method of any of paragraphs 82-84 or 86-93, wherein the level of one or more cytokines is increased within about 24 hours (e.g., within about 1, 2, 3, 4, 5, 6, 7, 8, 9, 10, 11, 12, 13, 14, 16, 17, 18, 19, 20, 21, 22, or 23 hours) after administration of the anti-HA antibody molecule.

95. The antibody molecule for use of paragraph 94, or the method of paragraph 94, wherein the level of one or more cytokines is increased within about 1 hour after administration of the anti-HA antibody molecule.

96. The antibody molecule for use of paragraph 94 or 95, or the method of paragraph 94 or 95, wherein the level of one or more cytokines is further decreased within about 36 hours (e.g., within about 12, 13, 14, 15, 16, 17, 18, 19, 20, 21, 22, 23, 24, 25, 26, 27, 28, 29, 30, 31, 32, 33, 34, or 35 hours), e.g., returned to about the same level (e.g., within about ±25%, ±20%, ±15%, ±10%, or ±5%) prior to administration of the anti-HA molecules.

97. The antibody molecule for use of any of paragraphs 81, 83-85, or 87-96, or the method of any of paragraphs 82-84 or 86-96, wherein the one or more cytokines comprise one, two, three, four, five, or all of IL-6, IL-8, IL-10, IFN-γ, TNF-α, or IL-33.

98. The antibody molecule for use of paragraph 97, or the method of paragraph 97, wherein the one or more cytokines comprise one, two, three, or all of IL-8, IFN-γ, IL-6, or TNF-α, e.g., one, two, or all of IL-8, IFN-γ, or TNF-α, or one, two, or all of IL-8, IFN-γ, or IL-6.

99. The antibody molecule for use of paragraph 98, or the method of paragraph 98, wherein the one or more cytokines comprise IL-8.

100. The antibody molecule for use of paragraph 99, or the method of paragraph 99, wherein the one or more cytokines further comprise IFN-γ, TNF-α, or both.

101. The antibody molecule for use of any of paragraphs 81, 83-85, or 87-100, or the method of any of paragraphs 82-84 or 86-100, further comprising administering a therapeutic agent or modality to treat or prevent an adverse event in the subject, e.g., to reduce the severity of the adverse event.

102. The antibody molecule for use of paragraph 101, or the method of paragraph 101, wherein the therapeutic agent or modality is administered prior to, concurrently with, or after administration of the anti-HA antibody molecule, e.g., at least 1, 2, 3, 4, 5, 6, 7, 8, 9, 10, 12, 15, 18, 21, 24, 27, 30, 33, or 36 hours, or within 1, 2, 3, 4, 5, 6, 7, 8, 9, 10, 12, 15, 18, 21, 24, 27, 30, 33, or 36 hours, prior to administration of the anti-HA antibody molecule.

103. The antibody molecule for use of paragraph 101 or 102, or the method of paragraph 101 or 102, wherein the therapeutic agent or modality comprises one, two, three, four, or all the following:

(a) diphenhydramine (e.g., one dose of diphenhydramine, e.g., about 25 mg to about 100 mg, e.g., about 50 mg, of diphenhydramine), (b) ibuprofen (e.g., one dose of ibuprofen, e.g., about 300 mg to about 1000 mg ibuprofen, e.g., about 600 mg, of ibuprofen), (c) aspirin (e.g., one dose of aspirin), (d) montelukast (e.g., one dose of montelukast, e.g., about 5 mg to about 25 mg, e.g., 10 mg, of montelukast), or (e) ranitidine (e.g., oral ranitidine, e.g., one dose of ranitidine, e.g., about 100 mg to about 200 mg, e.g., about 150 mg, of ranitidine).

104. The antibody molecule for use of paragraph 103, or the method of paragraph 103, wherein the therapeutic agent or modality comprises (a) and (b), or (a) and (c). 105. A method of evaluating an influenza therapy, the method comprising:

acquiring acknowledge that the level of one or more cytokines is elevated (e.g., transiently elevated) in a subject (e.g., a human subject) after administration of an anti-HA antibody molecule described herein, e.g., VIS410, wherein an elevated level of one or more cytokines is indicative that the anti-HA antibody molecule is effective in treating or preventing an influenza infection, or a symptom thereof.

106. A method of evaluating an influenza therapy, the method comprising:

acquiring acknowledge that the level of one or more cytokines is elevated (e.g., transiently elevated) in a subject (e.g., a human subject) after administration of an anti-HA antibody molecule described herein, e.g., VIS410, wherein an elevated level of one or more cytokines is indicative that the anti-HA antibody molecule is capable of causing an adverse event in the subject.

107. A method of evaluating a subject (e.g., a human subject), the method comprising:

acquiring acknowledge that the level of one or more cytokines is elevated (e.g., transiently elevated) in the subject after administration of an anti-HA antibody molecule described herein, e.g., VIS410; and selecting the subject as suitable for continued administration of the anti-HA antibody molecule.

108. A method of evaluating a therapy, the method comprising:

acquiring acknowledge that the level of one or more cytokines is elevated (e.g., transiently elevated) in a subject (e.g., a human subject) after administration of an anti-HA antibody molecule described herein, e.g., VIS410; and selecting the anti-HA antibody molecule as suitable for treating or preventing an influenza infection, or a symptom thereof, in the subject.

109. A method of evaluating a subject (e.g., a human subject), the method comprising:

acquiring acknowledge that the level of one or more cytokines is elevated (e.g., transiently elevated) in a subject after administration of an anti-HA antibody molecule described herein, e.g., VIS410; and selecting the subject as not suitable for continued administration of the anti-HA antibody molecule.

110. A method of evaluating a therapy, the method comprising:

acquiring acknowledge that the level of one or more cytokines is elevated (e.g., transiently elevated) in a subject (e.g., a human subject) after administration of an anti-HA antibody molecule described herein, e.g., VIS410; and selecting the anti-HA antibody molecule as not suitable for treating or preventing an influenza infection, or a symptom thereof, in the subject.

111. An anti-HA antibody molecule described herein, e.g., VIS410, for use in treating or preventing an influenza virus infection, or a symptom hereof, in a subject (e.g., a human subject), wherein the subject has one or more (e.g., 2, 3, 4, 5, 6, 7, 8, 9, 10, 11, 12, 13, 14, or all) of the following characteristics:

(a) is at least about 60 years old, e.g., at least about 65, 70, 75, or 80 years old;

(b) has received, or has not received, a second antiviral therapy (e.g., oseltamivir), e.g., within about 1, 2, or 3 days prior to administration of the anti-HA antibody molecule;

(c) has an onset of influenza, at least about 24, 36, 48, 60, 72, or 96 hours (e.g., at least about 60, 61, 62, 63, 64, 65, 66, 67, 68, 69, 70, 71, 72, 73, 74, 75, 76, 77, 78, 79, or 80 hours), or within about 24, 36, 48, 60, 72, 96, or 120 hours, prior to administration of the anti-HA antibody molecule;

(d) has received, or has not received, an influenza vaccine, e.g., within about 1, 2, 3, 4, 5, or 6 months, prior to administration of the anti-HA antibody molecule;

(e) is identified as being infected with an influenza A virus, e.g., within about 12, 24, 36, or 48 hours, prior to administration of the anti-HA antibody molecule;

(f) is infected with, is at risk of being infected with, an H1 influenza virus (e.g., an H1N1 virus), an H3 influenza virus (e.g., an H3N2 virus), or an H7 influenza virus (e.g., an H7N9 virus);

(g) receives, or is more likely to receive, an oxygen therapy, positive pressure ventilation, or a therapy to treat or prevent bacterial pneumonia;

(h) is, or is more likely to be, intubated, or receives, or is more likely to receive mechanical ventilation;

(i) has an ordinal scale score above about 2.0 (e.g., above about 2.0, 2.1, 2.2, 2.25, 2.3, 2.4, or 2.5), optionally wherein the ordinal scale scores are based on one or more (e.g., all) parameters chosen from death, ICU stay with mechanical ventilation, ICU stay without mechanical ventilation, non-ICU hospitalization, or discharge;

(j) requires greater intensity of care (e.g., ICU care);

(k) has a clinical response (e.g., as determined by one, two, three, four, or five vital signs described herein, e.g., meeting a specified threshold described herein), within about 24, 36, 48, 60, 72, 84, 96, 108, or 120 hours, after administration of the anti-HA antibody molecule;

(l) has a symptom score (e.g., determined by FluPRO) that is decreased by at least about 10%, 20%, 30%, 40%, 50%, 60%, 70%, 80%, 90%, or more), within 1, 2, 3, 4, 5, 6, 7, 8, 9, 10, 11, 12, 13, or 14 days, after administration of the anti-HA antibody molecule;

(m) has a symptom score (e.g., determined by visual analog score (VAS)) that is increased by at least about 2, 3, 4, 5, 6, 7, 8, 9, or 10-fold), within 1, 2, 3, 4, 5, 6, 7, 8, 9, 10, 11, 12, 13, or 14 days, after administration of the anti-HA antibody molecule;

(n) is negative for viral titer (e.g., determined by TCID50), within 1, 2, 3, 4, 5, 6, 7, 8, 9, 10, 11, 12, 13, or 14 days, after administration of the anti-HA antibody molecule; or (o) does not develop, or develops no more than 1, treatment emergent adverse event (TEAE) described herein (e.g., a serious TEAE described herein).

112. A method of treating or preventing an influenza virus infection, or a symptom thereof, in a subject (e.g., a human subject), comprising administering to the subject an anti-HA antibody molecule described herein, e.g., VIS410, wherein the subject has one or more (e.g., 2, 3, 4, 5, 6, 7, 8, 9, 10, 11, 12, 13, 14, or all) of the following characteristics:

(a) is at least about 60 years old, e.g., at least about 65, 70, 75, or 80 years old;

(b) has received, or has not received, a second antiviral therapy (e.g., oseltamivir), e.g., within about 1, 2, or 3 days prior to administration of the anti-HA antibody molecule;

(c) has an onset of influenza, at least about 24, 36, 48, 60, 72, or 96 hours (e.g., at least about 60, 61, 62, 63, 64, 65, 66, 67, 68, 69, 70, 71, 72, 73, 74, 75, 76, 77, 78, 79, or 80 hours), or within about 24, 36, 48, 60, 72, 96, or 120 hours, prior to administration of the anti-HA antibody molecule;

(d) has received, or has not received, an influenza vaccine, e.g., within about 1, 2, 3, 4, 5, or 6 months, prior to administration of the anti-HA antibody molecule;

(e) is identified as being infected with an influenza A virus, e.g., within about 12, 24, 36, or 48 hours, prior to administration of the anti-HA antibody molecule;

(f) is infected with, is at risk of being infected with, an H1 influenza virus (e.g., an H1N1 virus), an H3 influenza virus (e.g., an H3N2 virus), or an H7 influenza virus (e.g., an H7N9 virus);

(g) receives, or is more likely to receive, an oxygen therapy, positive pressure ventilation, or a therapy to treat or prevent bacterial pneumonia;

(h) is, or is more likely to be, intubated, or receives, or is more likely to receive mechanical ventilation;

(i) has an ordinal scale score above about 2.0 (e.g., above about 2.0, 2.1, 2.2, 2.25, 2.3, 2.4, or 2.5), optionally wherein the ordinal scale score is based one or more (e.g., all) parameters chosen from death, ICU stay with mechanical ventilation, ICU stay without mechanical ventilation, non-ICU hospitalization, or discharge;

(j) requires greater intensity of care (e.g., ICU care);

(k) has a clinical response (e.g., as determined by one, two, three, four, or five vital signs described herein, e.g., meeting a specified threshold described herein), within about 24, 36, 48, 60, 72, 84, 96, 108, or 120 hours, after administration of the anti-HA antibody molecule;

(l) has a symptom score (e.g., determined by FluPRO) that is decreased by at least about 10%, 20%, 30%, 40%, 50%, 60%, 70%, 80%, 90%, or more), within 1, 2, 3, 4, 5, 6, 7, 8, 9, 10, 11, 12, 13, or 14 days, after administration of the anti-HA antibody molecule;

(m) has a symptom score (e.g., determined by visual analog score (VAS)) that is increased by at least about 2, 3, 4, 5, 6, 7, 8, 9, or 10-fold), within 1, 2, 3, 4, 5, 6, 7, 8, 9, 10, 11, 12, 13, or 14 days, after administration of the anti-HA antibody molecule;

(n) is negative for viral titer (e.g., determined by TCID50), within 1, 2, 3, 4, 5, 6, 7, 8, 9, 10, 11, 12, 13, or 14 days, after administration of the anti-HA antibody molecule; or (o) does not develop, or develops no more than 1, treatment emergent adverse event (TEAE) described herein (e.g., a serious TEAE described herein).

113. The antibody molecule for use of paragraph 111, or the method of paragraph 112, further comprising knowledge that the subject has one or more (e.g., 2, 3, 4, 5, 6, 7, 8, 9, 10, 11, 12, 13, 14, or all) of the characteristics (a)-(o).

114. The antibody molecule for use of paragraph 111 or 113, or the method of paragraph 112 or 113, further comprising determining that the subject has one or more (e.g., 2, 3, 4, 5, 6, 7, 8, 9, 10, 11, 12, 13, 14, or all) of the characteristics (a)-(o).

115. The antibody molecule for use of any of paragraphs 111 or 113-114, or the method of any of paragraphs 112-114, wherein the anti-HA antibody molecule is administered, responsive to a determination that the subject has one or more (e.g., 2, 3, 4, 5, 6, 7, 8, 9, 10, 11, 12, 13, 14, or all) of the characteristics (a)-(o).

116. The combination for use of any of paragraphs 1 or 3-55, the antibody molecule for use of any of paragraphs 56, 58-78, 81, 83-85, 87-104, 111, or 113-115, or the method of any of paragraphs 2-55, 57-80, 82-84, 86-110, or 112-115, wherein the antibody molecule comprises:

(a) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y -A-D-S-V-Q-G (SEQ ID NO:69); and a CDR3 comprising the sequence D-S-R-L-R-S-L-L-Y-F-E-W-L -S-Q-G-Y-F-N-P (SEQ ID NO:70); and (b) a light chain immunoglobulin variable region segment comprising: a CDR1 comprising the sequence Q-S-I-T-F-D-Y-K-N-Y-L-A (SEQ ID NO: 145); a CDR2 comprising the sequence W-G-S-Y-L -E-S (SEQ ID NO:72); and a CDR3 comprising the sequence Q-Q-H-Y-R-T-P-P-S (SEQ ID NO:73).

117. The combination for use of any of paragraphs 1 or 3-55, the antibody molecule for use of any of paragraphs 56, 58-78, 81, 83-85, 87-104, 111, or 113-116, or the method of any of paragraphs 2-55, 57-80, 82-84, 86-110, or 112-116, wherein the antibody molecule comprises a heavy chain immunoglobulin variable region segment that comprises SEQ ID NO: 25.

118. The combination for use of any of paragraphs 1 or 3-55, the antibody molecule for use of any of paragraphs 56, 58-78, 81, 83-85, 87-104, 111, or 113-117, or the method of any of paragraphs 2-55, 57-80, 82-84, 86-110, or 112-117, wherein the antibody molecule comprises a light chain immunoglobulin variable region segment that comprises SEQ ID NO: 52.

119. The combination for use of any of paragraphs 1 or 3-55, the antibody molecule for use of any of paragraphs 56, 58-78, 81, 83-85, 87-104, 111, or 113-118, or the method of any of paragraphs 2-55, 57-80, 82-84, 86-110, or 112-118, wherein the antibody molecule comprises: a heavy chain immunoglobulin variable region segment that comprises SEQ ID NO: 25 and a light chain immunoglobulin variable region segment that comprises SEQ ID NO: 52.

120. The combination for use of any of paragraphs 1 or 3-55, the antibody molecule for use of any of paragraphs 56, 58-78, 81, 83-85, 87-104, 111, or 113-119, or the method of any of paragraphs 2-55, 57-80, 82-84, 86-110, or 112-119, wherein the antibody molecule comprises a tetramer of: two heavy chain immunoglobulin variable region segments, each comprising SEQ ID NO: 25 and two light chain immunoglobulin variable region segments, each comprising SEQ ID NO: 52.

121. The combination for use of any of paragraphs 1 or 3-55, the antibody molecule for use of any of paragraphs 56, 58-78, 81, 83-85, 87-104, 111, or 113-120, or the method of any of paragraphs 2-55, 57-80, 82-84, 86-110, or 112-120, wherein the antibody molecule comprises a full-length antibody.

122. The combination for use of any of paragraphs 1 or 3-55, the antibody molecule for use of any of paragraphs 56, 58-78, 81, 83-85, 87-104, 111, or 113-121, or the method of any of paragraphs 2-55, 57-80, 82-84, 86-110, or 112-121, wherein the antibody molecule comprises a humanized antibody molecule.

123. The combination for use of any of paragraphs 1 or 3-55, the antibody molecule for use of any of paragraphs 56, 58-78, 81, 83-85, 87-104, 111, or 113-122, or the method of any of paragraphs 2-55, 57-80, 82-84, 86-110, or 112-122, wherein the antibody molecule comprises two heavy paragraph variable regions and two light chain variable regions.

124. The combination for use of any of paragraphs 1 or 3-55, the antibody molecule for use of any of paragraphs 56, 58-78, 81, 83-85, 87-104, 111, or 113-123, or the method of any of paragraphs 2-55, 57-80, 82-84, 86-110, or 112-123, wherein the antibody molecule is an IgG antibody.

125. The combination for use of any of paragraphs 1 or 3-55, the antibody molecule for use of any of paragraphs 56, 58-78, 81, 83-85, 87-104, 111, or 113-124, or the method of any of paragraphs 2-55, 57-80, 82-84, 86-110, or 112-124, wherein the antibody molecule is a single chain antibody (scFv), a F(ab')$_2$ fragment, a Fab fragment, or an Fd fragment.

EXAMPLES

Example 1: In Vitro Antiviral Assessment of VIS410 in Combination with Baloxavir and Neuraminidase Inhibitors Four drugs have been approved for the treatment of acute influenza: three drugs that target the viral neuraminidase (NA) activity (oseltamivir, peramivir, and zanamivir) and a drug targeting the PA subunit of the viral RNA polymerase (baloxavir-marboxil) that was recently approved in Japan and the US in 2018. The neuraminidase inhibitors (NAIs) are used off label as standard-of-care for critically ill hospitalized patients with influenza. Baloxavir marboxil may also be used for treating hospitalized patients with influenza.

VIS410 is a broadly active monoclonal antibody targeting the highly conserved hemagglutinin (HA) stem region of Influenza A. VIS410 is currently being evaluated in a Phase 2b clinical study in combination with oseltamivir (versus oseltamivir alone) in patients hospitalized with influenza A. VIS410 was evaluated in combination with oseltamivir in in vitro cell culture infection assays. These data demonstrated improved antiviral activity when VIS410 and oseltamivir were combined at concentrations near the EC$_{50}$ for each drug with no evidence of antagonism. These data provided support for the use of VIS410 in combination with oseltamivir in the present study.

Further clinical studies will evaluate VIS410 in combination with standard of care therapies for hospitalized influenza A including peramivir, zanamivir, and baloxavir. Therefore, VIS410 antiviral activity in combination with other NAIs or baloxavir was assessed in vitro prior to dosing any subjects with these combinations in a clinical trial.

Methods and Materials

Anti-Viral Reagents

Monoclonal antibody VIS410 lot B16090058a was used for all experiments in this study. Small molecule anti-influenza drugs were obtained from MedChemExpress: Baloxavir (Cat. No. HY-109025A), Oseltamivir acid (Cat. No.: HY-13318), Zanamivir (Cat. No.: HY-13210), and Peramivir trihydrate (Cat. No.: HY-17015).

In Vitro Antiviral Assays—NP ELISA

Experiments for assessing antiviral activity of VIS410 in combination with small molecules utilized a protocol adapted from a standard WHO microneutralization method. An overview of the assay is presented in FIG. 1. Briefly, VIS410 and antivirals (individually and in combinations) were prepared in 96 well plates (FIG. 1, Step 1). Typically, eight concentrations of VIS410 were tested against 6-7 small molecule concentrations. Preliminary microneutralization tests of individual compounds was performed to determined $EC_{50}$ drug concentrations against specific viruses tested. For combination drug testing, all drug concentrations spanned the $EC_{50}$ concentrations of the individual compounds against the virus being tested. Viruses were then added to drug combinations (FIG. 1, Step 2). A/HongKong/4801/2014 (H3N2) and A/California/04/2009 (H1N1) Influenza A strains were used. Viruses and antiviral drugs mixtures were then preincubated at 37° C. for 1 hour prior to adding MDCK-London cells (FIG. 1, Step 3). Virus input and incubation period for virus infection were modified for the different molecules being tested (FIG. 1, Step 4). For tests comparing VIS410, baloxavir, and combinations of VIS410 and baloxavir, virus input of 50 $TCID_{50}$/well and 18-20 h incubation for infection were used. For tests comparing VIS410, neuraminidase inhibitors (NAIs), and combinations of VIS410 and NAIs, virus input of 1 $TCID_{50}$/well and 40 h incubation for infection were used (as explained in section 4.2.1).

After virus infection, cells were washed with PBS and fixed with PBS-acetone (20% PBS-80% acetone) (FIG. 1, Step 5). Infection was detected by ELISA using primary staining with a broadly reactive anti-nucleoprotein mouse monoclonal antibody (Anti-Influenza A Antibody nucleoprotein clones A1 A3 Blend, EMD Millipore Catalog #MAB8215), secondary staining with Horse-radish peroxidase (HRP)-conjugated goat anti-mouse polyclonal antibody (Jackson ImmunoResearch Catalog #115-035-071), and developed using TMB Microwell Peroxidase Substrate Kit (KPL Catalog #50-76-03) and 0.1 N sulfuric acid stop solution (FIG. 1, Step 6). Absorbance at 450 nm was measured using a standard plate reader, and data was analyzed using GraphPad Prism 7.0 software. Percent virus infection was calculated as signal of virus detected (OD450 nm) under various conditions with or without antiviral drugs normalized to virus only control (average of eight wells for each experiment).

In Vitro Antiviral Assays—CPE Assays

VIS410 and NAI combinations were assessed using in vitro antiviral assays with a cytopathic effect (CPE) readout. These assays evaluated drug combinations against A/Michigan/45/2015 (H1N1) and were performed in three independent replicates. NAI compounds were serially diluted using seven half-log dilutions in test medium (MEM supplemented with 10 U/ml trypsin, 1 µg/ml EDTA, and 50 µg/ml gentamicin). Final high concentrations of NAI inhibitors were as follows: 1 µM oseltamivir and zanamivir and 0.1 µM peramivir. VIS410 was similarly serially diluted using eight half-log dilutions to obtain final high starting concentrations of 10 µg/mL.

Each concentration of NAI was combined with each concentration of VIS410 in 5 wells of a 96-well plate. Each compound was also tested alone (i.e., not combined with another compound). Three wells of each compound combination were infected with virus inoculum prepared at the lowest concentration that would yield >90% CPE by day 3 p.i. Two wells were uninfected and used as cytotoxicity controls. Each plate contained six virus control wells and six cell control wells. Virus and compounds were incubated for one hour at room temperature. Following the incubation, combinations were transferred to 96-well plated containing confluent MDCK monolayers. Plates were incubated at 37±2° C., 5% $CO_2$.

Drug Synergy Analysis Using MacSynergy II

The MacSynergy II program was used to analyze in vitro antiviral assay data and determine additive, synergistic, or antagonistic activity of drug combinations. MacSynergy was used to generated three-dimensional (3D) surface plots using the drug combination assay results from replicate data, and the 95% confidence intervals for volumes of synergy and antagonism are calculated. Synergy was defined as drug combinations that yielded synergy volumes greater than 50, with synergy volume of 50 to 100 considered to indicate mild synergism and synergy volume >100 considered highly synergistic. Additive drug interactions had synergy volumes in the range of −50 to 50, while synergy volumes ≤−50 were considered antagonistic.

Results

VIS410 in Combination with Baloxavir

Figure 2B:
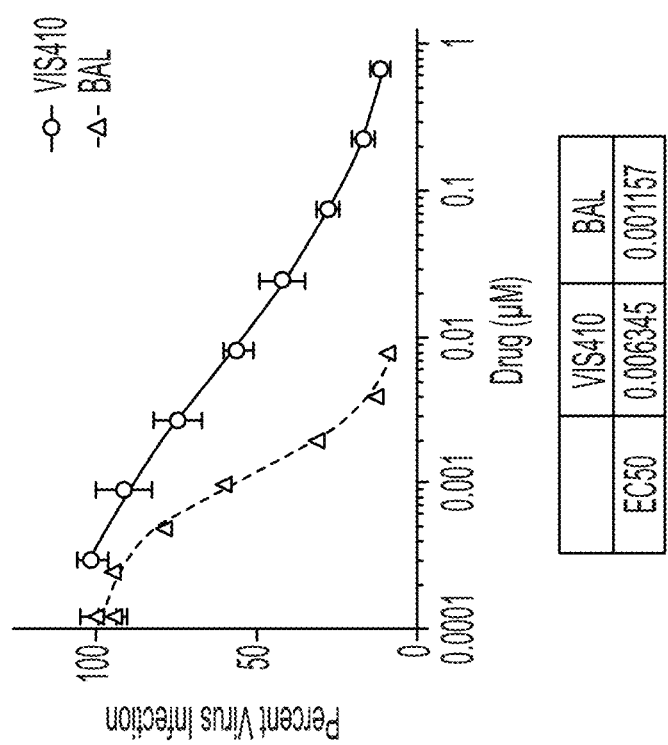
FIGS. 2A-2B are a series of graphs showing antiviral activity of individual compounds (VIS410 or baloxavir (BAL)) against A/Hong Kong/4801/2014 (A) and A/California/04/2009 (B). $EC_{50}$ concentrations (µM) are presented in the table below each plot. Data points and error bars represent average and standard error for at least three tests.
Figure 2A:
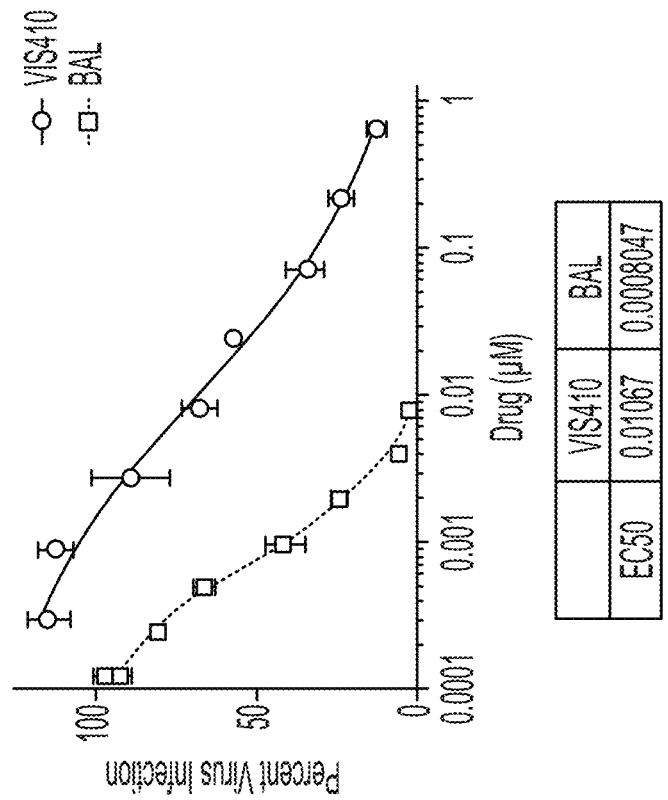
Figure 3A:
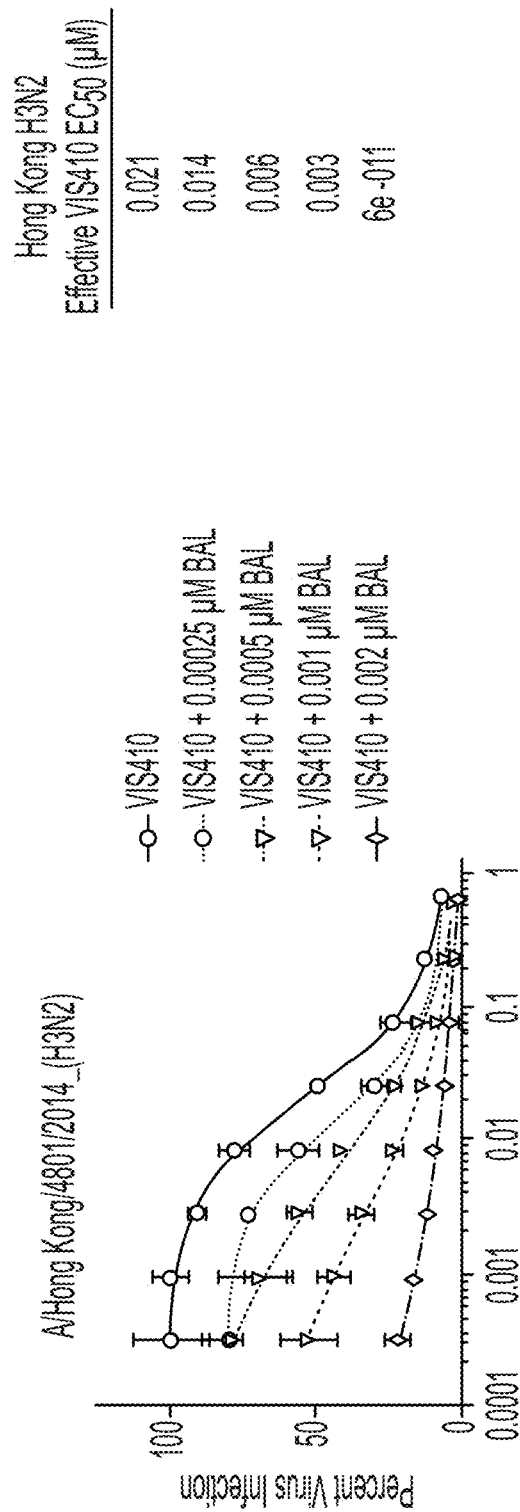
FIGS. 3A-3B are a series of graphs showing 2D curve analyses of VIS410 alone (8 concentration points) versus VIS410 in combination with select baloxavir concentrations against A/Hong Kong/4801/2014 (A) and A/California/04/2009 (B). The baloxavir $EC_{50}$ concentrations were 0.0008 µM against A/HongKong/4801/2014 and 0.001 µM against A/California/04/2009 (FIG. 2). Four baloxavir concentrations surrounding these $EC_{50}$ concentrations in combination with VIS410 and VIS410 alone were assessed as listed in the legends. The effective VIS410 $EC_{50}$ when combined with baloxavir is listed next to the drug combinations in the legend. Data points and error bars represent average and standard error for triplicate (A) and duplicate tests (B).
Figure 3B:
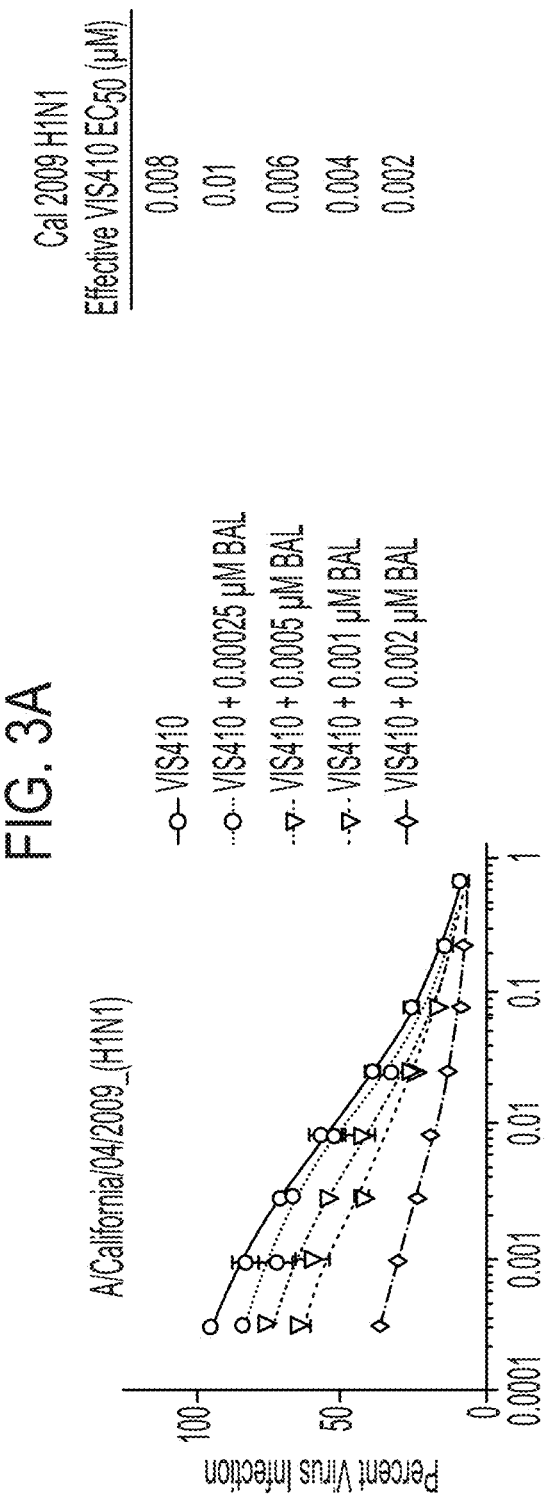

Cell culture-based infection assays using an NP-ELISA readout were performed to assess the antiviral activity of combinations of VIS410 and baloxavir. Recent circulating vaccines strains representative of the breadth of VIS410 reactivity—across group 1 and group 2 influenza A—were selected for testing, including A/Hong Kong/4801/2014 (H3N2-Group 2 Influenza A) and A/California/04/2009 (H1N1-Group 1 influenza A). Initial tests of individual compounds evaluated a range of baloxavir and VIS410 concentrations to identify the $EC_{50}$ concentrations of drugs against these influenza A viruses (FIGS. 2A-2B). These studies demonstrated VIS410 $EC_{50}$ of approximately 0.01 µM (1.5 µg/ml) against A/Hong Kong/4801/2014 and 0.006 µM (0.9 µg/ml) against A/California/04/2009 and baloxavir $EC_{50}$ of approximately 0.0008 µM against A/Hong Kong/4801/2014 and 0.001 µM against A/California/04/2009, consistent with previous reports of baloxavir activity.

Next a series of VIS410 concentrations that spanned the VIS410 $EC_{50}$ was tested in combination with a series of baloxavir concentrations that spanned the baloxavir $EC_{50}$. Six to seven baloxavir concentrations were evaluated (0.008 µM, 0.004 µM, 0.002 µM, 0.001 µM, 0.0005 µM, 0.00025 µM, and 0.000125 µM) against eight VIS410 concentrations (0.67 µM, 0.22 µM, 0.075 µM, 0.025 µM, 0.008 µM, 0.003 µM, 0.0009 µM, and 0.0003 µM) for both A/Hong Kong/4801/2014 (H3N2) and A/California/04/2009 (H1N1). Note: the 0.008 µM baloxavir concentration was not included in every experiment. The antiviral activity of the combinations was assessed using two-dimensional (2D) (FIGS. 3A-3B and FIGS. 4A-4B) and three-dimensional (3D) analyses, including examination of synergy (FIGS. 6A-6B).

Figure 4A:
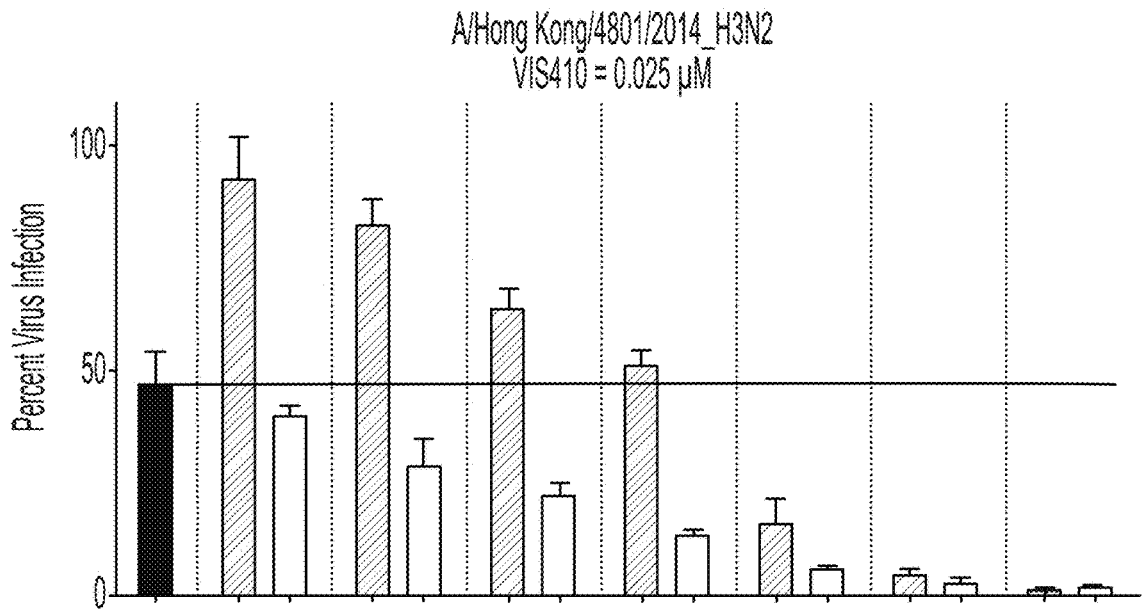
FIGS. 4A-4B are a series of graphs showing 2D histogram analyses of one VIS410 concentration close to the VIS410 $EC_{50}$ versus in combination with 7 baloxavir concentrations against A/Hong Kong/4801/2014 (A) and A/California/04/2009 (B). The concentrations closest to the VIS410 $EC_{50}$ were 0.025 µM against A/HongKong/4801/2014 and 0.008 µM against A/California/04/2009 (FIG. 2). Black bars represent percent virus infection with VIS410 alone, gray bars represent BAL alone, and white bars represent combination of VIS410 and baloxavir. A dark line across the histogram bars denotes antiviral activity of VIS410 alone. Data points and error bars represent average and standard error for triplicate (A) and duplicate tests (B).
Figure 4B:
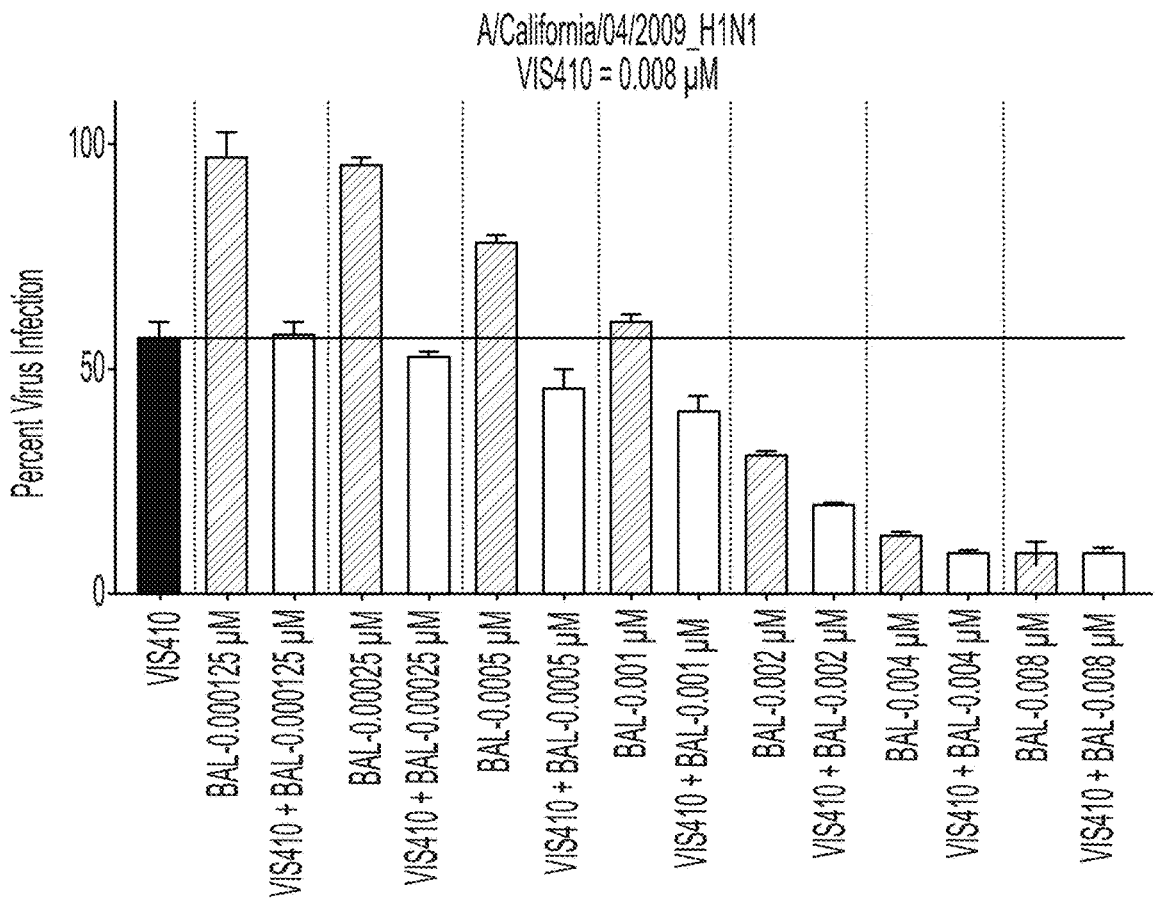
Figure 5A:
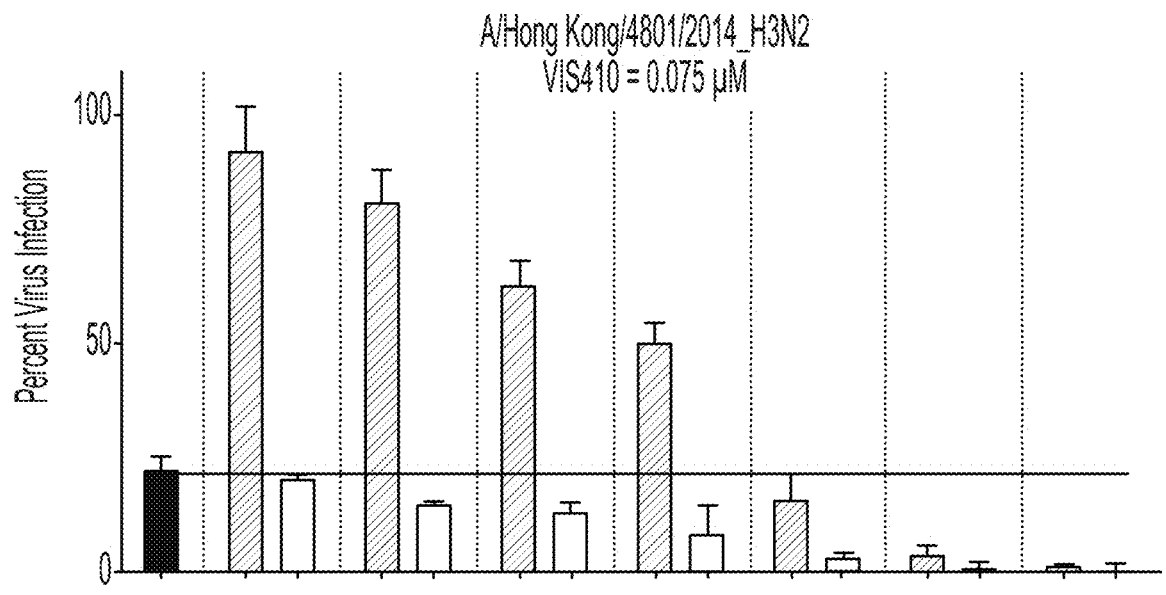
FIGS. 5A-5B are a series of graphs showing 2D histogram analyses of a higher (A) and lower (B) VIS410 concentration compared to $EC_{50}$ VIS410 versus in combination with 7 baloxavir concentrations against A/Hong Kong/4801/2014. Black bars represent percent virus infection with VIS410 alone, gray bars represent BAL alone, and white bars represent combination of VIS410 and baloxavir. A dark line across the histogram bars denotes antiviral activity of VIS410 alone. Data points and error bars represent average and standard error for triplicate (A) and duplicate tests (B).
Figure 5B:
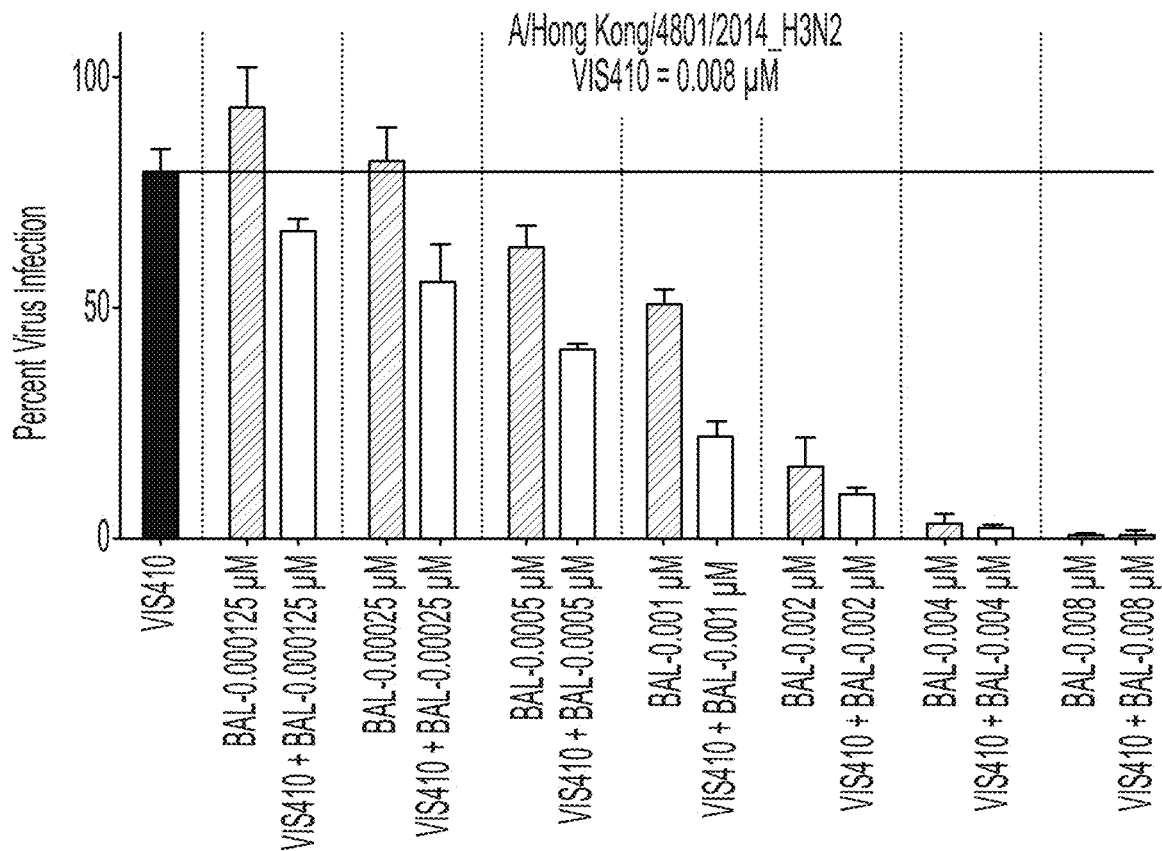

A 2D histogram analysis compared the antiviral activity of one select VIS410 concentration closest to the VIS410 $EC_{50}$ alone and in combination with the 6-7 baloxavir concentrations (FIG. 4A-4B). The VIS410 concentration of 0.025 µM for A/HongKong/4801/2014 (FIG. 4A) and 0.008 µM for A/California/04/2009 (FIG. 4B) were chosen for the histogram analysis based on FIG. 2. The data demonstrate that at concentrations where baloxavir is only partially active—e.g. from 0.00025 µM to 0.002 µM—the addition of VIS410 in combination with baloxavir enhanced antiviral activity compared to either drug individually, where the green bars (combinations) represent lower levels of virus infection compared to the blue bar (VIS410 alone) or the grey bars (BAL alone) (FIG. 4A-4B). Similar enhanced antiviral activity for combinations compared to individual drugs was observed when selecting higher (0.075 µM) or lower (0.008 µM) VIS410 concentrations (FIG. 5A-5B).

Figure 6A:
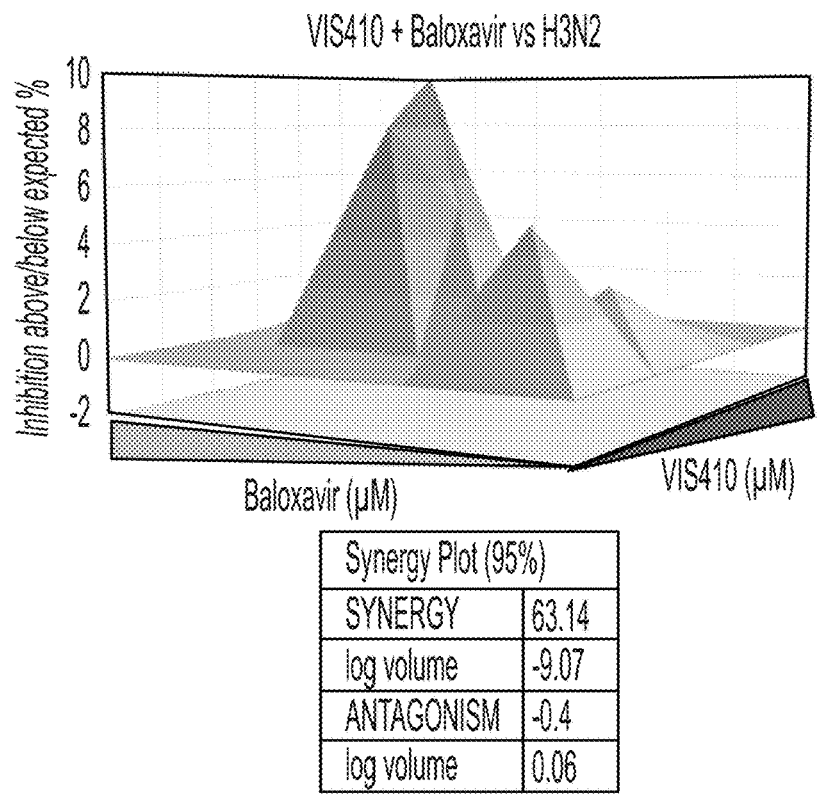
FIGS. 6A-6B are a series of graphs showing that the combination of VIS410 and baloxavir demonstrated synergistic antiviral activity. MacSynergy II was used to assess 3D antiviral activity and synergy of VIS410 in combination with baloxavir against A/Hong Kong/4801/2014_H3N2 (A) and A/California/04/2009_H1N1 (B). The plane at 0% inhibition above/below expected represents additive antiviral activity for drugs in combination. Peaks above the plane are regions of synergy, and dips below the plane are regions of antagonism. The volume of synergy and antagonism (in $\mu M^2$%) at the 95% confidence interval is displayed in the table beneath panels (A) and (B). Data for synergy plots were generated from tests run in triplicate (A) or duplicate (B).
Figure 6B:
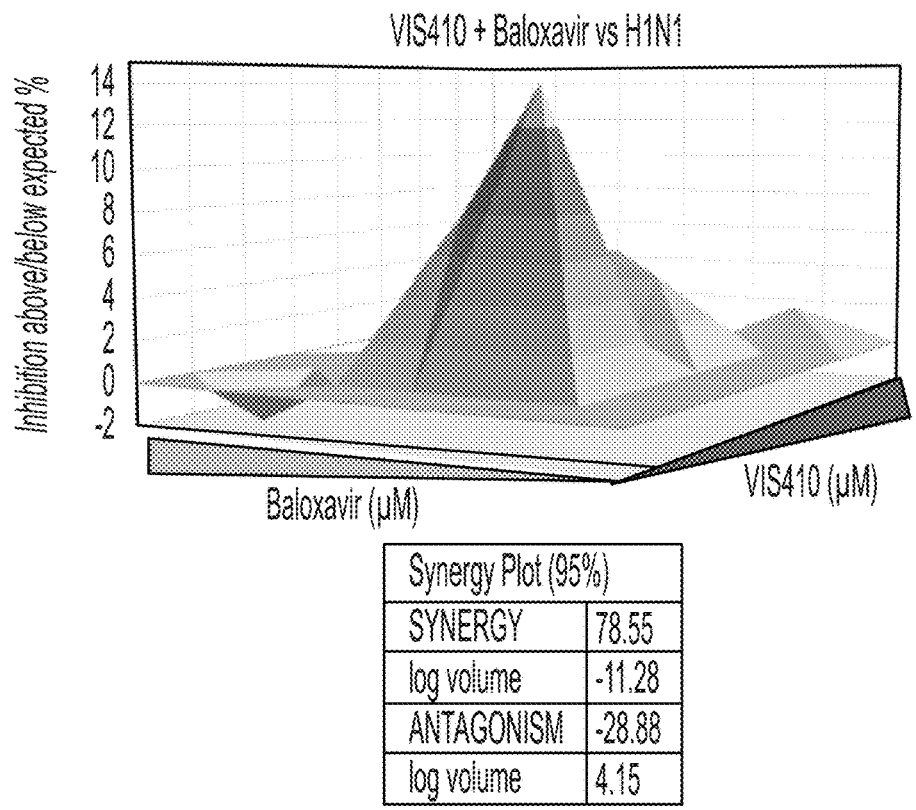

In order to understand if the enhanced antiviral activity of VIS410 and baloxavir combinations was synergistic, analysis was performed using MacSynergy II and 3D drug interaction plots were generated (FIG. 6A-6B). Peaks of synergy were observed at concentrations of baloxavir and VIS410 where the single drugs were only partially active (e.g. near the $EC_{50}$ of each drug individually). At concentrations where the single drugs were not active or were fully active, such as very high or low BAL or VIS410 concentrations, only additivity or minor antagonism dips below the plane of additivity were observed. Antagonism was only observed at the edges of the 3D plot where drug concentrations were most extreme, and no antagonism volumes of potential clinical significance ($\leq -50$) were observed. On the other hand, the synergy volumes ($\geq 50$) indicate mild to moderate synergy for VIS410 and baloxavir at the concentrations tested, with potential clinical significance of the synergistic activity.

VIS410 in Combination with NAIs Versus H3N2

Similar to VIS410-baloxavir combination studies, two influenza A viruses representative of VIS410 breadth across group 1 and group 2 influenza A viruses were selected for testing combinations of VIS410 and NAIs—including oseltamivir, peramivir, and zanamivir. Combination assays with the group 2 representative (A/Hong Kong/4801/2014, H3N2) used an in vitro cell culture infection assay with an NP-ELISA readout, and assays with the group 1 representative (A/Michigan/45/2015, H1N1) were performed using the CPE readout.

Figure 7:
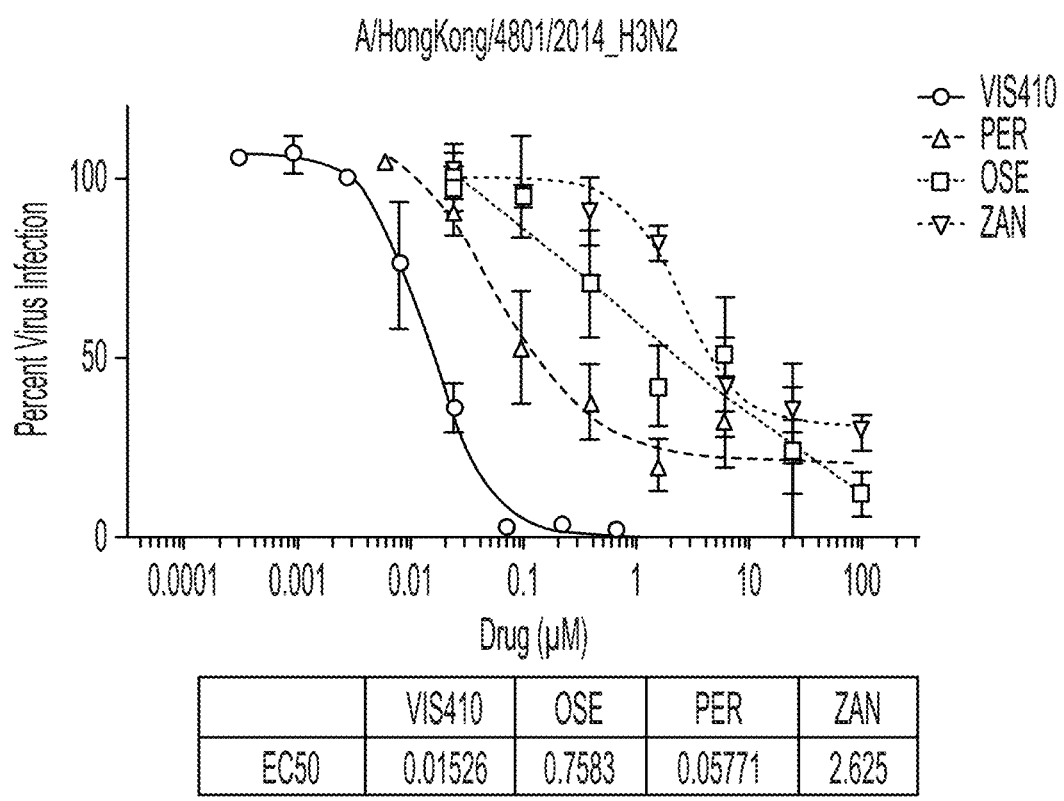
FIG. 7 is a graph showing antiviral activity of individual compounds (VIS410, peramivir (PER), oseltamivir (OSE), or zanamivir (ZAN)) against A/Hong Kong/4801/2014. $EC_{50}$ concentrations ($\mu M$) are presented in the table below the plot. Data points and error bars represent average and standard error for at least three tests.

The mechanism of action (MOA) for the NAIs is to inhibit release of new virus progeny; NAIs do not block initial virus infection. Therefore, experimental conditions were modified to optimize the level of antiviral effect observed from the NAIs using conditions that would detect inhibition of viral spread, including a lower virus inoculum (1 $TCID_{50}$/ml) and longer virus infection period (40 hours). Initial tests of individual compounds evaluated a range of NAI and VIS410 concentrations to identify the $EC_{50}$ concentrations of individual drugs against A/Hong Kong/4801/2014 (H3N2) using the modified assay conditions (FIG. 7). VIS410 activity and $EC_{50}$ against A/Hong Kong/4801/2014 were similar in the modified assay as the previous test ($EC_{50}$ range for both assay formats=0.01-0.02 µM, FIG. 2 and FIG. 7). The NAIs did not achieve complete inhibition of virus infection, consistent with an MOA of preventing release of virus particles and not blocking initial virus infection. However, the NAIs demonstrated antiviral activity under the conditions tested, with peramivir (PER) the most potent NAI against A/Hong Kong/4801/2014.

Eight VIS410 concentrations (0.67 µM, 0.22 µM, 0.075 µM, 0.025 µM, 0.008 µM, 0.003 µM, 0.0009 µM, and 0.0003 µM) that spanned the VIS410 $EC_{50}$ against A/Hong Kong/4801/2014 were tested in combination with six NAI concentrations over 3-logs that spanned the NAI $EC_{50}$. The six concentrations of all NAIs (PER, OSE, and ZAN) were 25 µM, 6.25 µM, 1.56 µM, 0.4 µM, 0.1 µM, and 0.024 µM to overlap the $EC_{50}$ of 0.057 µM, 0.76 µM, and 2.6 µM of PER, OSE, and ZAN, respectively (FIG. 7).

Figure 8A:
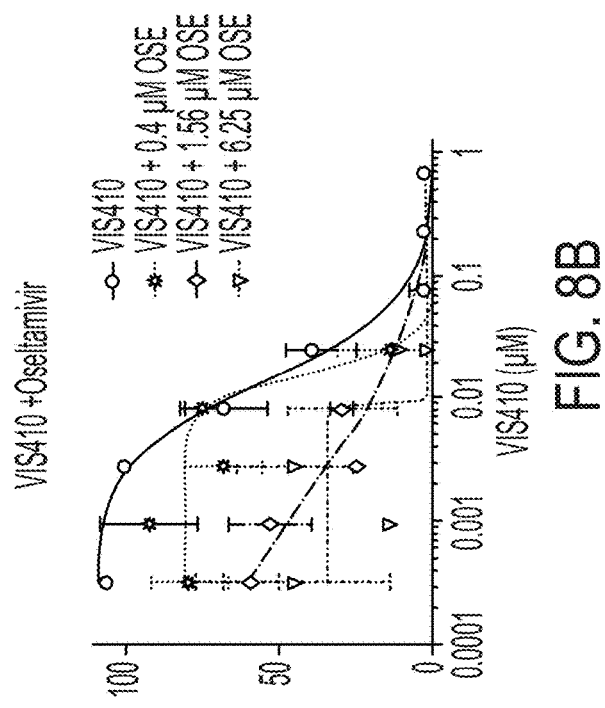
FIGS. 8A-8C are a series of graphs showing 2D curve analyses of VIS410 alone (8 concentration points) versus VIS410 in combination with select NAI concentrations against A/Hong Kong/4801/2014, peramivir (PER) (A), oseltamivir (OSE) (B), and zanamivir (ZAN) (C) as determined using the NP ELISA. The NAI $EC_{50}$ concentrations were 0.057 $\mu M$, 0.76 $\mu M$, and 2.6 $\mu M$ for PER, OSE, and ZAN, respectively, against A/Hong Kong/4801/2014 (FIG. 7). Three NAI concentrations surrounding the $EC_{50}$ concentrations in combination with VIS410 and VIS410 alone were assessed as listed in the legends. Data points and error bars represent average and standard error for duplicate tests.
Figure 8B:
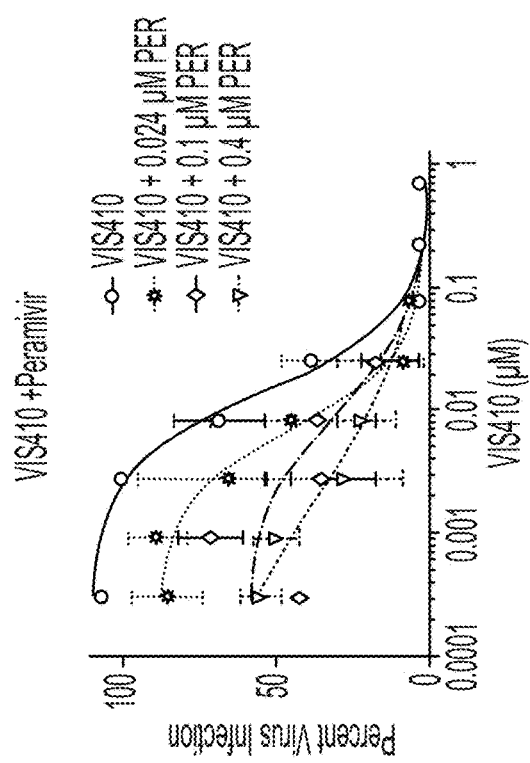
Figure 8C:
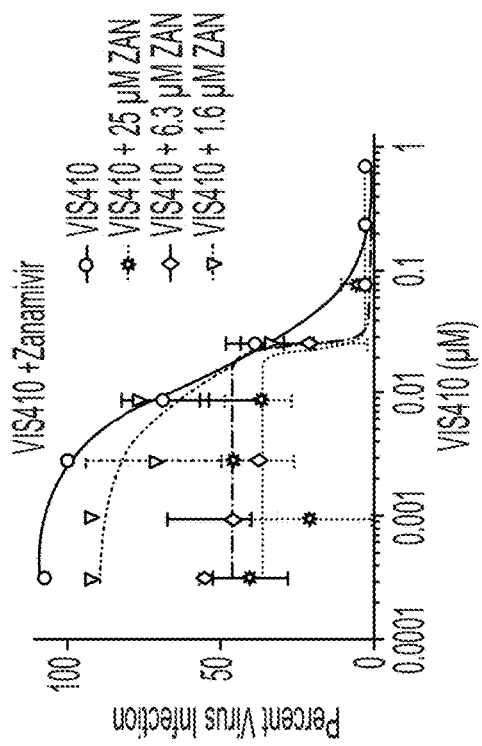

A 2D curve analysis compared the curve of antiviral activity for VIS410 alone to the curves for combinations of VIS410 with select NAI concentrations close to the NAI $EC_{50}$ (or partially active) against A/Hong Kong/4801/2014 (H3N2) (FIG. 8A-8C). Overall there was improved antiviral activity when VIS410 was in combination with NAI concentrations near the NAI $EC_{50}$ compared to VIS410 alone. These data demonstrate VIS410 and NAI in combination enhance antiviral activity in combination.

VIS410 in Combination with NAIs Versus H1N1

Combination antiviral activity assessments with VIS410 and NAIs—including oseltamivir, peramivir, and zanamivir—were performed against A/Michigan/45/2015 (H1N1) using CPE assay readout [17]. Compounds were first tested individually to determine the $EC_{50}$ of each drug against A/Michigan/45/2015 (H1N1) (Table 5). The results of the individual compounds demonstrated similarities in $EC_{50}$ values across replicates for VIS410, but higher variability across replicates was observed for the NAIs, particularly OSE and PER. For example, the $EC_{50}$ values between replicates for OSE were 7.5-fold different, and an $EC_{50}$ value could not be determined for one of the PER replicates.

TABLE 5

Antiviral activity of VIS410 and NAI compounds against influenza A/Michigan/45/2015 (H1N1)pdm09 using the CPE assay.

| Compound | $EC_{50}$ (µM) - Replicate 1 | $EC_{50}$ (µM) - Replicate 2 |
|---|---|---|
| VIS410 | 0.013 | 0.011 |
| Oseltamivir (OSE) | 0.18 | 0.024 |
| Peramivir (PER) | 0.01 | <0.006 |
| Zanamivir (ZAN) | 0.06 | 0.034 |

Next, combination studies with VIS410 and NAIs against A/Michigan/45/2015 were carried out. Eight VIS410 concentrations (0.067 µM, 0.021 µM, 0.0067 µM, 0.0021 µM, 0.00067 µM, 0.0002 µM, 0.000067 µM, and 0.00002 µM) that spanned the VIS410 $EC_{50}$ were tested against seven NAI concentrations spanning the NAI $EC_{50}$ individually. Concentrations for PER were (0.1 µM, 0.03 µM, 0.01 µM, 0.003 µM, 0.001 µM, 0.0003 µM, and 0.0001 µM). Concentrations for OSE and ZAN were (1.0 µM, 0.32 µM, 0.1 µM, 0.032 µM, 0.01 µM, 0.0032 µM, and 0.001 µM).

Figure 9A:
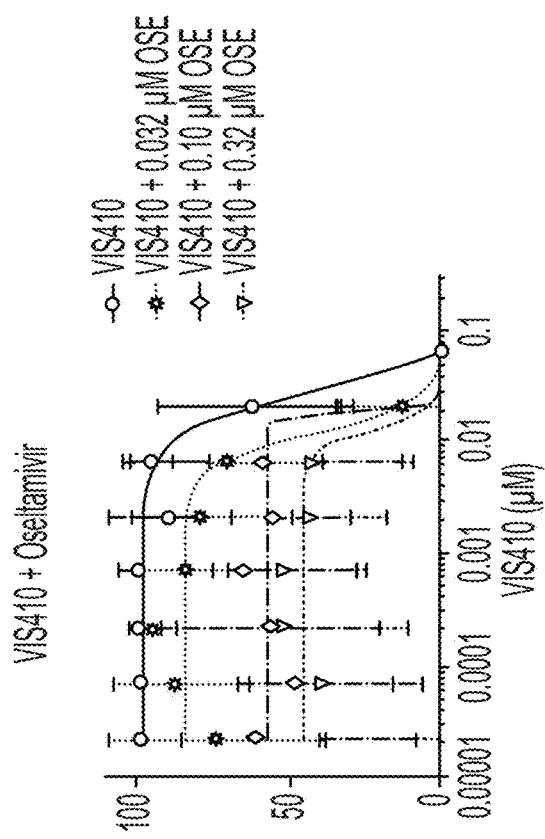
FIGS. 9A-9C are a series of graphs showing 2D curve analyses of VIS410 alone (8 concentration points) versus VIS410 in combination with select NAI concentrations against A/Michigan/45/2015 (H1N1), for peramivir (PER) (A), oseltamivir (OSE) (B), and zanamivir (ZAN) (C) as determined using the CPE assay. The NAI $EC_{50}$ concentrations against A/Michigan/45/2015 are shown in red for the NAI in each panel and also in Table 5. Three NAI concentrations surrounding the $EC_{50}$ concentrations in combination with VIS410 and VIS410 alone were assessed as listed in the legends. Data points and error bars represent average and standard error for triplicate tests.
Figure 9B:
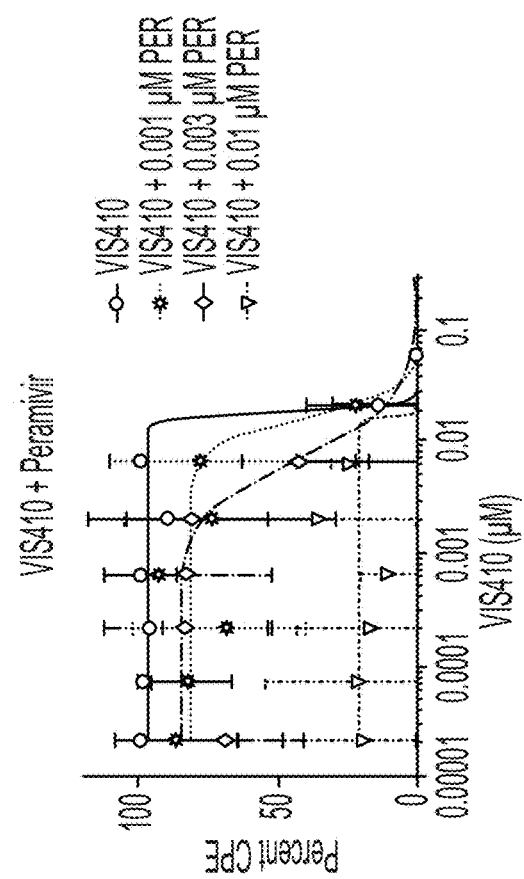
Figure 9C:
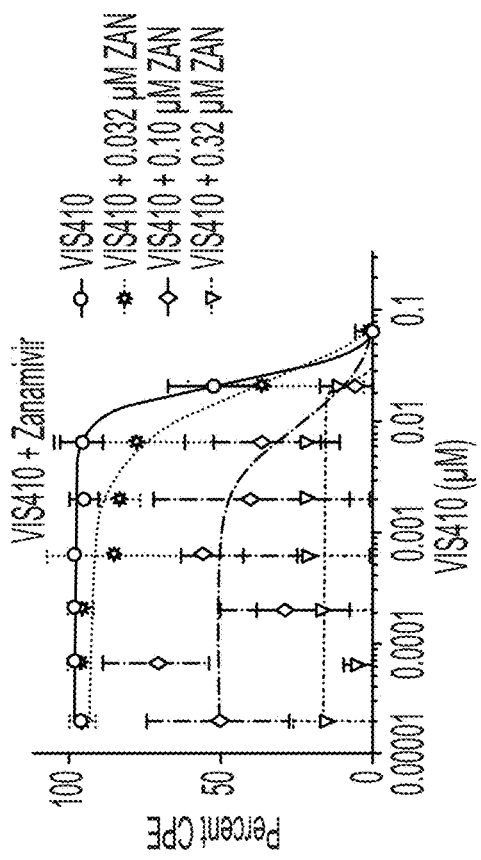

A 2D curve analysis compared the curve of antiviral activity for VIS410 alone to the curves for combinations of VIS410 with select NAI concentrations close to the NAI $EC_{50}$ (or partially active) against A/Michigan/45/2015 (H1N1) (FIG. 9A-9C). Overall there was improved antiviral activity when VIS410 was in combination with NAI concentrations near the NAI $EC_{50}$ compared to VIS410 alone (black, gray, and tan curves compared to blue curve, FIG. 9A-9C). These data are consistent with combination studies using NP-ELISA against A/Hong Kong/4801/2014 (H3N2) (FIG. 8) that demonstrate VIS410 and NAI in combination provide enhanced antiviral activity.

VIS410 in Combinations with NAIs—MacSynergy II Analysis

Replicate drug combination assay data was analyzed using MacSynergy II to generate 3D surface plots and calculate volumes of synergy and antagonism for VIS410 and NAI combinations. A summary of the analysis is shown in Table 6. Some VIS410 and NAI combinations demonstrated drug concentrations that resulted in synergy (or synergy volume >50)—particularly VIS410+OSE (vs H3N2), VIS410+PER (vs H1N1), and VIS410+ZAN (vs H1N1). The volumes of synergy observed were mild to moderate synergy, indicating potential clinical significance of the synergy. Other combinations of VIS410 and NAI at the concentrations evaluated did not demonstrate volumes of synergy or antagonism of significance (volumes between −50 and 50) and represent only additive effects of the drugs in combination—including VIS410+OSE (vs H1N1), VIS410+PER (vs H3N2), and VIS410+ZAN (vs H3N2). Higher assay variability using the NAIs in an infection assay (where NAIs do not block the initial infection) may contribute to varied drug combination outcomes using the different influenza viruses. Notably, no significant antagonistic antiviral effects were observed with any of drug combinations and viruses tested. These data demonstrate VIS410 and NAIs are not antagonistic, and mild drug synergy between VIS410 and NAIs is evident under some assay conditions.

TABLE 6

Combinations of VIS410 and NAIs Demonstrate Additive or Synergistic Antiviral Activity.

| Combination | A/Hong Kong/4801/2014 (H3N2)[1] | | | A/Michigan/45/2015 (H1N1)[2] | | |
| --- | --- | --- | --- | --- | --- | --- |
| | Synergy Volume ($\mu M^2$%) | Antagonism Volume ($\mu M^2$%) | Antiviral Effect | Synergy Volume ($\mu M^2$%) | Antagonism Volume ($\mu M^2$%) | Antiviral Effect |
| VIS410 + OSE | 109.04 | −20.14 | Synergy | 19.23 | −41.18 | Additive |
| VIS410 + PER | 38.16 | −7.42 | Additive | 72.96 | −38.12 | Synergy |
| VIS410 + ZAN | 18.68 | −16.18 | Additive | 53.78 | −34.48 | Synergy |

[1]MacSynergy II analysis performed on duplicate assay data.
[2]MacSynergy II analysis performed on triplicate assay data.

CONCLUSION

VIS410 is a broadly neutralizing, therapeutic monoclonal antibody being developed to treat patients hospitalized with influenza A. VIS410 was assessed in combination with oseltamivir in in vitro infection assays prior to the initiation of the present study in hospitalized patients. In these previous studies, VIS410 in combination with oseltamivir demonstrated improved antiviral effects compared to either drug individually with no antagonism observed against the Group 1 and Group 2 representative viruses tested. For this report, combinations of VIS410 with oseltamivir, peramivir, zanamivir, and baloxavir were evaluated as these four small molecules may be used as standard of care therapies for hospitalized influenza A and used in combination with VIS410.

These studies demonstrated that VIS410 in combination with baloxavir resulted in synergistic antiviral activity at a level that translated to potential clinical significance against both H1N1 and H3N2 viruses. Antiviral effects of VIS410 in combination with NAIs (oseltamivir, peramivir, and zanamivir) ranged from additive to moderately synergistic across conditions and viruses tested. No significant antagonistic antiviral effects were observed for any of the VIS410-small molecule combinations. Less assay variability and consistent synergistic antiviral activity across viruses was observed with baloxavir and VIS410 combinations. One possibility for the reduced variability of the VIS410-baloxavir combos is that both drugs block early in infection such that antiviral effects are clearly observed in the cell culture infection assays with VIS410 and baloxavir. On the other hand, the NAIs do not block the initial infection stages, so assay conditions needed to be modified to lower virus input and extend the infection period to allow for virus spread. Lowering the virus input could lead to stochastic effects with varying levels of initial infection for wells across the plate, contributing to assay variability.

All assessments included an initial phase of testing to determine the $EC_{50}$ value of each drug individually. Then, a series of concentrations spanning the $EC_{50}$ value of each drug individually were used for combination studies. Improved antiviral activity was observed for combinations of VIS410 with all four small molecule antivirals when drugs were combined at concentrations close to the $EC_{50}$ for both drugs (FIG. 3, FIG. 4, FIG. 8, and FIG. 9). In addition, MacSynergy II analysis showed peaks of synergy occur particularly at drug concentrations where the individual drugs are only partially active (For Baloxavir and VIS410, see FIG. 6). These data show that when VIS410 is combined with baloxavir or NAIs, lower concentrations of each drug individually can obtain the same antiviral effect.

These studies support the use of VIS410 in combination with other NAIs (peramivir and zanamivir) or baloxavir in future clinical trials evaluating VIS410. Combination antiviral therapy may be the most effective treatment to combat high viral loads and shedding in hospitalized patients. High rates of virus resistance have been observed in clinical trials with baloxavir marboxil, and high frequencies of oseltamivir-resistant viruses have circulated in previous years. Given the potential for the development of resistance to small molecules, it may be most effective to interfere with virus replication by targeting virus replication cycle at multiple stages. The combination of VIS410 with baloxavir or NAIs provides a multifaceted inhibition of viral replication that has the potential to translate into true clinical benefit for patients critically ill with influenza A infection.

Example 2: VIS410 Neutralization of Baloxavir-Resistant Virus

During the Phase II trial for baloxavir, the PA I38T and I38F substitutions emerged after baloxavir treatment in four (3.6%) of 112 A(H1N1)pdm09 viruses isolated from adults aged 20-64 years. In the Phase III trials, the PA I38T and I38M substitutions emerged in 36 (9.7%) of 370 A(H3N2) viruses obtained from patients aged 12-64 years and in 18 (23.4%) of 77 A(H3N2) viruses obtained from children aged 6 months to <12 years. Recent surveillance demonstrates PA I38T viruses in children treated with baloxavir in Japan.

Figure 10:
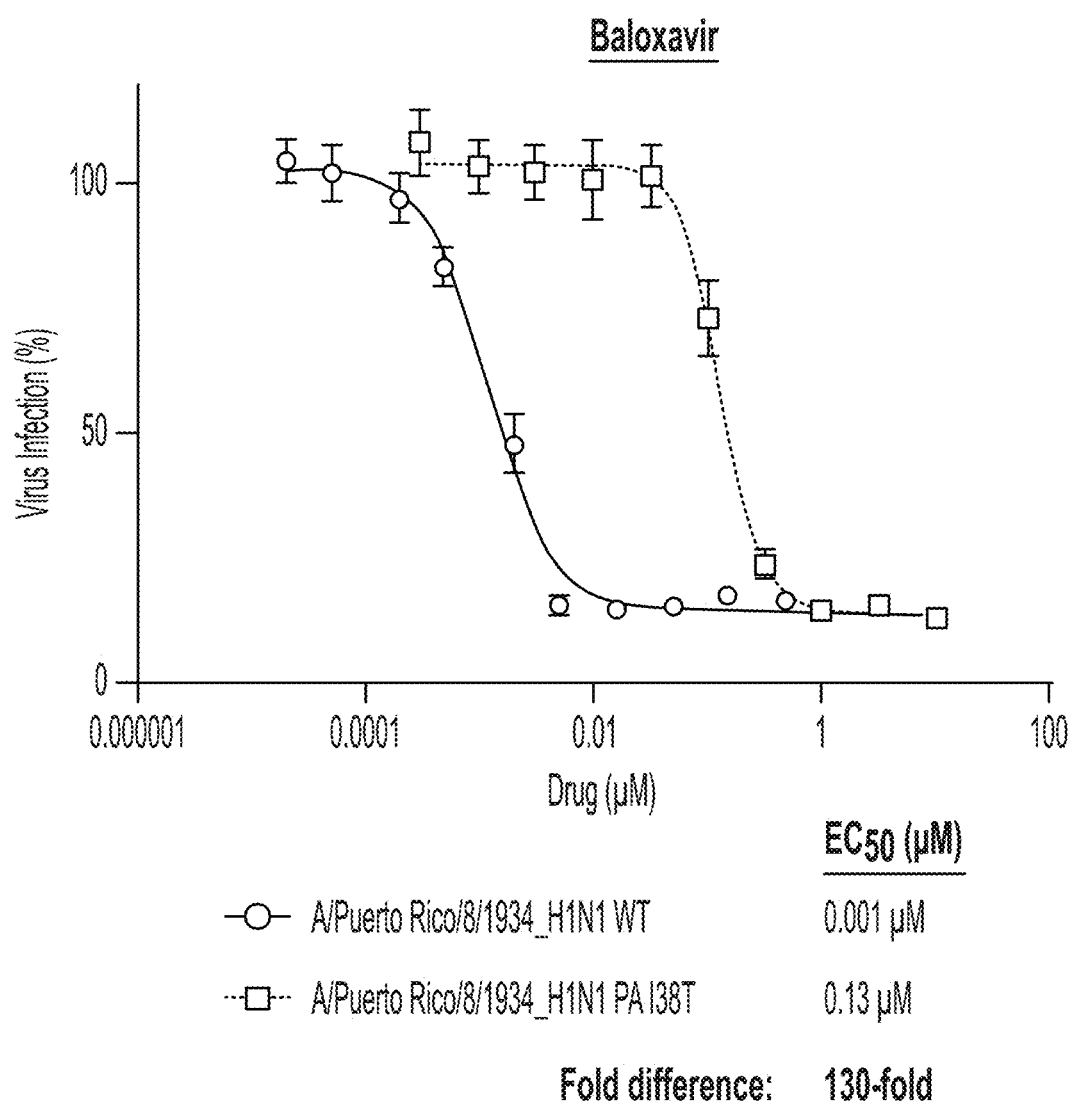
FIG. 10 is a graph showing that the PA I38T mutant for A/PR/8/1934 (H1N1) influenza virus showed approximately 100-fold lower sensitivity to baloxavir treatment compared to wild-type virus.
Figure 11:
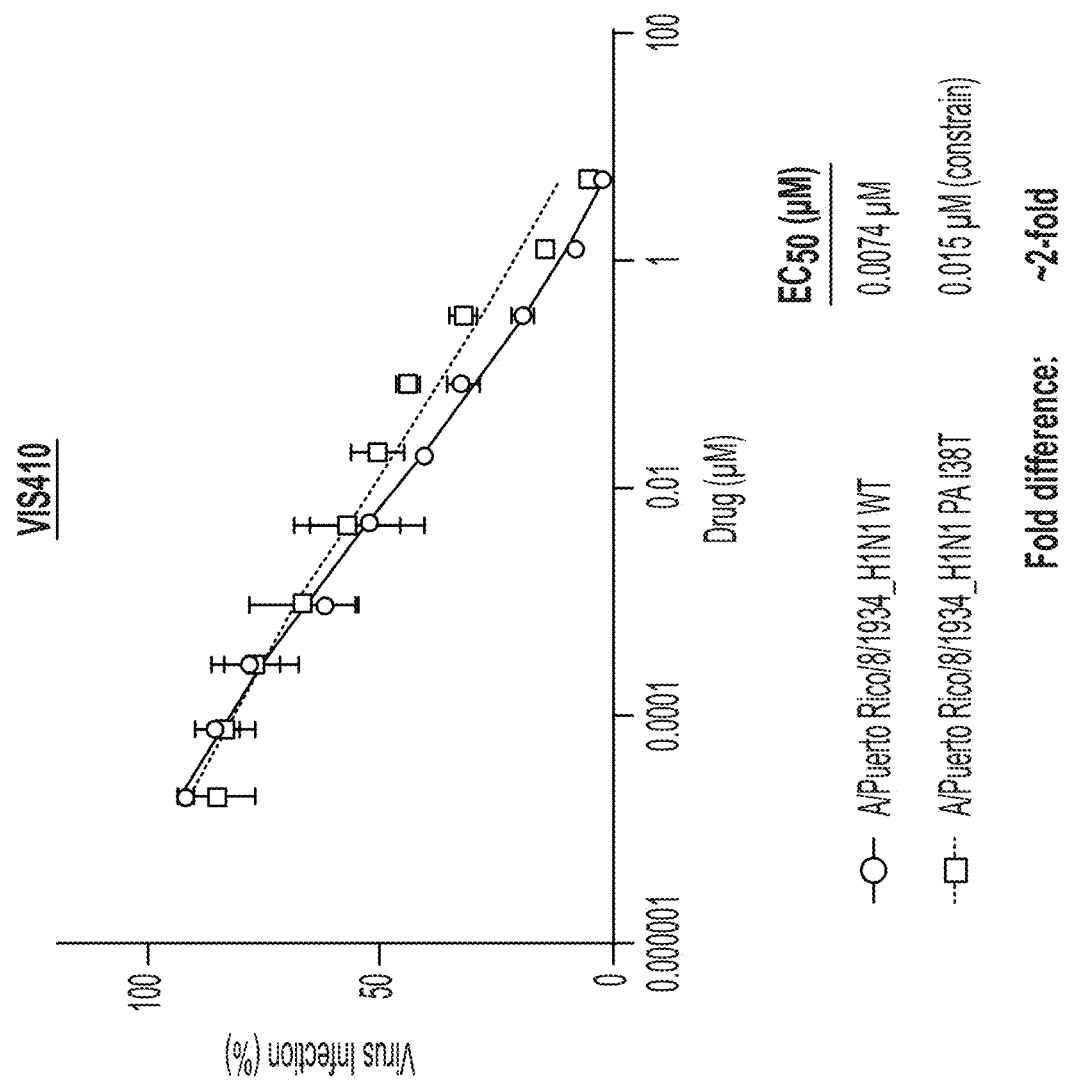
FIG. 11 is a graph showing that VIS410 exhibited similar antiviral activity against both wild-type and PA I38T mutant A/PR/8/1934 (H1N1) influenza viruses.

In this example, H1N1 viral stocks were used to test PA I38T strains for sensitivity to baloxavir and VIS410. The strains tested were A/PR/8/1934 (H1N1) (wild-type) and A/PR/8/1934 (H1N1) with PA I38T. As shown in FIG. 10, the PA I38T mutant exhibited about a 100-fold lower susceptibility to treatment with baloxavir alone compared to the wild-type virus. Specifically, the EC50 for the wild-type virus was about 1 nM, whereas the EC50 for the PA I38T mutant was about 130 nM (corresponding to 74.3 ng/ml based on a molecular weight of 571.55). The observed $IC_{50}$ for baloxavir was consistent with that observed in other studies. The observed $C_{max}$ for 40 mg was found to be 96.4 ng/ml and for 80 mg was 107 ng/ml. In contrast, as shown in FIG. 11, wild-type and PA I38T mutant viruses showed comparable sensitivity to VIS410 treatment. The observed EC50 for wild-type and PA I38T mutant viruses were 7.4 nM and 15 nM, respectively. VIS410 $EC_{50}$ against the wild-type PR/8 virus was consistent with previous data. VIS410 was found to bind to PR8 HA and protect against lethal challenge of PR8.

Example 3: VIS410 Treatment Induces Increase in Cytokine Levels

In this example, human patients were administered VIS410 or placebo and the levels of a set of cytokines was measured at various time points before and after treatment. Patients were divided into three cohorts (referred to as Parts 1, 2, and 3). Part 1 patients received either placebo or 2300 mg of VIS410. Part 2 patients received 2300 mg of VIS410 and either: (i) diphenhydramine and montelukast, or (ii) diphenhydramine and ibuprofen. Part 3 patients received 4600 mg of VIS410, in combination with diphenhydramine and ibuprofen. Part 2 and 3 patients were tested for cytokine levels starting at 1-hour after VIS410 infusion. As described in detail below, patients receiving VIS410 exhibited spikes in the level of IL-8, TNF-α, and interferon-γ after VIS410 infusion, particularly at the 1-hour post-infusion time point.
IL-8

In Part 1 patients, an increase in IL-8 levels was detected 12 hours after VIS410 administration, whereas no change in IL-8 levels was detected at the same time point in placebo-treated patients (FIG. 12).

Figure 13A:
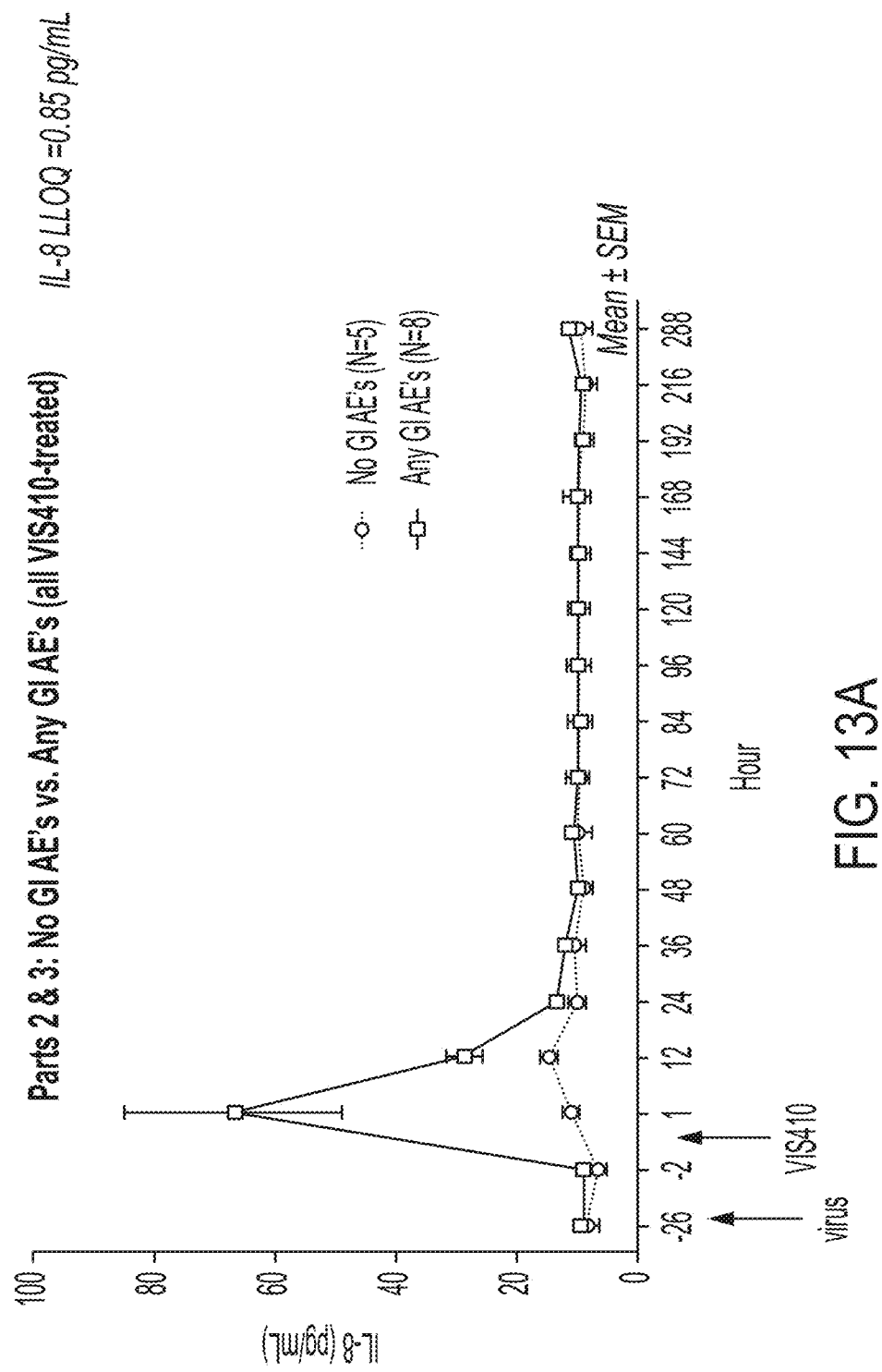
FIG. 13A is a graph showing serum IL-8 levels in VIS410-treated patients that either experienced a gastrointestinal adverse event (GI AE) or did not. The patient population shown here included all VIS410-treated patients. In this part of the study, the serum IL-8 levels were first measured post infusion at one hour, and again at 12 hours.
Figure 13B:
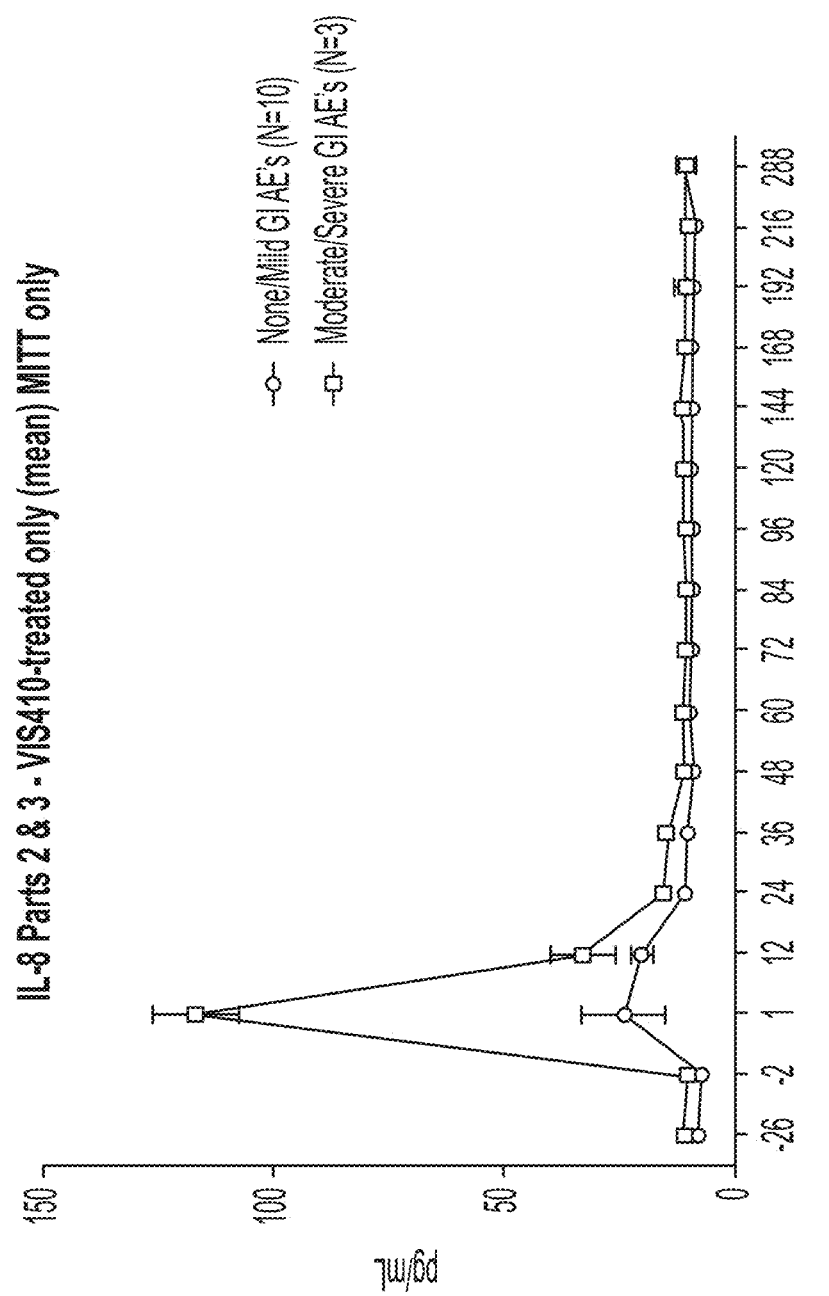
FIG. 13B is a graph showing serum IL-8 levels in VIS410-treated patients in the MITT population (those with confirmed influenza infection following virus challenge) that either experienced a moderate or severe gastrointestinal adverse event (GI AE), or experienced either a mild GI AE or no GI AE at all.

It was also observed that IL-8 spikes at an early time point (1 hour after VIS410 administration) were correlated with gastrointestinal (GI) adverse events (AEs). As shown in FIG. 13A, patients treated with VIS410 that did not experience any GI AEs showed only a small increase in IL-8 level to about 10 pg/ml at one hour after VIS410 infusion, increasing to about 15 pg/ml at 12 hours after infusion, and then decreasing thereafter. In contrast, patients treated with VIS410 that did experience GI AEs showed a large increase in IL-8 levels at the 1 hour post-VIS410 infusion time point to about 65 pg/ml. When looking at MITT patients, a similarly large IL-8 spike to about 120 pg/ml was detected at 1 hour post-VIS410 infusion in patients that experienced a moderate or severe GI AE, whereas patients that experience mild or no GI AEs only showed a small increase in IL-8 level to about 25 pg/ml at 1 hour post-infusion (FIG. 13B).

Figure 14A:
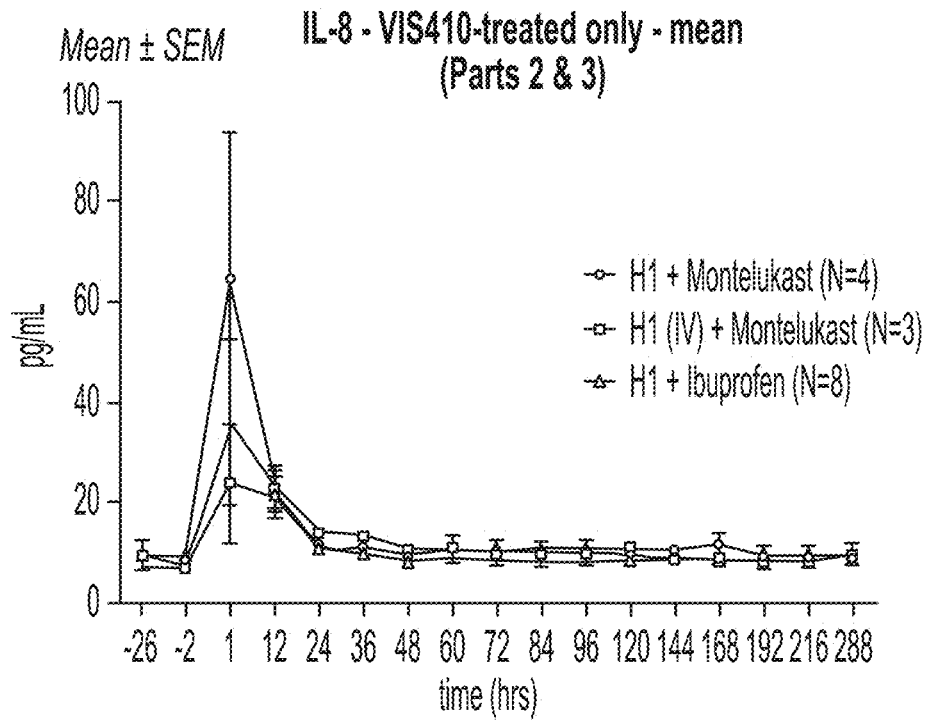
FIGS. 14A-14B are a series of graphs showing mean serum IL-8 profiles for patients receiving VIS410 and particular pre-treatment regimens (oral diphenhydramine+montelukast.
Figure 14B:
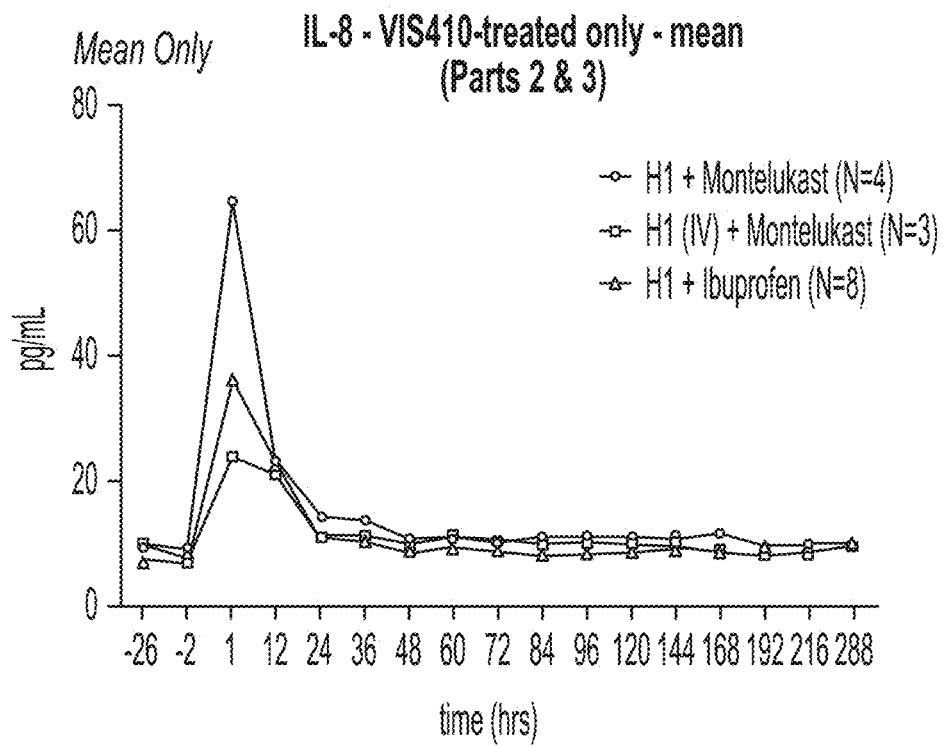

The level of IL-8 was also assessed for the various patient populations according to the additional agents administered alongside VIS410. As shown in FIGS. 14A-14B, patients also treated with montelukast showed higher levels of IL-8 at the 1-hour time point compared to patients administered ibuprofen. However, patients administered H1 (IV) and montelukast showed lower IL-8 spikes than either of the previous groups.
TNF-α

TNF-α spikes at an early time point (1 hour after VIS410 administration) were also correlated with GI AEs. In MITT patients from Parts 2 and 3, a substantial TNF-α spike to about 11 pg/ml was detected at 1 hour post-VIS410 infusion in patients that experienced a GI AE, whereas patients that did not experience a GI AE only showed a small increase in TNF-α level to about 4 pg/ml at 1 hour post-infusion (FIG. 15). Patients that exhibited either moderate or severe GI AEs showed a greater spike in TNF-α level (about 14 pg/ml) at 1 hour after infusion compared to patients that exhibited mild or no GI AEs (about 6 pg/ml) (FIG. 16).

Example 4: Phase 2b Influenza Trial for VIS410

In one example, VIS410 was evaluated in a Phase 2b influenza trial, e.g., for hospitalized patients with influenza A requiring oxygen therapy. Briefly, patients with symptom onset within 120 hours were administered one of: 2000 mg VIS410 (n=30), 4000 mg VIS410 (n=29), or placebo (n=30), each in combination with oseltamivir. Patients were assigned to each treatment group randomly. Safety was monitored through Day 56. Efficacy endpoints for the Phase 2b trial included: seven level ordinal scale (SLOS), oxygen normalization, clinical response, mortality, hospital/ICU stay, viral load, and patient reported outcomes. The endpoint analysis conducted for the trial is summarized in Table 7.

Overall, patients assigned to receive VIS410 were approximately four years older and exhibited greater average disease severity prior to treatment (e.g., greater proportion in the ICU, on mechanical ventilation, and also presenting with bacterial pneumonia), as shown using a 5-level ordinal scale. Despite this profound baseline imbalance favoring the placebo group, median time to normal oxygenation and time to complete clinical response (CCR) were not significantly different across the three treatment groups, as can be seen in Table 7. As shown in FIG. 17, patients administered VIS410 showed greater reduction in symptom severity from baseline by day 10 after treatment compared to placebo recipients. This reduction appeared to be dose-dependent, as patients receiving 4000 mg VIS410 showed more reduction in symptom severity compared to patients receiving 2000 mg VIS410. As shown in FIG. 18, the percentage of patients requiring an ICU stay decreased in VIS410 patients starting as early as day 2 after treatment and continued to decrease over the first week, whereas the percentage of patients requiring an ICU stay remained constant over the first week after treatment in patients receiving placebo. Additionally, as shown in Table 7, administration of VIS410 led to faster times to oxygenation and vital sign normalization for non-ICU-hospitalized patients. These differences were significant in the patient subgroups presenting within 72 hours of reported symptom onset or had positive baseline viral cultures. During the study, three patients receiving the placebo died, compared to only one patient receiving 4000 mg of VIS410 and two patients receiving 2000 mg of VIS410. This demonstrated a trend toward reduced mortality when patients are treated with VIS410 with oseltamivir.

Patients were also assessed for viral levels after treatment. As shown in FIGS. 19A-19B, the percentage of unresolved patients was lower for patients receiving VIS410 compared to patients receiving placebo. The percentage of patients with negative virology TCID50 was also higher for VIS410-treated patients compared to placebo-treated patients at days 3 and 5 after treatment (FIGS. 20A-20B). Additionally, as shown in Table 7, administration of VIS410 significantly improved time to clearance of infectious virus in those patients that were viral culture positive prior to treatment.

These data strongly support the paradigm of broadly neutralizing antibody therapy for influenza and can be used to inform designs for registrational studies for VIS410.

TABLE 7

Summary of VIS410 Endpoint Analysis

| Endpoint | Study Population | VIS410-Total (N)/Result | Placebo (N)/Result | P value |
|---|---|---|---|---|
| Median Time to First Room Air $O_2$ Sat > 94% (hours, h) | mITT* mITT, SLOS4** mITT, SLOS4, BL culture+† | (56)/96.9 h (35)/46.4 h (29)/45.5 h | (28)/86.3 h (24)/82.5 h (19)/88.2 h | 0.883 0.133 0.035 |
| Median Time to CCR - 5 out of 5 vital signs resolved (hours, h) | mITT mITT, SLOS4 mITT, SLOS4, BL culture+ | (57)/103.0 h (36)/61.8 h (30)/56.0 h | (28)/99.8 h (24)/82.5 h (19)/112.2 h | 0.549 0.075 0.021 |
| Percent Virus Culture Negative by Study Day 3 | mITT mITT, BL culture+ mITT, BL culture+, Onset < 72 h‡ | (57)/82.5% (45)/77.8% (21)/81.0% | (28)/67.9% (19)/52.6% (14)/42.9% | 0.127 0.047 0.023 |
| Median Time to Viral Load Clearance by $TCID_{50}$ (days, d) | mITT mITT, BL culture+ mITT, BL culture+, Onset < 72 h | (57)/1.7 d (45)/1.7 d (21)/1.7 d | (28)/1.8 d (19)/2.5 d (14)/3.1 d | 0.177 0.028 0.012 |

*mITT = modified intent-to-treat population (subjects with confirmed influenza A infection)
**SLOS4 = Subjects with baseline seven level ordinal scale score of 4 (non-ICU-hospitalized subjects)
†BL culture+ = Subjects with baseline positive viral culture
‡Onset < 72 h = Subjects with influenza onset < 72 h prior to study baseline

Example 5: VIS410 Neutralizes Oseltamivir-Resistant Virus In Vitro

In this example, in vitro assays were performed to determine the anti-viral activity of VIS410 against six oseltamivir-resistant influenza A virus strains. A panel of neuraminidase-inhibitor resistant strains were chosen based on availability and included representatives from the two main influenza A groups (1 and 2). A description of each strain is shown in Table 8.

TABLE 8

Description of Oseltamivir-resistant Strains

| Oseltamivir-resistant Influenza Virus Strain | Type | Year | Geography | Clinical Relevance |
|---|---|---|---|---|
| WSN/33 H274Y | H1N1 | 1933 | England | Mouse neurotropic-adapted historic laboratory strain, made resistant in the laboratory |
| Victoria/3/75-Os-R | H3N2 | 1975 | Australia | Human seasonal, made resistant in the laboratory; HA mutation confirmed |
| Mississippi/3/2001 H275Y | H1N1 | 2001 | North America | Oseltamivir-resistant clinical isolate |
| Hawaii/31/2007 H275Y | H1N1 | 2007 | North America | Oseltamivir-resistant clinical isolate, mouse-adapted |
| Pennsylvania/30/2009 H275Y, I223R | H1N1 | 2009 | North America | Resistant to oseltamivir and partially resistant to zanamivir |
| Hong Kong/2369/2009 H275Y | H1N1 | 2009 | Asia | Oseltamivir-resistant (see, e.g., Smee et al. Antiviral Res. 2012; 96: 13-20 |

An irrelevant human $IgG_1$, ribavirin, and oseltamivir-carboxylate were tested in parallel as controls. VIS410 was prepared in half-log dilutions in the test medium. Each dilution was added to 5 wells of a 96-well plate containing no cells. Three wells of each dilution were incubated with 10-124 $CCID_{50}$ of virus (see Table 9), and two wells remained uninfected as toxicity controls. The plates were incubated for an hour and then the contents of the wells were transferred to 96 well plates containing MDCK cells. The plates were incubated for 3-4 days or until >80% cytopathic effect (CPE) was observed in the untreated virus control wells. The plates were then stained with neutral red dye for approximately 2 hours, supernatant dye was removed from the wells, the incorporated dye was extracted in 50:50 Sorensen citrate buffer/ethanol, and the optical density was read on a spectrophotometer. Optical densities were converted to percent of cell controls and normalized to the virus control, and the concentration of test compound required to inhibit CPE by 50% ($EC_{50}$) was calculated. The concentration of VIS410 that would cause 50% CPE in the absence of virus was similarly calculated ($CC_{50}$). The selective index (SI) was the $CC_{50}$ divided by $EC_{50}$.

Table 8 describes the oseltamivir-resistant influenza A strains used in the study. The $EC_{50}$ results are presented in Table 9. As shown in Table 9, VIS410 inhibited viral replication in vitro with $EC_{50}$s of 0.071 to 22 µg/mL.

TABLE 9

Anti-viral Activity of VIS410 Against Oseltamivir-resistant Influenza A Strains

| Influenza Virus Strain | Inoc[a] | VIS410 | | | Human IgG-1 | | | Ribavirin | | | Oseltamivir-carboxylate | | |
|---|---|---|---|---|---|---|---|---|---|---|---|---|---|
| | | $EC_{50}$[b] | $CC_{50}$[c] | SI[d] | $EC_{50}$ | $CC_{50}$ | SI | $EC_{50}$ | $CC_{50}$ | SI | $EC_{50}$ | $CC_{50}$ | SI |
| WSN/33 H274Y | 124 | 0.071 | >100 | >1400 | >100 | >100 | 0 | 3.7 | >100 | >27 | 28 | >50 | >1.8 |
| Victoria/3/75-Os-R | 12 | 22 | >100 | >4.6 | >100 | >100 | 0 | 5.4 | >100 | >19 | >50 | >50 | 0 |
| Mississippi/3/2001 H275Y | 50 | 0.69 | >100 | >145 | >100 | >100 | 0 | 18 | >100 | >5.6 | >50 | >50 | 0 |
| Hawaii/31/2007 H275Y | 10 | 0.75 | >100 | >130 | >100 | >100 | 0 | 7.2 | >100 | >14 | >21 | >50 | <2.4 |
| Pennsylvania/30/2009 H275Y, I223R | 32 | 1.6 | >100 | >61 | >100 | >100 | 0 | 5.2 | >100 | >19 | >50 | >50 | 0 |
| Hong Kong/2369/2009 H275Y | 32 | 1.2 | >100 | >83 | >100 | >100 | 0 | 28 | >100 | >3.6 | >7.8 | >50 | <6.4 |

[a]$CCID_{50}$ per well
[b]$EC_{50}$ = 50% effective anti-viral concentration (μg/mL)
[c]$CC_{50}$ = 50% toxic concentration of compound without virus added (μg/mL)
[d]SI – $CC_{50}/EC50$
For VIS410 the reported value is the average of two assays performed in parallel
Viruses used:
A/Hawaii/31/2007 (H1N1): H1N1 virus with H275Y mutation in NA gene. Stock was passaged three times in MDCK cells, 12 times in BALB/c mice, then amplified once in MDCK cells. This virus strain was not fully oseltamivir-resistant. It yielded sporadic results with oseltamivir, with some activity observed above concentrations of 3.2 μg/mL, and an average $EC_{50}$ of ≥21 μg/mL over 3 independent replicate assays.
Mississippi/3/2001 H275Y (H1N1): Passaged twice in MDCK, 7 passages in mice, then amplified in MDCK cells. Oseltamivir-resistant.
Pennsylvania/30/2009 H275Y, I223R (H1N1): Resistant to oseltamivir and partially resistant to zanamivir. Amplified one time in MDCK cells.
WSN/33 H274Y (H1N1): Oseltamivir resistant virions isolated by plaque purification in the presence of oseltamivir and amplified in MDCK cells to produce stock
Hong Kong/2369/2009 H275Y (H1N1): Amplified one time in MDCK cells. This is an oseltamivir-resistant virus. Sporadic activity of oseltamivir was observed, with $EC_{50}$ ≥7.8, which agreed with the historical record for this strain.
Victoria/3/75-Os-R (H3N2): This is influenza A grown 2 passages in eggs, 2 passages in MDCK cells, then passaged 7 times in mice to adapt to mice. It was then passaged 10 times in MDCK in the presence of peramivir and clones were prepared by extinction dilution and tested. The sequencing revealed that this was VIC/3/75 with no differences found between the resistant and wild-type viruses in the NA gene but a point mutation resulting in a single amino acid change (Lys189Glu) was found in the resistant viral HA.

These data demonstrate that VIS410 exhibited anti-viral activity against oseltamivir-resistant influenza A strains.

Example 6: VIS410 Broadly Neutralizes Influenza A Viruses

In this example, VIS410 was tested for its capacity to neutralization of various influenza A strains from clinical samples. Briefly, the virus from each clinical sample was amplified by passaging once in culture on MDCK cells, virus titer was measured, and $IC_{50}$ was determined using a fixed amount of virus (aimed at 100 $TCID_{50}$/well in the final culturing step) mixed with increasing concentrations of VIS410 (10 concentrations, 0.5 Log steps, range 0.63-20,000 nM or 0.094-2980 μg/mL). After a one-day infection period, cells were immunostained for virus, and $IC_{50}$ concentrations determined based on percent of infection. The A/California/7/2009 strain was used as the reference for H1_2009 viruses and the A/Hongkong/4801/2014 strain for the influenza A H3N2 viruses.

Generally, samples with a positive $TCID_{50}$ titer (preferably ≥1 Log 10 TCID50/mL) were selected for phenotypic $IC_{50}$. Twenty-five samples (mostly baseline samples) from 25 VIS410-202 subjects were selected for determining $IC_{50}$.

$IC_{50}$ Data

The phenotypic $IC_{50}$ assay was used to determine VIS410 activity against strains that circulated during the VIS410-202 and VIS410-203 studies. Clinical samples were selected prior to VIS410 treatment or from placebo subjects such that treatment did not influence the virus sample being tested. For the $IC_{50}$ methods, the primary clinical isolate was passaged once in MDCK cells to obtain sufficient viral input for the assay, then the P1 virus was titered and used in the $IC_{50}$ assay. There were 25 VIS410-202 virus isolates and 25 VIS410-203 virus isolates selected for $IC_{50}$ determination. One H3N2 isolate (the baseline sample from subject 70301) did not yield sufficient virus in the P1 culture for $IC_{50}$ analysis. Coincidentally, the HA genotype of subject 70301 was identical to subject 70303 baseline HA sequence (which did yield sufficient virus titer for $IC_{50}$ assay). VIS410 $IC_{50}$ was determined for 24 viruses with unique HA sequences.

The viruses tested represented diverse HA sequences from different geographic regions and influenza seasons (Table 10). Nineteen isolates were influenza A H3N2 subtype and five were H1N1. Fifty percent were from the northern hemisphere 2016-2017 influenza season, and 50% were from South Africa, isolated during the 2017 southern hemisphere season. Vaccine strains from the same influenza seasons were also tested for comparison. All isolates tested were Baseline samples, prior to drug treatment, except for one virus (from subject 80839, who received placebo). The treatment for each subject is indicated in Table 10; however, treatment is irrelevant to the reported $IC_{50}$ as samples tested were baseline prior to treatment or post-baseline from placebo-treated subjects. Two viruses tested, from subjects 71307 and 70609, had untested polymorphisms at VIS410 epitope residues, HA2 D53 and HA2 R57, respectively. The other 22 viruses had VIS410 epitope residues identical to vaccine strains. Four H3N2 viruses had baseline polymorphisms at HA residues adjacent to epitope positions as shown in Table 10.

TABLE 10

Phenotypic $IC_{50}$ Testing of Recent Vaccine Strains and Clinical Study Isolates

| Clinical Study of Virus or Vaccine strain | Virus* | Subtype | $IC_{50}$ (μg/mL) | Subject Treatment | Polymorphisms at VIS410 epitope or adjacent residues** |
|---|---|---|---|---|---|
| Vaccine strain | A/Hong Kong/4801/2014 | H3N2 | 1.65 | N/A | None |
| Vaccine strain | A/Singapore/INFIMH-16 0019/2016 | H3N2 | 1.35 | N/A | None |
| Vaccine strain | A/Switzerland/8060/2017 | H3N2 | 1.07 | N/A | None |
| Vaccine strain | A/Kansas/14/2017 | H3N2 | 2.65 | N/A | None |
| VIS410-202 | A/Bulgaria/10101/2017 | H3N2 | 0.22 | Placebo | HA2__R58 adjacent |
| VIS410-202 | A/Latvia/30101/2017 | H3N2 | 0.28 | VIS410-4000 mg | None |
| VIS410-202 | A/Latvia/30314/2017 | H3N2 | 1.00 | VIS410-4000 mg | None |
| VIS410-202 | A/Florida/70303/2017 | H3N2 | 0.34 | VIS410-2000 mg | None |
| VIS410-202 | A/Florida/70327/2017 | H3N2 | 0.67 | VIS410-2000 mg | None |
| VIS410-202 | A/Florida/70604/2017 | H3N2 | 1.23 | Placebo | None |
| VIS410-202 | A/Florida/70609/2017 | H3N2 | 2.41 | VIS410-4000 mg | HA2__R57 epitope |
| VIS410-202 | A/Florida/71210/2017 | H3N2 | 0.97 | VIS410-4000 mg | None |
| VIS410-202 | A/Florida/71268/2017 | H3N2 | 3.14 | Placebo | None |
| VIS410-202 | A/North Carolina/71307/2017 | H3N2 | 39.4 | VIS410-2000 mg | HA2__D53 epitope |
| VIS410-202 | A/North Carolina/71330/2017 | H3N2 | 0.92 | VIS410-2000 mg | None |
| VIS410-202 | A/South Africa/80308/2017 | H3N2 | 0.91 | Placebo | HA1__Y279 adjacent |
| VIS410-202 | A/South Africa/80316/2017 | H3N2 | 0.57 | Placebo | None |
| VIS410-202 | A/South Africa/80521/2017 | H3N2 | 1.09 | VIS410-4000 mg | HA1__Y279 adjacent |
| VIS410-202 | A/South Africa/80714/2017 | H3N2 | 0.13 | VIS410-4000 mg | HA1__Y279 adjacent |
| VIS410-202 | A/South Africa/80839/2017 | H3N2 | 0.41 | Placebo | None |
| VIS410-202 | A/South Africa/80919/2017 | H3N2 | 2.55 | VIS410-2000 mg | None |
| VIS410-202 | A/South Africa/81130/2017 | H3N2 | 1.00 | Placebo | HA1__Y279 adjacent |
| VIS410-202 | A/South Africa/81313/2017 | H3N2 | 1.38 | VIS410-4000 mg | None |
| VIS410-203 | A/Bulgaria/0106011/2018 | H3N2 | 1.67 | VIS410-4000 mg | None |
| VIS410-203 | A/Latvia/0303004/2018 | H3N2 | 4.47 | Placebo | HA2__N46 epitope |
| VIS410-203 | A/Ohio/0717002/2018 | H3N2 | 0.81 | VIS410-4000 mg | None |
| VIS410-203 | A/Georgia/0720003/2018 | H3N2 | 0.49 | VIS410-4000 mg | None |
| VIS410-203 | A/Georgia/0720004/2018 | H3N2 | 0.97 | VIS410-2000 mg | None |
| VIS410-203 | A/Pennsylvania/0725005/2018 | H3N2 | 2.20 | Placebo | None |
| VIS410-203 | A/Pennsylvania/0725006/2018 | H3N2 | 1.50 | VIS410-2000 mg | None |
| VIS410-203 | A/Sydney/0903001/2018 | H3N2 | 1.49 | VIS410-2000 mg | None |
| VIS410-203 | A/Belarus/1003001/2018 | H3N2 | 1.26 | VIS410-4000 mg | None |
| VIS410-203 | A/Singapore/2401001/2018 | H3N2 | 1.17 | Placebo | None |
| VIS410-203 | A/Spain/2604004/2018 | H3N2 | 0.92 | VIS410-2000 mg | None |
| VIS410-203 | A/Thailand/2702006/2018 | H3N2 | 1.13 | VIS410-2000 mg | None |
| Vaccine strain | A/California/7/2009 | H1N1 | 0.52 | N/A | None |

TABLE 10-continued

Phenotypic IC$_{50}$ Testing of Recent Vaccine Strains and Clinical Study Isolates

| Clinical Study of Virus or Vaccine strain | Virus* | Subtype | IC$_{50}$ (μg/mL) | Subject Treatment | Polymorphisms at VIS410 epitope or adjacent residues** |
|---|---|---|---|---|---|
| Vaccine strain | A/Michigan/45/2015 | H1N1 | 0.89 | N/A | None |
| Vaccine strain | A/Brisbane/02/2018 | H1N1 | 0.55 | N/A | None |
| VIS410-202 | A/Florida/70702/2017 | H1N1 | 0.41 | VIS410-4000 mg | None |
| VIS410-202 | A/South Africa/80811/2017 | H1N1 | 0.38 | Placebo | None |
| VIS410-202 | A/South Africa/80836/2017 | H1N1 | 0.73 | VIS410-4000 mg | None |
| VIS410-202 | A/South Africa/80837/2017 | H1N1 | 0.25 | VIS410-2000 mg | None |
| VIS410-202 | A/South Africa/80860/2017 | H1N1 | 0.26 | Placebo | None |
| VIS410-203 | A/Latvia/0303005/2018 | H1N1 | 0.87 | VIS410-4000 mg | None |
| VIS410-203 | A/Latvia/0304001/2018 | H1N1 | 0.57 | Placebo | None |
| VIS410-203 | A/Serbia/0502013/2018 | H1N1 | 0.67 | VIS410-4000 mg | None |
| VIS410-203 | A/Serbia/0502016/2018 | H1N1 | 0.37 | VIS410-2000 mg | None |
| VIS410-203 | A/Georgia/0720001/2018 | H1N1 | 0.71 | VIS410-2000 mg | None |
| VIS410-203 | A/South Africa/0808006/2018 | H1N1 | 0.42 | VIS410-4000 mg | None |
| VIS410-203 | A/France/1302001/2018 | H1N1 | 0.86 | Placebo | None |
| VIS410-203 | A/France/1306001/2018 | H1N1 | 0.91 | VIS410-2000 mg | None |
| VIS410-203 | A/France/1307001/2018 | H1N1 | 0.86 | VIS410-4000 mg | None |
| VIS410-203 | A/Malay sia/1701001/2018 | H1N1 | 0.40 | VIS410-4000 mg | None |
| VIS410-203 | A/Spain/2602001/2018 | H1N1 | 0.42 | VIS410-2000 mg | None |
| VIS410-203 | A/Spain/2609001/2018 | H1N1 | 0.43 | Placebo | None |
| VIS410-203 | A/Thailand/2702008/2018 | H1N1 | 0.55 | VIS410-4000 mg | None |
| Oseltamivir Resistant | A/WSN/1933 | H1N1 | 0.07 | N/A | NA H275Y‡ |
| Oseltamivir Resistant | A/Mississippi/3/2001 | H1N1 | 0.69 | N/A | NA H275Y‡ |
| Oseltamivir Resistant | A/Hawaii/31/2007 | H1N1 | 0.75 | N/A | NA H275Y‡ |
| Oseltamivir Resistant | A/Pennsylvania/30/2009 | H1N1 | 1.6 | N/A | NA H275Y‡ |
| Oseltamivir Resistant | A/Hong Kong/2369/2009 | H1N1 | 1.2 | N/A | NA H275Y‡ |
| Baloxavir Sensitive | A/Puerto Rico/8/1934_H1N1 WT | H1N1 | 0.3 | N/A | WT |
| Baloxavir Resistant | A/Puerto Rico/8/1934_H1N1 PA I38T | H1N1 | 0.7 | N/A | PA I38T |

IC$_{50}$ = 50% Inhibitory Concentration
*All clinical isolates were from baseline nasopharyngeal samples prior to drug treatment except A/Singapore/2401001/2018 (Post-dose Day 1) and A/South Africa/80839/2017 (Day 3) from placebo subjects.
**Polymorphisms were at a VIS410 epitope residue or at a residue adjacent to an epitope position.
‡N1 NA numbering Mean IC$_{50}$ of H3N2 circulating viruses (n=30) and vaccines strains (n=4)=1.3 ug/ml—this excludes 71307 with HA2 D53
Mean IC$_{50}$ of H1N1 circulating viruses (n=18) and vaccines strains (n=3)=0.6 ug/ml
Median IC$_{50}$ of all H3N2 and H1N1 circulating strains and vaccines strains (n=55 viruses)=0.9 ug/ml VIS410 demonstrated a potent IC$_{50}$, similar to season-matched H1N1 and H3N2 vaccines strains (IC$_{50}$ range=0.13-3.1 μg/ml (Table 10), for nearly all viruses (23 out of 24, excluding A/North Carolina/71307/2017). This group included the four viruses with polymorphisms at residues adjacent to epitope positions (including polymorphisms HA2_R58 and HA1_Y279), suggesting these polymorphisms do not alter VIS410 activity. Of the 2 viruses containing untested HA polymorphisms at VIS410 epitope residues, the HA2 R57 virus (subject 70609) was fully VIS410-sensitive [IC$_{50}$ 2.4 μg/mL], but the HA2 D53 virus [subject 71307, IC$_{50}$ 39.4 μg/mL] demonstrated reduced VIS410 susceptibility compared to other viruses tested in parallel, considering variations in $IC_{50}$ values based on differences in methodology. The genotype of passage 1 virus stocks from subjects 70609 and 71307 was unchanged from the clinical isolates.

The phenotypic $IC_{50}$ data indicate that reduced influenza A susceptibility to VIS410 was rarely observed in VIS410-202. All viruses except one were neutralized by VIS410 with similar $IC_{50}$s as the matched vaccines strains. The HA2 D53 variant was present in subject 71307 at baseline prior to treatment with VIS410, and this H3N2 variant demonstrated lower sensitivity to VIS410 consistent with previous epitope definition and preclinical resistance studies.

In another example, VIS410 was tested against recent vaccine strains and a panel of 51 influenza A clinical isolates (n=31 H3N2 and n=18 H1N1) from various geographical regions and seven vaccine strains (n=56 total influenza A viruses). VIS410 demonstrated broad activity, with $IC_{50}$ values ranging from 0.1 to 4.5 μg/mL against sensitive strains, and with one subject containing a virus with reduced susceptibility excluded. The median $IC_{50}$ of the sensitive strains was 0.9 μg/mL.

In a further example, HA sequences from clinical isolates were used to make phylogenetic trees for each of H3N2 and H1N1, which were constructed in Geneious Prime software using the Neighbor-Joining Method with Jukes-Cantor protein distance measurement (FIGS. 21A-21B).

H3N2 viruses with diverse HA genotypes (n=35 total; 4 vaccine strains (red) and 31 clinical circulating strains) were tested for VIS410 $IC_{50}$ by NP-ELISA. An $IC_{50}$ range of 0.1-4.5 μg/ml was observed across 34 viruses with a mean $IC_{50}$=1.3 μg/ml. This range excluded A/North Carolina/71307/2017* ($IC_{50}$=39.4 μg/ml), which possessed a rare polymorphism at VIS410 epitope residue HA2 D53.

H1N1 viruses with diverse HA genotypes (n=21 total; 3 vaccine strains (red) and 18 clinical circulating strains) were tested for VIS410 $IC_{50}$ by NP-ELISA. An $IC_{50}$ range of 0.3-0.9 μg/ml was observed across 21 viruses, with a mean $IC_{50}$=0.6 μg/ml.

Example 7: Clinical and Virological Responses to a Broad-Spectrum Human Monoclonal Antibody in an Influenza Virus Challenge Study Summary Influenza A infections cause significant seasonal morbidity and mortality as well as periodic pandemic infections. Currently, no approved therapies exist for patients hospitalized with influenza. In this example, the efficacy of VIS410, a broadly neutralizing human immunoglobulin IgG1 monoclonal antibody engineered to bind to the stem region of group 1 and 2 influenza A hemagglutinins, was explored in experimental human influenza infection. Healthy volunteers were inoculated with influenza A/California/07/2009 (H1N1) and received a single dose of VIS410 or placebo 24 hours later. Subjects were monitored for symptoms, viral shedding, and safety, including cytokine measurements. The primary efficacy endpoint was the area under the curve (AUC) of viral load (VL) in the VIS410 group versus placebo. VIS410 treatment was associated with a 76% reduction in median VL AUC as measured by qRT-PCR (p=0.024) Similar VIS410 antiviral activity was observed by virus culture, with a 91% reduction in median VL AUC by $TCID_{50}$ (p=0.019) compared to placebo-treated volunteers. Influenza symptoms were generally mild or moderate, with a trend toward faster resolution in VIS410-treated subjects. Treatment with VIS410 was generally safe, with an increase in gastrointestinal events that were largely mitigated by pre-treatment with oral diphenhydramine (50 mg) in combination with 600 mg of ibuprofen. Transient elevation of specific cytokines (IL-8 and TNFα) were associated with gastrointestinal adverse events. Treatment with VIS410 did not interfere with the endogenous immune response to influenza A. These data show that VIS410 provides therapeutic benefit in influenza A infection.

Materials and Methods

Randomization and Masking

In this study, a randomized, placebo-controlled, blinded Phase 2a single-center human challenge study was conducted. In the placebo-controlled arm of the trial (Part 1), a total of 31 subjects were randomized in a ratio of 7:5 to receive either a single dose of VIS410 2300 mg or placebo. Fifteen subjects were enrolled in the VIS410 open-label portion of the study; 11 received 2300 mg VIS410 (Part 2) and four received 4600 mg VIS410 (Part 3).

Healthy subjects between 18 and 45 years of age, who had low serum titers (hemagglutination inhibition (HA1) titer ≤10) of neutralizing antibodies against the challenge virus, were eligible for participation in this study. Eligible subjects were admitted to the clinical unit and inoculated intranasally with $10^{-6}$ $TCID_{50}$ of A/California/7/2009 H1N1 on Day −1. Twenty-four hours following inoculation on Day 0, subjects received either an IV infusion of VIS410 or placebo (0.9% sodium chloride). Subjects were confined to the clinical center for 10 days and three outpatient visits were conducted between Days 10-Day 84.

Endpoint Assessments

Safety of VIS410 administration was determined through assessment of adverse events, vital signs, electrocardiographs, physical examinations, clinical laboratory values, and use of concomitant medications through the last follow-up visit. A symptom score card was completed by study personnel by interview. Virus levels were measured in nasopharyngeal secretions (NP) by qRT-PCR and $TCID_{50}$. Virologic endpoints for both assays included virus AUC, percentage change in peak viral load, and reduction of viral shedding in subjects treated with VIS410. For biological secondary endpoints, serum levels of cytokines and chemokines (TNFα, IFNγ, IL-6, IL-8, and IL-10) were measured by ELISA and serum HA1 titers were determined. VIS410 concentrations in serum and NP were measured by ELISA.

Statistical Analysis

The primary efficacy endpoint was virological, measured as the difference in viral AUC by qRT-PCR from nasopharyngeal swabs between VIS410 (2300 mg) and placebo in Part 1 of the study. A pre-specified interim analysis of the primary endpoint after randomization of 31 subjects led to termination of enrollment in Part 1 of the study because the primary endpoint had been met.

Virology and clinical efficacy endpoint assessments were limited to subjects within the mITT population, defined as subjects who were seronegative (strain specific HA1 titer of ≤1:10) at baseline and had confirmed infection following viral challenge, demonstrated either by repeated positive viral qRT-PCR or by HA1 seroconversion (4-fold increase in HA1 titer from Baseline to Day 14 or 28). PK analysis was performed on all subjects who received VIS410. All additional test and P-values presented in the results were performed with Prism software (Graphpad, version 7). Safety analyses were performed for all subjects who were inoculated with challenge virus (N=46).

Antibody Dependent Cellular Cytotoxicity (ADCC) Assay

Pre-dose and $C_{max}$ serum samples from VIS410- and placebo-treated individuals were assessed using the ADCC Reporter Bioassay (Promega), as described by the manufacturer. Briefly, HEK293T-17 cells (ATCC) were transiently transfected to express the H7 hemagglutinin (HA) from A/Anhui/01/2013 or A/Hong Kong/125/2016. H7 HA-expressing target cells were incubated with dilutions of sera. Jurkat T cells engineered to stably express the high-affinity human FcγRIIIa (V/V 158) were used as effector cells and were added to wells, and following incubation, luciferase induction as a measure of ADCC was assessed using Bio-Glo Luciferase Assay reagent (Promega). Data were expressed as fold induction relative to no sera control and fitted to a four-parameter curve using Prism software (GraphPad, version 5.03).

Results

Study Overview

This virus challenge study enrolled 46 subjects total. In randomized and placebo-controlled Part 1 of the study, 31 subjects were enrolled: 18 received VIS410 (2300 mg) and 13 received placebo. Two additional open-label, cohorts without placebo control were evaluated to assess the safety and tolerability of different pre-treatment regimens as well as a higher VIS410 dose (Part 2, VIS410-2300 mg; and Part 3, VIS410-4600 mg). One subject in Part 3 discontinued study involvement during follow up but had completed treatment and is included in safety and efficacy analyses. All other subjects completed scheduled follow-up in the study. The study design is diagrammed in FIG. 22.

Most subjects were Caucasian, and about half were male, with an age range of 20-45 years (Table 11). Among the 46 study subjects inoculated with challenge virus, 72% (33/46) had confirmation of infection, in addition to low baseline HA1 titers (Table 11), constituting the mITT population. Eight study subjects had HA1 titers >1:10 at baseline (8/46); among this group, detection of influenza RNA by qRT-PCR was confirmed for only 25% (2/8). The remaining five non-mITT population study subjects did not have confirmed establishment of infection by viral RNA detection or seroconversion, despite low baseline HA1 titers.

TABLE 11

Subject demographics and results of virus challenge

| Parameter | Part-1 (RCT) ITT Population | | Part-1 (RCT) mITT Population | | Part-2 Open-Label ITT population | Part-3 Open-Label ITT population |
|---|---|---|---|---|---|---|
| | Placebo N = 13 | VIS410 2300 mg N = 18 | Placebo N = 7 | VIS410 2300 mg N = 13 | VIS410 2300 mg N = 11 | VIS410 4600 mg N = 4 |
| Age, years Median (range) | 37.0 (23; 45) | 36.0 (20; 45) | 34 (23; 45) | 36 (20; 45) | 32.0 (22; 44) | 32.5 (20; 40) |
| Weight, kg Median (range) | 82.50 (51.4; 115.6) | 77.85 (53.4; 116.0) | 70.6 (55.5; 111.6) | 73.6 (53.4; 116.0) | 87.00 (65.4; 112.0) | 73.70 (55.6; 86.7) |
| BMI (kg/m$^2$) Median (range) | 25.00 (18.7; 32.0) | 24.90 (20.3; 39.1) | 25.00 (20.3; 30.0) | 24.6 (20.3; 39.1) | 30.00 (23.1; 34.9) | 26.10 (16.3; 27.7) |
| Sex, n (%) | | | | | | |
| Male | 7 (53.8) | 10 (55.6) | 4 (57.1) | 6 (46.2) | 7 (63.6) | 2 (50.0) |
| Female | 6 (46.2) | 8 (44.4) | 3 (42.9) | 7 (53.8) | 4 (36.4) | 2 (50.0) |
| Race, n (%) | | | | | | |
| White | 12 (92.3) | 14 (82.4) | 7 (100) | 12 (92.3) | 11 (100) | 4 (100) |
| Black or African American | 1 (7.7) | 2 (11.8) | 0 | 1 (7.7) | 0 | 0 |
| Asian | 0 | 1 (5.9) | 0 | 0 | 0 | 0 |
| Unknown | 0 | 1$^a$ | 0 | 0 | 0 | 0 |
| Proportion with HAI titer >1:10 at Baseline: n (%)[1] | 4 (30.7) | 3 (16.7) | 0 | 0 | 1 (9.0) | 0 |
| Subset: All confirmed infections with repeated detection of viral RNA by qRT-PCR[2]: n (%) | 8 (61.5) | 9 (50.0) | 7 (100) | 9 (69.2) | 7 (63.6) | 3 (75.0) |

N = Number of subjects; n = number of subjects with that observation.
$^a$Excluded from the denominator for the percentage calculation.
[1] If subject has multiple Day 1 HAI measurements, subject is considered HAI > 10 only if all Day HAI titers are >10.
[2] Positive viral load by qRT-PCR is defined as having 2 consecutive qRT-PCR time points above the level of quantification.

Virological Data

Viral load (VL) profiles by qRT-PCR and virus culture ($TCID_{50}$) were compared across treatment arms for Part 1 of the study. For subjects in the mITT population with confirmed infection, the VIS410-treatment group (2300 mg) demonstrated reduced mean and median viral shedding by qRT-PCR (FIGS. 23A and 23C) and $TCID_{50}$ (FIGS. 23B and 23D) compared to placebo.

VIS410 treatment was associated with a 76% reduction in median VL AUC by qRT-PCR (p=0.024, Table 12) and significantly lower peak viral load (PVL) by qRT-PCR (p=0.043, Table 12) compared to the placebo group. Similar VIS410 antiviral activity was observed by $TCID_{50}$, with a 91% reduction in median VL AUC by $TCID_{50}$ (p=0.019, Table 12) and significantly lower PVL by $TCID_{50}$ (p=0.009, Table 12) for the VIS410 vs. placebo group.

TABLE 12

Part 1 (mITT population): Influenza RNA qRT-PCR and virus culture outcomes

| Part I (mITT) | VL-Area Under the Curve (VL AUC**) (h × $\log_{10}$ vp/mL) | | Peak Viral Load (PVL***) ($\log_{10}$ vp/mL) | |
|---|---|---|---|---|
| | VIS410 2300 mg (N=13) | Placebo (N=7) | VIS410 2300 mg (N=13) | Placebo (N=7) |
| VL* by qRT-PCR | | | | |
| Minimum | 0.00 | 157 | 0.00 | 5.36 |
| Maximum | 953 | 1,201 | 7.50 | 7.86 |
| Median | 232 | 1,033 | 5.61 | 7.14 |
| Arithmetic Mean | 365 | 819 | 4.54 | 6.73 |
| Coefficient of Variation | 0.98 | 0.50 | 0.56 | 0.15 |
| P-value VIS410 group vs Placebo (Mann-Whitney U test) | 0.024 | | 0.043 | |
| VL by Virus Culture | | | | |
| Minimum | 0.00 | 31.3 | 0.00 | 3.00 |
| Maximum | 438 | 605 | 5.00 | 5.75 |
| Median | 47.1 | 552 | 2.75 | 5.00 |
| Arithmetic Mean | 126 | 396 | 2.27 | 4.54 |
| Coefficient of Variation | 1.32 | 0.60 | 0.83 | 0.23 |
| P-value VIS410 group vs Placebo (Mann-Whitney U test) | 0.019 | | 0.009 | |

*VL = Viral load
**VL AUC units are h × $\log_{10}$ vp/mL for VL AUC by qRT-PCR and h × $\log_{10}$ $TCID_{50}$/mL for VL AUC by virus culture. Vp = viral particles
***PVL units are $\log_{10}$ vp/mL for PVL by qRT-PCR and $\log_{10}$ $TCID_{50}$/mL for PVL by virus culture.

Figure 23A:
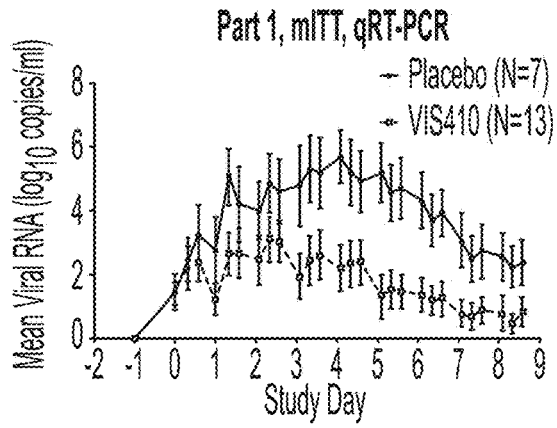
Figure 23B:
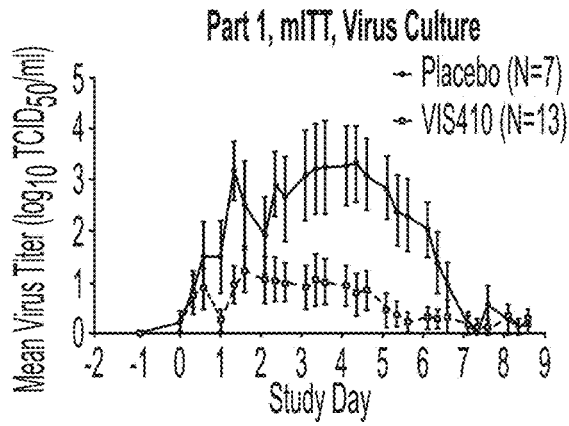
Figure 23C:
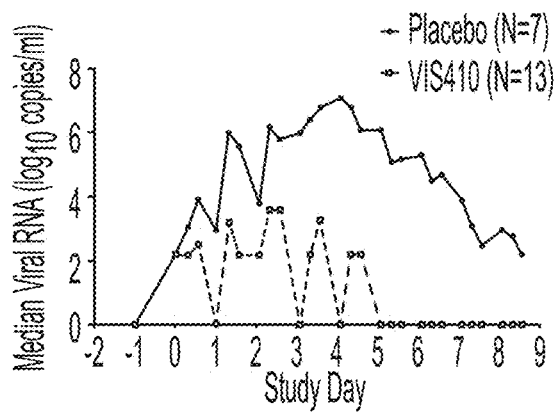
Figure 23D:
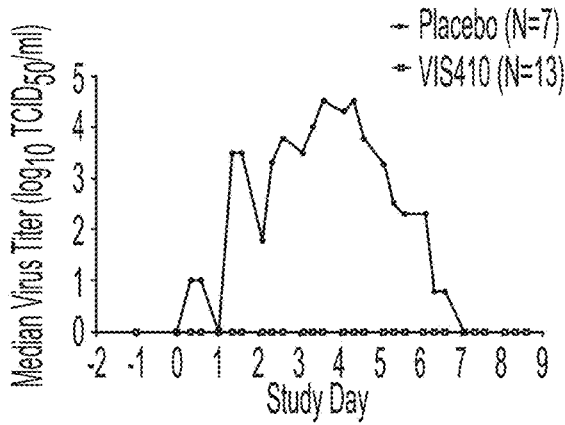
Figure 23E:
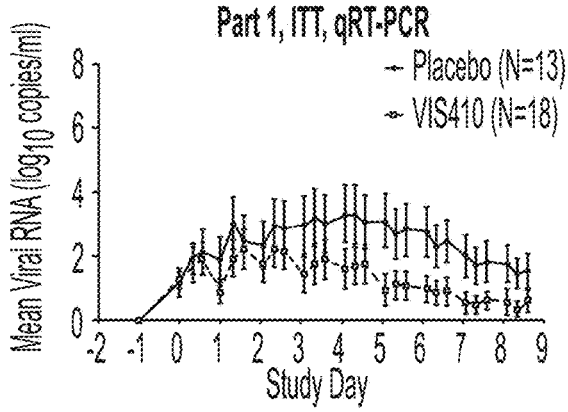
Figure 23F:
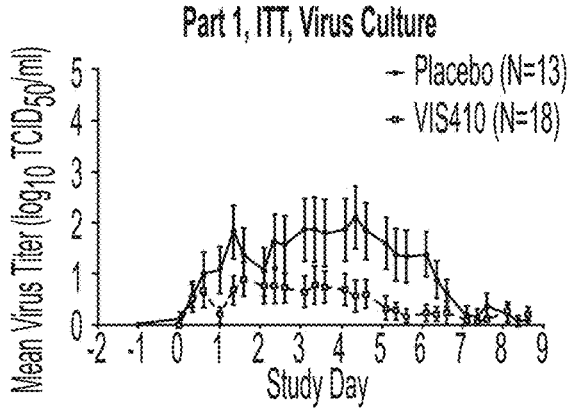

Viral infection profiles were also evaluated for all Part 1 subjects (ITT population, including those without confirmed virus infection) to eliminate potential bias from analysis of the mITT population subset alone. VIS410 treatment was associated with reduced mean viral shedding by qRT-PCR (FIG. 23E) and $TCID_{50}$ (FIG. 23F).

Finally, analysis of virus shedding from Parts 2 and 3 (open-label, VIS410 treatment only), demonstrated consistently lower virus shedding by qRT-PCR and $TCID_{50}$ for all VIS410-treatment arms versus placebo in all Parts of the study (FIGS. 24A-24B).

Influenza Symptom Resolution

Generally, only mild to moderate symptoms were observed following virus challenge in these healthy adults, as anticipated based on previous clinical experience with the challenge strain and inoculum. Mean daily symptom scores for total symptoms and upper respiratory tract (URT) symptoms were analyzed for the mITT population in placebo-controlled Part 1 of the study. VIS410-treated subjects reported higher total symptom scores prior to study drug dosing on Day 0 (FIG. 25A), with lower scores reported from Days 3-8. URT symptoms scores were equivalent for VIS410 and placebo treated groups immediately after infection and study drug administration but were improved Days 2-8 post-administration in VIS410-treated subjects (FIG. 25B). Time to resolution of total symptoms was similar between VIS410 and placebo-treated subjects (FIG. 25C). However, there was a trend toward faster time to resolution from peak URT symptom score observed with VIS410 treatment compared to placebo (FIG. 25D).

Safety and Tolerability

Treatment emergent adverse events (TEAEs) were recorded for 32 of 33 (97%) VIS410 recipients, and 10 of 13 (77%) placebo recipients (Table 13). The most frequently reported AEs occurring in the VIS410-treated cohort were abdominal pain (occurring in 71% of VIS410 recipients who did not receive pre-treatment prophylaxis versus 0% of placebo recipients) and diarrhea (occurring in 57% of VIS410 recipients who did not receive pre-treatment prophylaxis versus 0% of placebo recipients). Influenza-like symptoms (expected as a result of virus challenge) were well-balanced and occurred in 48% of VIS410 recipients and 54% of placebo recipients). Most adverse events were of mild to moderate severity. However, four VIS410 recipients experienced severe cramping, diarrhea, or both. These notable gastrointestinal adverse events were first observed during dosing of the initial 12 subjects (all seven VIS410 recipients in this group did not receive pre-treatment prophylaxis and experienced cramping, diarrhea, and nausea or vomiting). All events occurred within three hours of infusion and the majority resolved spontaneously within 12 hours of infusion. Following this observation, the protocol was amended to incorporate pretreatment with an antihistamine-based regimen consisting of a single dose of diphenhydramine (50 mg) in various combinations with a single dose of either oral ranitidine (150 mg), montelukast (10 mg), or ibuprofen (600 mg) (Table 13). The various oral pretreatment regimens were administered 60 minutes prior to VIS410 infusion. Pretreatment appeared to significantly ameliorate post-infusion gastrointestinal adverse event symptom severity, with a single dose of 50 mg of diphenhydramine in combination with 600 mg of ibuprofen appearing to largely ameliorate GI symptoms in both the 2300 mg and 4600 mg dosing groups.

TABLE 13

Primary safety endpoint (safety population)

| | Part 1 | | | | | | Part 2 | | | Part 3 |
|---|---|---|---|---|---|---|---|---|---|---|
| | No Pre-treatment | | Pretreatment with H1/H2 | | Pretreatment with H1/H2/M | | H1/M | H1/I | H1(IV)/M | H1/I |
| n (%) | Placebo N = 5 | VIS410 2300 mg N = 7 | Placebo N = 4 | VIS410 2300 mg N = 5 | Placebo N = 4 | VIS410 2300 mg N = 6 | VIS410-2300 mg N = 4 | VIS410-2300 mg N = 4 | VIS410-2300 mg N = 3 | VIS410-4600 mg N = 4 |
| TEAEs | 3 (60.0) [14.7; 94.7] | 7 (100) [59.0; 100] | 4 (100) [39.8; 100] | 5 (100) [47.8; 100] | 3 (75.0) [19.4; 99.4] | 5 (83.3) [35.9; 99.6] | 4 (100) [39.8; 100] | 4 (100) [39.8; 100] | 3 (100) [29.2; 100] | 4 (100) [39.8; 100] |
| 1-hour post-infusion AEs | 0 | 6 (85.7) [42.1; 99.6] | 0 | 4 (80.0) [28.4; 99.5] | 1 (25.0) [0.6; 80.6] | 4 (66.7) [22.3; 95.7] | 3 (75.0) [19.4; 99.4] | 0 | 1 (33.3) [0.8; 90.6] | 0 |
| SAEs | 0 | 0 | 0 | 0 | 0 | 0 | 0 | 0 | 0 | 0 |
| Severe AEs | 0 | 2 (28.6) | 0 | 0 | 0 | 1 (16.7) | 1 (25.0) | 0 | 0 | 1 (25.0) |
| Most frequently Reported TEAEs: | | | | | | | | | | |
| Abdominal Pain | 0 | 5 (71.4) | 0 | 3 (60.0) | 0 | 3 (50.0) | 3 (75.0) | 0 | 0 | 0 |
| Diarrhea | 0 | 4 (57.1) | 0 | 4 (80.0) | 1 (25.0) | 2 (33.3) | 3 (75.0) | 2 (50.0) | 3 (100) | 3 (75.0) |
| Influenza | 3 (60.0) | 3 (42.9) | 3 (75.0) | 4 (80.0) | 2 (50.0) | 3 (50.0) | 2 (50.0) | 2 (50.0) | 1 (33.3) | 1 (25.0) |

N = Number of subjects; n = number of subjects with that observation; 95% CI: Confidence interval.
1-hour post-infusion AEs: AEs that occurred within 1 h of completion of the infusion with VIS410/placebo.
H1: diphenhydramine, H2: ranitidine, M: montelukast, I: ibuprofen, H1 (IV): diphenhydramine administered intravenously.

Figure 26A:
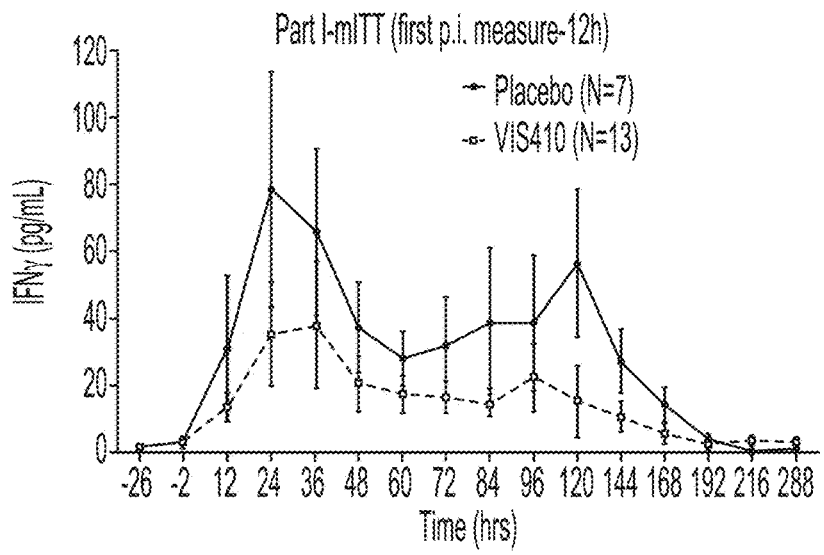
Figure 26B:
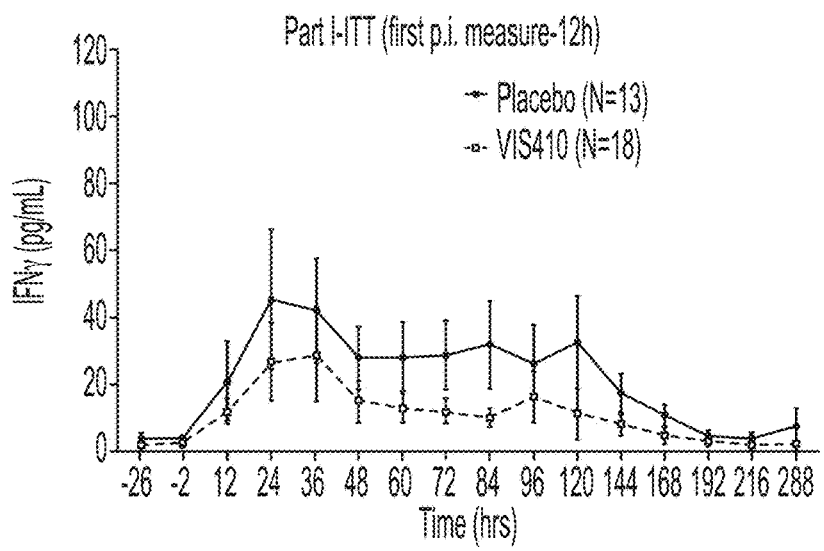
Figure 26C:
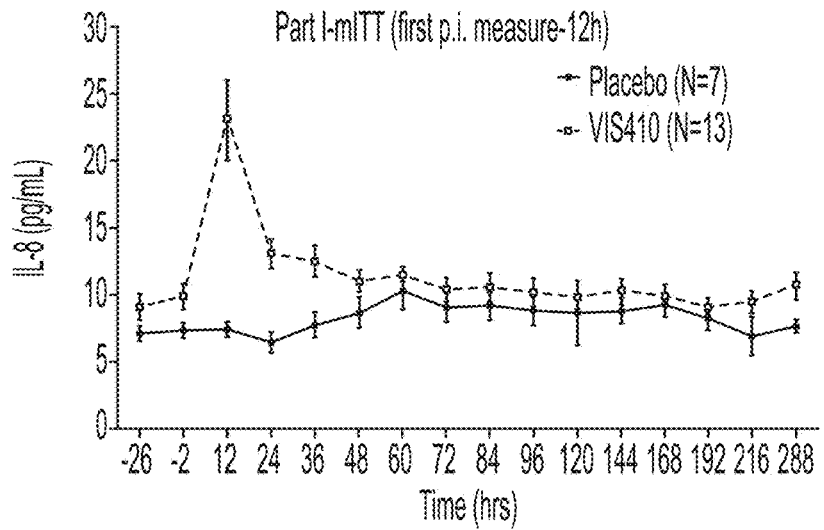
Figure 26D:
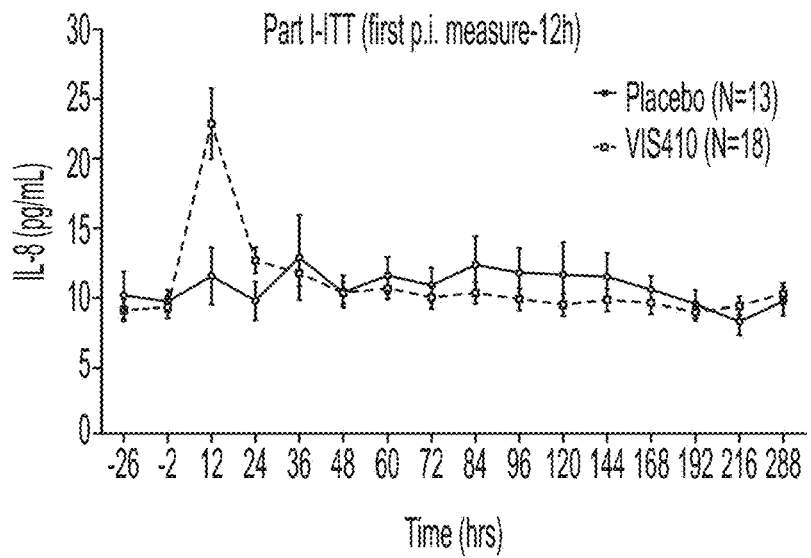
Figure 26E:
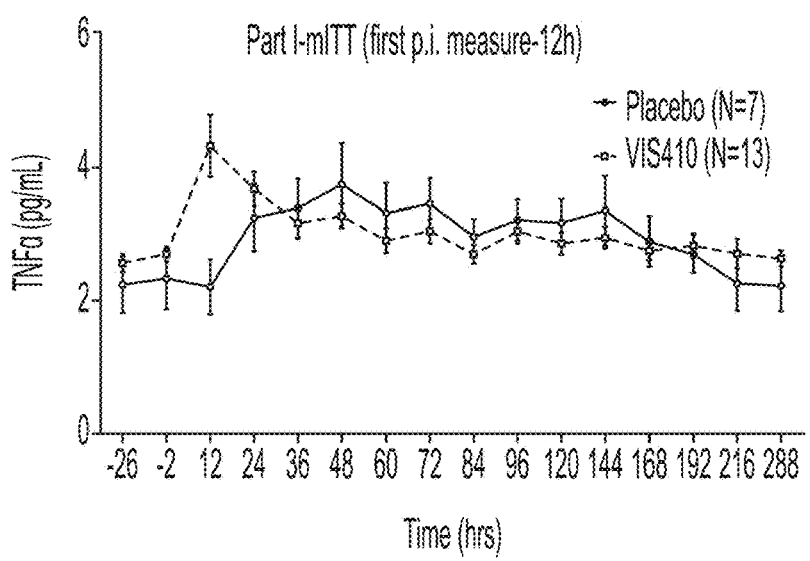
Figure 26F:
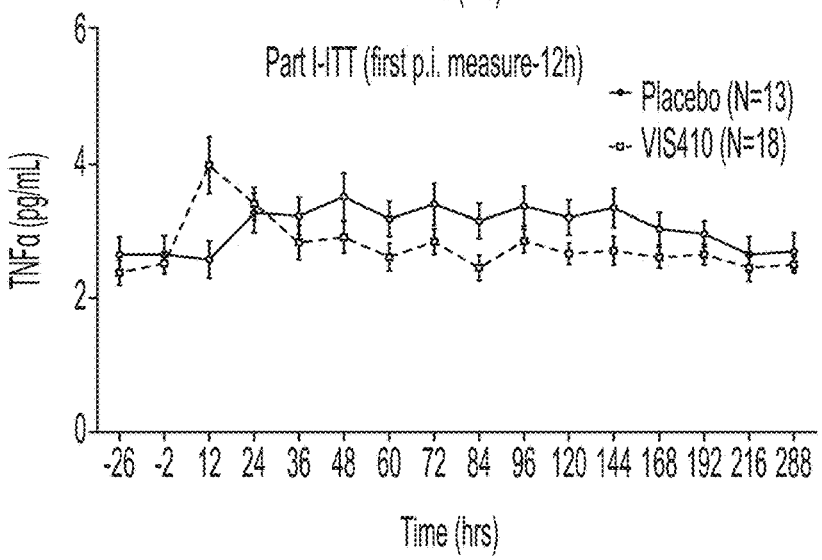

Multiple serum cytokine concentrations, including IFNγ, TNFα, IL-6, IL-8, and IL-10, were quantified to examine the effect of virus infection and the type and extent of the acute inflammatory response. For the placebo-controlled Part 1 of the study (mITT population), serum IFNγ levels increased with infection in both placebo and VIS410-treatment groups, with lower levels of IFNγ observed in the VIS410-treated group, likely reflecting a treatment effect of lower viral loads in these individuals (FIG. 26A). Interestingly, VIS410 treatment was associated with higher serum concentrations of IL-8 and TNFα in comparison with both baseline levels and levels measured in placebo-treated individuals at 12 hours following dosing. This increase was transient and returned to baseline/placebo levels by about Day two (FIGS. 26C and 26E, respectively). Similar relative profiles for IFNγ, IL-8, and TNFα levels were observed for the ITT population in Part 1 (FIGS. 26B, 26D, and 26F and Table 14). Minor increases in IL-6 were observed in Parts 2 and 3 but no significant differences were observed for IL-10 (Table 14).

TABLE 14

Detailed summary of cytokine profiles

| | | Part 1 Placebo (ITT, n = 13) | | Part 1 VIS410-2300 mg (ITT, n = 18) | | Part 2 VIS410-2300 mg (ITT n = 11) | | Part 3 VIS410-4600 mg (ITT, n = 4) | |
|---|---|---|---|---|---|---|---|---|---|
| | Time (hours) | mean | s.e. | mean | s.e. | mean | s.e. | mean | s.e. |
| TNF-α (pg/ml) | −26 | 2.74 | 0.20 | 2.44 | 0.13 | 2.54 | 0.15 | 2.31 | 0.15 |
| | −2 | 2.74 | 0.22 | 2.50 | 0.12 | 2.49 | 0.14 | 2.11 | 0.26 |
| | 1 | n.d. | n.d. | n.d. | n.d. | 5.50 | 0.99 | 14.38 | 4.52 |
| | 12 | 2.66 | 0.19 | 4.00 | 0.38 | 4.43 | 0.78 | 4.47 | 0.66 |
| | 24 | 3.22 | 0.28 | 3.35 | 0.24 | 3.39 | 0.40 | 3.20 | 0.40 |
| | 36 | 3.19 | 0.27 | 2.89 | 0.20 | 3.11 | 0.33 | 2.75 | 0.38 |
| | 48 | 3.46 | 0.35 | 2.95 | 0.20 | 3.10 | 0.29 | 2.64 | 0.17 | n.d. = not determined.

Lower and upper limits of quantification (LLOQ and ULOQ) for each of the cytokine assays are: IL-6 (0.828 and 324 pg/mL); IL-8 (0.852 and 406 pg/mL); IL-10 (0.422 and 216 pg/mL); IFN-γ (6.34 and 928 pg/mL), and TNF-α (1.39 and 274 pg/mL).

Parts 2 and 3 of the study added a one-hour post-infusion timepoint for evaluation of cytokine responses. IL-8 and TNFα levels were ~2 to 8-fold greater from baseline levels one hour following VIS410-infusion, with a rapid return to baseline. There was some evidence of a dose-response (n=4 at the high dose) with greater cytokine elevations associated with the 4600 mg dose of VIS410 (FIGS. 27A and 27C).

The relationship of IL-8 and TNFα profiles in Parts 2 and 3 to gastrointestinal adverse events (GI AEs) was also evaluated. Subjects reporting moderate or severe GI AEs following VIS410 administration demonstrated IL-8 and TNFα serum elevations approximately five-fold and two-fold higher, respectively, than subjects reporting no or mild GI AEs (FIGS. 27B and 27D). Importantly, despite transient elevations, mean IL-8 and TNF-α serum levels returned to baseline for VIS410-treated subjects within 48-60 hours post-infusion.

VIS410 Mechanism of Action

Figure 28A:
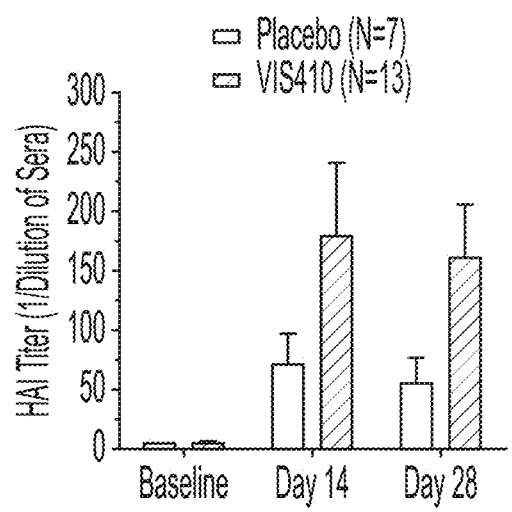

VIS410 targets the influenza HA stalk and does not inhibit binding of HA to its receptors, nor does it inhibit HA-induced erythrocyte agglutination. For example, when spiked into control sera at increasing concentrations, VIS410 had no effect on HA1 activity of the serum. To examine if VIS410 therapy impacted the endogenous humoral response to influenza infection, serum HA1 titers from placebo and VIS410-treated subjects were measured against the challenge strain. Mean HA1 titers in mITT population for VIS410-treated subjects (Part 1) were higher than mean values in placebo-treated subjects on days 14 and 28 following infection (FIG. 28A). These data indicate that treatment with VIS410 does not inhibit the antibody response to influenza, and, indeed, may facilitate a more robust host humoral response to the virus.

Figure 28B:
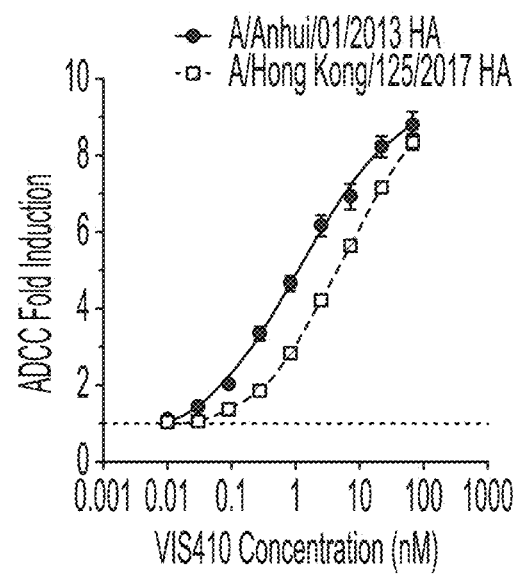
Figure 28C:
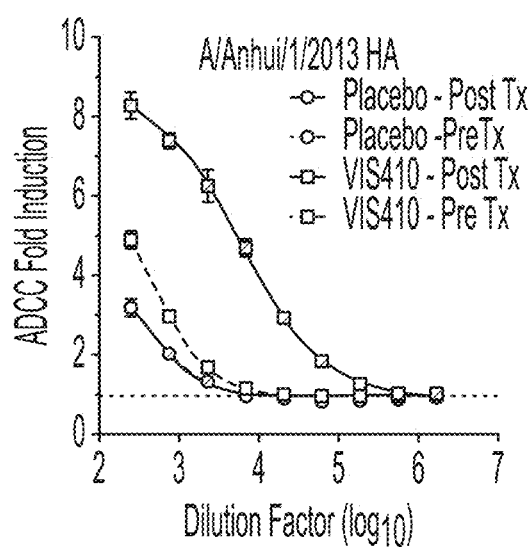
Figure 28D:
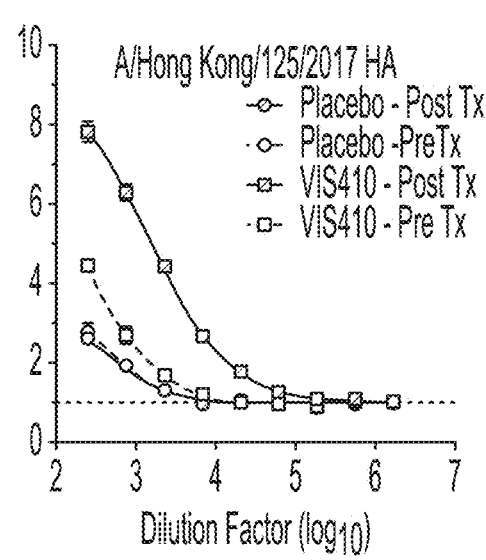

In addition to direct virus neutralization, VIS410 elicits antibody-dependent cellular cytotoxicity (ADCC), through broad recognition of influenza A HA, including HA from recent H7N9 strains (FIG. 28B). To further characterize the mechanism of action of VIS410 in patient serum, an ADCC reporter assay was conducted with serum from placebo and VIS410-treated subjects. (FIGS. 28C and 28D). Sera from VIS410-treated subjects induced a substantial increase in ADCC activity against two clinically important H7N9-strains compared to placebo. These H7N9 strains are serologically unrelated to the H1N1 strain used to challenge the subjects of this study, thus demonstrating the broad functional protection associated with VIS410 against different subtypes of influenza A.

VIS410 Pharmacokinetics

VIS410 demonstrated dose-dependent pharmacokinetics, with higher serum concentrations observed for the 4600 mg dose vs 2300 mg as expected (FIG. 29, Table 15). Mean serum $C_{max}$ was 873 µg/ml (2300 mg) and 1650 µg/ml (4600 mg). The drug serum half-life was similar for both doses (Median $t_{1/2}$ was 11.7 days (2300 mg) and 11.5 days (4600 mg). Nasal concentrations of VIS410 were variable with mean nasal $C_{max}$ of 35.9 µg/ml (2300 mg) and 110 µg/ml (4600 mg) (FIG. 29).

TABLE 15

| VIS410 serum and nasopharyngeal pharmacokinetics | | | | | | |
|---|---|---|---|---|---|---|
| | $C_{max}$ (ug/mL) | $T_{max}$ (day) | $AUC_{0-last}$ (day*ug/mL) | Vd (mL) | CL (mL/day) | $t_{1/2}$ (day) |
| VIS410- 2300 mg (Serum PK*) | | | | | | |
| N | 29 | 29 | 29 | 29 | 29 | 29 |
| Mean | 873 | 0.235 | 7010 | 5570 | 330 | 11.7 |
| SD | 289 | 0.204 | 1300 | 1300 | 63.4 | 1.63 |
| Min | 371 | 0.103 | 4310 | 3310 | 223 | 9.39 |
| Median | 869 | 0.107 | 7080 | 5320 | 316 | 11.7 |
| Max | 1820 | 1.08 | 10100 | 9440 | 501 | 15.3 |
| CV % | 33.1 | 86.8 | 18.6 | 23.4 | 19.2 | 13.9 |
| VIS410- 4600 mg (Serum PK) | | | | | | |
| N | 4 | 4 | 4 | 4 | 4 | 4 |
| Mean | 1650 | 0.260 | 16200 | 4900 | 280 | 12.1 |
| SD | 195 | 0.226 | 586 | 911 | 9.67 | 1.89 |
| Min | 1470 | 0.104 | 15500 | 4270 | 268 | 10.6 |
| Median | 1660 | 0.177 | 16200 | 4540 | 280 | 11.5 |
| Max | 1830 | 0.583 | 16900 | 6250 | 292 | 14.9 |
| CV % | 11.8 | 86.8 | 3.62 | 18.6 | 3.46 | 15.6. |

*The following PK parameters were determined for VIS410 in serum: $C_{max}$: max observed serum concentration, $T_{max}$: time of $C_{max}$, $AUC_{0-last}$: area under the serum concentration-time curve from time 0 to the last measurable concentration, Vd: volume of distribution, CL: total clearance, and $t_{1/2}$: terminal elimination half-life.

| | $C_{max}$ (ug/mL) | $T_{max}$ (day) | $AUC_{0-last}$ (day*ug/mL) | $T_{last}$ (day) | $C_{last}$ (ug/mL) |
|---|---|---|---|---|---|
| VIS410- 2300 mg (Nasal PK**) | | | | | |
| N | 29 | 29 | 29 | 29 | 29 |
| Mean | 35.9 | 3.11 | 98.0 | 8.05 | 10.9 |
| SD | 39.1 | 2.45 | 88.2 | 0.0329 | 11.9 |
| Min | 4.52 | 0.323 | 17.0 | 7.97 | 0.980 |

TABLE 15-continued

VIS410 serum and nasopharyngeal pharmacokinetics

| | | | | | |
|---|---|---|---|---|---|
| Median | 19.0 | 2.06 | 60.4 | 8.06 | 7.74 |
| Max | 170 | 8.01 | 346 | 8.08 | 45.4 |
| CV % | 109 | 78.8 | 90.0 | 0.409 | 109 |
| VIS410- 4600 mg (Nasal PK) | | | | | |
| N | 4 | 4 | 4 | 4 | 4 |
| Mean | 110 | 2.12 | 349 | 12.1 | 8.50 |
| SD | 112 | 2.08 | 260 | 0.00793 | 11.7 |
| Min | 46.3 | 0.311 | 150 | 12.1 | 1.34 |
| Median | 57.5 | 1.57 | 265 | 12.1 | 3.34 |
| Max | 278 | 5.05 | 717 | 12.1 | 26.0 |
| CV % | 102 | 97.9 | 74.4 | 0.0657 | 138 |

**The following PK parameters were determined for VIS410 in nasal mucosa: $C_{max}$: max observed nasal mucosa concentration, $T_{max}$: time of $C_{max}$, $AUC_{0-last}$: area under the nasal mucosa concentration-time curve from time 0 to the last measurable concentration, $T_{last}$: time of the last measurable concentration, and $C_{last}$: last measurable concentration.

In this human challenge study using A/California/7/2009 (H1N1) influenza virus, it was demonstrated that VIS410, a broad spectrum human monoclonal antibody to the hemagglutinin stalk, represents an effective immune-based therapeutic for treating influenza infection. VIS410 treatment was associated with a significant reduction in VL AUC by qRT-PCR (primary endpoint), VL AUC by virus culture ($TCID_{50}$), and peak viral load by qRT-PCR and $TCID_{50}$ measurements. Trends were observed for improvement in upper respiratory symptoms with VIS410 treatment.

While HA-stem epitope binding by VIS410 resulted in inhibition of virus replication, it is a non-immunodominant epitope and therefore was not expected to interfere with endogenous immune responses to the virus. To verify this, HA1 was examined as a surrogate for endogenous response to influenza. VIS410 did not interfere with HA1 titers and hence the endogenous immune response to influenza. In contrast, the ADCC data demonstrated that VIS410 can facilitate clearance of infected cells and can act even on cells infected with a heterotypic virus. Without wishing to be bound by theory, it is believed that in an embodiment this breadth of response can, at least in part, be due to in situ formation of antibody-virus complexes that can be readily phagocytosed and thereby present antigens common to multiple influenza strains.

Genotypic and phenotypic resistance monitoring demonstrated that no VIS410 epitope HA polymorphisms emerged, nor was there evidence for emergence of viral resistance. Evidence for VIS410 dual mechanism of actions, including direct antiviral effects and indirect potentiation of host immunity, were also demonstrated in this trial.

VIS410 treatment was unexpectedly associated with transient elevation of specific cytokines (IL-8, TNFα, and IL-6), as well as gastrointestinal adverse events (GI AEs). Cytokine elevation was associated with GI AEs of greater severity in this study, and the time course of elevated cytokine levels and GI AEs were similar, both rapidly resolving.

Without wishing to be bound by theory, it is believed that in an embodiment mild increases in the cytokines can have a therapeutic significance that can help accelerate viral clearance. IL-8 mediates the inflammatory response as a chemoattractant for neutrophils, basophils, and lymphocytes, and TNFα functions to activate the immune response to influenza. It is important to differentiate this transient and selective cytokine elevation from the hyper-inflammatory response observed in severe influenza. No evidence of hyper-inflammatory response was observed in the VIS410-treated group.

Treatment-emergent GI adverse events were effectively mitigated by the combination of an H1 blocker plus a prostaglandin inhibitor. Similar pretreatment regimens have been used successfully with other monoclonal antibodies. Without wishing to be bound by theory, it is believed that VIS410 can engage macrophage or monocyte Fcγ receptors, resulting in transient cytokine elevation. There was no evidence for a histamine release syndrome in this study, nor did mast cell blockade with montelukast prevent the occurrence of adverse events.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating or preventing an influenza virus infection, or a symptom thereof, in a human subject, comprising administering to the subject a combination of an anti-HA antibody molecule, and one or more anti-viral agents comprising an endonuclease inhibitor, a polymerase basic protein 2 (PB2) inhibitor, or both,
wherein the antibody molecule comprises:

(a) a heavy chain immunoglobulin variable region segment comprising:
            (SEQ ID NO: 68)
a CDR1 comprising the sequence
S-Y-A-M-H;

(SEQ ID NO: 69)
a CDR2 comprising the sequence
V-V-S-Y-D-G-N-Y-K-Y-Y-A-D-S-V-Q-G;
and (SEQ ID NO: 70)
a CDR3 comprising the sequence
D-S-R-L-R-S-L-L-Y-F-E-W-L-S-Q-G-Y-F-N-P;
and (b) a light chain immunoglobulin variable region segment comprising:
            (SEQ ID NO: 145)
a CDR1 comprising the sequence
Q-S-I-T-F-D-Y-K-N-Y-L-A;

(SEQ ID NO: 72)
a CDR2 comprising the sequence
W-G-S-Y-L-E-S;
and (SEQ ID NO: 73)
a CDR3 comprising the sequence
Q-Q-H-Y-R-T-P-P-S.

2. The method of claim 1, wherein the one or more anti-viral agents comprises an endonuclease inhibitor, and wherein the endonuclease inhibitor comprises a cap-dependent endonuclease inhibitor or baloxavir marboxil.

3. The method of claim 1, wherein the one or more anti-viral agents comprises a PB2 inhibitor, and wherein the PB2 inhibitor comprises pimodivir.

4. The method of claim 1, wherein the one or more anti-viral agents further comprise a neuraminidase inhibitor, wherein the neuraminidase inhibitor comprises one, two, or all of oseltamivir, peramivir, or zanamivir.

5. The method of claim 1, wherein the anti-HA antibody molecule is administered prior to, concurrently with, or subsequent to, the one or more anti-viral agents.

6. The method of claim 2, wherein the anti-HA antibody molecule is administered intravenously at a dose of between 1500 mg and 2500 mg or between 3500 mg and 4500 mg.

7. The method of claim 1, wherein the antibody molecule comprises a heavy chain immunoglobulin variable region segment that comprises SEQ ID NO: 25, a light chain immunoglobulin variable region segment that comprises SEQ ID NO: 52, or both.

8. The method of claim 1, wherein the subject is infected with, or is at risk of being infected with, an influenza virus A.

9. The method of claim 1, wherein the subject is infected with, or is at risk of being infected with, an H1N1, H1N2, H2N2, H3N2, H5N1, H6N1, H7N2, H7N3, H7N7, H7N9, H9N2, or H10N7 influenza virus, or a combination thereof.

10. A method of treating or preventing an influenza virus infection, or a symptom thereof, in a human subject, comprising responsive to a determination of the presence of an influenza virus that is resistant to the antiviral agent administering to the subject an anti-HA antibody molecule,
wherein the antibody molecule comprises:

(a) a heavy chain immunoglobulin variable region segment comprising:
            (SEQ ID NO: 68)
a CDR1 comprising the sequence
S-Y-A-M-H;

(SEQ ID NO: 69)
a CDR2 comprising the sequence
V-V-S-Y-D-G-N-Y-K-Y-Y-A-D-S-V-Q-G;
and (SEQ ID NO: 70)
a CDR3 comprising the sequence
D-S-R-L-R-S-L-L-Y-F-E-W-L-S-Q-G-Y-F-N-P;
and (b) a light chain immunoglobulin variable region segment comprising:
            (SEQ ID NO: 145)
a CDR1 comprising the sequence
Q-S-I-T-F-D-Y-K-N-Y-L-A;

(SEQ ID NO: 72)
a CDR2 comprising the sequence
W-G-S-Y-L-E-S;
and (SEQ ID NO: 73)
a CDR3 comprising the sequence
Q-Q-H-Y-R-T-P-P-S,
and wherein the subject is infected with, or is at risk of being infected with, an influenza virus that is resistant to an antiviral agent chosen from an endonuclease inhibitor, a neuraminidase inhibitor, a PB2 inhibitor, or a combination thereof.

11. The method of claim 10, wherein the antiviral agent comprises an endonuclease inhibitor, and wherein the endonuclease inhibitor comprises a cap-dependent endonuclease inhibitor or baloxavir marboxil.

12. The method of claim 10, wherein the antiviral agent comprises a neuraminidase inhibitor, and wherein the neuraminidase inhibitor comprises oseltamivir, peramivir, zanamivir, or a combination thereof.

13. The method of claim 10, wherein the antiviral agent comprises a PB2 inhibitor, and wherein the PB2 inhibitor comprises pimodivir.

14. A method of evaluating a human subject or a therapy, the method comprising:
acquiring acknowledge that a human subject is infected with, or is at risk of being infected with, an influenza virus that is resistant to an antiviral agent chosen from an endonuclease inhibitor, a neuraminidase inhibitor, a PB2 inhibitor, or a combination thereof; and
selecting the subject for a therapy comprising an anti-HA antibody molecule, or selecting a therapy comprising an anti-HA antibody molecule for treating or preventing influenza in the subject,
wherein the anti-HA antibody molecule comprises:

(a) a heavy chain immunoglobulin variable region segment comprising:
            (SEQ ID NO: 68)
a CDR1 comprising the sequence
S-Y-A-M-H;

-continued a CDR2 comprising the sequence (SEQ ID NO: 69)
V-V-S-Y-D-G-N-Y-K-Y-Y-A-D-S-V-Q-G;
and a CDR3 comprising the sequence (SEQ ID NO: 70)
D-S-R-L-R-S-L-L-Y-F-E-W-L-S-Q-G-Y-F-N-P;
and (b) a light chain immunoglobulin variable region segment comprising:
 (SEQ ID NO: 145)
a CDR1 comprising the sequence
Q-S-I-T-F-D-Y-K-N-Y-L-A;

a CDR2 comprising the sequence (SEQ ID NO: 72)
W-G-S-Y-L-E-S;
and a CDR3 comprising the sequence (SEQ ID NO: 73)
Q-Q-H-Y-R-T-P-P-S.

15. A method of treating or preventing an influenza virus infection, or a symptom thereof, in a human subject, comprising administering to the subject an anti-HA antibody molecule or modifying the administration of an anti-HA antibody molecule to the subject, responsive to a change in the level of 1, 2, 3, 4, 5, or all of the cytokines comprising IL-6, IL-8, IL-10, IFN-γ, TNF-α, or IL-33 in the subject,
 wherein the antibody molecule comprises:

(a) a heavy chain immunoglobulin variable region segment comprising:
 (SEQ ID NO: 68)
a CDR1 comprising the sequence
S-Y-A-M-H;

a CDR2 comprising the sequence (SEQ ID NO: 69)
V-V-S-Y-D-G-N-Y-K-Y-Y-A-D-S-V-Q-G;

and a CDR3 comprising the sequence (SEQ ID NO: 70)
D-S-R-L-R-S-L-L-Y-F-E-W-L-S-Q-G-Y-F-N-P;
and (b) a light chain immunoglobulin variable region segment comprising:
 (SEQ ID NO: 145)
a CDR1 comprising the sequence
Q-S-I-T-F-D-Y-K-N-Y-L-A;

a CDR2 comprising the sequence (SEQ ID NO: 72)
W-G-S-Y-L-E-S;
and a CDR3 comprising the sequence (SEQ ID NO: 73)
Q-Q-H-Y-R-T-P-P-S.

16. The method of claim 15, further comprising determining that the level of one or more cytokines is changed, wherein the level of one or more cytokines is determined every week, every two weeks, every three weeks, every four weeks, every six weeks, or every eight weeks.

17. A method of evaluating an influenza therapy or a human subject, the method comprising:
 acquiring acknowledge that the level of one or more cytokines is elevated in a human subject after administration of an influenza therapy comprising an anti-HA antibody molecule,
 wherein an elevated level of one or more cytokines is indicative that the anti-HA antibody molecule is effective in treating or preventing an influenza infection, or a symptom thereof, and
 selecting the anti-HA antibody molecule as suitable for treating or preventing an influenza infection, or a symptom thereof, in the subject, or selecting the subject as suitable for continued administration of the anti-HA antibody molecule,
 wherein the antibody molecule comprises:

(a) a heavy chain immunoglobulin variable region segment comprising:
 (SEQ ID NO: 68)
a CDR1 comprising the sequence
S-Y-A-M-H;

a CDR2 comprising the sequence (SEQ ID NO: 69)
V-V-S-Y-D-G-N-Y-K-Y-Y-A-D-S-V-Q-G;
and a CDR3 comprising the sequence (SEQ ID NO: 70)
D-S-R-L-R-S-L-L-Y-F-E-W-L-S-Q-G-Y-F-N-P;
and (b) a light chain immunoglobulin variable region segment comprising:
 (SEQ ID NO: 145)
a CDR1 comprising the sequence
Q-S-I-T-F-D-Y-K-N-Y-L-A;

a CDR2 comprising the sequence (SEQ ID NO: 72)
W-G-S-Y-L-E-S;
and a CDR3 comprising the sequence (SEQ ID NO: 73)
Q-Q-H-Y-R-T-P-P-S.

18. A method of evaluating an influenza therapy or a human subject, the method comprising:
 acquiring acknowledge that the level of one or more cytokines is elevated in a human subject after administration of an influenza therapy comprising an anti-HA antibody molecule,
 wherein an elevated level of one or more cytokines is indicative that the anti-HA antibody molecule is capable of causing an adverse event in the subject, and
 selecting the anti-HA antibody molecule as not suitable for treating or preventing an influenza infection, or a symptom thereof, in the subject, or selecting the subject as not suitable for continued administration of the anti-HA antibody molecule,
 wherein the antibody molecule comprises:

(a) a heavy chain immunoglobulin variable region segment comprising:
 (SEQ ID NO: 68)
a CDR1 comprising the sequence
S-Y-A-M-H;

a CDR2 comprising the sequence (SEQ ID NO: 69)
V-V-S-Y-D-G-N-Y-K-Y-Y-A-D-S-V-Q-G;
and a CDR3 comprising the sequence (SEQ ID NO: 70)
D-S-R-L-R-S-L-L-Y-F-E-W-L-S-Q-G-Y-F-N-P;
and -continued (b) a light chain immunoglobulin variable region segment comprising:

a CDR1 comprising the sequence (SEQ ID NO: 145)
Q-S-I-T-F-D-Y-K-N-Y-L-A;

a CDR2 comprising the sequence (SEQ ID NO: 72)
W-G-S-Y-L-E-S;
and a CDR3 comprising the sequence (SEQ ID NO: 73)
Q-Q-H-Y-R-T-P-P-S.

19. A method of treating or preventing an influenza virus infection, or a symptom thereof, in a subject, comprising administering to the subject an anti-HA antibody molecule, wherein the antibody molecule comprises:

(a) a heavy chain immunoglobulin variable region segment comprising:

a CDR1 comprising the sequence (SEQ ID NO: 68)
S-Y-A-M-H;

a CDR2 comprising the sequence (SEQ ID NO: 69)
V-V-S-Y-D-G-N-Y-K-Y-Y-A-D-S-V-Q-G;
and a CDR3 comprising the sequence (SEQ ID NO: 70)
D-S-R-L-R-S-L-L-Y-F-E-W-L-S-Q-G-Y-F-N-P;
and (b) a light chain immunoglobulin variable region segment comprising:

a CDR1 comprising the sequence (SEQ ID NO: 145)
Q-S-I-T-F-D-Y-K-N-Y-L-A;

a CDR2 comprising the sequence (SEQ ID NO: 72)
W-G-S-Y-L-E-S;
and a CDR3 comprising the sequence (SEQ ID NO: 73)
Q-Q-H-Y-R-T-P-P-S,
and wherein the subject has the following characteristics:
(i) requires hospitalization or intensive care unit (ICU) care; and
(ii) receives, or is more likely to receive, an oxygen therapy, positive pressure ventilation, and/or a therapy to treat or prevent bacterial pneumonia; and/or is, or is more likely to be, incubated.

20. The method of claim 19, wherein the subject has 1, 2, 3, 4, 5, 6, 7, 8, 9, 10, 11, or all of the following characteristics:
(a) is at least about 60 years old, e.g., at least about 65, 70, 75, or 80 years old;
(b) has received, or has not received, a second antiviral therapy, within about 1, 2, or 3 days prior to administration of the anti-HA antibody molecule;
(c) has an onset of influenza, at least about 24, 36, 48, 60, 72, or 96 hours, or within about 24, 36, 48, 60, 72, 96, or 120 hours, prior to administration of the anti-HA antibody molecule;
(d) has received, or has not received, an influenza vaccine, within about 1, 2, 3, 4, 5, or 6 months, prior to administration of the anti-HA antibody molecule;
(e) is identified as being infected with an influenza A virus, within about 12, 24, 36, or 48 hours, prior to administration of the anti-HA antibody molecule;
(f) is infected with, is at risk of being infected with, an H1 influenza virus, an H3 influenza virus, or an H7 influenza virus;
(g) has an ordinal scale score above about 2.0, 2.1, 2.2, 2.25, 2.3, 2.4, or 2.5, wherein the ordinal scale score is based one or more parameters chosen from death, ICU stay with mechanical ventilation, ICU stay without mechanical ventilation, non-ICU hospitalization, or discharge;
(h) has a clinical response as determined by one, two, three, four, or five vital signs meeting a specified threshold, within about 24, 36, 48, 60, 72, 84, 96, 108, or 120 hours, after administration of the anti-HA antibody molecule;
(i) has a symptom score determined by FluPRO that is decreased by at least about 10%, 20%, 30%, 40%, 50%, 60%, 70%, 80%, 90%, or more, within 1, 2, 3, 4, 5, 6, 7, 8, 9, 10, 11, 12, 13, or 14 days, after administration of the anti-HA antibody molecule;
(j) has a symptom score determined by visual analog score (VAS) that is increased by at least about 2, 3, 4, 5, 6, 7, 8, 9, or 10-fold, within 1, 2, 3, 4, 5, 6, 7, 8, 9, 10, 11, 12, 13, or 14 days, after administration of the anti-HA antibody molecule;
(k) is negative for viral titer determined by TCID50, within 1, 2, 3, 4, 5, 6, 7, 8, 9, 10, 11, 12, 13, or 14 days, after administration of the anti-HA antibody molecule; or
(l) does not develop, or develops no more than 1, treatment emergent adverse event (TEAE).

* * * * *

UNITED STATES PATENT AND TRADEMARK OFFICE
CERTIFICATE OF CORRECTION

PATENT NO. : 11,230,593 B2
APPLICATION NO. : 16/829519
DATED : January 25, 2022
INVENTOR(S) : Kristin Narayan It is certified that error appears in the above-identified patent and that said Letters Patent is hereby corrected as shown below:

In the Specification

At Column 9, Line number 41, delete "acquiring acknowledge" and insert -- acquiring knowledge --.

At Column 10, Line number 61, delete "acquiring acknowledge" and insert -- acquiring knowledge --.

At Column 12, Line number 34, delete "acknowledge" and insert -- knowledge --.

At Column 15, Line number 8, delete "acknowledge" and insert -- knowledge --.

At Column 17, Line number 40, delete "acknowledge" and insert -- knowledge --.

At Column 19, Line number 38, delete "acknowledge" and insert -- knowledge --.

At Column 21, Line number 38, delete "acquiring acknowledge" and insert -- acquiring knowledge --.

At Column 24, Line number 2, delete "acquiring acknowledge" and insert -- acquiring knowledge --.

At Column 25, Line number 65, delete "acquiring acknowledge" and insert -- acquiring knowledge --.

At Column 28, Line number 30, delete "acquiring acknowledge" and insert -- acquiring knowledge --.

At Column 164, Line number 8, delete "acknowledge" and insert -- knowledge --.

At Column 164, Line number 15, delete "acknowledge" and insert -- knowledge --.

At Column 165, Line number 10, delete "acknowledge" and insert -- knowledge --.

At Column 166, Line number 37, delete "acknowledge" and insert -- knowledge --.

Signed and Sealed this
Nineteenth Day of March, 2024

*Katherine Kelly Vidal*

Katherine Kelly Vidal
*Director of the United States Patent and Trademark Office*

CERTIFICATE OF CORRECTION (continued)
U.S. Pat. No. 11,230,593 B2

At Column 166, Line number 47, delete "acknowledge" and insert -- knowledge --.

At Column 166, Line number 56, delete "acknowledge" and insert -- knowledge --.

At Column 166, Line number 64, delete "acknowledge" and insert -- knowledge --.

At Column 167, Line number 6, delete "acknowledge" and insert -- knowledge --.

At Column 167, Line number 14, delete "acknowledge" and insert -- knowledge --.

In the Claims

At Column 352, Claim number 14, Line number 50, delete "acquiring acknowledge" and insert -- acquiring knowledge --.

At Column 353, Claim number 17, Line number 64, delete "acquiring acknowledge" and insert -- acquiring knowledge --.

At Column 354, Claim number 18, Line number 40, delete "acquiring acknowledge" and insert -- acquiring knowledge --.